(12) United States Patent
Amberg et al.

(10) Patent No.: US 8,686,002 B2
(45) Date of Patent: Apr. 1, 2014

(54) HETEROCYCLIC COMPOUNDS AND THEIR USE AS BINDING PARTNERS FOR 5-HT$_5$ RECEPTORS

(75) Inventors: Wilhelm Amberg, Mannheim (DE); Astrid Netz, Mannheim (DE); Andreas Kling, Mannheim (DE); Michael Ochse, Bad Durkeim (DE); Udo Lange, Berlin (DE); Charles W. Hutchins, Green Oaks, IL (US); Francisco Javier Garcia-Ladona, Kandel (DE); Wolfgang Wernet, Neustadt (DE); Alfred Hahn, legal representative, Mannheim (DE)

(73) Assignee: AbbVie Deutschland GmbH & Co. KG, Wiesbaden (DE)

( * ) Notice: Subject to any disclaimer, the term of this patent is extended or adjusted under 35 U.S.C. 154(b) by 364 days.

(21) Appl. No.: 11/990,822

(22) PCT Filed: Aug. 21, 2006

(86) PCT No.: PCT/EP2006/008222
§ 371 (c)(1),
(2), (4) Date: Nov. 5, 2009

(87) PCT Pub. No.: WO2007/022946
PCT Pub. Date: Mar. 1, 2007

(65) Prior Publication Data
US 2010/0041698 A1 Feb. 18, 2010

Related U.S. Application Data

(60) Provisional application No. 60/711,075, filed on Aug. 24, 2005.

(30) Foreign Application Priority Data

Aug. 21, 2005 (DE) .......................... 10 2005 040 602
Feb. 9, 2006 (DE) .......................... 10 2006 005 916

(51) Int. Cl.
| | |
|---|---|
| *C07D 215/38* | (2006.01) |
| *C07D 239/84* | (2006.01) |
| *C07D 401/04* | (2006.01) |
| *C07D 405/06* | (2006.01) |
| *C07D 409/04* | (2006.01) |
| *C07D 409/12* | (2006.01) |
| *C07D 471/04* | (2006.01) |
| *C07D 491/04* | (2006.01) |
| *A61K 31/4706* | (2006.01) |
| *A61P 25/28* | (2006.01) |

(52) U.S. Cl.
USPC .......................................... 514/313; 546/159

(58) Field of Classification Search
None
See application file for complete search history.

(56) References Cited

U.S. PATENT DOCUMENTS

| | | | |
|---|---|---|---|
| 4,390,540 | A | 6/1983 | Chodnekar et al. |
| 4,455,311 | A | 6/1984 | Kienzle |
| 5,258,356 | A | 11/1993 | Saupe et al. |
| 5,470,975 | A | 11/1995 | Atwal |
| 6,114,349 | A | 9/2000 | Kirsch et al. |
| 6,284,796 | B1 | 9/2001 | Geyer et al. |
| 2004/0235828 | A1 | 11/2004 | Dorsch et al. |
| 2005/0101568 | A1 | 5/2005 | Kaila et al. |
| 2005/0101569 | A1 | 5/2005 | Kaila et al. |
| 2006/0247212 | A1 | 11/2006 | Murai et al. |

FOREIGN PATENT DOCUMENTS

| | | |
|---|---|---|
| BE | 722675 | 4/1969 |
| DE | 3907937 | 9/1990 |
| DE | 43 44 452 | 6/1995 |
| DE | 196 13 591 | 10/1997 |
| DE | 101 39 060 | 2/2003 |
| EP | 0 046 267 | 2/1982 |
| EP | 0 073 060 | 3/1983 |
| EP | 0 365 492 | 4/1990 |
| EP | 0 399 818 | 11/1990 |
| EP | 0 481 448 | 4/1992 |
| EP | 0 481 802 | 4/1992 |
| EP | 0 498 723 | 8/1992 |
| EP | 0 507 594 | 10/1992 |
| EP | 0 527 534 | 2/1993 |

(Continued)

OTHER PUBLICATIONS

Onoda et al., caplus an 1995:913405.*

(Continued)

*Primary Examiner* — Sun Jae Loewe
(74) *Attorney, Agent, or Firm* — Lisa V. Mueller; Michael Best & Friedrich LLP

(57) ABSTRACT

The invention relates to compounds of general formula (I), corresponding enantiomeric, diastereomeric and/or tautomeric forms thereof as well as pharmaceutically acceptable salts thereof and the prodrugs of said compounds. The invention also relates to the use of said compounds as binding partners for 5-HT5 receptors for treating diseases that are modulated by a 5-HT5 receptor activity, in particular, for treating neurodegenerative and neuropsychiatric disorders as well as signs, symptoms and dysfunctions.

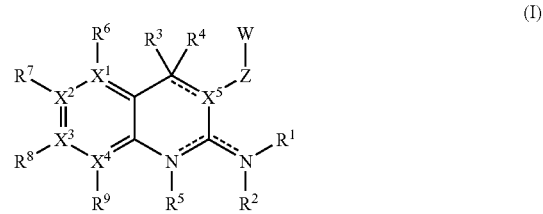

(I)

29 Claims, No Drawings

(56) References Cited

FOREIGN PATENT DOCUMENTS

| | | |
|---|---|---|
| EP | 0 530 994 | 3/1993 |
| EP | 0 603 712 | 6/1994 |
| EP | 0 735 025 | 10/1996 |
| EP | 1 661 889 | 5/2006 |
| FR | 7.865 | 6/1907 |
| GB | 2 105 331 | 3/1983 |
| JP | 55-27106 | 2/1980 |
| JP | 62-31713 | 2/1987 |
| JP | 5-25115 | 2/1993 |
| WO | WO 93/04047 | 3/1993 |
| WO | WO 95/21823 | 8/1995 |
| WO | WO 96/18616 | 6/1996 |
| WO | WO 96/18617 | 6/1996 |
| WO | WO 97/06161 | 2/1997 |
| WO | WO 97/44036 | 11/1997 |
| WO | WO 98/20007 | 5/1998 |
| WO | WO 98/34115 | 8/1998 |
| WO | WO 98/45268 | 10/1998 |
| WO | WO 99/05096 | 2/1999 |
| WO | WO 99/30969 | 6/1999 |
| WO | WO 00/64877 | 11/2000 |
| WO | WO 01/12187 | 2/2001 |
| WO | WO 01/38315 | 5/2001 |
| WO | WO 02/02548 | 1/2002 |
| WO | WO 02/20489 | 3/2002 |
| WO | WO 02/26713 | 4/2002 |
| WO | WO 02/36734 | 5/2002 |
| WO | WO 02/060382 | 8/2002 |
| WO | WO 02/064594 | 8/2002 |
| WO | WO 03/13523 | 2/2003 |
| WO | WO 03/045313 | 6/2003 |
| WO | WO 03/045920 | 6/2003 |
| WO | WO 03/066604 | 8/2003 |
| WO | WO 03/068749 | 8/2003 |
| WO | WO 03/103575 | 12/2003 |
| WO | WO 2004/011436 | 2/2004 |
| WO | WO 2004/024693 | 3/2004 |
| WO | WO 2004/087053 | 10/2004 |
| WO | WO 2004/087160 | 10/2004 |
| WO | WO 2004/099159 | 11/2004 |
| WO | WO 2005/007672 | 1/2005 |
| WO | WO 2005/020897 | 3/2005 |
| WO | WO 2005/028624 | 3/2005 |
| WO | WO 2005/037223 | 4/2005 |
| WO | WO 2005/046698 | 5/2005 |
| WO | WO 2005/070924 | 8/2005 |
| WO | WO 2005/117875 | 12/2005 |
| WO | WO 2005/007672 | 2/2006 |
| WO | WO 2006/017844 | 2/2006 |
| WO | WO 2006/020959 | 2/2006 |
| WO | WO 2006/024932 | 3/2006 |
| WO | WO 2006/039718 | 4/2006 |

OTHER PUBLICATIONS

Latrepirdine, 2013, http://en.wikipedia.org/wiki/Latrepirdine.*
SB-699,551, 2013, http://en.wikipedia.org/wiki/SB-699,551.*
AD-prevention, 2013, http://www.mayoclinic.com/health/alzheimers-disease/DS00161/DSECTION=prevention.*
Kennet G.A., 5-HT Receptors and Their Ligands; Serotonin Receptors and Their Function, TOCRIS Review (http://www.tocris.com/serotonin.htm), May 1997.
Peroutka S.J., 1994, Molecular Biology of Serotonin (5-HT) Receptors, Synapse 18, 241-260.
Nelson, D.L., Current Drug Targets—CNS & Neurological Disorders 2004 Issue 1.
Erlander et al., Proc. Natl. Acad. Sci. USA, "Two Members of a Distinct Subfamily of 5-Hydroxytryptamine Receptors Differentially Expressed in Rat Brain", vol. 90. pp. 3452-3456 (1993).
Oliver et al., Brain Research, "Localization of 5-ht5A Receptor-Like Immunoreactivity in the Rat Brain", 867 (2000) pp. 131-142.
Pasqualetti et al., Molecular Brain Research, "Distribution of the 5-HT5A Serotonin Receptor mRNA in the Human Brain", 56 (1998), pp. 1-8.
Diener, H. C. et al., Arzneimitteltherapie, "Behandlung der Migraneattacke und Migraneprophylaxe Empfehlungen der Deutschen Migrane—und Kopfschmerzgesellschaft". 15:387-394 (1997).
Badawneh, M. et al., IL Farmaco, "Synthesis of Variously Substituted 1,8-naphthyridine Derivatives and Evaluation of Their Antimycobacterial Activity", 57 (2002) 631-639.
Erba, E. et al., J. Chem. Soc. Perkin Trans., "v-Triazolines, Part 38, New Synthesis of 4-Aminoquinazolines and 6-Aminopurines", 1, (1997) 3021-3024.
Sayed, A. A. et al., J. Chem. Research (S), "A Novel Synthesis of 2-Diethylamino-3-o-nitrobenzylquinolines", (2003), 36-37.
Singh, J. et al., Z. Naturforsch, Chemotherapy of Filariasis—On the Search of New Agents Effective on the Reproductive System of Female Adult Worms [1], 45c, (1990), 1210-1214.
Communications Syntheses, A Convenient Synthesis of 2,3-Disubstituted Benzol[6][1,8]naphthyridines; A Novel Annelation Reaction of 2,3-Disubstituted Quinolines, May 1987, 512-514.
Song et al., Tetrahedron Letters, "Solid-phase Synthesis of 3-alkyl-2-arylamino-3,4-dihydroquinazolines", 45, (2004) 2727-2730.
Kienzle, F. et al., Eur. J. Med. Chem.—Chim. Ther., "1,5-Dihydroimidazoquinazolinones as Blood Platelet Aggregation Inhibitors", 1982-17, No. 6, pp. 547-556.
Khimiko-Farmatsevticheskii Zhurnal (1976), 10, pp. 28-33.
Hawes et al., College of Pharmacy, University of Saskatchewan, Sakatoon, Canada, "2-Amino-3-substituted 1,6-Naphthyridines", Dec. 17, 1971, vol. 9, pp. 703-706.
Thomas et al., Neuropharmacology, "SB-699551-A (3-cyclopentyl-N-[2[(dimethylamino)ethyl]-N-[(4'-{[(2-phenylethyl)amino]methyl}-4-biphenylyl)methyl]propanamide dihydrochloride), a novel 5-ht5A receptor-selective antagonist, enhances 5-HT neuronal function: Evidence for an autoreceptor role for the 5-ht5A receptor in guinea pig brain", 51, (2006) pp. 566-577.
Ishikawa F., et al., Chemical and Pharmaceutical Bulletin, "Cyclic Guanidines. IX, Synthesis of 2-Amino-3,4-dihydroquinazolines as Blood Platelet Aggregation Inhibitors", Aug. 22, 1979, No. 5, 1357-1364.
Plassat et al., The EMBO Journal, "The Mouse 5HT5 Receptor Reveals a Remarkable Heterogeneity Within the 5HT1D Receptor Family", 1992 vol. 11 No. 13, pp. 4779-4786.
Carson et al., GLIA, "The 5-HT5A Serotonin Receptor is Expressed Predominantly by Astrocytes in Which it InhibitscAMP Accumulation of Reactive Astrocytes", 1996, pp. 317-326.
Pfaffenrath, MMW Seminar, "Triptane Gegen Migraneattacken", 1998, pp. 625-626.
Ishikawa F., et al., Chemical and Pharmaceutical Bulletin, "Cyclic Guanidines. IX, Synthesis of 2-Amino-3,4-dihydroquinazolines as Blood Platelet Aggregation Inhibitors", Aug. 22, 1979, No. 5, 1357-1364, XP001247938.

* cited by examiner

HETEROCYCLIC COMPOUNDS AND THEIR USE AS BINDING PARTNERS FOR 5-HT$_5$ RECEPTORS

FIELD OF THE INVENTION

The present invention relates to novel heterocyclic compounds and the use of these compounds as binding partners for 5-HT$_5$ receptors for treatment of diseases modulated by a 5-HT$_5$ receptor activity, in particular for treatment of neurodegenerative and neuropsychiatric disorders as well as the associated signs, symptoms and dysfunctions.

BACKGROUND OF THE INVENTION

At least seven different receptor classes mediate the physiological activities attributed to involvement of the neurotransmitter serotonin (5-hydroxytryptamine, abbreviated 5-HT). They are designated as 5-HT$_1$, 5-HT$_2$, 5-HT$_3$, 5-HT$_4$, 5-HT$_5$, 5-HT$_6$ and 5-HT$_7$ according to an internationally recognized classification system. Most of these classes also include other receptor subtypes that can be differentiated; for example, the 5-HT$_1$ class includes receptors that can be subdivided into at least five subclasses, namely 5-HT$_{1A}$, 5-HT$_{1B}$, 5-HT$_{1C}$, 5-HT$_{1D}$ and 5-HT$_{1E}$ (Martin Boess; Neuropharmacology 33:275-317 (1994)).

The properties, function and pharmacology of these receptor subtypes have been summarized, e.g., by (a) G. A. Kennet, Serotonin Receptors and their Function," TOCRIS Review (http://www.tocris.com/serotonin.htm), published May 1997; (b) S. J. Peroutka, 1994, "Molecular Biology of Serotonin (5-HT) Receptors, Synapse 18, 241-260 and Current Drug Targets—CNS & Neurological Disorders 2004, 3, No. 1.

The 5-HT$_5$ class was described for the first time by Plassat et al., The EMBO Journal, vol. 11, no. 13, pp. 4779-4786 (1992). A distinction is made between 5-HT$_{5A}$ and 5-HT$_{5B}$ receptors (Erlander et al., Proc. Natl. Acad. Sci. USA 90:3452-3456 (1993)). Although there are only minor sequence homologies between 5-HT$_5$ and other 5-HT receptors, the pharmacological profile of these receptors is definitely different.

5-HT$_5$ receptors have been localized with the help of the techniques of molecular biology in the olfactory bulb, the hippocampus, the cortex, the cerebral ventricles, the corpus callosum and the cerebellum. By using immunohistochemical methods, it has been demonstrated that 5-HT$_5$ receptors are expressed by neurons in various areas of the brain (Oliver et al., Brain Res 2000, 867, 131-142; Pasqualetti et al., Mol Brain Res 1998, 56, 1-8). These 5-HT$_5$ receptors can modulate important brain functions either directly or indirectly, but they may also be involved in mechanisms that play a role in neuropathological, neurodegenerative and neuropsychiatric diseases. 5-HT$_5$ receptors have also been localized in astrocytes (Carson et al., GLIA 17:317-326 (1996)). Astrocytes are situated directly on the basal membrane of cerebral capillaries of the blood-brain barrier, and an abnormal astrocyte-endothelium structure is associated with a loss of blood-brain barrier. The precise function of astrocytes is unclear. They appear to execute transport tasks and connective functions. Reactive astrocytes have been observed in conjunction with reactive gliosis in a number of pathological cerebral changes and neuropsychiatric disorders. These astrocytes undergo a change in morphology as a result of brain injuries. The protein expression pattern changes and growth factors are produced. In vitro studies on cultured astrocytes show 5-HT$_5$ receptor-mediated responses. For this reason, it is assumed first that 5-HT$_5$ receptors are involved in recovery processes in the brain after a trauma, but on the other hand, the possibility cannot be ruled out that they play a role in the damage itself or may even contribute toward increasing the injury.

Diseases of the central nervous system today affect large portions of the population, and the number of patients is steadily increasing especially due to the growing elderly population. Neuropathological conditions such as cerebral ischemia, cerebral vascular accident, epilepsy and seizures in general, chronic schizophrenia, other psychotic diseases, depression, anxiety states, bipolar disorder, dementia, especially Alzheimer's disease, demyelinizing diseases, in particular multiple sclerosis and brain tumors lead to damage to the brain and the neural deficiencies associated with such damage. Therapeutic treatments of the neurodegenerative and neuropsychiatric disorders mentioned here have so far been directed at various membrane receptors with the goal of compensating for deficiencies in neurotransmission processes. Although neuroprotective effects have been achieved with various serotonergic compounds in animal models for neuropathological states such as ischemia, cerebral stroke and excitotoxicity, positive effects on mood disorders such as depression or anxiety have also been observed to some extent. Examples that can be mentioned here include 5-HT$_{1A}$ agonists such as buspirone or the compound 8-hydroxy-2-(di-n-propylamino)tetraline (8-OH-DPAT), which is characterized as a selective 5-HT$_{1A}$ receptor ligand. However, these active ingredients relieve the neurological deficiencies described here only to a limited extent, but at the present time there is still no effective treatment for these diseases.

Migraines are another neuropathological disease affecting large portions of the population. Migraines are in most cases manifested as recurring headaches, which have been estimated as affecting eight million people, i.e., 3-5% of all children, 7% of all men and 14% of all women. Although a genetic predisposition has been suggested, the causes appear to be varied (H. C. Diener et al., Arzneimitteltherapie 15:387-394 (1997)). Two hypotheses are dominant. The vascular theory, which has been known for a long time, suggests a dilatation process of the internal and external cerebrovascular system as the cause. The neurogenic theory is based on secretion of vasoactive neurotransmitters, mainly neuropeptides, such as substance P and neurokinin from axons of the vasculature due to stimulation of certain ganglia innervating the cerebral tissue, leading to inflammatory reactions and thus to pain.

There is not yet a causal therapy for treatment of migraines. Two different treatment methods are presently being used: the first is a prophylactic treatment for prevention of recurring migraine attacks and the second is a symptomatic treatment for suppression of acute symptoms once an attack has occurred. Migraine-specific active ingredients such as Sanmigran®, Nocerton®, Desernil® and Vidora® are used prophylactically, but active ingredients normally used for other indications such as β-blockers, antiemetic active ingredients such as Sibelium®, antidepressants such as Laroxyl® or anti-epileptic agents such as Depakin® are also administered. For acute therapy, analgesics such as aspirin, paracetamol or Optalidon®, NSAIDs (non-steroidal anti-inflammatory drugs) such as Cebutid®, Voltaren®, Brufen®, Ponstyl®, Profenid®, Apranx® and Naprosyn® are administered to relieve the pain and inflammation, while ergot alkaloids such as ergotamine, dihydroergotamine, which can trigger vasoconstriction, or substances of the triptan family, such as sumatriptan, Naramig® and AscoTop®, which have a high affinity for 5-HT$_{1D}$ receptors, are also administered. The latter substances act as agonists and block vasodilation.

However, the active ingredients mentioned above are not optimal for treatment of migraines. Nonopioid analgesics often have side effects. The complex mechanism of action of the ergot alkaloids leads to side effects such as hypertension or even gangrene due to the strong peripheral vasoconstriction effect. Compounds belonging to the triptan family are also not completely satisfactory (V. Pfaffenrath, Münch. Med. Wschr. 625-626 (1998)).

$5-HT_5$ receptors have a high affinity for various antidepressants and antipsychotics. Previous studies indicate a role of $5-HT_5$ receptors in the following syndromes:

Psychosis, depression, chronic schizophrenia, other psychotic diseases, anxiety states, bipolar disorders, dementia, especially Alzheimer's disease, demyelinizing diseases, in particular multiple sclerosis, ischemia, cerebral stroke and migraines.

The use of $5-HT_5$ receptor ligands in general for treatment of migraines and other cerebrovascular diseases is described in WO00/041472 and their use for treatment of neurodegenerative and neuropsychiatric diseases is described in WO00/041696.

There is therefore a demand for substances that trigger modulation of the $5-HT_{5A}$ receptor activity.

PRIOR ART

Quinoline and dihydroquinazoline derivatives have not previously been used as $5-HT_5$ ligands.

WO05/007672 describes low-molecular Toll-like receptor antagonists, including quinoline derivatives.

WO04/011436 describes the synthesis and use of quinoline derivatives as mycobacterial inhibitors.

WO04/024693 and WO02/036734 describe, among other thing, the synthesis of quinoline and naphtheridine derivatives and their use as HIV integrase inhibitors.

WO03/045313 and WO03/045920 describe the synthesis of 2-aminoquinoline derivatives and their use as "melanin concentrating hormone" receptor antagonists (MCHII-1R) for treatment of obesity, eating disorders, osteoarthritis, cancer and mental disorders, perception disorders, reproductive disorders, renal dysfunctions, movement disorders, ADD and epilepsy, among other things.

WO02/202489 describes the synthesis of quinoline derivatives and their use as cGMP phosphodiesterase inhibitors.

WO02/02548 also describes substituted 2-aminoquinoline derivatives as catechol-O-methyltransferase inhibitors, among other things.

WO02/064594 describes 6-substituted pyridopyrimidines and their use for treatment of p38-mediated diseases.

WO98/20007 describes the synthesis of 5-hetaryl-substituted quinoline derivatives and their use as PDE and TNF inhibitors for treatment of inflammation, among other things.

WO97/44036 describes the synthesis of 5-substituted quinoline carboxamide derivatives and their use as phosphodiesterase IV inhibitors.

EP 603712 describes substituted quinoline derivatives as angiotensin II antagonists, among other things.

EP 507594 describes the synthesis of quinoline derivatives and their use as angiotensin II antagonists.

The formation of 3-substituted 2-aminoquinoline derivatives as a byproduct of synthesis of isoquinoline derivatives is described in Chemistry of Heterocyclic Compounds (2004), 40, 888. Synthesis of 3-substituted 1,8-naphtheridine derivatives and their antimicrobial effect is described in Farmaco (2002), 57, 631.

Synthesis of 4-chloro-3-mercaptophenyl-2-(N-methylpiperazinyl)quinoline and receptor binding to $D_2$, $D_4$ and $5-HT_{1A}$ are described in Bioorganic & Medicinal Chemistry Letters (2004), 11, 1141.

Synthesis of 4-amino-3-benzyl-2-morpholinoquinoline is described in Journal of the Chemical Society, Perkin Transactions 1 (1997), 3021.

Synthesis of 2-N,N-diethylamino-3-benzylquinoline derivatives is described in Journal of Chemical Research Synopsis (2003), 36-37.

The antifilarial effect of 3-(4-chloromercaptophenyl)-2-(N-methylpiperazinyl)[b][1.8]-naphtheridine is described in Zeitschrift für Naturforschung C [Journal of Natural Research C], Journal of Biosciences (1990), 45, 1210.

Synthesis of 3-substituted 2-amino[b][1.8]naphtheridine derivatives is described in Synthesis (1987), 512.

Synthesis of 2-arylamino-3-alkylquinoline and 2-arylamino-3-phenylquinoline derivatives from 2-aminophenyl ketones and carboxylic acids or carboxylic acid anhydrides is described in Journal für Praktische Chemie (1977), 319, 589-600.

WO05/020897 describes the use of 4-oxo-3,4-dihydroquinazonine derivative as Trp-p8 modulators, among other things.

WO04/087053 describes the use of 3,4-dihydroquinazoline derivatives as dipeptidyl peptidase inhibitors, among other things.

WO03/103575 describes the synthesis and use of pyrimidinone derivatives as inhibitors of "mitotic kinesin KSP."

EP 0073060 describes the synthesis of 3-substituted 2-aminodihydroquinazoline derivatives as intermediates for the synthesis of imidazoquinoline derivatives and their use for the production of pharmaceutical drugs, e.g., as blood platelet aggregation inhibitors, gastric acid secretion inhibitors and for treatment of heart failure.

EP 0046267 also describes the synthesis of 3-substituted 2-aminodihydroquinazoline derivatives as intermediates for the synthesis of imidazoquinoline derivatives and their use for the production of pharmaceutical drugs, e.g., as blood platelet aggregation inhibitors, gastric acid secretion inhibitors and their use as substances with a cardiovascular activity.

EP 530994 describes the synthesis of quinazoline derivatives and their use as HIV reverse transcriptase inhibitors.

JP62047186 describes the synthesis of 2-amino-3-benzyl-3,4-dihydroquinoline derivatives and their use as intermediates for the production of blood platelet aggregation inhibitors.

JP62031713 describes the synthesis of 3-substituted 2-amino-3,4-dihydroquinazoline derivatives and their use as blood platelet aggregation inhibitors.

WO93/04047 describes the synthesis and use of quinazolinone derivatives as HIV reverse transcriptase inhibitors.

BE 722675 describes the synthesis of dihydroquinazoline derivatives and their use as antihypertensive agents.

Solid-phase synthesis of 3-alkyl-2-arylamino-3,4-dihydroquinazoline-4-acetamide derivatives is described in Tetrahedron Letters (2004), 45, 2727-2730.

The synthesis of 3-(p-methoxybenzyl)-3,4-dihydroquinazoline derivatives and their use as intermediates for synthesis of blood platelet aggregation inhibitors are described in the European Journal of Medicinal Chemistry (1982), 17, 547-556.

The synthesis of 2-amino-3,4-dihydroquinazoline derivatives and their use as blood platelet aggregation inhibitors are described in Chemical Pharmaceutical Bulletin (1980), 28, 1357-1364. The synthesis of 1-benzyl-1H-perimidin-2-amine and other 1H-perimidin-2-amine derivatives and their neurotropic activity are described in Khimiko-Farmatsevticheskii Zhurnal (1976), 10, 28-33.

WO06/024932, WO06/017836 and WO06/017844 describe the synthesis of 2-aminoquinazoline derivatives and their use as β-secretase inhibitors for treatment of Alzheimer's disease and related diseases.

The following compounds are listed in the SciFinder Database but are not otherwise described in the literature: 3-(2-methylbenzyl)-3,4-dihydroquinazolin-2-amine, 3-(2-chlorobenzyl)-3,4-dihydroquinazolin-2-amine, 3-(2-chlorobenzyl)-4-methyl-3,4-dihydroquinazolin-2-amine, 3-(2,3-dimethylbenzyl)-3,4-dihydroquinazolin-2-amine, 3-[2-(methoxymethyl)benzyl]-3,4-dihydroquinazolin-2-amine, 3-[2-ethylbenzyl]-3,4-dihydroquinazolin-2-amine, 3-[1-(2-chlorophenyl)ethyl]-3,4-dihydroquinazolin-2-amine, 3-[1-(2-methylphenyl)ethyl]-3,4-dihydroquinazolin-2-amine, 3-(2-chlorobenzyl)-1-methyl-3,4-dihydroquinazolin-2(1H)-imine, 3-(2,4-dimethylbenzyl)-3,4-dihydroquinazolin-2-amine, 4-methyl-3-(2-methylbenzyl)-3,4-dihydroquinazolin-2-amine, 3-(2,6-dimethylbenzyl)-3,4-dihydroquinazolin-2-amine.

The following compounds are listed in the Beilstein database but are not otherwise described in the literature: 2-{3-(2,6-dichlorobenzyl)-2-[(3,4-dichlorphenyl)amino]-3,4-dihydroquinazolin-4-yl}acetamide, 2-{2-[(4-methoxyphenyl)amino]-3-(2-methylbenzyl)-3,4-dihydroquinazolin-4-yl}acetamide, N,N-diethyl-7-[(6-nitro-1,3-benzodioxol-5-yl)methyl][1.3]dioxolo[4.5-g]-quinolin-6-amine, N,N-diethyl-6,7-dimethoxy-3-[(6-nitro-1,3-benzodioxol-5-yl)methyl]-quinoline-2-amine, 7-(4,5-dimethoxy-2-nitrobenzyl)-N,N-diethyl[1.3]dioxolo[4.5-g]quinolin-6-amine, 3-(4,5-dimethoxy-2-nitrobenzyl)-N,N-diethyl-6,7-dimethoxyquinolin-2-amine.

EP 1661889 describes, among other things, substituted quinolines and naphthyridines as well as their use for treatment of chemokine receptor-mediated diseases such as allergies.

WO03/013523 describes the synthesis of aminopyridines, aminoquinolines and aminoisoquinolines as well as their use of modulators of the activity of proteins having SH3 domains for treatment of diseases such as osteoarthritis, cancer, viral infections and autoimmune diseases.

WO97/06161 describes the synthesis of 8-aminoquinoline derivatives and their use to combat protozoan parasites.

WO96/18617 and WO96/18616 describe the synthesis of 2-aminopyridine derivatives and their use for treatment of nitrogen oxide synthase-mediated diseases, including Parkinson's disease, schizophrenia, depression and drug addiction.

U.S. Pat. No. 5,470,975 describes the synthesis of dihydropyrimidine derivatives and their use as angiotensin II receptor antagonists for treatment of hypertension and cognitive disorders.

EP 527534 describes the synthesis of quinolines and naphthyridines and their use as angiotensin II receptor antagonists for treatment of hypertension and cognitive disorders, among other things.

EP 0481802 describes the synthesis of pyridinone derivatives and their use as HIV reverse transcriptase inhibitors.

EP 481448 describes the synthesis of pyrimidinones and their use as angiotensin II inhibitors for treatment of hypertension and loss of cognitive abilities, among other things.

DE 3907937 describes the synthesis of 2-amino-1,8-naphthyridines and their use as an antidote for herbicides.

WO05/046698 describes quinoline derivatives as inhibitors of interleukin-12 production and osteoclast production for treatment of arthritis, for example, among other things.

U.S. Pat. No. 6,284,796 describes quinoline and naphthyridine derivatives, among other things, as urokinase inhibitors for treatment of inflammations and cancer, for example.

EP 735025 describes the synthesis of aminonitropyridine derivatives and their use for production of medicines and agrochemicals.

WO06/039718 describes the synthesis of naphthyridine derivatives and their use as protein kinase modulators for treatment of inflammations and cancer, among other things.

WO02/060382 describes the synthesis of 2-aminonaphthyridine derivatives and their use for treatment of TIE-mediated diseases such as cancer and arthritis.

Journal of Heterocyclic Chemistry, 1972, 9, 703 describes the synthesis of 2-aminonaphthyridines from 4-aminopyridin-3-carbaldehyde and acetonitrile derivatives.

WO05/037223 describes quinoline derivatives as immunomodulators, among other things.

WO05/028624 describes quinoline derivatives as kinase ligands for treatment of inflammations and cancer for example.

WO04/099159 describes substituted hetaryl compounds as protein tyrosine phosphatase inhibitors and their use for treatment of diabetes, for example.

WO04/087160 describes the synthesis of quinoline derivatives and their use for treatment of neurological disorders such as schizophrenia.

DE 10139060 describes quinoline and dihydroquinazoline derivatives as factor Xa and VIIa inhibitors for treatment of thromboses, inflammations and tumors, among other things.

WO03/068749 describes the synthesis of quinoline and isoquinoline derivatives and their use as vallinoid [sic; vanilloid] receptor antagonists for treatment of pain and asthma, for example.

WO02/026713 describes the synthesis of substituted quinoline derivatives and their use for treatment or prevention of infections caused by parasitic intestinal worms or arthropod ectoparasites.

WO01/012187 describes dihydroquinazolines and their use as peroxisome proliferation activator (PPAR) agonists for treatment of diabetes, among other things.

WO00/064877 describes the synthesis of 2-aminoquinoline carboxamide compounds and their use for treatment of Alzheimer's disease, neuropathy, anxiety, depression and drug addiction, among other things.

WO99/30696 describes quinoline derivatives for prevention and treatment of myocardial diseases, among other things.

WO99/05096 describes quinoline derivatives as urokinase inhibitors for treatment of inflammations and cancer, for example.

WO98/45268 describes quinoline and naphthyridine derivatives and their use as phosphodiesterase and tumor necrosis factor inhibitors for treatment of asthma, arthritis, depression and dementia, for example.

WO98/34115 describes the synthesis of 4-substituted quinoline derivatives and their use for treatment of infections and pain.

DE 19613591 describes the synthesis of quinoline derivatives and their use for treatment of retroviral infections.

WO95/21823 describes the synthesis of quinoline derivatives and their use as potassium channel blockers for treatment of CNS diseases such as depression, pain and psychoses and to improve memory and learning ability.

DE 4344452 describes the synthesis of naphthyridine derivatives and their use as antiviral compounds, among other things.

EP 635492 describes naphthyridine derivatives and their use as glycoprotein IIb/IIIa antagonists and as platelet aggregation inhibitors, e.g., for treatment of angina, among other things.

JP 05025115 describes substituted quinolines and their use as ACAT inhibitors to lower the cholesterol level, among other things.

EP 498723 describes the synthesis of substituted quinolines and quinazolines and their use as angiotensin II antagonists, e.g., for treatment of cardiovascular disorders, asthma, Alzheimer's disease and cognitive disorders.

EP 399818 describes the synthesis of substituted quinolines and their use as SRS-A and leukotriene antagonists, e.g., for treatment of allergies and inflammations.

WO05/117875 describes the synthesis of substituted quinolines and their use to prepare medicines for treatment of infections with drug-resistant strains of mycobacteria.

WO05/070924 describes the synthesis of substituted quinolines and their use for treatment of mycobacterial diseases.

US 2005101568 describes the synthesis of quinoline derivatives and their use as antagonists for adhesion proteins for treatment of inflammations, metastases and thrombotic diseases, for example.

US 2005/101569 describes the synthesis of quinoline derivatives and their use as inhibitors for selectin-mediated intracellular adhesion for treatment of inflammations, cancer and restenosis, for example.

WO06/020959 describes the synthesis of substituted quinazolines and their use as ghrelin receptor antagonists for treatment of obesity, diabetes, cardiovascular disorders and inflammations, for example.

French Patent No. 7.865 M describes 3,4-dihydroquinazoline derivatives that may be substituted with an amino group in position 2 and with an arylalkyl group in position 3 on the nitrogen atom, and the arylalkyl group in the aryl part may have up to seven carbon atoms and in the alkyl part may have up to three carbon atoms, for treatment of arterial hypertension.

David R. Thomas et al. describe in Neuropharmacology (2006) (at press) 3-cyclopentyl-N-[2-(dimethylamino)ethyl]-N-[(40-{[(2-phenylethyl)amino]methyl}-4-biphenylyl)methyl]-propanamide dihydrochloride (SB-699551) as selective 5-$HT_{5A}$ receptor antagonists and pharmacological studies with this substance to investigate the role of 5-$HT_{5A}$ in the brain of guinea pigs.

SUMMARY OF THE INVENTION

The object of the present invention is to make available compounds that allow the treatment of neuropathological, neuropsychiatric and neurodegenerative disorders with sufficient efficacy and a low incidence of side effects.

It has now surprisingly been found that substances of general formula I or IA act as ligands of the 5-$HT_5$ receptor and therefore allow treatment of the disease states described above that are associated with this receptor as well as the related symptoms and dysfunctions.

According to one aspect of the present invention, at least one compound of general formula I

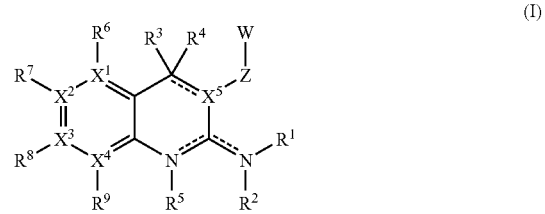

as well as corresponding enantiomeric, diastereomeric and/or tautomeric forms thereof and/or pharmaceutically acceptable salts thereof and/or the active ingredient precursors ("prodrugs") thereof are made available, such that the stated radicals have the following definitions:

$R^1$ and $R^2$ independently of one another denote
hydrogen, a free electron pair, OH, CN or,
in each case optionally substituted, $C_1$-$C_6$ alkyl, O—$C_1$-$C_6$ alkyl, $C_1$-$C_6$ alkylene-O—$C_1$-$C_6$ alkyl, $C_2$-$C_6$ alkenyl, $C_2$-$C_6$ alkynyl, CO—$C_1$-$C_6$ alkyl, CO—O—$C_1$-$C_6$ alkyl, $SO_2$—$C_1$-$C_6$ alkyl, $C_3$-$C_7$ cycloalkyl, $C_1$-$C_4$ alkylene-cycloalkyl, aryl, $C_1$-$C_4$ alkylene-aryl, CO—O-arylalkyl, CO—$C_1$-$C_4$ alkylene-aryl, CO-aryl, $SO_2$-aryl, hetaryl, $C_1$-$C_4$ alkylene-hetaryl, CO-hetaryl or $SO_2$—$C_1$-$C_4$ alkylene-aryl, heterocycloalkyl, $C_1$-$C_4$ alkylene-heterocycloalkyl, indanyl or $R^1$ and $R^2$ together with the nitrogen may form a three- to six-membered, optionally substituted, saturated or aromatic heterocycle, which may contain another heteroatom selected from the group consisting of O, N and S, such that the heterocycle may optionally be substituted once, twice or three times with the same or different substituents, $R^3$ denotes
hydrogen, $NO_2$, $NH_2$, OH, CN, $CF_3$, $OCF_3$, $CHF_2$, $OCHF_2$, COOH, O—$CH_2$—COOH, halogen, SH or,
in each case optionally substituted, $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-hetaryl or $C_1$-$C_4$ alkylene-aryl or O—$R_3^1$, CO—$R_3^1$, S—$R_3^1$, SO—$R_3^1$, CO—O—$R_3^1$, $NR_3^4$—CO—O—$R_3^1$, O—$CH_2$—COO—$R_3^1$, $NR_3^2R_3^3$, $CONH_2$, $SO_2NH_2$, $NR_3^4$—CO—$R_3^1$, $SO_2$—$R_3^1$, $NR_3^4$—$SO_2$—$R_3^1$, $SO_2$—$NR_3^2R_3^3$ or CO—$NR_3^2R_3^3$ in which $R_3^1$ denotes,
in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-aryl, $C_2$-$C_6$ alkylene-aryl or $C_1$-$C_6$ alkylene-hetaryl;

$R_3^2$ denotes
hydrogen, OH, CN or,
in each case optionally substituted $C_1$-$C_6$ alkyl, $C_2$-$C_6$ alkenyl, $C_2$-$C_6$ alkynyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-aryl, $C_1$-$C_4$ alkylene-hetaryl, $C_1$-$C_6$ alkylene-O—$C_1$-$C_6$ alkyl, CO—$C_1$-$C_6$ alkyl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O—$C_1$-$C_4$ alkylene-aryl, CO—O-hetaryl, CO—O—$C_1$-$C_4$ alkylene-hetaryl, $SO_2$—$C_1$-$C_6$ alkyl, $SO_2$-aryl, $SO_2$-hetaryl, $SO_2$—$C_1$-$C_4$ alkylene-aryl or $SO_2$—$C_1$-$C_4$ alkylene-hetaryl;

$R_3^3$ denotes, in each case optionally substituted $C_1$-$C_6$ alkyl, $C_2$-$C_6$ alkenyl, $C_2$-$C_6$ alkynyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-aryl, $C_1$-$C_4$ alkylene-hetaryl, $C_1$-$C_6$ alkylene-O—$C_1$-$C_6$-alkyl, CO—$C_1$-$C_6$ alkyl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O—$C_1$-$C_4$ alkylene-aryl, CO—O-hetaryl, CO—O—$C_1$-$C_4$ alkylene-hetaryl, $SO_2$—$C_1$-$C_6$ alkyl, $SO_2$-aryl, $SO_2$-hetaryl, $SO_2$—$C_1$-$C_4$ alkylene-aryl or $SO_2$—$C_1$-$C_4$ alkylene-hetaryl;

or the radicals $R_3^2$ and $R_3^3$ together with the nitrogen may form a three- to seven-membered, optionally substituted, saturated or aromatic heterocycle, which may contain one, two or three additional heteroatoms, which may be the same or different and are selected from the group consisting of O, N and S, such that optionally two of the substituted radicals on this heterocycle together may form an anellated, optionally substituted, saturated, unsaturated or aromatic carbocycle or heterocycle, such that the heterocycle may contain up to three heteroatoms that are the same or different and are selected from the groups consisting of O, N and S and the cyclic group thereby formed may optionally be substituted and/or another optionally substituted cyclic group may be condensed onto this cyclic group;

$R_3^4$ denotes hydrogen or, in each case optionally substituted $C_1$-$C_6$ alkyl, $C_1$-$C_6$ alkenyl-O—$C_1$-$C_6$ alkyl, $C_2$-$C_6$ alkenyl, $C_3$-$C_{12}$ alkynyl, CO—$C_1$-$C_6$ alkyl, CO—O—$C_1$-$C_6$ alkyl, $SO_2$—$C_1$-$C_6$ alkyl, $C_3$-$C_7$ cycloalkyl, aryl, $C_1$-$C_4$ alkylene-aryl, CO—O-arylalkyl, CO—O—$C_1$-$C_4$ alkylene-aryl, CO—$C_1$-$C_4$ alkylene-aryl, CO-aryl, $SO_2$-aryl, hetaryl, CO-hetaryl or $SO_2$—$C_1$-$C_4$ alkylene-aryl;

$R^4$ denotes a bond in the ring to $X^5$ while maintaining a C=C double bond for the case when $X^5$=C or for the case when $X^5$=N, it may denote a radical selected from the group consisting of hydrogen, CN, $CF_3$, $CHF_2$, COOH, halogen or, in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-hetaryl or $C_1$-$C_4$ alkylene-aryl; or $R^3$ and $R^4$ together with the respective carbon atom to which they are bound may form a three-membered, optionally substituted carbocycle, $R^5$ denotes hydrogen, a free electron pair or in each case optionally substituted O—$C_1$-$C_6$ alkyl, $C_1$-$C_6$ alkyl, CO—$C_1$-$C_6$ alkyl or —CO—O—$C_1$-$C_6$ alkyl;

$X^1$ denotes C or N, $X^2$ denotes C or N, $X^3$ denotes C or N, $X^4$ denotes C or N, such that at most one of radicals $X^1$ through $X^4$ may denote N at the same time, in which $R^6$, $R^7$, $R^8$ and $R^9$ denote, each independently of one another, a free electron pair when bound to a nitrogen atom (N), or when bound to a carbon atom (C), then they may denote, each independently of one another, the same or different radicals selected from groups 1), 2), 3), 4), 5), 6) or 7) above, which may be the same or different, such that groups 1) through 7) have the following meanings:

1) hydrogen, halogen, CN, $CF_3$, $CHF_2$, —$OCF_3$, —$NH_2$, —OH or optionally substituted $C_1$-$C_{10}$ alkyl, $C_2$-$C_{10}$ alkenyl, $C_2$-$C_{10}$ alkynyl or $NR_Q^7R_Q^8$ or $NHR_Q^7$, where $R_Q^7$ and $R_Q^8$ are defined below;

2) phenyl, which may be substituted with one, two or three radicals selected from the group consisting of $R_Q^2$, $R_Q^3$ and $R_Q^4$ such that $R_Q^2$, $R_Q^3$ and $R_Q^4$, each independently of one another, denotes a substituent from the following group:

hydrogen, $NO_2$, $NH_2$, OH, CN, $CF_3$, $CHF_2$, $OCF_3$, $OCHF_2$, COOH, O—$CH_2$—COOH, SH, halogen or in each case optionally substituted aryl, hetaryl, heterocycloalkyl, $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, $C_1$-$C_4$ alkylene-aryl or $C_1$-$C_4$ alkylene-hetaryl or O—$R_Q^5$, S—$R_Q^5$, $NR_Q^7R_Q^8$, CO—$OR_Q^6$, $NR_Q^7$—CO—O—$R_Q^6$, O—$CH_2$—COO—$R_Q^6$, $NR_Q^7$—CO—$R_Q^6$, $SO_2$—$R_Q^6$, $NR_Q^7$—$SO_2$—$R_Q^6$, $SO_2NH_2$, $CONH_2$, $SO_2$—$NR_Q^7R_Q^8$ or CO—$NR_Q^7R_Q^8$ or two radicals selected from the group consisting of $R_Q^2$, $R_Q^3$ and $R_Q^4$ together may form a three- to seven-membered, optionally substituted, saturated, unsaturated or aromatic carbocycle or an optionally substituted, saturated, unsaturated aromatic heterocycle that may contain one, two or three additional heteroatoms, which may be the same or different and are selected from the group consisting of O, N and S and optionally two substituted radicals on this heterocycle together may form an anellated, optionally substituted, saturated, unsaturated or aromatic carbocycle or heterocycle, such that the heterocycle may contain one, two or three heteroatoms that are the same or different and are selected from the group consisting of O, N and S, and the resulting cyclic group may optionally be substituted and/or another optionally substituted cyclic group may be condensed onto this cyclic group;

$R_Q^5$ denotes in each case optionally substituted $C_1$-$C_6$ alkyl, $C_2$-$C_6$ alkenyl, $C_2$-$C_6$ alkynyl, alkylene-$C_3$-$C_7$ cycloalkyl, $C_1$-$C_4$ alkylene-heterocycloalkyl, heterocycloalkyl or hetaryl or $C_1$-$C_4$ alkyl that is optionally substituted once or more with one or more substituents that may be the same or different and are selected from the group consisting of halogen, $NO_2$, $NH_2$, OH, CN, $CF_3$, $CHF_2$, $OCF_3$, $OCHF_2$, NH—($C_1$-$C_6$ alkyl) and N($C_1$-$C_6$ alkyl)$_2$;

$R_Q^6$ denotes in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, alkylene-heterocycloalkyl, aryl, hetaryl, heterocycloalkyl or $C_1$-$C_6$ alkylene-O—$C_1$-$C_6$ alkyl;

$R_Q^7$ denotes, independently of the respective incidence, hydrogen, CN or in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, C₁-C₄ alkylene-heterocycloalkyl, aryl, hetaryl, heterocycloalkyl, C₁-C₆ alkylene-O—C₁-C₆ alkyl, CO—C₁-C₆ alkyl, C₁-C₄ alkylene-aryl, C₁-C₄ alkylene-hetaryl, CO-aryl, CO-hetaryl, CO—C₁-C₄ alkylene-aryl, CO—C₁-C₄ alkylene-hetaryl, CO—O—C₁-C₆ alkyl, CO—O-aryl, CO—O—C₁-C₄ alkylene-aryl, CO—O-hetaryl, CO—O—C₁-C₄ alkylene-hetaryl, SO₂—C₁-C₆ alkyl, SO₂-aryl, SO₂-hetaryl, SO₂—C₁-C₄ alkylene-aryl or SO₂—C₁-C₄ alkylene-hetaryl;

$R_Q^8$ denotes, independently of the respective incidence, in each case optionally substituted C₁-C₆ alkyl, C₂-C₆ alkenyl, C₂-C₆ alkynyl, C₃-C₇ cycloalkyl, C₁-C₄ alkylene-C₃-C₇ cycloalkyl, C₁-C₄ alkylene-heterocycloalkyl, aryl, hetaryl, heterocycloalkyl, C₁-C₆ alkylene-O—C₁-C₆ alkyl, CO—C₁-C₆ alkyl, CO-aryl, CO-hetaryl, CO—C₁-C₄ alkylene-aryl, CO—C₁-C₄ alkylene-hetaryl, CO—O—C₁-C₆ alkyl, CO—O-aryl, CO—O—C₁-C₄ alkylene-aryl, CO—O-hetaryl, CO—O—C₁-C₄ alkylene-hetaryl, SO₂—C₁-C₆ alkyl, SO₂-aryl, SO₂-hetaryl, SO₂—C₁-C₄ alkylene-aryl or SO₂—C₁-C₄ alkylene-hetaryl;

or the radicals $R_Q^7$ and $R_Q^8$ together with the nitrogen may form a three- to seven-membered, optionally substituted, saturated or aromatic heterocycle that may contain one, two or three other heteroatoms, which may be the same or different and are selected from the group consisting of O, N and S; and optionally two substituted radicals on this heterocycle together may form an anellated, optionally substituted, saturated, unsaturated or aromatic carbocycle or heterocycle, such that the heterocycle may contain one, two or three heteroatoms that are the same or different and are selected from the group consisting of O, N and S, and the cyclic group thereby formed may optionally be substituted or another optionally substituted cyclic group may be condensed onto this cyclic group;

3) a five- or six-membered hetaryl radical, optionally substituted once or twice with substituents that are the same or different and are selected from the group consisting of:

2-thienyl, 3-thienyl, 2-pyrrolyl, 3-pyrrolyl, 2-thiazolyl, 4-thiazolyl, 5-thiazolyl, 2-oxazolyl, 4-oxazolyl, 5-oxazolyl, 1-pyrazolyl, 3-pyrazolyl, 4-pyrazolyl, 5-pyrazolyl, 3-isothiazolyl, 4-isothiazolyl, 5-isothiazolyl, 1-imidazolyl, 2-imidazolyl, 4-imidazolyl, 5-imidazolyl, 2-pyridyl, 3-pyridyl, 4-pyridyl, 2-pyrimidyl, 4-pyrimidyl, 5-pyrimidyl, 6-pyrimidyl, 3-pyridazinyl, 4-pyridazinyl, 5-pyridazinyl, 6-pyridazinyl, 3-isoxazolyl, 4-isoxazolyl, 5-isoxazolyl, thiadiazolyl, oxadiazolyl or triazinyl or their anellated derivatives indazolyl, benzothiophenyl, benzofuranyl, indolinyl, benzimidazolyl, benzothiazolyl, benzoxazolyl, quinolinyl and isoquinolinyl, such that the substituents are preferably selected from the group consisting of halogen, NO₂, NH₂, OH, CN, CF₃, OCF₃, CHF₂, OCHF₂, C₁-C₆ alkyl, O—C₁-C₆ alkyl, NH—(C₁-C₆ alkyl), N(C₁-C₆ alkyl)₂, NHCO—C₁-C₄ alkyl, NHSO₂—C₁-C₄ alkyl and SO₂—C₁-C₄ alkyl;

4) two of the radicals R⁶, R⁷, R⁸ or R⁹ together form a four- to seven-membered, optionally substituted, partially or fully saturated carbocycle or a five- or six-membered, optionally substituted, partially or fully saturated heterocycle, which may contain one, two or three heteroatoms that are the same or different and are selected from the group consisting of O, N and S;

5) an optionally substituted C₃-C₈ monocyclic saturated hydrocarbon radical;

6) an optionally substituted four- to seven-membered mono- or bicyclic, partially or fully saturated heterocyclic group, which may contain one, two or three heteroatoms that may be the same or different and are selected from the group consisting of O, N and S, such that this cyclic group may be substituted one or more times. For the case when the heterocyclic group contains a nitrogen atom, this nitrogen atom may be substituted with an $R_Q^7$ radical as defined above;

such that the following, optionally substituted radicals azetidin-1-yl, azetidin-2-yl, azetidin-3-yl, pyrrolin-1-yl, pyrrolin-3-yl, pyrrolidin-1-yl, pyrrolidin-2-yl, pyrrolidin-3-yl, 1,2,3,6-tetrahydropyridin-1-yl, 1,2,3,6-tetrahydropyridin-4-yl, piperidin-1-yl, piperidin-2-yl, piperidin-3-yl, piperidin-4-yl, tetrahydro-2H-pyran-4-yl, tetrahydrofuran-3-yl, azepan-4-yl, azepan-3-yl, azepan-2-yl, 1,4-diazepan-5-yl, morpholinyl or piperazinyl are preferred;

such that the following, optionally substituted radicals

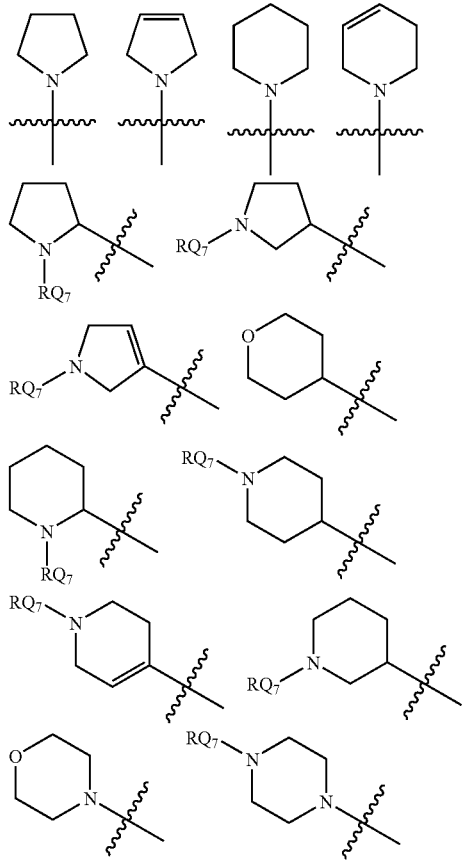

are especially preferred;

7) a radical of general formula V

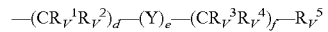

having the indices d=0-4 (i.e., an integer selected from 0, 1, 2, 3 or 4)

e=0-1 (i.e., an integer selected from 0 or 1)

f=0-4 (i.e., an integer selected from 0, 1, 2, 3 or 4)
such that the sum of d, e and f is 1, 2, 3, 4, 5, 6, 7 or 8;
$R_V^1$, $R_V^2$, $R_V^3$, $R_V^4$ independently of one another denote
hydrogen, halogen, OH or
in each case optionally substituted $C_1$-$C_4$ alkyl, $C_2$-$C_4$ alkenyl, $C_2$-$C_4$ alkynyl, $C_1$-$C_4$ alkylene-$C_3$-$C_7$ cycloalkyl, $C_3$-$C_7$ cycloalkyl, aryl, $C_1$-$C_4$ alkylene-aryl, hetaryl or $C_1$-$C_4$ alkylene-hetaryl or
independently of one another, two radicals $R_V^1$ and $R_V^2$ or $R_V^3$ and $R_V^4$ together may form a three- to seven-membered, optionally substituted, saturated or unsaturated carbocyclic or heterocyclic group, such that the heterocyclic group may contain one, two or three heteroatoms selected from the group consisting of O, N and S;
$R_V^5$ denotes
a radical as defined above in one of the groups 1), 2), 3), 5) or 6):
Y denotes
—CO—, —O—, —S—, —SO—, —SO$_2$—, —CS—NR$_Y^5$—, —COO—, —O—CO—, —CO—NR$_Y^5$, —NR$_Y^5$—CO—, —SO$_2$—NR$_Y^5$, —NR$_Y^5$—SO$_2$—;
such that
$R_Y^5$ denotes
hydrogen or
optionally substituted $C_1$-$C_6$ alkyl, $C_1$-$C_6$ alkylene-O—$C_1$-$C_6$ alkyl, $C_2$-$C_6$ alkenyl, $C_3$-$C_{12}$ alkynyl, CO—$C_1$-$C_6$ alkyl, CO—O—$C_1$-$C_6$ alkyl, SO$_2$—$C_1$-$C_6$ alkyl, $C_3$-$C_7$ cycloalkyl, aryl, $C_1$-$C_4$ alkylene-aryl, CO—O—$C_1$-$C_4$ alkylene-aryl, CO—$C_1$-$C_4$ alkylene-aryl, CO-aryl, SO$_2$ aryl, hetaryl, CO-hetaryl or SO$_2$—$C_1$-$C_4$ alkylene-aryl;
$X^5$ denotes
C or N,
Z denotes
a radical of general formula Z1

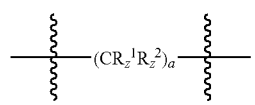

where
a=0, 1, 2, 3 or 4 (i.e., an integer selected from 0, 1, 2, 3 or 4),
preferably a=1, 2, 3 or 4,
especially preferably a=1 or 2,
most especially preferably a=1,
$R_Z^1$, $R_Z^2$ independently of one another denote
hydrogen, halogen, OH or
in each case optionally substituted $C_1$-$C_4$ alkyl, $C_2$-$C_4$ alkenyl, $C_2$-$C_4$ alkynyl, $C_1$-$C_4$ alkylene-$C_3$-$C_7$ cycloalkyl, $C_3$-$C_7$ cycloalkyl, aryl, $C_1$-$C_4$ alkylene-aryl, hetaryl or $C_1$-$C_4$ alkylene-hetaryl or
each independently of one another denote two radicals $R_Z^1$ and $R_Z^2$ which together form a three- to seven-membered, optionally substituted, saturated or unsaturated carbocyclic or heterocyclic group, such that the heterocyclic group may contain one, two or three heteroatoms, which may be the same or different and are selected from the group consisting of O, N and S, such that preferably $R_Z^1$ and $R_Z^2$ should not both be OH at the same time, W denotes a radical of general formula W

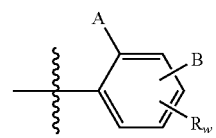

in which
A denotes OH, CN, OCF$_3$, CHF$_2$, CF$_3$, OCHF$_2$, COOH, O—CH$_2$—COOH, SH, SO$_2$H, alkylene-OH, NR$_A^4$—SO$_2$H, NR$_A^4$—COOH, SOH,
or
$R_A^1$, O—$R_A^1$, CO—$R_A^1$, S—$R_A^1$, SO—$R_A^1$, CO—O—$R_A^1$, NR$_A^4$—CO—O—$R_A^1$, O—CH$_2$—COO—$R_A^1$, NR$_A^2$R$_A^3$, NR$_A^4$—CO—$R_A^1$, SO$_2$—$R_A^1$, NR$_A^4$—SO$_2$—$R_A^1$, SO$_2$—NR$_A^2$R$_A^3$, CO—NR$_A^2$R$_A^3$, $C_1$-$C_4$ alkylene-NR$_A^2$R$_A^3$, alkylene-CO—NR$_A^2$R$_A^3$, $C_1$-$C_4$ alkylene-NR$_A^2$R$_A^3$, $C_1$-$C_4$ alkylene-CO—NR$_A^2$R$_A^3$, $C_1$-$C_4$ alkylene-SO$_2$—NR$_A^2$R$_A^3$ or $C_1$-$C_4$ alkylene-O—$R_A^1$;
preferably A=optionally substituted —O—$C_1$-$C_3$ alkyl or —O—$C_1$-$C_3$ haloalkyl, —N($C_1$-$C_3$ alkyl)$_2$, piperidinyl or morpholinyl,
especially preferably A=optionally substituted —O—$C_1$-$C_3$ alkyl or —O—$C_1$-$C_3$ alkyl substituted with one, two, three, four or five halogen atoms that may be the same or different and are selected from the group consisting of fluorine, chlorine, bromine and iodine;
most especially preferred is A=—O—CH$_3$, —OCF$_3$, —OCHF$_2$, —OCH$_2$F, —O—CH$_2$—CH$_3$, —O—CH$_2$—CF$_3$, —O—CH$_2$—CHF$_2$, —O—CH$_2$—CH$_2$F or O-isopropyl;
even more preferably A=—O—CH$_3$, —O—CH$_2$—CH$_3$, —O—CH$_2$—CF$_3$, —O—CH$_2$—CHF$_2$ or —O—CH$_2$—CH$_2$F;
most preferred is A=-O—CH$_3$;
in which
$R_A^1$ denotes
independently of the respective occurrence, in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-aryl, $C_2$-$C_6$ alkylene-aryl, $C_1$-$C_6$ alkylene-hetaryl, $C_1$-$C_4$ alkylene-NR$_A^2$R$_A^3$, $C_1$-$C_4$ alkylene-CO—NR$_A^2$R$_A^3$ or $C_1$-$C_4$ alkylene-O—$C_1$-$C_6$ alkyl;
$R_A^2$ denotes
independently of their respective occurrence, hydrogen, OH, CN
or
in each case optionally substituted $C_1$-$C_6$ alkyl, $C_2$-$C_6$ alkenyl, $C_2$-$C_6$ alkynyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-aryl, $C_1$-$C_4$ alkylene-hetaryl, $C_1$-$C_6$ alkylene-O—$C_1$-$C_6$ alkyl; CO—$C_1$-$C_6$ alkyl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O—$C_1$-$C_4$ alkylene-aryl, CO—O-hetaryl, CO—O—$C_1$-$C_4$ alkylene-hetaryl, SO$_2$—$C_1$-$C_6$ alkyl, SO$_2$-aryl, SO$_2$-hetaryl, SO$_2$—$C_1$-$C_4$ alkylene-aryl or SO$_2$—$C_1$-$C_4$ alkylene-hetaryl;

$R_A^3$ denotes
- independently of the respective occurrence, hydrogen or in each case optionally substituted $C_1$-$C_6$ alkyl, $C_2$-$C_6$ alkenyl, $C_2$-$C_6$ alkynyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-aryl, $C_1$-$C_4$ alkylene-hetaryl, $C_1$-$C_6$ alkylene-O—$C_1$-$C_6$ alkyl; CO—$C_1$-$C_6$ alkyl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O—$C_1$-$C_4$ alkylene-aryl, CO—O-hetaryl, CO—O—$C_1$-$C_4$ alkylene-hetaryl, $SO_2$—$C_1$-$C_6$ alkyl, $SO_2$-aryl, $SO_2$-hetaryl, $SO_2$—$C_1$-$C_4$ alkylene-aryl or $SO_2$—$C_1$-$C_4$ alkylene-hetaryl;
- or the radicals $R_A^2$ and $R_A^3$ together with the nitrogen to which they are attached may form a three- to seven-membered, optionally substituted, saturated or aromatic heterocycle, which may contain one, two or three additional heteroatoms, which may be the same or different and are selected from the group consisting of O, N and S; such that two optionally substituted radicals on this heterocycle together may form an anellated, optionally substituted, saturated, unsaturated or aromatic carbocycle or heterocycle, such that the heterocycle may contain one, two or three heteroatoms, which may be the same or different and are selected from the group consisting of O, N and S and such that the cyclic group thereby formed may optionally be substituted and/or another optionally substituted cyclic group may be condensed onto this cyclic group;

$R_A^4$ denotes
- independently of the respective occurrence, hydrogen or in each case optionally substituted $C_1$-$C_6$ alkyl, $C_1$-$C_6$ alkenyl-O—$C_1$-$C_6$ alkyl, $C_2$-$C_6$ alkenyl, $C_3$-$C_{12}$ alkynyl, CO—$C_1$-$C_6$ alkyl. CO—O—$C_1$-$C_6$ alkyl, $SO_2$—$C_1$-$C_6$ alkyl, $C_3$-$C_7$ cycloalkyl, aryl, $C_1$-$C_4$ alkylene-aryl, CO—O-arylalkyl, CO—$C_1$-$C_4$ alkylene-aryl, CO-aryl, CO-aryl, $SO_2$-aryl, hetaryl, CO-hetaryl or $SO_2$—$C_1$-$C_4$ alkylene-aryl;

B denotes
- hydrogen, $NO_2$, $NH_2$, OH, CN, $OCF_3$, $CHF_2$, $CF_3$, $OCHF_2$, COOH, O—$CH_2$—COOH, halogen, SH, $SO_2H$, $C_1$-$C_4$ alkylene-OH, $NR_A^4$—$SO_2H$, $NR_A^4$—COOH, SOH,
- or
- in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-hetaryl, $C_1$-$C_4$ alkylene-aryl, O—$R_A^1$, CO—$R_A^1$, S—$R_A^1$, SO—$R_A^1$, CO—O—$R_A^1$, $NR_A^4$—CO—O—$R_A^1$, O—$CH_2$—COO—$R_A^1$, $NR_A^2R_A^3$, $NR_A^4$—CO—$R_A^1$, $SO_2$—$R_A^1$, $NR_A^4$—$SO_2$—$R_A^1$, $SO_2$—$NR_A^2R_A^3$, CO—$NR_A^2R_A^3$, $C_1$-$C_4$ alkylene-$NR_A^2R_A^3$, $C_1$-$C_4$ alkylene-CO—$NR_A^2R_A^3$, $C_1$-$C_4$ alkylene-$SO_2$—$NR_A^2R_A^3$ or $C_1$-$C_4$ alkylene-O—$R_A^1$; or independently of one another, two of the radicals A, B or $R_W$ together with the respective carbon atom to which they are attached may form a five- to seven-membered, optionally substituted, saturated or unsaturated carbocycle or a five- to seven-membered, optionally substituted, saturated or unsaturated or aromatic heterocycle that may contain one, two or three additional heteroatoms, which may be the same or different and are selected from the group consisting of O, N and S; such that optionally two substituted radicals on this carbocycle or heterocycle together may form an anellated, optionally substituted, saturated, unsaturated or aromatic carbocycle or heterocycle, such that the heterocycle may contain one, two or three heteroatoms, which may be the same or different and are selected from the group consisting of O, N and S, and such that the cyclic group thus formed may optionally be substituted and/or another optionally substituted cyclic group may be condensed onto this cyclic group;

$R_W$ denotes
- hydrogen, OH, halogen, $NO_2$, $NH_2$, CN, $CF_3$, $CHF_2$, $OCF_3$, $OCHF_2$
- or
- in each case optionally substituted $C_1$-$C_6$ alkyl, $C_3$-$C_7$ cycloalkyl, $C_1$-$C_6$ alkylene-O—$C_1$-$C_6$ alkyl, $C_1$-$C_6$ thioalkyl, aryl, hetaryl, O—$C_1$-$C_6$ alkyl, O-aryl, O—$C_1$-$C_4$ alkylene-aryl, O-benzyl, $C_1$-$C_6$ alkylamino, $C_1$-$C_6$ dialkylamino, pyrrolidinyl, piperidinyl, morpholinyl, CO—$C_1$-$C_6$ alkyl, $SO_2$—$C_1$-$C_6$ alkyl, CO-aryl, $SO_2$-aryl, CO—$C_1$-$C_4$ alkylene-aryl, $SO_2$—$C_1$-$C_4$ alkylene-aryl, SO-aryl, $CONH_2$, CONH—$C_1$-$C_6$ alkyl, $SO_2NH$—$C_1$-$C_6$ alkyl, CON—($C_1$-$C_6$ alkyl)$_2$, $SO_2N$—($C_1$-$C_6$ alkyl)$_2$, NH—$SO_2$—$C_1$-$C_6$ alkyl or NH—CO—$C_1$-$C_6$ alkyl;
- optionally preferably with one, two, three, four or five measures selected from the group consisting of measures (i), (ii), (iii), (iv) and (v):
- measure (i): according to a preferred embodiment, at least one compound of general formula I, in which the radicals $R^1$, $R^2$, $R^3$, $R^4$, $R^5$, $R^6$, $R^7$, $R^8$, $R^9$, $X^1$, $X^2$, $X^3$, $X^4$, $X^5$, Z and W have the meanings given above, with the provision that when $X^5$=N, then $R^3$ and $R^4$ are each hydrogen and/or
- measure (ii): according to another preferred embodiment, at least one compound of general formula I, in which the radicals $R^1$, $R^2$, $R^3$, $R^4$, $R^5$, $R^6$, $R^7$, $R^8$, $R^9$, $X^1$, $X^2$, $X^3$, $X^4$, $X^5$, Z and W have the meanings given above, with the provision that when $X^2$=N and $X^5$=C, $R^8$ is not bound to the 1,6-naphthyridine ring by a nitrogen, oxygen or sulfur atom and/or
- measure (iii): according to another preferred embodiment, at least one compound of general formula I, in which the radicals $R^1$, $R^2$, $R^3$, $R^4$, $R^5$, $R^6$, $R^7$, $R^8$, $R^9$, $X^1$, $X^2$, $X^3$, $X^4$, $X^5$, Z and W have the meanings given above, with the provision that when $X^4$=N and $X^5$=C then $R^8$ is not bound to the 1,8-naphthyridine ring by a nitrogen atom and/or
- measure (iv): according to another preferred embodiment, at least one compound of general formula I, in which the radicals $R^1$, $R^2$, $R^3$, $R^4$, $R^5$, $R^6$, $R^7$, $R^8$, $R^9$, $X^1$, $X^2$, $X^3$, $X^4$, $X^5$, Z and W have the meanings given above, with the provision that when $X^1$, $X^2$, $X^3$, $X^4$ and $X^5$ each equal C, then $R^3$ does not denote COOH, $COOR_3$ or a pharmaceutically acceptable acid mimetic as defined in U.S. Patent Application No. US 2005/0101568, paragraph [0088], pages 6 and 7 and/or
- measure (v): according to a preferred embodiment, at least one compound of general formula I, in which the radicals $R^1$, $R^2$, $R^3$, $R^4$, $R^5$, $R^6$, $R^7$, $R^8$, $R^9$, $X^1$, $X^2$, $X^3$, $X^4$, $X^5$, Z and W have the meanings given above, with the provision that formula I does not denote 2-({2-[(2-benzoyl-4-chlorophenyl)amino]-6-chloro-4-phenylquinolin-3-yl}methyl)benzoic acid or 3-[2-(methoxymethyl)benzyl]-3,4-dihydroquinazolin-2-amine.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, at least one compound of general formula I as defined above or according to Claim 1, corresponding enantiomeric, diastereomeric and/or tautomeric forms thereof and/or the pharmaceutically acceptable salts thereof and/or the active ingredient precursors (prodrugs) thereof are made available, in which the radicals $R^1$, $R^2$, $R^3$, $R^4$, $R^5$, $R^6$, $R^7$, $R^8$, $R^9$, $X^1$, $X^2$, $X^3$, $X^4$, $X^5$, Z and W have the same meanings as given above, unless explicitly stated otherwise below, or have them in Claim 1 and in which the following radicals have the following definitions:

$R^1$ and $R^2$ independently of one another denote
  hydrogen, a free electron pair, OH, CN or optionally substituted O—$C_1$-$C_6$ alkyl, $C_1$-$C_6$ alkyl, CO—$C_1$-$C_6$ alkyl, CO—$OC_1$-$C_6$ alkyl.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, at least one compound of general formula I as described above or according to Claim 1 or 2, corresponding enantiomeric, diastereomeric and/or tautomeric forms thereof and/or the pharmaceutically acceptable salts thereof and/or the active ingredient precursors (prodrugs) thereof, are made available, in which the radicals $R^1$, $R^2$, $R^3$, $R^4$, $R^5$, $R^6$, $R^7$, $R^8$, $R^9$, $X^1$, $X^2$, $X^3$, $X^4$, $X^5$, Z and W have the same meanings as given above, unless explicitly stated otherwise below, or have them in Claim 1 or 2 and in which the radicals below are defined as follows:

A denotes OH, —O—$C_1$-$C_6$ alkyl, —$OCF_3$, —$OCHF_2$ or optionally substituted —NH—$C_1$-$C_6$ alkyl, —NH—CO—$C_1$-$C_6$ alkyl, —NH—$SO_2$—$C_1$-$C_6$ alkyl, —N($C_1$-$C_6$ alkyl)$_2$, piperidinyl, morpholinyl, —N($C_1$-$C_6$ alkyl)-CO—$C_1$-$C_6$ alkyl or —N($C_1$-$C_6$ alkyl)-$SO_2$—$C_1$-$C_6$ alkyl, $C_1$-$C_4$ alkylene-CO—N($CH_3$)$_2$, $C_1$-$C_4$ alkylene-CO—N-piperidyl, $C_1$-$C_4$ alkylene-CO—N-morpholinyl, $C_1$-$C_4$ alkylene-$SO_2$—N($CH_3$)$_2$, $C_1$-$C_4$ alkylene-$SO_2$—N-piperidyl, $C_1$-$C_4$ alkylene, $SO_2$—N-morpholinyl or $C_1$-$C_4$ alkyl-O—$C_1$-$C_4$ alkyl and B denotes hydrogen, CN, $CF_3$, $OCF_3$, $OCHF_2$, $CHF_2$, COOH, halogen, or optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-hetaryl, $C_1$-$C_4$ alkylene-aryl, $C_1$-$C_4$ alkylene-$NR_A^2R_A^3$, $C_1$-$C_4$ alkylene-CO—$NR_A^2R_A^3$, $C_1$-$C_4$ alkylene-$SO_2$—$NR_A^2R_A^3$, $NR_A^4$—CO—$R_A^1$, $NR_A^4$—$SO_2$—$R_A^1$, or $C_1$-$C_4$ alkylene-O—$R_A^1$, —O—$R_A^1$ or —$NR_A^2R_A^3$; in which $R_A^1$ denotes
  independently of its respective occurrence, optionally substituted $C_1$-$C_6$ alkyl, $C_3$-$C_6$ cycloalkyl, $C_1$-$C_4$ alkylene-heterocycloalkyl, aryl, hetaryl, $C_1$-$C_4$ alkylene-aryl, $C_1$-$C_6$ alkylene-hetaryl, $C_1$-$C_4$ alkylene-$NR_A^2R_A^3$, $C_1$-$C_4$ alkylene-CO—$NR_A^2R_A^3$ or $C_1$-$C_4$ alkylene-O—$C_1$-$C_6$ alkyl;

$R_A^2$ denotes
  independently of its respective occurrence, hydrogen, CN or optionally substituted $C_1$-$C_6$ alkyl, aryl, hetaryl, heterocycloalkyl, $C_1$-$C_4$ alkylene-aryl, $C_1$-$C_4$ alkylene-hetaryl, CO—$C_1$-$C_6$ alkyl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, $SO_2$-aryl or $SO_2$-hetaryl;

$R_A^3$ denotes
  independently of its respective occurrence, hydrogen or optionally substituted $C_1$-$C_6$ alkyl;
  or the radicals $R_A^2$ and $R_A^3$ together with the nitrogen may form a five- or six-membered, optionally substituted, saturated or aromatic heterocycle that may contain another heteroatom that may be the same or different and is selected from the group O, N, S;

$R_A^4$ denotes
  hydrogen or optionally substituted $C_1$-$C_6$ alkyl;

$R_W$ denotes hydrogen, CN, $CF_3$, $OCF_3$ or
  optionally substituted $C_1$-$C_6$ alkyl or O—$C_1$-$C_6$ alkyl or independently of one another, two radicals selected from the group consisting of A, B, or $R_W$ together with the respective carbon atom to which they are attached may form a five- or six-membered, optionally substituted, saturated or unsaturated carbocycle or a five- or six-membered, optionally substituted, saturated or unsaturated or aromatic heterocycle, which may contain one, two or three other heteroatoms, which may be the same or different and are selected from the group consisting of O, N and S.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, at least one compound of general formula I as described above or according to any one of Claims 1 through 3, corresponding enantiomeric, diastereomeric and/or tautomeric forms thereof and/or the pharmaceutically acceptable salts thereof and/or the active ingredient precursors (prodrugs) thereof are made available, where the radicals $R^1$, $R^2$, $R^3$, $R^4$, $R^5$, $R^6$, $R^7$, $R^8$, $R^9$, $X^1$, $X^2$, $X^3$, $X^4$, $X^5$, Z and W have the same meanings as given above, unless explicitly stated otherwise below, or have the same meanings in any one of Claims 1 through 3 and in which the radicals below are defined as follows:

Z denotes —$CH_2$—, —CH($C_1$-$C_3$ alkyl), optionally $C_1$-$C_3$ alkyl-substituted $C_1$-$C_3$ alkylene or —$CH_2$—C—($CH_2$—$CH_2$)—$CH_2$—.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, at least one compound of general formula I as described above or according to any one of Claims 1 through 4, corresponding enantiomeric, diastereomeric and/or tautomeric forms thereof and/or the pharmaceutically acceptable salts thereof and/or the active ingredient precursors (prodrugs) thereof are made available, where the radicals $R^1$, $R^2$, $R^3$, $R^4$, $R^5$, $R^6$, $R^7$, $R^8$, $R^9$, $X^1$, $X^2$, $X^3$, $X^4$, $X^5$, Z and W have the same meanings as given above, unless explicitly stated otherwise below, or have the same meanings in any one of Claims 1 through 4 and in which the radicals below are defined as follows:

Z denotes —CH$_2$—, —CH$_2$—CH$_2$— or —CH$_2$—CH$_2$—CH$_2$—.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, at least one compound of general formula I as described above or according to any one of Claims 1 through 5, corresponding enantiomeric, diastereomeric and/or tautomeric forms thereof and/or the pharmaceutically acceptable salts thereof and/or the active ingredient precursors (prodrugs) thereof are made available, where the radicals $R^1$, $R^2$, $R^3$, $R^4$, $R^5$, $R^6$, $R^7$, $R^8$, $R^9$, $X^1$, $X^2$, $X^3$, $X^4$, $X^5$, Z and W have the same meanings as given above, unless explicitly stated otherwise below, or have the same meanings in any one of Claims 1 through 5 and in which the radicals below are defined as follows:

Z denotes —CH$_2$—.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, at least one compound of general formula I as described above or according to any one of Claims 1 through 6, corresponding enantiomeric, diastereomeric and/or tautomeric forms thereof and/or the pharmaceutically acceptable salts thereof and/or the active ingredient precursors (prodrugs) thereof are made available, where the radicals $R^1$, $R^2$, $R^3$, $R^4$, $R^5$, $R^6$, $R^7$, $R^8$, $R^9$, $X^1$, $X^2$, $X^3$, $X^4$, $X^5$, Z and W have the same meanings as given above, unless explicitly stated otherwise below, or have the same meanings in any one of Claims 1 through 6 and in which the radicals below are defined as follows:

W denotes, with the provision that

A denotes optionally substituted —O—C$_1$-C$_6$ alkyl, —OCF$_3$, —OCHF$_2$, —N(C$_1$-C$_3$ alkyl)$_2$, piperidinyl, morpholinyl and B denotes
hydrogen, CN, CF$_3$, OCF$_3$, —OCHF$_2$, CHF$_2$, COOH, halogen, or optionally substituted C$_1$-C$_6$ alkyl, C$_3$-C$_7$ cycloalkyl, hetaryl, heterocycloalkyl, C$_1$-C$_4$ alkylene-NR$_A^2$R$_A^3$, C$_1$-C$_4$ alkylene-CO—NR$_A^2$R$_A^3$, C$_1$-C$_4$ alkylene-SO$_2$—NR$_A^2$R$_A^3$, NR$_A^4$—CO—R$_A^1$, NR$_A^4$—SO$_2$—R$_A^1$ or C$_1$-C$_4$ alkylene-O—R$_A^1$, —O—R$_A^1$ or —NR$_A^2$R$_A^3$, in which R$_A^1$ denotes
independently of its respective occurrence, optionally substituted C$_1$-C$_6$ alkyl, C$_3$-C$_6$ cycloalkyl, phenyl, pyridyl, C$_1$-C$_4$ alkylene-NR$_A^2$R$_A^3$ or C$_1$-C$_4$ alkylene-O—C$_1$-C$_6$ alkyl;

R$_A^2$ denotes
independently of its respective occurrence, hydrogen, CN or optionally substituted C$_1$-C$_6$ alkyl, phenyl or pyridyl;

R$_A^3$ denotes
independently of its respective occurrence, hydrogen or optionally substituted C$_1$-C$_6$ alkyl;

or the radicals R$_A^2$ and R$_A^3$ together with the nitrogen atom to which they are attached may form a five- or six-membered, optionally substituted, saturated heterocycle, which may contain another heteroatom which may be the same or different and is selected from the group consisting of O, N, S;

R$_A^4$ denotes
independently of its respective occurrence, hydrogen or optionally substituted C$_1$-C$_6$ alkyl;

R$_W$ denotes hydrogen or
independently of one another, two radicals selected from the group consisting of A, B and R$_W$ together with the respective carbon atom to which they are attached may form a five- or six-membered, optionally substituted, saturated or unsaturated or aromatic heterocycle, which may contain one or two or more heteroatoms, which may be the same or different and are selected from the group consisting of O, N and S.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, at least one compound of general formula I as described above or according to any one of Claims 1 through 7, corresponding enantiomeric, diastereomeric and/or tautomeric forms thereof and/or the pharmaceutically acceptable salts thereof and/or the active ingredient precursors (prodrugs) thereof are made available, such that formula I has one of the following meanings IIa, IIb or IIc (dihydroquinazoline compound), depending on the meaning of $R^1$, $R^2$, $R^4$ and $R^5$

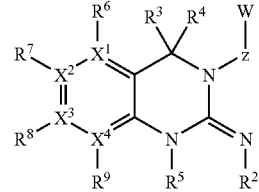

IIa

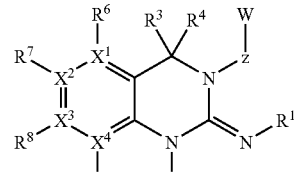

IIb

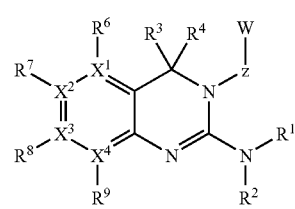

IIc in which the radicals $R^1$, $R^2$, $R^5$, $R^6$, $R^7$, $R^8$, $R^9$, $X^1$, $X^2$, $X^3$, $X^4$, Z and W have the same meanings as given above, unless explicitly stated otherwise below, or have the same meanings in any one of Claims 1 through 7 and in which the radicals below are defined as follows:
$R^3$ denotes hydrogen and
$R^4$ denotes hydrogen.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, at least one compound of general formula I as described above or according to any one of Claims 1 through 7, corresponding enantiomeric, diastereomeric and/or tautomeric forms thereof and/or the pharmaceutically acceptable salts thereof and/or the active ingredient precursors (prodrugs) thereof are made available, such that formula I has one of the following meanings IIa, IIb or IIc (dihydroquinazoline compound), depending on the meaning of $R^1$, $R^2$, $R^4$ and $R^5$

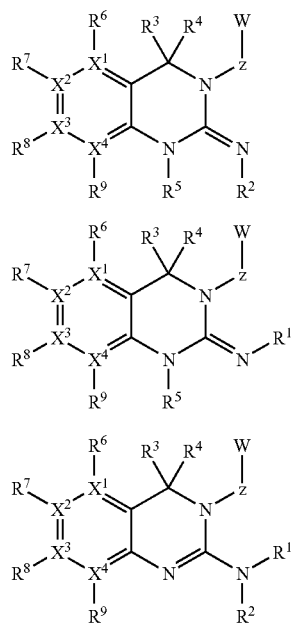

in which the radicals $R^1$, $R^2$, $R^3$, $R^4$, $R^5$, $R^6$, $R^7$, $R^8$, $R^9$, Z and W have the same meanings as given above, unless explicitly stated otherwise below, or have the same meanings in any one of Claims 1 through 7 and in which the radicals below are defined as follows:
$X^1$ denotes C,
$X^2$ denotes C,
$X^3$ denotes C,
$X^4$ denotes C.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, at least one compound of general formula I as described above or according to any one of Claims 1 through 7, corresponding enantiomeric, diastereomeric and/or tautomeric forms thereof and/or the pharmaceutically acceptable salts thereof and/or the active ingredient precursors (prodrugs) thereof are made available, such that formula I has one of the following meanings IIa, IIb or IIc (dihydroquinazoline compound), depending on the meaning of $R^1$, $R^2$, $R^4$ and $R^5$

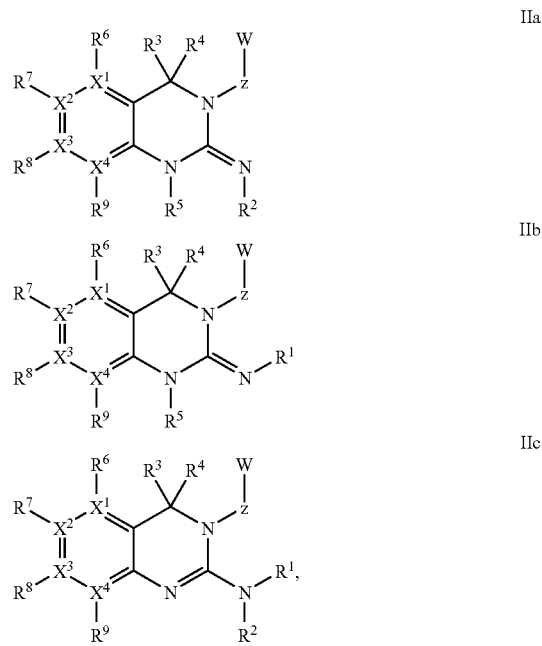

in which the radicals $R^1$, $R^2$, $R^3$, $R^4$, $R^5$, $X^1$, $X^2$, $X^3$, $X^4$, Z and W have the same meanings as given above, unless explicitly stated otherwise below, or have the same meanings in any one of Claims 1 through 7 and in which the radicals below are defined as follows:

$R^6$, $R^7$, $R^8$ and $R^9$ denote each independently of one another, a radical selected from groups 1), 2), 3), 4), 5), 6) or 7), which may the same or different where groups 1) through 7) have the following meanings:

1) hydrogen, halogen, CN, $CF_3$, —$OCF_3$, or optionally substituted $C_1$-$C_4$ alkyl, $C_2$-$C_4$ alkenyl or $NR_Q^7 R_Q^8$ or $NHR_Q^7$, in which $R_Q^7$ and $R_Q^8$ are defined as shown below 2) phenyl optionally substituted with one, two or three radicals which may be the same or different and are selected from the group consisting of $R_Q^2$, $R_Q^3$ and $R_Q^4$ in which
$R_Q^2$, $R_Q^3$ and $R_Q^4$, each independently of one another, denote a substituent from the following group:
hydrogen, $NO_2$, $NH_2$, OH, CN, $CF_3$, $CHF_2$, $OCF_3$, $OCHF_2$, COOH, O—$CH_2$—COOH, SH, halogen or
optionally substituted hetaryl, heterocycloalkyl, $C_1$-$C_4$ alkyl, O—$R_Q^5$, $NR_Q^7 R_Q^8$, or
two of the radicals selected from the group consisting of $R_Q^2$, $R_Q^3$ and $R_Q^4$ together with the respective atom to which they are attached may form a five- or six-membered, optionally substituted, saturated, unsaturated or aromatic heterocycle, which may contain one or two other different or same heteroatoms selected from the group consisting of O, N and S;
$R_Q^5$ denotes optionally substituted $C_1$-$C_4$ alkyl;

$R_Q^7$ denotes, independently of its respective occurrence, hydrogen or optionally substituted $C_1$-$C_4$ alkyl;

$R_Q^8$ denotes, independently of the respective occurrence, optionally substituted $C_1$-$C_4$ alkyl, aryl or hetaryl;

or the radicals $R_Q^7$ and $R_Q^8$ together with the nitrogen atom to which they are attached may form a five- or six-membered, optionally substituted, saturated or aromatic heterocycle, which may contain one or two additional heteroatoms, which may be the same or different and are selected from the group consisting of O, N and S;

3) a five- or six-membered hetaryl radical, optionally having one or two substituents that may be the same or different and are selected from the group consisting of:

2-thienyl, 3-thienyl, 2-thiazolyl, 4-thiazolyl, 5-thiazolyl, 1-pyrazolyl, 3-pyrazolyl, 4-pyrazolyl, 5-pyrazolyl, 1-imidazolyl, 2-imidazolyl, 4-imidazolyl, 5-imidazolyl, 2-pyridyl, 3-pyridyl, 4-pyridyl, in which the substituents are preferably selected from the group consisting of halogen, CN, $CF_3$, $OCF_3$, or optionally substituted $C_1$-$C_3$ alkyl, O—$C_1$-$C_4$ alkyl, NH—($C_1$-$C_4$ alkyl), N($C_1$-$C_4$ alkyl)$_2$;

4) two radicals selected from the group consisting of $R^6$, $R^7$, $R^8$ and $R^9$ together with the respective atom to which they are attached may form a five- or six-membered, optionally substituted, partially or fully saturated carbocycle or a five- or six-membered, optionally substituted, partially or fully saturated heterocycle, which may have one or two heteroatoms that are the same or different and are selected from the group consisting of O, N and S;

5) an optionally substituted $C_3$-$C_5$ monocyclic saturated hydrocarbon radical;

6) an optionally substituted five- or six-membered monocyclic, partially or fully saturated heterocycle selected from the following group:

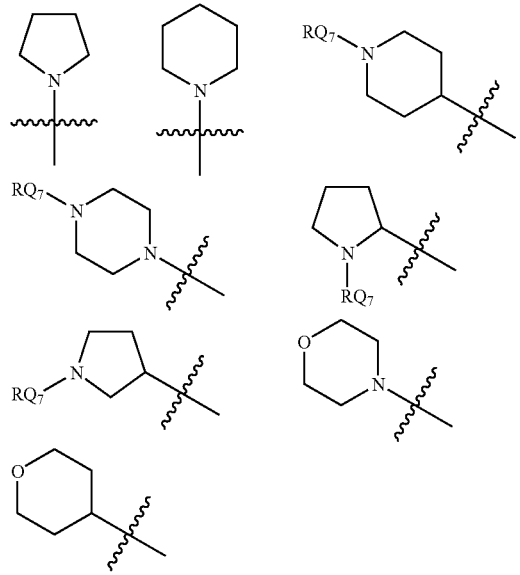

in which the radical $R_Q^7$ is defined as described above, independently of its occurrence;

7) a radical of general formula V $$—(CR_Y^1R_Y^2)_d—(Y)_e—(CR_Y^3R_Y^4)_f—R_Y^5 \qquad V$$

with the indices
d=0 or 1,
e=0 or 1,
f=0 or 1,
in which the sum of d, e and f is 1, 2 or 3;
$R_Y^2$, $R_Y^3$, $R_Y^4$ independently of one another denote hydrogen or $C_1$-$C_4$ alkyl,
$R_Y^5$ denotes a radical selected from the radicals as defined above in groups 1), 2), 3), 5) or 6);

Y denotes —CO—, —O—, —S—, —$NR_Y^5$—, —CO—$NR_Y^5$, —$NR_Y^5$—CO—, —$SO_2$—$NR_Y^5$, —$NR_Y^5$—$SO_2$—;

in which
$R_Y^5$ denotes
hydrogen or
optionally substituted $C_1$-$C_6$ alkyl.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, at least one compound of general formula I as described above or according to any one of Claims 1 through 7, corresponding enantiomeric, diastereomeric and/or tautomeric forms thereof and/or the pharmaceutically acceptable salts thereof and/or the active ingredient precursors (prodrugs) thereof are made available, such that formula I has one of the following meanings IIa, IIb or IIc (dihydroquinazoline compound), depending on the meaning of $R^1$, $R^2$, $R^4$ and $R^5$

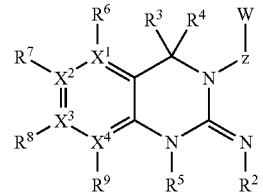

IIa

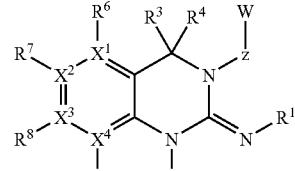

IIb

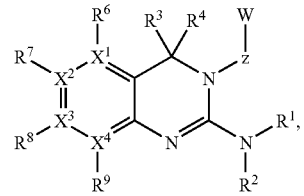

IIc in which the radicals $R^1$, $R^2$, $R^3$, $R^4$, $R^5$, $X^1$, $X^2$, $X^3$, $X^4$, Z and W have the same meanings as given above, unless explicitly stated otherwise below, or have the same meanings in any one of Claims 1 through 7 and in which the radicals below are defined as follows:

$R^6$, $R^7$, $R^8$ and $R^9$ denote
each independently of one another, a radical selected from the same or different radicals of groups 1), 2), 3), 4), 5), 6) or 7), in which groups 1) through 7) have the following meanings:

1) hydrogen, Cl, F, CN, $CF_3$, $-OCF_3$, or
   optionally substituted $C_1$-$C_4$ alkyl or $NR_Q^7R_Q^8$ in which $R_Q^7$ and $R_Q^8$ are defined as shown below
2) phenyl optionally substituted with one, two or three radicals selected from the group consisting of $R_Q^2$, $R_Q^3$ and $R_Q^4$ in which
   $R_Q^2$, $R_Q^3$ and $R_Q^4$, each independently of one another, denote a substituent that may be the same or different and is selected from the following group:
   hydrogen, CN, $CF_3$, Cl, F or
   optionally substituted $C_1$-$C_4$ alkyl, $O-R_Q^5$, $NR_Q^7R_Q^8$;
   $R_Q^5$ denotes optionally substituted $C_1$-$C_2$ alkyl;
   $R_Q^7$ denotes, independently of its respective occurrence, hydrogen
   or
   optionally substituted $C_1$-$C_2$ alkyl;
   $R_Q^8$ denotes, independently of its respective occurrence, optionally substituted $C_1$-$C_2$ alkyl;
3) optionally substituted 2-thienyl, 3-thienyl, 2-thiazolyl, 4-thiazolyl, 5-thiazolyl, 2-pyridyl, 3-pyridyl or 4-pyridyl;
4) two of the radicals $R^6$, $R^7$, $R^8$ or $R^9$ together with the respective atom to which they are attached may form an optionally substituted 1,3-dioxolane ring;
5) optionally substituted cyclopropyl or cyclopentyl;
6) a six-membered monocyclic, optionally substituted heterocycle selected from the following group:

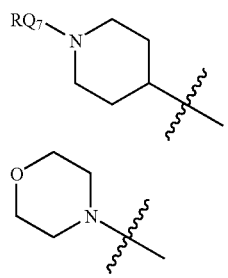

in which the radical $R_Q^7$ is defined as above, independently of its occurrence;

7) an optionally substituted radical of general formula V $$-(CR_V^1R_V^2)_d-(Y)_e-(CR_V^3R_V^4)_f-R_V^5 \qquad V$$

with the indices
d=0-1 (i.e., an integer selected from 0 or 1)
e=0 or 1
f=0 or 1
in which the sum of d, e and f is 1 or 2;
$R_V^1$, $R_V^2$, $R_V^3$ and $R_V^4$ each denotes hydrogen,
$R_V^5$ denotes, independently of its occurrence, a radical selected from radicals as defined above in groups 1), 2), 3), 5) or 6);
Y denotes
$-CO-$, $-O-$, $-NR_Y^5-$;
in which
$R_Y^5$ denotes
hydrogen or methyl.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, at least one compound of general formula I as described above or according to any one of Claims 1 through 7, corresponding enantiomeric, diastereomeric and/or tautomeric forms thereof and/or the pharmaceutically acceptable salts thereof and/or the active ingredient precursors (prodrugs) thereof are made available, such that formula I has one of the following meanings IIa, IIb or IIc (dihydroquinazoline compound), depending on the meaning of $R^1$, $R^2$, $R^4$ and $R^5$

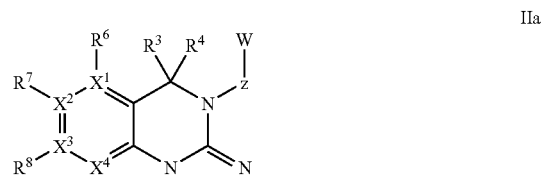

IIa

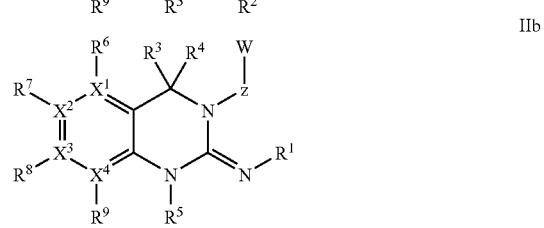

IIb

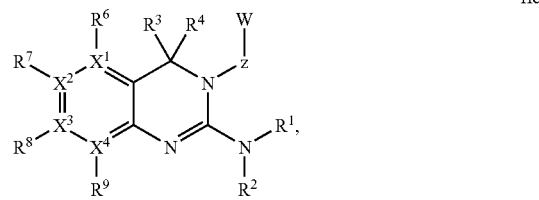

IIc in which the radicals $R^1$, $R^2$, $R^3$, $R^4$, $R^5$, $X^1$, $X^2$, $X^3$, $X^4$, Z and W have the same meanings as given above, unless explicitly stated otherwise below, or have the same meanings in any one of Claims 1 through 7 and in which the radicals below are defined as follows:

$R^6$, $R^7$, $R^8$ and $R^9$ denote
   each independently of one another, a radical that may be the same or different selected from the group consisting of:
   hydrogen, Cl, F, CN, $CF_3$, $-OCF_3$, $C_1$-$C_4$ alkyl, $NMe_2$, methoxy, ethoxy; phenyl, 2-thienyl, 3-thienyl, 2-pyridyl, 3-pyridyl, 4-pyridyl, morpholinyl or N-methylpiperazinyl which may optionally be substituted once, twice or three times with Cl, F, methyl or methoxy, where the substituents may be the same or different.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, at least one compound of general formula I as described above or according to any one of Claims 1 through 7, corresponding enantiomeric, diastereomeric and/or tautomeric forms thereof and/or the pharmaceutically acceptable salts thereof and/or the active ingredient precursors (prodrugs) thereof are made available, such that formula I has one of the following meanings IIa, IIb or IIc (dihydroquinazoline compound), depending on the meaning of $R^1$, $R^2$, $R^4$ and $R^5$

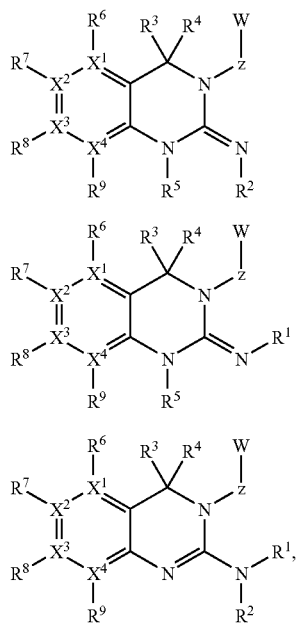

in which the radicals $R^3$, $R^4$, $R^6$, $R^7$, $R^8$, $R^9$, Z and W have the same meanings as given above, unless explicitly stated otherwise below, or have the same meanings in any one of Claims 1 through 7 and in which the radicals below are defined as follows:

$R^1$ denotes hydrogen $R^2$ denotes hydrogen and $R^5$ denotes hydrogen or a free electron pair.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, at least one compound of general formula I as described above or according to any one of Claims 1 through 7, corresponding enantiomeric, diastereomeric and/or tautomeric forms thereof and/or the pharmaceutically acceptable salts thereof and/or the active ingredient precursors (prodrugs) thereof are made available, such that formula I has one of the following meanings IIIa, IIIb or IIIc (quinoline compound), depending on the meaning of $R^1$, $R^2$ and $R^5$

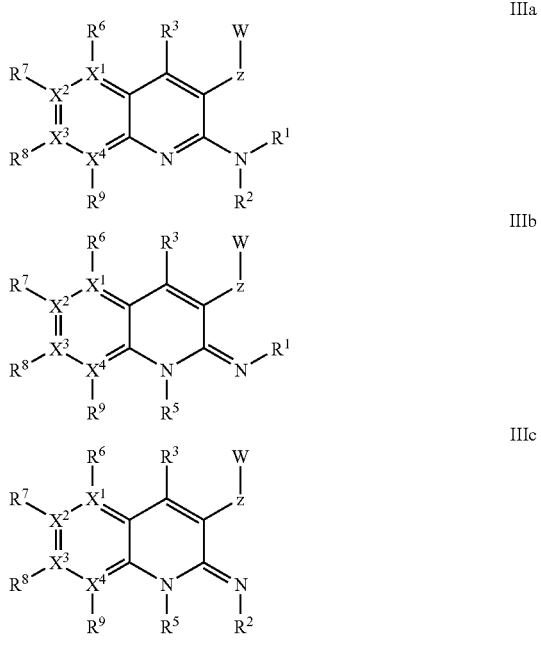

and $R^1$, $R^2$, $R^5$, $R^6$, $R^7$, $R^8$, $R^9$, $X^1$, $X^2$, $X^3$, $X^4$, Z and W have the same meanings as given above, unless explicitly stated otherwise below, or have the same meanings in any one of Claims 1 through 7 and in which the radicals below are defined as follows:

$R^3$ denotes hydrogen, CN, $CF_3$, Cl, F, methoxy, ethoxy, methyl, ethyl, optionally substituted phenyl.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, at least one compound of general formula I as described above or according to any one of Claims 1 through 8, corresponding enantiomeric, diastereomeric and/or tautomeric forms thereof and/or the pharmaceutically acceptable salts thereof and/or the active ingredient precursors (prodrugs) thereof are made available, such that formula I has one of the following meanings IIIa, IIIb or IIIc (quinoline compound), depending on the meaning of $R^1$, $R^2$ and $R^5$

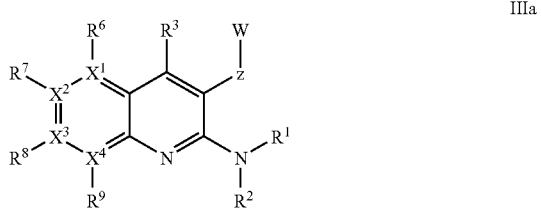

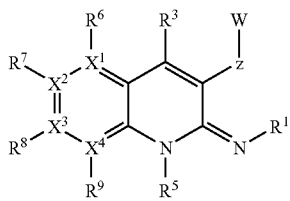

IIIb

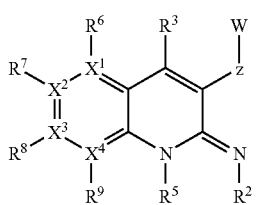

IIIc and $R^1$, $R^2$, $R^3$, $R^5$, $R^6$, $R^7$, $R^8$, $R^9$, Z and W have the same meanings as given above, unless explicitly stated otherwise below, or have the same meanings in any one of Claims 1 through 8 and in which the radicals below are defined as follows:

$X^1$ denotes C,
$X^2$ denotes C or N,
$X^3$ denotes C or N,
$X^4$ denotes C.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, at least one compound of general formula I as described above or according to any one of Claims 1 through 8, corresponding enantiomeric, diastereomeric and/or tautomeric forms thereof and/or the pharmaceutically acceptable salts thereof and/or the active ingredient precursors (prodrugs) thereof are made available, such that formula I has one of the following meanings IIIa, IIIb or IIIc (quinoline compound), depending on the meaning of $R^1$, $R^2$ and $R^5$

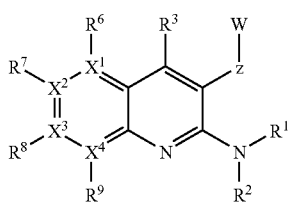

IIIa

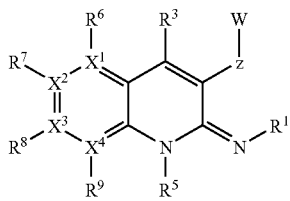

IIIb and $R^1$, $R^2$, $R^3$, $R^5$, $R^6$, $R^7$, $R^8$, $R^9$, Z and W have the same meanings as given above, unless explicitly stated otherwise below, or have the same meanings in any one of Claims 1 through 8, and in which the radicals below are defined as follows:

$X^1$ denotes C,
$X^2$ denotes C,
$X^3$ denotes C,
$X^4$ denotes C.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, at least one compound of general formula I as described above or according to any one of Claims 1 through 9, corresponding enantiomeric, diastereomeric and/or tautomeric forms thereof and/or the pharmaceutically acceptable salts thereof and/or the active ingredient precursors (prodrugs) thereof are made available, such that formula I has one of the following meanings IIIa, IIIb or IIIc (quinoline compound), depending on the meaning of $R^1$, $R^2$ and $R^5$

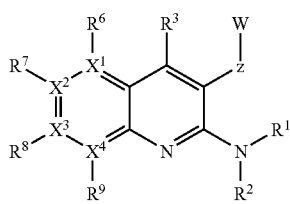

IIIa

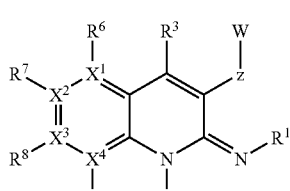

IIIb

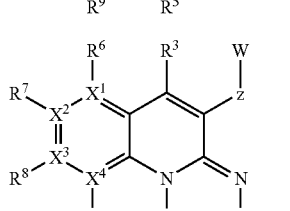

IIIc in which the radicals $R^1$, $R^2$, $R^3$, $R^5$, $X^1$, $X^2$, $X^3$, $X^4$, Z and W have the same meanings as given above, unless explicitly stated otherwise below, or have the same meanings in any one of Claims 1 through 9 and in which the radicals below are defined as follows:

$R^6$, $R^7$, $R^8$ and $R^9$ denote each independently of the others, a radical that may be the same or different is selected from the same or different radicals of the groups 1), 2), 3), 4), 5), 6) or 7), in which groups 1) through 7) have the following meanings:
1) hydrogen, halogen, CN, $CF_3$, $-OCF_3$, or
   optionally substituted $C_1$-$C_4$ alkyl, $C_2$-$C_4$ alkenyl or $NR_Q^7R_Q^8$
   in which $R_Q^7$ and $R_Q^8$ are defined as shown below
2) phenyl optionally substituted with one, two or three radicals which may be the same or different and are selected from the group consisting of $R_Q^2$, $R_Q^3$ and $R_Q^4$ in which
   $R_Q^2$, $R_Q^3$ and $R_Q^4$, independently of one another each denote a substituent that may be the same or different and is selected from the following group:
   hydrogen, $NO_2$, $NH_2$, OH, CN, $CF_3$, $CHF_2$, $OCF_3$, $OCHF_2$, COOH, O—$CH_2$—COOH, SH, halogen or
   optionally substituted hetaryl, heterocycloalkyl, $C_1$-$C_4$ alkyl, O—$R_Q^5$, $NR_Q^7R_Q^8$ or
   two of the radicals from $R_Q^2$, $R_Q^3$ or $R_Q^4$ together with the carbon atom to which they are attached may form a five- or six-membered, optionally substituted, saturated, unsaturated or aromatic heterocycle that may contain one or two additional different or the same heteroatoms selected from the group consisting of O, N and S, in which
   $R_Q^5$ denotes optionally substituted $C_1$-$C_4$ alkyl;
   $R_Q^7$ denotes, independently of its respective occurrence, hydrogen
   or
   in each case optionally substituted $C_1$-$C_4$ alkyl;
   $R_Q^8$ denotes, independently of its respective occurrence, optionally substituted $C_1$-$C_4$ alkyl, aryl or hetaryl;
   or the radicals $R_Q^7$ and $R_Q^8$ together with the nitrogen atom to which they are attached may form a five- or six-membered, optionally substituted, saturated or aromatic heterocycle, which may contain one or two additional heteroatoms, which may be the same or different and are selected from the group consisting of O, N and S;
3) a five- or six-membered hetaryl radical, which may optionally be substituted once or twice with substituents that may be the same or different and are selected from the group consisting of:
   2-thienyl, 3-thienyl, 2-thiazolyl, 4-thiazolyl, 5-thiazolyl, 1-pyrazolyl, 3-pyrazolyl, 4-pyrazolyl, 5-pyrazolyl, 1-imidazolyl, 2-imidazolyl, 4-imidazolyl, 5-imidazolyl, 2-pyridyl, 3-pyridyl, 4-pyridyl, in which the substituents are preferably selected from the group consisting of halogen, CN, $CF_3$, $OCF_3$, or optionally substituted $C_1$-$C_3$ alkyl, O—$C_1$-$C_4$ alkyl, NH—($C_1$-$C_4$ alkyl), N($C_1$-$C_4$ alkyl)$_2$;
4) two of the radicals $R^6$, $R^7$, $R^8$ or $R^9$ together may form a five- or six-membered, optionally substituted, partially or fully saturated carbocycle or a five- or six-membered, optionally substituted, partially or fully saturated heterocycle, which may contain one or two heteroatoms that are the same or different and are selected from the group consisting of O, N and S;
5) an optionally substituted $C_3$-$C_5$ monocyclic saturated hydrocarbon radical;
6) an optionally substituted five- or six-membered monocyclic, partially or fully saturated heterocycle selected from the following group:

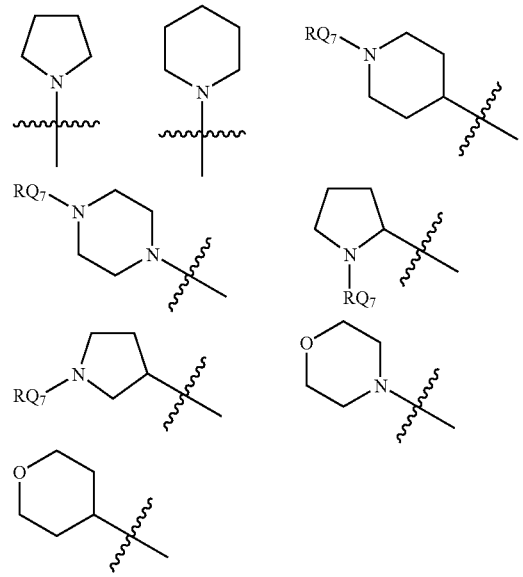

in which the radical $R_Q^7$, independently of its occurrence, is defined as above;
7) a radical of general formula V

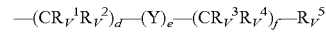    V with the indices
d=0 or 1,
e=0 or 1,
f=0 or 1,
in which the sum of d, e and f is 1, 2 or 3;
$R_V^1$, $R_V^2$, $R_V^3$, $R_V^4$ independently of one another denote hydrogen or optionally substituted $C_1$-$C_4$ alkyl,
$R_V^5$ denotes
a radical selected from radicals as defined above in one or more of the groups 1), 2), 3), 5) or 6);
Y denotes

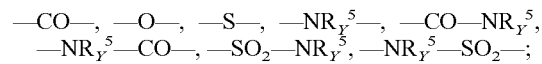

in which
$R_Y^5$ denotes
hydrogen or
optionally substituted $C_1$-$C_6$ alkyl.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, at least one compound of general formula I as described above or according to any one of Claims 1 through 10, corresponding enantiomeric, diastereomeric and/or tautomeric forms thereof and/or the pharmaceutically acceptable salts thereof and/or the active ingredient precursors (prodrugs) thereof are made available, such that formula I has one of the following meanings IIIa, IIIb or IIIc (quinoline compound), depending on the meaning of $R^1$, $R^2$ and $R^5$

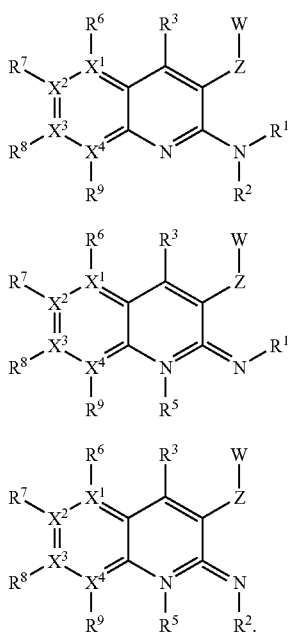

IIIa

IIIb

IIIc in which the radicals $R^2$, $R^3$, $R^5$, $X^1$, $X^2$, $X^3$, $X^4$, Z and W have the same meanings as given above, unless explicitly stated otherwise below, or have the same meanings in any one of Claims 1 through 10 and in which the radicals below are defined as follows:

$R^6$, $R^7$, $R^8$ and $R^9$ denote each independently of one another, a radical selected from the groups 1), 2), 3), 4), 5), 6) or 7) which may be the same or different, such that groups 1) through 7) have the following meanings:

1) hydrogen, Cl, F, CN, $CF_3$, —$OCF_3$, or
   optionally substituted $C_1$-$C_4$ alkyl or $NR_Q^7R_Q^8$
   in which $R_Q^7$ and $R_Q^8$ are defined as shown below
2) phenyl which may substituted with one, two or three radicals that may be the same or different and are selected from the group consisting of $R_Q^2$, $R_Q^3$ and $R_Q^4$ in which
   $R_Q^2$, $R_Q^3$ and $R_Q^4$ each independently of one another denotes a substituent that may be the same or different and is selected from the following group:
   hydrogen, CN, $CF_3$, $CHF_2$, $OCF_3$, $OCHF_2$, Cl, F or optionally substituted hetaryl, heterocycloalkyl, $C_1$-$C_4$ alkyl, O—$R_Q^5$, $NR_Q^7R_Q^8$ or
   two of the radicals from $R_Q^2$, $R_Q^3$ or $R_Q^4$ together with the carbon atom to which they are attached may form a five- or six-membered, optionally substituted, saturated, unsaturated or aromatic heterocycle, which may contain one or two additional heteroatoms, which may be the same or different and are selected from the group consisting of O, N and S;
   $R_Q^5$ denotes optionally substituted $C_1$-$C_4$ alkyl;
   $R_Q^7$ denotes, independently of its respective occurrence, hydrogen
   or
   in each case optionally substituted $C_1$-$C_4$ alkyl;
   $R_Q^8$ denotes, independently of its respective occurrence, optionally substituted $C_1$-$C_4$ alkyl, aryl or hetaryl;

or the radicals $R_Q^7$ and $R_Q^8$ together with the nitrogen atom to which they are attached may form a five- or six-membered, optionally substituted, saturated or aromatic heterocycle, which may contain another heteroatom selected from the group consisting of O, N and S;

3) a five- or six-membered hetaryl radical, optionally substituted once or twice with substituents that may be the same or different and are selected from the group consisting of:
   2-thienyl, 3-thienyl, 2-thiazolyl, 1-pyrazolyl, 1-imidazolyl, 2-imidazolyl, 2-pyridyl, 3-pyridyl, 4-pyridyl, in which the substituents are preferably selected from the group consisting of Cl, F, CN, $CF_3$, $OCF_3$, or optionally substituted $C_1$-$C_3$ alkyl, O—$C_1$-$C_4$ alkyl, NH—($C_1$-$C_4$ alkyl), N($C_1$-$C_4$ alkyl)$_2$;

4) two of the radicals $R^6$, $R^7$, $R^8$ or $R^9$ together with the respective atom to which they are attached may form an optionally substituted 1,3-dioxolane or morpholine ring;

5) optionally substituted cyclopropyl or cyclopentyl;

6) a five- or six-membered, optionally substituted monocyclic, partially or fully saturated heterocycle selected from the following group:

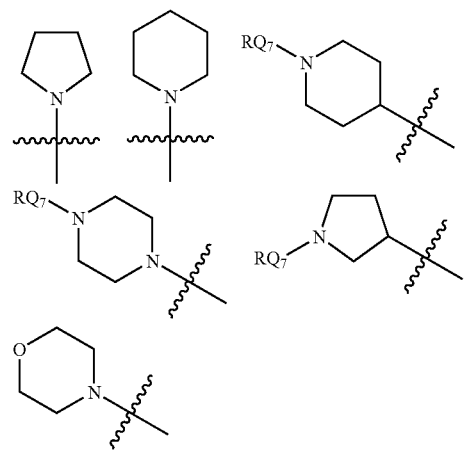

where the $R_Q^7$ radical, independently of its occurrence, is defined as above;

7) a radical of general formula V $$-(CR_V^1R_V^2)_d-(Y)_e-(CR_V^3R_V^4)_f-R_V^5 \qquad V$$

with the indices d=0-1 (i.e., 0 or 1)

e=0-1 (i.e., 0 or 1)

f=0-1 (i.e., 0 or 1)

in which the sum of d, e and f is 1 or 2;

$R_V^2$, $R_V^2$, $R_V^3$ and $R_V^4$ each denotes hydrogen, $R_V^5$ denotes a radical selected from the radicals as defined above in one or more of groups 1), 2), 3), 5) or 6);

Y denotes

—CO—, —O—, —$NR_Y^5$—;

in which $R_Y^5$ denotes hydrogen or methyl.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, at least one compound of general formula I as described above or according to any one of Claims 1 through 11, corresponding enantiomeric, diastereomeric and/or tautomeric forms thereof and/or the pharmaceutically acceptable salts thereof and/or the active ingredient precursors (prodrugs) thereof are made available, such that formula I has one of the following meanings IIIa, IIIb or IIIc (quinoline compound), depending on the meaning of $R^1$, $R^2$ and $R^5$

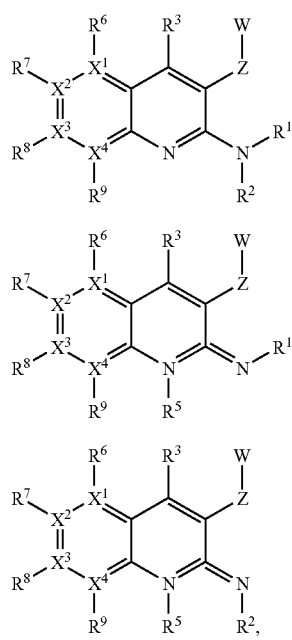

in which the radicals $R^1$, $R^2$, $R^3$, $R^5$, $X^1$, $X^2$, $X^3$, $X^4$, Z and W have the same meanings as given above, unless explicitly stated otherwise below, or have the same meanings in any one of Claims 1 through 11 and in which the radicals below are defined as follows:

$R^6$, $R^7$, $R^8$ and $R^9$ denote each independently of one another, a radical selected from the group: hydrogen, Cl, F, CN, $CF_3$, $-OCF_3$, optionally substituted $C_1$-$C_4$ alkyl, dimethylamino, diethylamino, methoxy, ethoxy, propoxy, isopropoxy, pyrrolidinyl, piperidinyl, morpholinyl or N-methylpiperazinyl or aryl or hetaryl, optionally substituted once or more with substituents that may be the same or different and are selected from Cl, F, methyl or methoxy, the aryl or hetaryl being selected from the group consisting of phenyl, 2-thienyl, 3-thienyl, 2-thiazolyl, 1-imidazolyl, 1-pyrazolyl, 2-pyridyl, 3-pyridyl or 4-pyridyl.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, at least one compound of general formula I as described above or according to any one of Claims 1 through 12, corresponding enantiomeric, diastereomeric and/or tautomeric forms thereof and/or the pharmaceutically acceptable salts thereof and/or the active ingredient precursors (prodrugs) thereof are made available, such that formula I has one of the following meanings IIIa, IIIb or IIIc (quinoline compound), depending on the meaning of $R^1$, $R^2$ and $R^5$

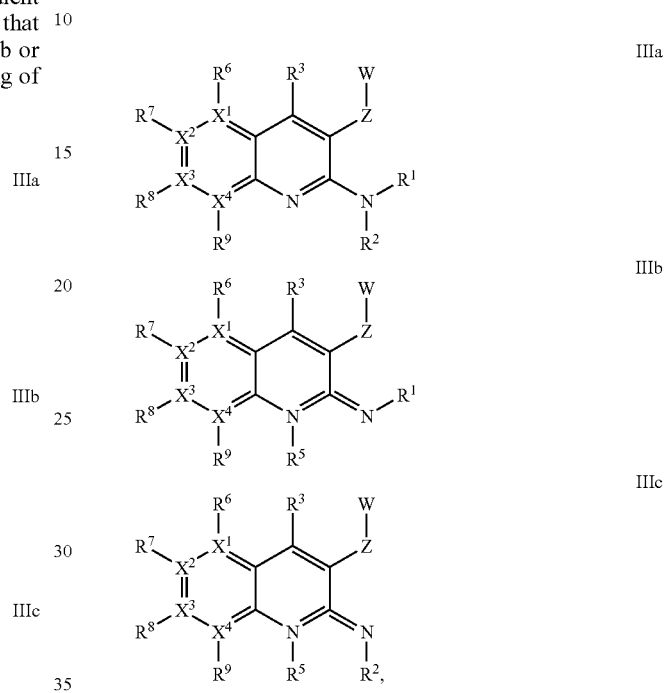

in which the radicals $R^1$, $R^2$, $R^3$, $R^5$, $R^6$, $R^7$, $R^8$, $R^9$, Z and W have the same meanings as given above, unless explicitly stated otherwise below, or have the same meanings in any one of Claims 1 through 12 and in which the radicals below are defined as follows:

$R^1$ denotes hydrogen, $R^2$ denotes hydrogen and $R^5$ denotes hydrogen or a free electron pair.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, at least one compound of general formula I as described above or according to any one of Claims 1 through 13, in particular in any one of Claims 1 through 7 and 8 through 13, corresponding enantiomeric, diastereomeric and/or tautomeric forms thereof and/or the pharmaceutically acceptable salts thereof and/or the active ingredient precursors (prodrugs) thereof are made available, in which the radicals $R^1$, $R^2$, $R^3$, $R^4$, $R^5$, $R^6$, $R^7$, $R^8$, $R^9$, $X^1$, $X^2$, $X^3$, $X^4$, $X^5$, Z and W have the same meanings as given above, unless explicitly stated otherwise below, or have the same meanings in any one of Claims 1 through 13, in particular in any one of Claims 1 through 7 and 8 through 13 and in which the radicals below are defined as follows:

$R^1$ and $R^2$ independently of one another denote
hydrogen, a free electron pair, OH, CN or
  optionally substituted O—$C_1$-$C_6$ alkyl, $C_1$-$C_6$ alkyl, CO—$C_1$-$C_6$ alkyl, CO—O—$C_1$-$C_6$ alkyl,
$R^3$ denotes hydrogen, CN, $CF_3$, Cl, F, methoxy, ethoxy, methyl, ethyl,
  optionally substituted phenyl,
$R^4$ denotes a bond to $X^5$ while preserving a C=C double bond,
$R^5$ denotes hydrogen or a free electron pair,
$R^6$, $R^7$, $R^8$ and $R^9$
  denote each independently of one another, a radical selected from the group
    consisting of hydrogen, Cl, F, CN, $CF_3$, —$OCF_3$, optionally substituted $C_1$-$C_4$ alkyl, dimethylamino, diethylamino, methoxy, ethoxy, propoxy, isopropoxy, pyrrolidinyl, piperidinyl, morpholinyl or N-methylpiperazinyl or aryl or hetaryl selected from the group consisting of phenyl, 2-thienyl, 3-thienyl, 2-thiazolyl, 1-imidazolyl, 1-pyrazolyl, 2-pyridyl, 3-pyridyl or 4-pyridyl, each optionally substituted once or more with substituents that may be the same or different and are selected from Cl, F, methyl or methoxy;
$X^1$ denotes C,
$X^2$ denotes C,
$X^3$ denotes C,
$X^4$ denotes C,
$X^5$ denotes C,
Z denotes —$CH_2$—, —$CH_2$—$CH_2$— or —$CH_2$—$CH_2$—$CH_2$— and
W with
A denotes optionally substituted —O—$C_1$-$C_6$ alkyl, —$OCF_3$, —$OCHF_2$, —NH—$C_1$-$C_6$ alkyl, —NH—CO—$C_1$-$C_6$ alkyl, —NH—$SO_2$—$C_1$-$C_6$ alkyl, —N($C_1$-$C_6$ alkyl)$_2$, piperidinyl, morpholinyl, —N($C_1$-$C_6$ alkyl)-CO—$C_1$-$C_6$ alkyl or —N($C_1$-$C_6$ alkyl)-$SO_2$—$C_1$-$C_6$ alkyl, $C_1$-$C_4$ alkylene-CO—N($CH_3$)$_2$, $C_1$-$C_4$ alkylene-CO—N-piperidyl, $C_1$-$C_4$ alkylene-CO—N-morpholinyl, $C_1$-$C_4$ alkylene-$SO_2$—N($CH_3$)$_2$, alkylene-$SO_2$—N-piperidyl, $C_1$-$C_4$ alkylene, $SO_2$—N-morpholinyl or $C_1$-$C_4$ alkyl-O—$C_1$-$C_4$ alkyl and
B denotes hydrogen, CN, $CF_3$, $OCF_3$, —$OCHF_2$, $CHF_2$, COOH, halogen, or optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-hetaryl, $C_1$-$C_4$ alkylene-aryl, $C_1$-$C_4$ alkylene-$NR_A^2R_A^3$, $C_1$-$C_4$ alkylene-CO—$NR_A^2R_A^3$, $C_1$-$C_4$ alkylene-$SO_2$—$NR_A^2R_A^3$, $NR_A^4$—CO—$R_A^1$, $NR_A^4$—$SO_2$—$R_A^1$, or $C_1$-$C_4$ alkylene-O—$R_A^1$, —O—$R_A^1$ or —$NR_A^2R_A^3$; in which
$R_A^1$ denotes
  optionally substituted $C_1$-$C_6$ alkyl, $C_3$-$C_6$ cycloalkyl, $C_1$-$C_4$ alkylene-heterocycloalkyl, aryl, hetaryl, $C_1$-$C_4$ alkylene-aryl, $C_1$-$C_6$ alkylene-hetaryl, $C_1$-$C_4$ alkylene-$NR_A^2R_A^3$, $C_1$-$C_4$ alkylene-CO—$NR_A^2R_A^3$ or $C_1$-$C_4$ alkylene-O—$C_1$-$C_6$ alkyl;
$R_A^2$ denotes
  hydrogen, CN or
  optionally substituted $C_1$-$C_6$ alkyl, aryl, hetaryl, heterocycloalkyl, $C_1$-$C_4$ alkylene-aryl, $C_1$-$C_4$ alkylene-hetaryl, CO—$C_1$-$C_6$ alkyl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, $SO_2$-aryl or $SO_2$-hetaryl;
$R_A^3$ denotes
  hydrogen or optionally substituted $C_1$-$C_6$ alkyl;
  or the radicals $R_A^2$ and $R_A^3$ together with the nitrogen atom to which they are attached may form a five- or six-membered, optionally substituted, saturated or aromatic heterocycle, which may contain another heteroatom that may be the same or different and is selected from the group consisting of O, N and S;
$R_A^4$ denotes
  hydrogen or
  optionally substituted $C_1$-$C_6$ alkyl;
$R_W$ denotes hydrogen, CN, $CF_3$, $OCF_3$ or
  optionally substituted $C_1$-$C_6$ alkyl or O—$C_1$-$C_6$ alkyl
  or, independently of one another, two of the radicals A, B, or $R_W$ together with the carbon atom to which they are attached may form a five- or six-membered, optionally substituted, saturated or unsaturated carbocycle or a five- or six-membered, optionally substituted, saturated or unsaturated or aromatic heterocycle, which may contain one, two or three additional heteroatoms, which may be the same or different and are selected from the group consisting of O, N and S.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, at least one compound of general formula I as described above or according to any one of Claims 1 through 14, in particular Claims 1 through 7 and 8 through 14, corresponding enantiomeric, diastereomeric and/or tautomeric forms thereof and/or the pharmaceutically acceptable salts thereof and/or the active ingredient precursors (prodrugs) thereof are made available, in which the radicals $R^1$, $R^2$, $R^3$, $R^4$, $R^5$, $R^6$, $R^7$, $R^8$, $R^9$, $X^1$, $X^2$, $X^3$, $X^4$, $X^5$, Z and W have the same meanings as given above, unless explicitly stated otherwise below, or have the same meanings in any one of Claims 1 through 14, in particular in any one of Claims 1 through 7 and 8 through 14 and in which the radicals below are defined as follows:
$R^1$ denotes hydrogen,
$R^2$ denotes hydrogen and
$R^3$ denotes hydrogen, CN, $CF_3$, Cl, F, methoxy, ethoxy, methyl, ethyl, optionally substituted phenyl,
$R^4$ denotes a bond to $X^5$ while preserving a C=C double bond,
$R^5$ denotes hydrogen or a free electron pair,
$R^6$, $R^7$, $R^8$ and $R^9$
  denote, each independently of one another, a radical that may be the same or different and is selected from the group consisting of
    hydrogen, Cl, F, CN, $CF_3$, —$OCF_3$, $C_1$-$C_4$ alkyl, dimethylamino, diethylamino, methoxy, ethoxy, propoxy, isopropoxy, pyrrolidinyl, piperidinyl, morpholinyl or N-methylpiperazinyl or
    aryl or hetaryl selected from the group consisting of phenyl, 2-thienyl, 3-thienyl, 2-thiazolyl, 1-imidazolyl, 1-pyrazolyl, 2-pyridyl, 3-pyridyl and 4-pyridyl, optionally substituted once or more with substituents that may be the same or different and are selected from Cl, F, methyl or methoxy;
$X^1$ denotes C,
$X^2$ denotes C,
$X^3$ denotes C,
$X^4$ denotes C,
$X^5$ denotes C, Z denotes —CH$_2$—, and W with A denotes optionally substituted —O—C$_1$-C$_6$ alkyl, —OCF$_3$, —OCHF$_2$, —N(C$_1$-C$_3$ alkyl)$_2$, piperidinyl or morpholinyl and B denotes hydrogen, CN, CF$_3$, OCF$_3$, —OCHF$_2$, CHF$_2$, COOH, halogen or optionally substituted C$_1$-C$_6$ alkyl, C$_3$-C$_7$ cycloalkyl, hetaryl, heterocycloalkyl, C$_1$-C$_4$ alkylene-NR$_A$$^2$R$_A$$^3$, C$_1$-C$_4$ alkylene-CO—NR$_A$$^2$R$_A$$^3$, C$_1$-C$_4$ alkylene-SO$_2$—NR$_A$$^2$R$_A$$^3$, NR$_A$$^4$—CO—R$_A$$^1$, NR$_A$$^4$—SO$_2$—R$_A$$^1$ or C$_1$-C$_4$ alkylene-O—R$_A$$^1$, —O—R$_A$$^1$ or —NR$_A$$^2$R$_A$$^3$; in which R$_A$$^1$ denotes optionally substituted C$_1$-C$_6$ alkyl, C$_3$-C$_6$ cycloalkyl, phenyl, pyridyl, C$_1$-C$_4$ alkylene-NR$_A$$^2$R$_A$$^3$ or C$_1$-C$_4$ alkylene-O—C$_1$-C$_6$ alkyl;

R$_A$$^2$ denotes hydrogen, CN or optionally substituted C$_1$-C$_6$ alkyl, phenyl or pyridyl;

R$_A$$^3$ denotes hydrogen or optionally substituted C$_1$-C$_6$ alkyl;

or the radicals R$_A$$^2$ and R$_A$$^3$ together with the nitrogen atom to which they are attached may form a five- to six-membered saturated heterocycle, which may contain another heteroatom that may be the same or different and is selected from the group consisting of O, N and S;

R$_A$$^4$ denotes hydrogen or optionally substituted C$_1$-C$_6$ alkyl;

R$_W$ denotes hydrogen or independently of one another, two of the radicals A, B, or R$_W$ together with the carbon atom to which they are attached may form a five- or six-membered, optionally substituted, saturated or unsaturated or aromatic heterocycle that may contain one or two or three heteroatoms that are the same or different and are selected from the group consisting of O, N and S.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, at least one compound of general formula I as described above or according to any one of Claims 1 through 15, in particular Claims 1 through 7 and 8 through 15, corresponding enantiomeric, diastereomeric and/or tautomeric forms thereof and/or the pharmaceutically acceptable salts thereof and/or the active ingredient precursors (prodrugs) thereof are made available, in which the radicals R$^1$, R$^2$, R$^3$, R$^4$, R$^5$, R$^6$, R$^7$, R$^8$, R$^9$, X$^1$, X$^2$, X$^3$, X$^4$, X$^5$, Z and W have the same meanings as given above, unless explicitly stated otherwise below, or have the same meanings in any one of Claims 1 through 15, in particular in any one of Claims 1 through 7 and 8 through 15 and in which the radicals below are defined as follows:

R$^1$ denotes hydrogen,

R$^2$ denotes hydrogen and

R$^3$ denotes hydrogen, CN, CF$_3$, Cl, F, methoxy, ethoxy, methyl, ethyl, optionally substituted phenyl, R$^4$ denotes a bond to X$^5$ while preserving a C=C double bond, R$^5$ denotes hydrogen or a free electron pair, R$^6$, R$^7$, R$^8$ and R$^9$ denote each independently of one another, a radical that may be the same or different and is selected from the group consisting of hydrogen, Cl, F, CN, CF$_3$, —OCF$_3$, optionally substituted C$_1$-C$_4$ alkyl, dimethylamino, diethylamino, methoxy, ethoxy, propoxy, isopropoxy, pyrrolidinyl, piperidinyl, morpholinyl or N-methylpiperazinyl or aryl or hetaryl selected from the group consisting of phenyl, 2-thienyl, 3-thienyl, 2-thiazolyl, 1-imidazolyl, 1-pyrazolyl, 2-pyridyl, 3-pyridyl and 4-pyridyl, optionally substituted once or more with substituents that may be the same or different and are selected from Cl, F, methyl or methoxy;

X$^1$ denotes C,

X$^2$ denotes C,

X$^3$ denotes C,

X$^4$ denotes C,

X$^5$ denotes C,

Z denotes —CH$_2$—, and

W with

A denotes optionally substituted —O—C$_1$-C$_6$ alkyl, —OCF$_3$, —OCHF$_2$, —N(C$_1$-C$_3$ alkyl)$_2$, piperidinyl or morpholinyl and B denotes hydrogen, CN, CF$_3$, OCF$_3$, —OCHF$_2$, CHF$_2$, halogen or optionally substituted C$_1$-C$_6$ alkyl, C$_3$-C$_7$ cycloalkyl, C$_1$-C$_4$ alkylene-NR$_A$$^2$R$_A$$^3$, NR$_A$$^4$—CO—R$_A$$^1$, NR$_A$$^4$—SO$_2$—R$_A$$^1$ or C$_1$-C$_4$ alkylene-O—R$_A$$^1$, —O—R$_A$$^1$ or —NR$_A$$^2$R$_A$$^3$; in which R$_A$$^1$ denotes optionally substituted C$_1$-C$_6$ alkyl, C$_3$-C$_6$ cycloalkyl, phenyl, pyridyl, C$_1$-C$_4$ alkylene-NR$_A$$^2$R$_A$$^3$ or C$_1$-C$_4$ alkylene-O—C$_1$-C$_6$ alkyl;

R$_A$$^2$ denotes hydrogen, CN or optionally substituted C$_1$-C$_6$ alkyl, phenyl or pyridyl;

R$_A$$^3$ denotes hydrogen or optionally substituted C$_1$-C$_6$ alkyl;

or the radicals R$_A$$^2$ and R$_A$$^3$ together with the nitrogen atom to which they are attached may form a five- to six-membered, optionally substituted, saturated heterocycle, which may contain another heteroatom that may be the same or different and is selected from the group consisting of O, N and S;

R$_A$$^4$ denotes hydrogen or methyl;

R$_W$ denotes hydrogen.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, at least one compound of general formula I as described above or according to any one of Claims 1 through 16, in particular Claims 1 through 7, corresponding enantiomeric, diastereomeric and/or tautomeric forms thereof and/or the pharmaceutically acceptable salts thereof and/or the active ingredient precursors (prodrugs) thereof are made available, in which the radicals R$^1$, R$^2$, R$^3$, R$^4$, R$^5$, X$^1$, X$^2$, X$^3$, X$^4$, Z and W have the same meanings as given above, unless explicitly stated otherwise below, or have the same meanings in any one of Claims 1 through 16, in particular in any one of Claims 1 through 7 and in which the radicals below are defined as follows:

$R^1$ and $R^2$ independently of one another denotes
hydrogen, a free electron pair, OH or optionally substituted O—$C_1$-$C_6$ alkyl, $C_1$-$C_6$ alkyl, CO—$C_1$-$C_6$ alkyl, CO—O—$C_1$-$C_6$ alkyl, $R^3$ denotes hydrogen, $R^4$ denotes hydrogen, $R^5$ denotes hydrogen or a free electron pair, $R^6$, $R^7$, $R^8$ and $R^9$
 each independently of one another denotes a radical selected from the group consisting of
 hydrogen, Cl, F, CN, $CF_3$, —$OCF_3$, $C_1$-$C_4$ alkyl, $NMe_2$, methoxy, ethoxy; phenyl, 2-thienyl, 3-thienyl, 2-thiazolyl, 1-imidazolyl, 1-pyrazolyl, 2-pyridyl, 3-pyridyl and 4-pyridyl, optionally substituted once or more with substituents that may be the same or different and are selected from Cl, F, methyl or methoxy;

$X^1$ denotes C, $X^2$ denotes C, $X^3$ denotes C, $X^4$ denotes C, $X^5$ denotes C, Z denotes —$CH_2$—, and W with A denotes optionally substituted —O—$C_1$-$C_6$ alkyl, —$OCF_3$, —$OCHF_2$, —NH—$C_1$-$C_6$ alkyl, —NH—CO—$C_1$-$C_6$ alkyl, —NH—$SO_2$—$C_1$-$C_6$ alkyl, —N($C_1$-$C_6$ alkyl)$_2$, piperidinyl, morpholinyl, —N($C_1$-$C_6$ alkyl)-CO—$C_1$-$C_6$ alkyl or —N($C_1$-$C_6$ alkyl)-$SO_2$—$C_1$-$C_6$ alkyl, $C_1$-$C_4$ alkylene-CO—N($CH_3$)$_2$, $C_1$-$C_4$ alkylene-CO—N-piperidyl, $C_1$-$C_4$ alkylene-CO—N-morpholinyl, $C_1$-$C_4$ alkylene-$SO_2$—N($CH_3$)$_2$, $C_1$-$C_4$ alkylene-$SO_2$—N-piperidyl, $C_1$-$C_4$ alkylene, $SO_2$—N-morpholinyl or $C_1$-$C_4$ alkyl-O—$C_1$-$C_6$ alkyl and B denotes hydrogen, CN, $CF_3$, $OCF_3$, —$OCHF_2$, $CHF_2$, COOH, halogen, or optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-hetaryl, $C_1$-$C_4$ alkylene-aryl, $C_1$-$C_4$ alkylene-$NR_A^2R_A^3$, $C_1$-$C_4$ alkylene-CO—$NR_A^2R_A^3$, $C_1$-$C_4$ alkylene-$SO_2$—$NR_A^2R_A^3$, $NR_A^4$—CO—$R_A^1$, $NR_A^4$—$SO_2$—$R_A^1$, or $C_1$-$C_4$ alkylene-O—$R_A^1$, —O—$R_A^1$ or —$NR_A^2R_A^3$; in which $R_A^1$ denotes
 optionally substituted $C_1$-$C_6$ alkyl, $C_3$-$C_6$ cycloalkyl, $C_1$-$C_4$ alkylene-heterocycloalkyl, aryl, hetaryl, $C_1$-$C_4$ alkylene-aryl, $C_1$-$C_6$ alkylene-hetaryl, $C_1$-$C_4$ alkylene-$NR_A^2R_A^3$, $C_1$-$C_4$ alkylene-CO—$NR_A^2R_A^3$ or $C_1$-$C_4$ alkylene-O—$C_1$-$C_6$ alkyl;

$R_A^2$ denotes
 hydrogen, CN or optionally substituted $C_1$-$C_6$ alkyl, aryl, hetaryl, heterocycloalkyl, $C_1$-$C_4$ alkylene-aryl, $C_1$-$C_4$ alkylene-hetaryl, CO—$C_1$-$C_6$ alkyl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, $SO_2$-aryl or $SO_2$-hetaryl;

$R_A^3$ denotes
 hydrogen or optionally substituted $C_1$-$C_6$ alkyl;
 or the radicals $R_A^2$ and $R_A^3$ together with the nitrogen atom to which they are attached may form a five- or six-membered, optionally substituted, saturated or aromatic heterocycle, which may contain another heteroatom that may be the same or different and is selected from the group consisting of O, N and S;

$R_A^4$ denotes
 hydrogen or optionally substituted $C_1$-$C_6$ alkyl;

$R_W$ denotes hydrogen, CN, $CF_3$, $OCF_3$ or
 optionally substituted $C_1$-$C_6$ alkyl or O—$C_1$-$C_6$ alkyl
 or independently of one another, two of the radicals A, B or $R_W$ together with the carbon atom to which they are attached may form a five- or six-membered, optionally substituted, saturated or unsaturated carbocycle or a five- or six-membered, optionally substituted, saturated or unsaturated or aromatic heterocycle, which may contain one, two or three additional heteroatoms, which may be the same or different and are selected from the group consisting of O, N and S.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, at least one compound of general formula I as described above or according to any one of Claims 1 through 17, in particular Claims 1 through 7 and 17, corresponding enantiomeric, diastereomeric and/or tautomeric forms thereof and/or the pharmaceutically acceptable salts thereof and/or the active ingredient precursors (prodrugs) thereof are made available, in which the radicals $R^1$, $R^2$, $R^3$, $R^4$, $R^5$, $X^1$, $X^2$, $X^3$, $X^4$, Z and W have the same meanings as given above, unless explicitly stated otherwise below, or have the same meanings in any one of Claims 1 through 17, in particular in any one of Claims 1 through 7 and 17 and in which the radicals below are defined as follows:

$R^1$ denotes hydrogen, $R^2$ denotes hydrogen, $R^3$ denotes hydrogen, $R^4$ denotes hydrogen, $R^5$ denotes hydrogen or a free electron pair, $R^6$, $R^7$, $R^8$ and $R^9$
 each independently of one another denotes a radical that may be the same or different and is selected from the group consisting of
 hydrogen, Cl, F, CN, $CF_3$, —$OCF_3$, $C_1$-$C_4$ alkyl, $NMe_2$, methoxy, ethoxy; phenyl, 2-thienyl, 3-thienyl, 2-pyridyl, 3-pyridyl, 4-pyridyl, morpholinyl or N-methylpiperazinyl, optionally substituted once or more with substituents that may be the same or different and are selected from Cl, F, methyl or methoxy;

$X^1$ denotes C, $X^2$ denotes C, $X^3$ denotes C, $X^4$ denotes C, $X^5$ denotes N, Z denotes —$CH_2$—, and W with A denotes —O—$C_1$-$C_6$ alkyl, —$OCF_3$, —$OCHF_2$, —N(($C_1$-$C_3$ alkyl)$_2$, piperidinyl or morpholinyl and B denotes hydrogen, CN, $CF_3$, $OCF_3$, —$OCHF_2$, $CHF_2$, COOH, halogen, or optionally substituted $C_1$-$C_6$ alkyl, $C_3$-$C_7$ cycloalkyl, hetaryl, heterocycloalkyl, $C_1$-$C_4$ alkylene-$NR_A^2R_A^3$, $C_1$-$C_4$ alkylene-CO—$NR_A^2R_A^3$, $C_1$-$C_4$ alkylene-$SO_2$—$NR_A^2R_A^3$, $NR_A^4$—CO—$R_A^1$, $NR_A^4$—$SO_2$—$R_A^1$ or $C_1$-$C_4$ alkylene-O—$R_A^1$, —O—$R_A^1$, —$NR_A^2R_A^3$; in which $R_A^1$ denotes
 optionally substituted $C_1$-$C_6$ alkyl, $C_3$-$C_6$ cycloalkyl, phenyl, pyridyl, $C_1$-$C_4$ alkylene-$NR_A^2R_A^3$ or $C_1$-$C_4$ alkylene-O—$C_1$-$C_6$ alkyl;

$R_A^2$ denotes
  hydrogen, CN or optionally substituted $C_1$-$C_6$ alkyl, phenyl or pyridyl;
$R_A^3$ denotes
  hydrogen or optionally substituted $C_1$-$C_6$ alkyl;
  or the radicals $R_A^2$ and $R_A^3$ together with the nitrogen atom to which they are attached may form a five- or six-membered, optionally substituted, saturated heterocycle, which may contain another heteroatom that may be the same or different and is selected from the group consisting of O, N and S;
$R_A^4$ denotes
  hydrogen or optionally substituted $C_1$-$C_6$ alkyl;
$R_W$ denotes hydrogen
  or independently of one another, two of the radicals A, B or $R_W$ together with the carbon atom to which they are attached may form a five- or six-membered, optionally substituted, saturated or unsaturated or aromatic heterocycle that may contain one or two additional heteroatoms, which may be the same or different and are selected from the group consisting of O, N and S.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, at least one compound of general formula I as described above or according to any one of Claims 1 through 17, in particular Claims 1 through 7 and 17, corresponding enantiomeric, diastereomeric and/or tautomeric forms thereof and/or the pharmaceutically acceptable salts thereof and/or the active ingredient precursors (prodrugs) thereof are made available, in which the radicals $R^1$, $R^2$, $R^3$, $R^4$, $R^5$, $X^1$, $X^2$, $X^3$, $X^4$, Z and W have the same meanings as given above, unless explicitly stated otherwise below, or have the same meanings in any one of Claims 1 through 17, in particular in any one of Claims 1 through 7 and 17 and in which the radicals below are defined as follows:

$R^1$ denotes hydrogen,
$R^2$ denotes hydrogen,
$R^3$ denotes hydrogen,
$R^4$ denotes hydrogen,
$R^5$ denotes hydrogen or a free electron pair,
$R^6$, $R^7$, $R^8$ and $R^9$
  each independently of one another denotes a radical selected from the group consisting of
    hydrogen, Cl, F, CN, $CF_3$, —$OCF_3$, $C_1$-$C_4$ alkyl, $NMe_2$, methoxy, ethoxy; phenyl, 2-thienyl, 3-thienyl, 2-pyridyl, 3-pyridyl, 4-pyridyl, morpholinyl or N-methylpiperazinyl, optionally substituted once or more with substituents that may be the same and are selected from Cl, F, methyl or methoxy;
$X^1$ denotes C,
$X^2$ denotes C,
$X^3$ denotes C,
$X^4$ denotes C,
$X^5$ denotes N,
Z denotes —$CH_2$—, and
W with
  A denotes optionally substituted —O—$C_1$-$C_6$ alkyl, —$OCF_3$, —$OCHF_2$, —$N(C_1$-$C_3$ alkyl$)_2$, piperidinyl or morpholinyl and
  B denotes hydrogen, CN, $CF_3$, $OCF_3$, —$OCHF_2$, $CHF_2$, halogen, or optionally substituted $C_1$-$C_6$ alkyl, $C_3$-$C_7$ cycloalkyl, $C_1$-$C_4$ alkylene-$NR_A^2R_A^3$, $NR_A^4$—CO—$R_A^1$, $NR_A^4$—$SO_2$—$R_A^1$ or $C_1$-$C_4$ alkylene-O—$R_A^1$, —O—$R_A^1$, —$NR_A^2R_A^3$; in which
$R_A^1$ denotes
  optionally substituted $C_1$-$C_6$ alkyl, $C_3$-$C_6$ cycloalkyl, phenyl, pyridyl, $C_1$-$C_4$ alkylene-$NR_A^2R_A^3$ or $C_1$-$C_4$ alkylene-O—$C_1$-$C_6$ alkyl;
$R_A^2$ denotes
  hydrogen, CN or optionally substituted $C_1$-$C_6$ alkyl, phenyl or pyridyl;
$R_A^3$ denotes
  hydrogen or optionally substituted $C_1$-$C_6$ alkyl;
  or the radicals $R_A^2$ and $R_A^3$ together with the nitrogen atom to which they are attached may form a five- to six-membered, optionally substituted, saturated heterocycle, which may contain an additional heteroatom that may be the same or different and is selected from the group consisting of O, N and S;
$R_A^4$ denotes
  hydrogen or methyl;
$R_W$ denotes hydrogen.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, at least one compound of general formula I as described above or according to any one of Claims 1 through 17, in particular Claims 1 through 7 and 17 or in particular Claims 1 through 7 and 8 through 16, corresponding enantiomeric, diastereomeric and/or tautomeric forms thereof and/or the pharmaceutically acceptable salts thereof and/or the active ingredient precursors (prodrugs) thereof are made available, in which the radicals $R^1$, $R^2$, $R^3$, $R^4$, $R^5$, $X^1$, $X^2$, $X^3$, $X^4$, Z B and W have the same meanings as given above, unless explicitly stated otherwise below, or have the same meanings in any one of Claims 1 through 17, in particular in any one of Claims 1 through 7 and 17, in particular in any one of Claims 1 through 7 and 8 through 16, and in which the radicals below are defined as follows:

A denotes optionally substituted —O—$C_1$-$C_3$ alkyl, —O—$C_1$-$C_3$ haloalkyl, —$N(C_1$-$C_3$ alkyl$)_2$, piperidinyl or morpholinyl.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, at least one compound of general formula I as described above or according to any one of Claims 1 through 17, in particular Claims 1 through 7 and 17 or in particular Claims 1 through 7 and 8 through 16, corresponding enantiomeric, diastereomeric and/or tautomeric forms thereof and/or the pharmaceutically acceptable salts thereof and/or the active ingredient precursors (prodrugs) thereof are made available, in which the radicals $R^1$, $R^2$, $R^3$, $R^4$, $R^5$, $X^1$, $X^2$, $X^3$, $X^4$, Z and W have the same meanings as given above, unless explicitly stated otherwise below, or have the same meanings in any one of Claims 1 through 17, in particular in any one of Claims 1 through 7 and 17, in particular in any one of Claims 1 through 7 and 8 through 16, and in which the radicals below are defined as follows:

A denotes optionally substituted —O—$C_1$-$C_3$ alkyl or —O—$C_1$-$C_3$ alkyl that is substituted with one, two, three, four or five halogen atoms that are the same or different and are selected from the group consisting of fluorine, chlorine, bromine and iodine.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, at least one compound of general formula I as described above or according to any one of Claims 1 through 17, in particular Claims 1 through 7 and 17 or in particular Claims 1 through 7 and 8 through 16, corresponding enantiomeric, diastereomeric and/or tautomeric forms thereof and/or the pharmaceutically acceptable salts thereof and/or the active ingredient precursors (prodrugs) thereof are made available, in which the radicals $R^1$, $R^2$, $R^3$, $R^4$, $R^5$, $X^1$, $X^2$, $X^3$, $X^4$, Z and W have the same meanings as given above, unless explicitly stated otherwise below, or have the same meanings in any one of Claims 1 through 25, in particular in any one of Claims 1 through 7 and 17, in particular in any one of Claims 1 through 7 and 8 through 16, and in which the radicals below are defined as follows:

A denotes —O—$CH_3$, —$OCF_3$, —$OCHF_2$, —$OCH_2F$, —O—$CH_2$—$CH_3$, —O—$CH_2$—$CF_3$, —O—$CH_2$—$CHF_2$, —O—$CH_2$—$CH_2F$ or O-isopropyl.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, at least one compound of general formula I as described above or according to any one of Claims 1 through 17, in particular Claims 1 through 7 and 17 or in particular Claims 1 through 7 and 8 through 16, corresponding enantiomeric, diastereomeric and/or tautomeric forms thereof and/or the pharmaceutically acceptable salts thereof and/or the active ingredient precursors (prodrugs) thereof are made available, in which the radicals $R^1$, $R^2$, $R^3$, $R^4$, $R^5$, $X^1$, $X^2$, $X^3$, $X^4$, Z and W have the same meanings as given above, unless explicitly stated otherwise below, or have the same meanings in any one of Claims 1 through 17, in particular in any one of Claims 1 through 7 and 17, in particular in any one of Claims 1 through 7 and 8 through 16, and in which the radicals below are defined as follows:

A denotes —O—$CH_3$, —O—$CH_2$—$CH_3$, —O—$CH_2$—$CF_3$, —O—$CH_2$—$CHF_2$ or —O—$CH_2$—$CH_2F$.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, at least one compound of general formula I as described above or according to any one of Claims 1 through 17, in particular Claims 1 through 7 and 17 or in particular Claims 1 through 7 and 8 through 16, corresponding enantiomeric, diastereomeric and/or tautomeric forms thereof and/or the pharmaceutically acceptable salts thereof and/or the active ingredient precursors (prodrugs) thereof are made available, in which the radicals $R^1$, $R^2$, $R^3$, $R^4$, $R^5$, $X^1$, $X^2$, $X^3$, $X^4$, Z and W have the same meanings as given above, unless explicitly stated otherwise below, or have the same meanings in any one of Claims 1 through 25, in particular in any one of Claims 1 through 7 and 17, in particular in any one of Claims 1 through 7 and 8 through 16, and in which the radicals below are defined as follows:

A denotes —O—$CH_3$.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, at least one compound of general formula I as described above or according to any one of Claims 1 through 21, corresponding enantiomeric, diastereomeric and/or tautomeric forms thereof and/or the pharmaceutically acceptable salts thereof and/or the active ingredient precursors (prodrugs) are made available for use as pharmaceutical drugs.

Each of the definitions of one variable as given above may be combined with any of the definitions of the remaining variables as given above. This is true in particular of the combination of preferred definitions of one variable with any definitions or any preferred definitions of the remaining variables.

According to another aspect of the present invention, a pharmaceutical composition containing at least one compound of general formula I as described above or according to any one of Claims 1 through 21 and/or corresponding enantiomeric, diastereomeric and/or tautomeric forms thereof and/or the pharmaceutically acceptable salts thereof and/or the active ingredient precursors (prodrugs) and optionally at least one pharmaceutically acceptable vehicle and/or diluent are made available.

Each of the definitions of one variable as given above may be combined with any of the definitions of the remaining variables as given above. This is true in particular of the combination of preferred definitions of one variable with any definitions or any preferred definitions of the remaining variables.

According to another aspect of the present invention, the use of at least one compound of general formula I as described above or according to any one of Claims 1 through 21 and/or corresponding enantiomeric, diastereomeric and/or tautomeric forms thereof and/or the pharmaceutically acceptable salts thereof and/or the active ingredient precursors (prodrugs) are made available for treatment and/or prevention and/or for production of a pharmaceutical drug for treatment and/or prevention of at least one disease that can be treated and/or prevented prophylactically by modulation of the 5-$HT_5$ receptor activity in a patient requiring such a treatment and/or prevention.

Each of the definitions of one variable as given above may be combined with any of the definitions of the remaining variables as given above. This is true in particular of the combination of preferred definitions of one variable with any definitions or any preferred definitions of the remaining variables.

According to another aspect of the present invention, the use of at least one compound of general formula I as described above or according to any one of Claims 1 through 21 and/or corresponding enantiomeric, diastereomeric and/or tautomeric forms thereof and/or the pharmaceutically acceptable salts thereof and/or the active ingredient precursors (prodrugs) are made available for treatment and/or prevention and/or for production of a pharmaceutical drug for treatment and/or prevention of at least one disease that can be treated and/or prevented prophylactically by modulation of the 5-HT$_5$ receptor activity with simultaneous binding affinity for the 5-HT$_{5A}$ receptor of less than or equal to 10 μM (K$_i$), preferably less than or equal to 300 nM (K$_i$) in a patient requiring such a treatment and/or prevention.

Each of the definitions of one variable as given above may be combined with any of the definitions of the remaining variables as given above. This is true in particular of the combination of preferred definitions of one variable with any definitions or any preferred definitions of the remaining variables.

According to another aspect of the present invention, the use of at least one compound of general formula I as described above or according to any one of Claims 1 through 21 and/or corresponding enantiomeric, diastereomeric and/or tautomeric forms thereof and/or the pharmaceutically acceptable salts thereof and/or the active ingredient precursors (prodrugs) are made available for treatment and/or prevention and/or for production of a pharmaceutical drug for treatment and/or prevention of at least one disease selected from the group consisting of neuropathological, neuropsychiatric and neurodegenerative disorders; neuropathological, neuropsychiatric and neurodegenerative symptoms and neuropathological, neuropsychiatric and neurodegenerative dysfunctions in a patient requiring such a treatment and/or prevention.

Each of the definitions of one variable as given above may be combined with any of the definitions of the remaining variables as given above. This is true in particular of the combination of preferred definitions of one variable with any definitions or any preferred definitions of the remaining variables.

According to another aspect of the present invention, the use of at least one compound of general formula I as described above or according to any one of Claims 1 through 21 and/or corresponding enantiomeric, diastereomeric and/or tautomeric forms thereof and/or the pharmaceutically acceptable salts thereof and/or the active ingredient precursors (prodrugs) are made available for treatment and/or prevention and/or for production of a pharmaceutical drug for treatment and/or prevention of migraines and brain injuries in a patient requiring such treatment and/or prevention.

Each of the definitions of one variable as given above may be combined with any of the definitions of the remaining variables as given above. This is true in particular of the combination of preferred definitions of one variable with any definitions or any preferred definitions of the remaining variables.

According to another aspect of the present invention, the use of at least one compound of general formula I as described above or according to any one of Claims 1 through 21 and/or corresponding enantiomeric, diastereomeric and/or tautomeric forms thereof and/or the pharmaceutically acceptable salts thereof and/or the active ingredient precursors (prodrugs) is made available for treatment and/or prevention and/or for production of a pharmaceutical drug for treatment and/or prevention of at least one neuropathological, neuropsychiatric and neurodegenerative disease selected from the group consisting of cerebral ischemia, stroke, epilepsy and seizures in general, psychoses, schizophrenia, autism, OCD syndrome, cognitive disorders, attention disorders, depression, bipolar and/or unipolar depression, anxiety, dementia, senile dementia, Alzheimer's disease, demyelinizing diseases, multiple sclerosis and brain tumors in a patient requiring such a treatment and/or prevention.

Each of the definitions of one variable as given above may be combined with any of the definitions of the remaining variables as given above. This is true in particular of the combination of preferred definitions of one variable with any definitions or any preferred definitions of the remaining variables.

According to another aspect of the present invention, the use of at least one compound of general formula I as described above or according to any one of Claims 1 through 21 and/or corresponding enantiomeric, diastereomeric and/or tautomeric forms thereof and/or the pharmaceutically acceptable salts thereof and/or the active ingredient precursors (prodrugs) are made available for treatment and/or prevention and/or for production of a pharmaceutical drug for treatment and/or prevention of at least one disease selected from the group consisting of cerebrovascular disorders, pain, pain-induced disorders, addiction, drug-induced disorders, amnesia, alcoholism, drug abuse, disorders of the circadian rhythm and Cushing's syndrome in a patient requiring such treatment and/or prevention.

Each of the definitions of one variable as given above may be combined with any of the definitions of the remaining variables as given above. This is true in particular of the combination of preferred definitions of one variable with any definitions or any preferred definitions of the remaining variables.

According to another aspect of the present invention, the use of at least one compound of general formula I as described above or according to any one of Claims 1 through 21 and/or corresponding enantiomeric, diastereomeric and/or tautomeric forms thereof and/or the pharmaceutically acceptable salts thereof and/or the active ingredient precursors (prodrugs) are made available, characterized in that the treatment and/or prevention is based on modulation of the 5-HT$_5$ receptor activity in the patient.

Each of the definitions of one variable as given above may be combined with any of the definitions of the remaining variables as given above. This is true in particular of the combination of preferred definitions of one variable with any definitions or any preferred definitions of the remaining variables.

According to another aspect of the present invention, the use of at least one compound of general formula I as described above or according to any one of Claims 1 through 21 and/or corresponding enantiomeric, diastereomeric and/or tautomeric forms thereof and/or the pharmaceutically acceptable salts thereof and/or the active ingredient precursors (prodrugs) are made available, characterized in that the treatment and/or prevention is based on a binding affinity for the 5-HT$_{5A}$ receptor of less than or equal to 10 μM (Ki), determined according to a suitable test model.

Each of the definitions of one variable as given above may be combined with any of the definitions of the remaining variables as given above. This is true in particular of the combination of preferred definitions of one variable with any definitions or any preferred definitions of the remaining variables.

According to another aspect of the present invention, the use of at least one compound of general formula I as described above or according to any one of Claims 1 through 21 and/or corresponding enantiomeric, diastereomeric and/or tautomeric forms thereof and/or the pharmaceutically acceptable salts thereof and/or the active ingredient precursors (prodrugs) are made available, characterized in that the treatment and/or prevention is based on a binding affinity for the 5-HT$_{5A}$ receptor of less than or equal to 300 nM (K$_i$), determined according to a suitable test model.

Each of the definitions of one variable as given above may be combined with any of the definitions of the remaining variables as given above. This is true in particular of the combination of preferred definitions of one variable with any definitions or any preferred definitions of the remaining variables.

According to another aspect of the present invention, the use of at least one compound of general formula I as described above or according to any one of Claims 1 through 21 and/or corresponding enantiomeric, diastereomeric and/or tautomeric forms thereof and/or the pharmaceutically acceptable salts thereof and/or the active ingredient precursors (prodrugs) are made available, characterized in that the treatment and/or prevention is based on a binding affinity for the 5-HT$_{5A}$ receptor of less than or equal to 10 µM (K$_i$), preferably less than or equal to 300 nM (K$_i$) each determined according to a suitable test model with simultaneous modulation of another 5-HT$_5$ receptor activity.

Each of the definitions of one variable as given above may be combined with any of the definitions of the remaining variables as given above. This is true in particular of the combination of preferred definitions of one variable with any definitions or any preferred definitions of the remaining variables.

According to another aspect of the present invention, the use of at least one compound of general formula I

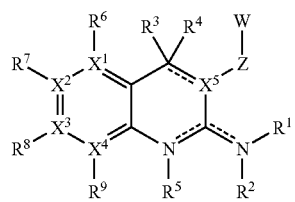

(I)

corresponding enantiomeric, diastereomeric and/or tautomeric forms thereof and/or the pharmaceutically acceptable salts thereof and/or the active ingredient precursors (prodrugs) thereof are made available, where the radicals listed have the following definitions:

R$^1$ and R$^2$ independently of one another denote
hydrogen, a free electron pair, OH, CN or,
optionally substituted, C$_1$-C$_6$ alkyl, O—C$_1$-C$_6$ alkyl, C$_1$-C$_6$ alkylene-O—C$_1$-C$_6$ alkyl, C$_2$-C$_6$ alkenyl, C$_2$-C$_6$ alkynyl, C$_3$-C$_{12}$ alkynyl, CO—C$_1$-C$_6$ alkyl, CO—O—C$_1$-C$_6$ alkyl, SO$_2$—C$_1$-C$_6$ alkyl, C$_3$-C$_7$ cycloalkyl, aryl, C$_1$-C$_4$ alkylene-aryl, CO—O-arylalkyl, CO—C$_1$-C$_4$ alkylene-aryl, CO-aryl, SO$_2$-aryl, hetaryl, CO-hetaryl or SO$_2$—C$_1$-C$_4$ alkylene-aryl, C$_1$-C$_4$ alkylene-hetaryl, C$_1$-C$_4$ alkylene-heterocycloalkyl, heterocycloalkyl, C$_1$-C$_4$ cycloalkyl, indanyl or R$^1$ and R$^2$ together with the nitrogen atom to which they are attached may form a three- to six-membered, optionally substituted, saturated or aromatic heterocycle, which may contain another heteroatom selected from the group consisting of O, N and S, such that the heterocycle may optionally have one, two or three substituents which may be the same or different, R$^3$ denotes
hydrogen, NO$_2$, NH$_2$, OH, CN, CF$_3$, OCF$_3$, CHF$_2$, OCHF$_2$, COOH, O—CH$_2$—COOH, halogen, SH or, optionally substituted, C$_1$-C$_6$ alkyl, C$_2$-C$_6$ alkenyl, C$_2$-C$_6$ alkynyl, C$_3$-C$_7$ cycloalkyl, C$_1$-C$_4$ alkylene-C$_3$-C$_7$ cycloalkyl, C$_1$-C$_4$ alkylene-heterocycloalkyl, aryl, hetaryl, heterocycloalkyl, C$_1$-C$_4$ alkylene-hetaryl or C$_1$-C$_4$ alkylene-aryl or optionally substituted O—R$_3^1$, CO—R$_3^1$, S—R$_3^1$, SO—R$_3^1$, CO—O—R$_3^1$, NR$_3^4$—CO—O—R$_3^1$, O—CH$_2$—COO—R$_3^1$, NR$_3^2$R$_3^3$, CONH$_2$, SO$_2$NH$_2$, NR$_3^4$—CO—R$_3^1$, SO$_2$—R$_3^1$, NR$_3^4$—SO$_2$—R$_3^1$, SO$_2$—NR$_3^2$R$_3^3$ or CO—NR$_3^2$R$_3^3$
in which
R$_3^1$ denotes
optionally substituted C$_1$-C$_6$ alkyl, C$_2$-C$_6$ alkenyl, C$_2$-C$_6$ alkynyl, C$_3$-C$_7$ cycloalkyl, C$_1$-C$_4$ alkylene-C$_3$-C$_7$ cycloalkyl, C$_1$-C$_4$ alkylene-heterocycloalkyl, aryl, hetaryl, heterocycloalkyl, C$_1$-C$_4$ alkylene-aryl, C$_2$-C$_6$ alkylene-aryl or C$_1$-C$_6$ alkylene-hetaryl;

R$_3^2$ denotes
hydrogen, OH, CN or,
optionally substituted C$_1$-C$_6$ alkyl, C$_2$-C$_6$ alkenyl, C$_2$-C$_6$ alkynyl, C$_1$-C$_4$ alkylene-C$_3$-C$_7$ cycloalkyl, C$_1$-C$_4$ alkylene-heterocycloalkyl, aryl, hetaryl, heterocycloalkyl, C$_1$-C$_4$ alkylene-aryl, C$_1$-C$_4$ alkylene-hetaryl, C$_1$-C$_6$ alkylene-O—C$_1$-C$_6$ alkyl, CO—C$_1$-C$_6$ alkyl, CO-aryl, CO-hetaryl, CO—C$_1$-C$_4$ alkylene-aryl, CO—C$_1$-C$_4$ alkylene-hetaryl, CO—O—C$_1$-C$_6$ alkyl, CO—O-aryl, CO—O—C$_1$-C$_4$ alkylene-aryl, CO—O-hetaryl, CO—O—C$_1$-C$_4$ alkylene-hetaryl, SO$_2$—C$_1$-C$_6$ alkyl, SO$_2$-aryl, SO$_2$-hetaryl, SO$_2$—C$_1$-C$_4$ alkylene-aryl or SO$_2$—C$_1$-C$_4$ alkylene-hetaryl;

R$_3^3$ denotes
optionally substituted C$_1$-C$_6$ alkyl, C$_2$-C$_6$ alkenyl, C$_2$-C$_6$ alkynyl, C$_1$-C$_4$ alkylene-C$_3$-C$_7$ cycloalkyl, C$_1$-C$_4$ alkylene-heterocycloalkyl, aryl, hetaryl, heterocycloalkyl, C$_1$-C$_4$ alkylene-aryl, C$_1$-C$_4$ alkylene-hetaryl, C$_1$-C$_6$ alkylene-O—C$_1$-C$_6$ alkyl, CO—C$_1$-C$_6$ alkyl, CO-aryl, CO-hetaryl, CO—C$_1$-C$_4$ alkylene-aryl, CO—C$_1$-C$_4$ alkylene-hetaryl, CO—O—C$_1$-C$_6$ alkyl, CO—O-aryl, CO—O—C$_1$-C$_4$ alkylene-aryl, CO—O-hetaryl, CO—O—C$_1$-C$_4$ alkylene-hetaryl, SO$_2$—C$_1$-C$_6$ alkyl, SO$_2$-aryl, SO$_2$-hetaryl, SO$_2$—C$_1$-C$_4$ alkylene-aryl or SO$_2$—C$_1$-C$_4$ alkylene-hetaryl;

or the radicals R$_3^2$ and R$_3^3$ together with the nitrogen atom to which they are attached may form a three- to seven-membered, optionally substituted, saturated or aromatic heterocycle that may contain one, two or three other heteroatoms, which may be the same or different and are selected from the group consisting of O, N and S, such that two optionally substituted radicals on this heterocycle together with the respective atom to which they are attached may form an anellated, optionally substituted, saturated, unsaturated or aromatic carbocycle or heterocycle, such that the heterocycle may contain one, two or three heteroatoms that are the same or different and are selected from the group consisting of O, N and S and the cyclic group thereby formed may be optionally substituted and/or another optionally substituted cyclic group may be condensed onto this cyclic group;

R$_3^4$ denotes
hydrogen or optionally substituted C$_1$-C$_6$ alkyl, C$_1$-C$_6$ alkenyl-O—C$_1$-C$_6$ alkyl, C$_2$-C$_6$ alkenyl, C$_3$-C$_{12}$ alkynyl, CO—C$_1$-C$_6$ alkyl, CO—O—C$_1$-C$_6$ alkyl, SO$_2$—C$_1$-C$_6$ alkyl, C$_3$-C$_7$ cycloalkyl, aryl, C$_1$-C$_4$ alkylene-aryl, CO—O-arylalkyl, CO—$C_1$-$C_4$ alkylene-aryl, CO-aryl, $SO_2$-aryl, hetaryl, CO-hetaryl or $SO_2$—$C_1$-$C_4$ alkylene-aryl;

$R^4$ denotes
a bond in the ring to $X^5$ while maintaining a C═C double bond for the case when $X^5$═C or a radical selected from hydrogen, CN, $CF_3$, $CHF_2$, COOH, halogen or, optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-hetaryl or $C_1$-$C_4$ alkylene-aryl,
for the case when $X^5$═N; or
$R^3$ and $R^4$ together with the atom to which they are bound may form an optionally substituted three-membered carbocycle, $R^5$ denotes
hydrogen, a electron pair or
optionally substituted O—$C_1$-$C_6$ alkyl, $C_1$-$C_6$ alkyl, CO—$C_1$-$C_6$ alkyl, —CO—O—$C_1$-$C_6$ alkyl $X^4$ denotes C or N,
$X^2$ denotes C or N,
$X^3$ denotes C or N,
$X^4$ denotes C or N,
such that at most one of radicals $X^1$ through $X^4$ may denote N at the same time,
in which
$R^6$, $R^7$, $R^8$ and $R^9$ denote, each independently of one another, a radical that may be the same or different and is selected from the same or different moieties of the groups 1), 2), 3), 4), 5), 6) or 7), such that the groups 1) through 7) have the following meanings:

1) hydrogen, halogen, CN, $CF_3$, $CHF_2$, —$OCF_3$, —$NH_2$, —OH or optionally substituted $C_1$-$C_{10}$ alkyl, $C_2$-$C_{10}$ alkenyl, $C_2$-$C_{10}$ alkynyl or $NR_Q^7R_Q^8$, in which $R_Q^7$ and $R_Q^8$ are defined as shown below;

2) phenyl, optionally substituted with one, two or three radicals that may be the same or different and are selected from the group consisting of $R_Q^2$, $R_Q^3$ and $R_Q^4$
in which
$R_Q^2$, $R_Q^3$ and $R_Q^4$ each independently of one another denotes a substituent from the following group:
hydrogen, $NO_2$, $NH_2$, OH, CN, $CF_3$, $CHF_2$, $OCF_3$, $OCHF_2$, COOH, O—$CH_2$—COOH, SH, halogen or optionally substituted aryl, hetaryl, heterocycloalkyl, $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, $C_1$-$C_4$ alkylene-aryl or $C_1$-$C_4$ alkylene-hetaryl or O—$R_Q^5$, S—$R_Q^5$, $NR_Q^7R_Q^8$, CO—$OR_Q^6$, $NR_Q^7$—CO—O—$R_Q^6$, O—$CH_2$—COO—$R_Q^6$, $NR_Q^7$—CO—$R_Q^6$, $SO_2$—$R_Q^6$, $NR_Q^7$—$SO_2$—$R_Q^6$, $SO_2NH_2$, $CONH_2$, $SO_2$—$NR_Q^7R_Q^8$ or CO—$NR_Q^7R_Q^8$ or
two or the radicals $R_Q^2$, $R_Q^3$ and $R_Q^4$ together with the atom to which they are attached may form a three- to seven-membered, optionally substituted, saturated, unsaturated or aromatic carbocycle or a three- to seven-membered, optionally substituted, saturated, unsaturated aromatic heterocycle that may contain one, two or three additional heteroatoms, which may be the same or different and are selected from the group consisting of O, N and S and optionally two substituted radicals on this heterocycle together may form an anellated, optionally substituted, saturated, unsaturated or aromatic carbocycle or heterocycle, such that the heterocycle may contain one, two or three heteroatoms that are the same or different and are selected from the group consisting of O, N and S, and the resulting cyclic group may optionally be substituted or another optionally substituted cyclic group may be condensed onto this cyclic group;

$R_Q^5$ denotes optionally substituted $C_1$-$C_6$ alkyl, $C_2$-$C_6$ alkenyl, $C_2$-$C_6$ alkynyl, $C_1$-$C_4$ alkylene-$C_3$-$C_7$ cycloalkyl, $C_1$-$C_4$ alkylene-heterocycloalkyl, heterocycloalkyl or hetaryl or $C_1$-$C_4$ alkyl optionally substituted with one, two or three substituents selected, independently of one another, from the group consisting of halogen, $NO_2$, $NH_2$, OH, CN, $CF_3$, $CHF_2$, $OCF_3$, $OCHF_2$ or optionally substituted NH—($C_1$-$C_6$ alkyl) and N($C_1$-$C_6$ alkyl)$_2$;

$R_Q^6$ denotes optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl or $C_1$-$C_6$ alkylene-O—$C_1$-$C_6$ alkyl;

$R_Q^7$ denotes, independently of its respective occurrence, hydrogen, CN or optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_6$ alkylene-O—$C_1$-$C_6$ alkyl, CO—$C_1$-$C_6$ alkyl, $C_1$-$C_4$ alkylene-aryl, $C_1$-$C_4$ alkylene-hetaryl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O—$C_1$-$C_4$ alkylene-aryl, CO—O-hetaryl, CO—O—$C_1$-$C_4$ alkylene-hetaryl, $SO_2$—$C_1$-$C_6$ alkyl, $SO_2$-aryl, $SO_2$-hetaryl, $SO_2$—$C_1$-$C_4$ alkylene-aryl or $SO_2$—$C_1$-$C_4$ alkylene-hetaryl;

$R_Q^8$ denotes, independently of its respective occurrence, optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_6$ alkylene-O—$C_1$-$C_6$ alkyl, CO—$C_1$-$C_6$ alkyl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O—$C_1$-$C_4$ alkylene-aryl, CO—O-hetaryl, CO—O—$C_1$-$C_4$ alkylene-hetaryl, $SO_2$—$C_1$-$C_6$ alkyl, $SO_2$-aryl, $SO_2$-hetaryl, $SO_2$—$C_1$-$C_4$ alkylene-aryl or $SO_2$—$C_1$-$C_4$ alkylene-hetaryl;

or the radicals $R_Q^7$ and $R_Q^8$ together with the nitrogen atom to which they are attached may form a three- to seven-membered, optionally substituted, saturated or aromatic heterocycle that may contain one, two or three other heteroatoms, which may be the same or different and are selected from the group consisting of O, N and S; and optionally two substituted radicals on this heterocycle together may form an anellated, optionally substituted, saturated, unsaturated or aromatic carbocycle or heterocycle, such that the heterocycle may contain one, two or three heteroatoms, which may be the same or different and are selected from the group consisting of O, N and S, and the resulting cyclic group may optionally be substituted and/or another cyclic group, optionally substituted, may be condensed onto this cyclic group;

3) a five- or six-membered hetaryl radical, optionally substituted once or twice with substituents that may be the same or different and are selected from the group consisting of:
2-thienyl, 3-thienyl, 2-pyrrolyl, 3-pyrrolyl, 2-thiazolyl, 4-thiazolyl, 5-thiazolyl, 2-oxazolyl, 4-oxazolyl, 5-oxazolyl, 1-pyrazolyl, 3-pyrazolyl, 4-pyrazolyl, 5-pyrazolyl, 3-isothiazolyl, 4-isothiazolyl, 5-isothiazolyl, 1-imidazolyl, 2-imidazolyl, 4-imidazolyl, 5-imidazolyl, 2-pyridyl, 3-pyridyl, 4-pyridyl, 2-pyrimidyl, 4-pyrimidyl, 5-pyrimidyl, 6-pyrimidyl, 3-pyridazinyl, 4-pyridazinyl, 5-pyridazinyl, 6-pyridazinyl, 3-isoxazolyl, 4-isoxazolyl, 5-isoxazolyl, thiadiazolyl, oxadiazolyl or triazinyl or the anellated derivatives thereof indazolyl, benzothiophenyl, benzofuranyl, indolinyl, benzimidazolyl, benzothiazolyl, benzoxazolyl, quinolinyl and isoquinolinyl, such that the substituents are preferably selected from the group consisting of halogen, $NO_2$, $NH_2$, OH, CN, $CF_3$, $OCF_3$, $CHF_2$, O—$CHF_2$, optionally substituted $C_1$-$C_6$ alkyl, O—$C_1$-$C_6$ alkyl, NH—($C_1$-$C_6$ alkyl), N($C_1$-$C_6$ alkyl)$_2$, NHCO—$C_1$-$C_4$ alkyl, NHSO$_2$—$C_1$-$C_4$ alkyl and SO$_2$—$C_1$-$C_4$ alkyl;

4) two of the radicals $R^6$, $R^7$, $R^8$ or $R^9$ together with the respective atom to which they are attached may form a four- to seven-membered, optionally substituted, fully or partially saturated carbocycle or a five- or six-membered, optionally substituted, fully or partially saturated heterocycle that may contain two or three heteroatoms that are the same or different and are selected from the group consisting of O, N and S;

5) an optionally substituted $C_3$-$C_8$ monocyclic saturated hydrocarbon radical;

6) an optionally substituted four- to seven-membered mono- or bicyclic, fully or partially saturated heterocycle that may contain one or two heteroatoms that are the same or different and are selected from the group consisting of O, N and/or S, such that this cyclic group may also contain one, two, three or more substituents, and in the event the heterocycle contains a nitrogen atom, this nitrogen atom may be substituted with an $R_Q^7$ radical, which may have one of the meanings defined above, independently of its occurrence, such that preferably the following, optionally substituted radicals are azetidin-1-yl, azetidin-2-yl, azetidin-3-yl, pyrrolin-1-yl, pyrrolin-3-yl, pyrrolidin-1-yl, pyrrolidin-2-yl, pyrrolidin-3-yl, 1,2,3,6-tetrahydropyridin-1-yl, 1,2,3,6-tetrahydropyridin-4-yl, piperidin-1-yl, piperidin-2-yl, piperidin-3-yl, piperidin-4-yl, tetrahydro-2H-pyran-4-yl, tetrahydrofuran-3-yl, azepan-4-yl, azepan-3-yl, azepan-2-yl, 1,4-diazepan-5-yl, morpholinyl, piperazinyl, such that the following optionally substituted radicals preferably include:

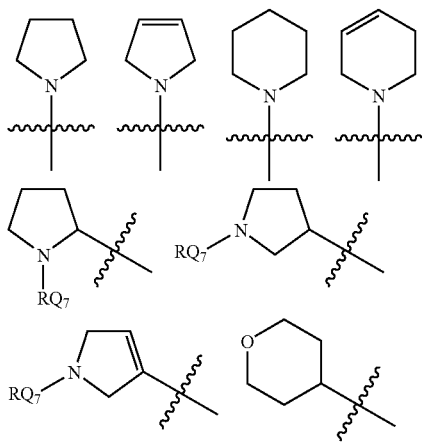

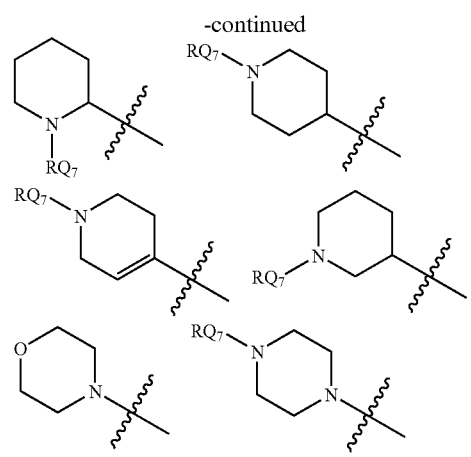

7) a radical of general formula V $$—(CR_V^1R_V^2)_d—(Y)_e—(CR_V^3R_V^4)_f—R_V^5 \qquad V$$

having the indices d=0-4 (i.e., an integer selected from 0, 1, 2, 3 or 4)

e=0-1 (i.e., an integer selected from 0 or 1)

f=0-4 (i.e., an integer selected from 0, 1, 2, 3 or 4), such that the sum of d, e and f is 1, 2, 3, 4, 5, 6, 7 or 8;

$R_V^1$, $R_V^2$, $R_V^3$, $R_V^4$ each independently denotes hydrogen, halogen, OH or optionally substituted $C_1$-$C_4$ alkyl, $C_2$-$C_4$ alkenyl, $C_2$-$C_4$ alkynyl, $C_1$-$C_4$ alkylene-$C_3$-$C_7$ cycloalkyl, $C_3$-$C_7$ cycloalkyl, aryl, $C_1$-$C_4$ alkylene-aryl, hetaryl or $C_1$-$C_4$ alkylene-hetaryl or, independently of one another, two radicals $R_V^1$ and $R_V^2$ or $R_V^3$ and $R_V^4$ together with the carbon atom to which they are attached may form a three- to seven-membered, optionally substituted, saturated or unsaturated carbocycle or heterocycle in which the heterocycle may contain one, two or three heteroatoms selected from the group consisting of O, N and S;

$R_V^5$ denotes a radical selected from the radicals as defined above in the same or different moieties of groups 1), 2), 3), 5) or 6):

Y denotes

—CO—, —O—, —S—, —SO—, SO$_2$—, CS—, —NR$_Y^5$—, —COO—, —O—CO—, —CO—NR$_Y^5$, —NR$_Y^5$—CO—, —SO$_2$—NR$_Y^5$, —NR$_Y^5$, SO$_2$—;

in which $R_Y^5$ denotes hydrogen or optionally substituted $C_1$-$C_6$ alkyl, $C_1$-$C_6$ alkylene-O—$C_1$-$C_6$ alkyl, $C_2$-$C_6$ alkenyl, $C_3$-$C_{12}$ alkynyl, CO—$C_1$-$C_6$ alkyl, CO—O—$C_1$-$C_6$ alkyl, SO$_2$—$C_1$-$C_6$ alkyl, $C_3$-$C_7$ cycloalkyl, aryl, $C_1$-$C_4$ alkylene-aryl, CO—O—$C_1$-$C_4$ alkylene-aryl, CO—$C_1$-$C_4$ alkylene-aryl, CO-aryl, SO$_2$ aryl, hetaryl, CO-hetaryl or SO$_2$—$C_1$-$C_4$ alkylene-aryl;

$X^5$ denotes

C or N

Z denotes
a radical of general formula Z1

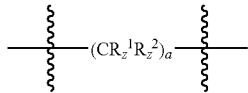

where
a=0, 1, 2, 3 or 4,
preferably a=1, 2, 3 or 4,
especially preferably a=1 or 2,
most especially preferably a=1;
$R_Z^1$, $R_Z^2$ independently of one another denote
hydrogen, halogen, OH or
optionally substituted $C_1$-$C_4$ alkyl, $C_2$-$C_4$ alkenyl, $C_2$-$C_4$ alkynyl, $C_1$-$C_4$ alkylene-$C_3$-$C_7$ cycloalkyl, $C_3$-$C_7$ cycloalkyl, aryl, $C_1$-$C_4$ alkylene-aryl, hetaryl or $C_1$-$C_4$ alkylene-hetaryl or
independently of one another, two radicals $R_Z^1$ and $R_Z^2$ together with the carbon atom to which they are attached may form a three- to seven-membered, optionally substituted, saturated or unsaturated carbocycle or heterocycle, such that the heterocycle may contain one, two or three heteroatoms selected from the group consisting of O, N and S, such that preferably $R_Z^1$ and $R_Z^2$ should not both denote OH at the same time;
W denotes a radical of general formula W

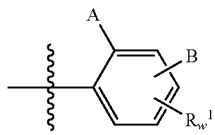

in which
A denotes
OH, CN, OCF$_3$, CHF$_2$, CF$_3$, OCHF$_2$, COOH, O—CH$_2$—COOH, SH, SO$_2$H, C$_1$-C$_4$ alkylene-OH, NR$_A^4$—SO$_2$H, NR$_A^4$—COOH, SOH,
or optionally substituted
O—R$_A^1$, CO—R$_A^1$, S—R$_A^1$, SO—R$_A^1$, CO—O—R$_A^1$, NR$_A^4$—CO—O—R$_A^1$, O—CH$_2$—COO—R$_A^1$, NR$_A^2$R$_A^3$, NR$_A^4$—CO—R$_A^1$, SO$_2$—R$_A^1$, NR$_A^4$—SO$_2$—R$_A^1$, SO$_2$—NR$_A^2$R$_A^3$, CO—NR$_A^2$R$_A^3$, C$_1$-C$_4$ alkylene-NR$_A^2$R$_A^3$, alkylene-CO—NR$_A^2$R$_A^3$, C$_1$-C$_4$ alkylene-SO$_2$—NR$_A^2$R$_A^3$ or C$_1$-C$_4$ alkylene-O—R$_A^1$;
preferably A=optionally substituted —O—C$_1$-C$_3$ alkyl or —O—C$_1$-C$_3$ haloalkyl, —N(C$_1$-C$_3$ alkyl)$_2$, piperidinyl or morpholinyl,
especially preferably A=optionally substituted —O—C$_1$-C$_3$ alkyl or —O—C$_1$-C$_3$ alkyl substituted with one, two, three, four or five halogen atoms that may be the same or different and are selected from the group consisting of fluorine, chlorine, bromine and iodine;
most especially preferably A=-OCF$_3$, —OCHF$_2$, —OCH$_2$F, —O—CH$_2$—CH$_3$, —O—CH$_2$—CF$_3$, —O—CH$_2$—CHF$_2$, —O—CH$_2$—CH$_2$F or O-isopropyl;
even more preferably A=-O—CH$_3$, —O—CH$_2$—CH$_3$, —O—CH$_2$—CF$_3$, —O—CH$_2$—CHF$_2$ or —O—CH$_2$—CH$_2$F;
most preferred is A=-O—CH$_3$,
$R_A^1$ denotes
independently of its respective occurrence, optionally substituted C$_1$-C$_6$ alkyl, C$_2$-C$_6$ alkenyl, C$_2$-C$_6$ alkynyl, C$_3$-C$_7$ cycloalkyl, C$_1$-C$_4$ alkylene-C$_3$-C$_7$ cycloalkyl, C$_1$-C$_4$ alkylene-heterocycloalkyl, aryl, hetaryl, heterocycloalkyl, C$_1$-C$_4$ alkylene-aryl, C$_2$-C$_6$ alkylene-aryl, C$_1$-C$_6$ alkylene-hetaryl, C$_1$-C$_4$ alkylene-NR$_A^2$R$_A^3$, C$_1$-C$_4$ alkylene-CO—NR$_A^2$R$_A^3$ or C$_1$-C$_4$ alkylene-O—C$_1$-C$_6$ alkyl;
$R_A^2$ denotes
independently of its respective occurrence, hydrogen, OH, CN
or
optionally substituted C$_1$-C$_6$ alkyl, C$_2$-C$_6$ alkenyl, C$_2$-C$_6$ alkynyl, C$_1$-C$_4$ alkylene-C$_3$-C$_7$ cycloalkyl, C$_1$-C$_4$ alkylene-heterocycloalkyl, aryl, hetaryl, heterocycloalkyl, C$_1$-C$_4$ alkylene-aryl, C$_1$-C$_4$ alkylene-hetaryl, C$_1$-C$_6$ alkylene-O—C$_1$-C$_6$ alkyl; CO—C$_1$-C$_6$ alkyl, CO-aryl, CO-hetaryl, CO—C$_1$-C$_4$ alkylene-aryl, CO—C$_1$-C$_4$ alkylene-hetaryl, CO—O—C$_1$-C$_6$ alkyl, CO—O-aryl, CO—O—C$_1$-C$_4$ alkylene-aryl, CO—O-hetaryl, CO—O—C$_1$-C$_4$ alkylene-hetaryl, SO$_2$—C$_1$-C$_6$ alkyl, SO$_2$-aryl, SO$_2$-hetaryl, SO$_2$—C$_1$-C$_4$ alkylene-aryl or SO$_2$—C$_1$-C$_4$ alkylene-hetaryl;
$R_A^3$ denotes
independently of its respective occurrence, hydrogen or optionally substituted C$_1$-C$_6$ alkyl, C$_2$-C$_6$ alkenyl, C$_2$-C$_6$ alkynyl, C$_1$-C$_4$ alkylene-C$_3$-C$_7$ cycloalkyl, C$_1$-C$_4$ alkylene-heterocycloalkyl, aryl, hetaryl, heterocycloalkyl, C$_1$-C$_4$ alkylene-aryl, C$_1$-C$_4$ alkylene-hetaryl, C$_1$-C$_6$ alkylene-O—C$_1$-C$_6$ alkyl; CO—C$_1$-C$_6$ alkyl, CO-aryl, CO-hetaryl, CO—C$_1$-C$_4$ alkylene-aryl, CO—C$_1$-C$_4$ alkylene-hetaryl, CO—O—C$_1$-C$_6$ alkyl, CO—O-aryl, CO—O—C$_1$-C$_4$ alkylene-aryl, CO—O-hetaryl, CO—O—C$_1$-C$_4$ alkylene-hetaryl, SO$_2$—C$_1$-C$_6$ alkyl, SO$_2$-aryl, SO$_2$-hetaryl, SO$_2$—C$_1$-C$_4$ alkylene-aryl or SO$_2$—C$_1$-C$_4$ alkylene-hetaryl;
or the radicals $R_A^2$ and $R_A^3$ together with the nitrogen atom to which they are attached may form a three- to seven-membered, optionally substituted, saturated or aromatic heterocycle that may contain one, two or three additional heteroatoms, which may be the same or different and are selected from the group consisting of O, N and S; such that optionally two substituted radicals on this heterocycle together may form an anellated, optionally substituted, saturated, unsaturated or aromatic carbocycle or heterocycle, such that the heterocycle may contain one, two or three heteroatoms that are the same or different and are selected from the group consisting of O, N and S and such that the resulting cyclic group may optionally be substituted and/or another optionally substituted cyclic group may be condensed onto this cyclic group;
$R_A^4$ denotes
independently of its respective occurrence, hydrogen or optionally substituted C$_1$-C$_6$ alkyl, C$_1$-C$_6$ alkenyl-O—C$_1$-C$_6$ alkyl, C$_2$-C$_6$ alkenyl, C$_3$-C$_{12}$ alkynyl, CO—C$_1$-C$_6$ alkyl. CO—O—C$_1$-C$_6$ alkyl, SO$_2$—C$_1$-C$_6$ alkyl, C$_3$-C$_7$ cycloalkyl, aryl, C$_1$-C$_4$ alkylene-aryl, CO—O-arylalkyl, CO—C$_1$-C$_4$ alkylene-aryl, CO-aryl, CO-aryl, SO$_2$-aryl, hetaryl, CO-hetaryl or SO$_2$—C$_1$-C$_4$ alkylene-aryl;

B denotes
hydrogen, $NO_2$, $NH_2$, OH, CN, $OCF_3$, $CHF_2$, $CF_3$, $OCHF_2$, COOH, o—$CH_2$—COOH, halogen, SH or optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-hetaryl, $C_1$-$C_4$ alkylene-aryl, O—$R_A^1$, CO—$R_A^1$, S—$R_A^1$, SO—$R_A^1$, CO—O—$R_A^1$, $NR_A^4$—CO—O—$R_A^1$, O—$CH_2$—COO—$R_A^1$, $NR_A^2R_A^3$, $NR_A^4$—CO—$R_A^1$, $SO_2$—$R_A^1$, $NR_A^4$—$SO_2$—$R_A^1$, $SO_2$—$NR_A^2R_A^3$, CO—$NR_A^2R_A^3$, $C_1$-$C_4$ alkylene-$NR_A^2R_A^3$, $C_1$-$C_4$ alkylene-CO—$NR_A^2R_A^3$, $C_1$-$C_4$ alkylene-$SO_2$—$NR_A^2R_A^3$ or $C_1$-$C_4$ alkylene-O—$R_A^1$;

or, independently of one another, two of the radicals A, B or $R_W$ together with the carbon atom to which they are each attached may form a five- to seven-membered, optionally substituted, saturated or unsaturated carbocycle or a five- to seven-membered, optionally substituted, saturated or unsaturated or aromatic heterocycle, which may have one, two or three additional heteroatoms, which may be the same or different and are selected from the group consisting of O, N and S; such that optionally two substituted radicals on this carbocycle or heterocycle together may form an anellated, optionally substituted, saturated, unsaturated or aromatic carbocycle or heterocycle, such that the heterocycle may have one, two or three heteroatoms, which may be the same or different and are selected from the group consisting of O, N and S and such that the cyclic group thus formed may optionally be substituted and/or another optionally substituted cyclic group may be condensed onto this cyclic group;

$R_W$ denotes
hydrogen, OH, halogen, $NO_2$, $NH_2$, CN, $CF_3$, $CHF_2$, $OCF_3$, $OCHF_2$
or
optionally substituted $C_1$-$C_6$ alkyl, $C_3$-$C_7$ cycloalkyl, $C_1$-$C_6$ alkylene-O—$C_1$-$C_6$ alkyl, $C_1$-$C_6$ thioalkyl, aryl, hetaryl, O—$C_1$-$C_6$ alkyl, O-aryl, O-benzyl, $C_1$-$C_6$ alkylamino, $C_1$-$C_6$ dialkylamino, pyrrolidinyl, piperidinyl, morpholinyl, CO—$C_1$-$C_6$ alkyl, $SO_2$—$C_1$-$C_6$ alkyl, CO-aryl, $SO_2$-aryl, CO—$C_1$-$C_4$ alkylene-aryl, $SO_2$—$C_1$-$C_4$ alkylene-aryl, SO-aryl, $CONH_2$, CONH—$C_1$-$C_6$ alkyl, $SO_2NH$—$C_1$-$C_6$ alkyl, CON—$(C_1$-$C_6$ alkyl$)_2$, $SO_2N$—$(C_1$-$C_6$ alkyl$)_2$, NH—$SO_2$—$C_1$-$C_6$ alkyl or NH—CO—$C_1$-$C_6$ alkyl;

for treatment and/or prevention and/or production of a medication for treatment and/or prevention of CNS diseases or CNS-related diseases in a patient requiring such treatment and/or prevention.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, the use of at least one compound of general formula I as described above and/or corresponding enantiomeric, diastereomeric and/or tautomeric forms thereof and/or the pharmaceutically acceptable salts thereof and/or the active ingredient precursors (prodrugs) thereof is made available in which the radicals $R^1$, $R^2$, $R^3$, $R^4$, $R^5$, $R^6$, $R^7$, $R^8$, $R^9$, $X^1$, $X^2$, $X^3$, $X^4$, $X^5$, Z and W have the same meanings as given above, unless explicitly stated otherwise below, and the following radical is defined as below:

A denotes optionally substituted —O—$C_1$-$C_3$ alkyl, —O—$C_1$-$C_3$ haloalkyl, —N($C_1$-$C_3$ alkyl)$_2$, piperidinyl or morpholinyl.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, the use of at least one compound of general formula I as described above and/or corresponding enantiomeric, diastereomeric and/or tautomeric forms thereof and/or the pharmaceutically acceptable salts thereof and/or the active ingredient precursors (prodrugs) thereof is made available in which the radicals $R^1$, $R^2$, $R^3$, $R^4$, $R^5$, $R^6$, $R^7$, $R^8$, $R^9$, $X^1$, $X^2$, $X^3$, $X^4$, $X^5$, Z and W have the same meanings as given above, unless explicitly stated otherwise below, and the following radical is defined as below:

A denotes optionally substituted —O—$C_1$-$C_3$ alkyl, —O—$C_1$-$C_3$ alkyl substituted with 1, 2, 3, 4 or 5 halogen atoms that may be the same or different and are selected from the group comprising fluorine, chlorine, bromine and iodine.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, the use of at least one compound of general formula I as described above and/or corresponding enantiomeric, diastereomeric and/or tautomeric forms thereof and/or the pharmaceutically acceptable salts thereof and/or the active ingredient precursors (prodrugs) thereof is made available in which the radicals $R^1$, $R^2$, $R^3$, $R^4$, $R^5$, $R^6$, $R^7$, $R^8$, $R^9$, $X^1$, $X^2$, $X^3$, $X^4$, $X^5$, Z and W have the same meanings as given above, unless explicitly stated otherwise below, and the following radical is defined as below:

A denotes —O—$CH_3$, —$OCF_3$, —$OCHF_2$, —$OCH_2F$, —O—$CH_2$—$CF_3$, —O—$CH_2$—$CHF_2$, —O—$CH_2$—$CH_2F$ or O-isopropyl.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, the use of at least one compound of general formula I as described above and/or corresponding enantiomeric, diastereomeric and/or tautomeric forms thereof and/or the pharmaceutically acceptable salts thereof and/or the active ingredient precursors (prodrugs) thereof is made available in which the radicals $R^1$, $R^2$, $R^3$, $R^4$, $R^5$, $R^6$, $R^7$, $R^8$, $R^9$, $X^1$, $X^2$, $X^3$, $X^4$, $X^5$, Z and W have the same meanings as given above, unless explicitly stated otherwise below, and the following radical is defined as below:

A denotes —O—$CH_3$, —O—$CH_2$—$CH_3$, —O—$CH_2$—$CF_3$, —O—$CH_2$—$CHF_2$ or —O—$CH_2$—$CHF_2$.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, the use of at least one compound of general formula I as described above and/or corresponding enantiomeric, diastereomeric and/or tautomeric forms thereof and/or the pharmaceutically acceptable salts thereof and/or the active ingredient precursors (prodrugs) thereof is made available in which the radicals $R^1, R^2, R^3, R^4, R^5, R^6, R^7, R^8, R^9, X^1, X^2, X^3, X^4, X^5$, Z and W have the same meanings as given above, unless explicitly stated otherwise below, and the following radical is defined as below:

A denotes —O—CH$_3$.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, the use of at least one compound of general formula I as described above and/or corresponding enantiomeric, diastereomeric and/or tautomeric forms thereof and/or the pharmaceutically acceptable salts thereof and/or the active ingredient precursors (prodrugs) thereof is made available in which the radicals $R^1, R^2, R^3, R^4, R^5, R^6, R^7, R^8, R^9, X^1, X^2, X^3, X^4, X^5$, Z and W have the same meanings as given above, unless explicitly stated otherwise below, and the following radical is defined as below:

$X^5$ denotes C and $R^4$ denotes a bond in the ring to $X^5$ while maintaining a C=C double bond.

Each of the definitions of one variable as given above may be combined with any of the definitions of the remaining variables as given above. This is true in particular of the combination of preferred definitions of one variable with any definitions or any preferred definitions of the remaining variables.

According to another preferred aspect of the present invention, the use of at least one compound of general formula I as described above or according to any one of Claims 1 through 22 is disclosed for treatment and/or prevention and/or for production of a medication for treatment and/or prevention of CNS diseases or CNS-related diseases in a patient requiring such a treatment and/or prevention without any and/or any significant simultaneous nitrogen monoxide modulation (nitric oxide modulation).

According to another preferred aspect of the present invention, the use of at least one compound of general formula I as described above or according to any one of Claims 1 through 22 is disclosed for treatment and/or prevention and/or for production of a medication for treatment and/or prevention of CNS diseases or CNS-related diseases in a patient requiring such a treatment and/or prevention without any and/or any significant simultaneous interacting or binding to the SH3 protein domain or homologs thereof.

According to another preferred aspect of the present invention, the use of at least one compound of general formula I as described above or according to any one of Claims 1 through 22 is disclosed for treatment and/or prevention and/or for production of a medication for treatment and/or prevention of CNS diseases or CNS-related diseases in a patient requiring such a treatment and/or prevention without or without any significant simultaneous antagonism of the chemokine receptor in particular without antagonizing the chemokine receptor CCR4 and/or CCR5.

According to another preferred aspect of the present invention, the use of at least one compound of general formula I as described above or according to any one of Claims 1 through 22 is disclosed and/or corresponding enantiomeric, diastereomeric and/or tautomeric forms thereof and/or the pharmaceutically acceptable salts thereof and/or the active ingredient precursors (prodrugs) thereof, characterized in that the treatment and/or prevention is accomplished by modulation of the 5-HT$_5$ receptor activity.

According to another preferred aspect of the present invention, the use of at least one compound of general formula I as described above or according to any one of Claims 1 through 22 is disclosed and/or corresponding enantiomeric, diastereomeric and/or tautomeric forms thereof and/or the pharmaceutically acceptable salts thereof and/or the active ingredient precursors (prodrugs) thereof, characterized in that the treatment and/or prevention is accomplished by modulation of the 5-HT$_5$ receptor activity but without or without any significant simultaneous nitric oxide modulation.

According to another preferred aspect of the present invention, the use of at least one compound of general formula I as described above or according to any one of Claims 1 through 22 and/or corresponding enantiomeric, diastereomeric and/or tautomeric forms thereof and/or the pharmaceutically acceptable salts thereof and/or the active ingredient precursors (prodrugs) thereof is made available, characterized in that the treatment and/or prevention is accomplished by modulation of the 5-HT$_5$ receptor activity but without or without any significant simultaneous interacting or binding to the SH3 protein domain or homologs thereof.

According to another preferred aspect of the present invention, the use of at least one compound of general formula I as described above or according to any one of Claims 1 through 22 and/or corresponding enantiomeric, diastereomeric and/or tautomeric forms thereof and/or the pharmaceutically acceptable salts thereof and/or the active ingredient precursors (prodrugs) thereof is made available, characterized in that the treatment and/or prevention is accomplished by modulation of the 5-HT$_5$ receptor activity but without or without any significant simultaneous antagonism of the chemokine receptor in particular without antagonizing the chemokine receptor CCR4 and/or CCR5.

According to another preferred aspect of the present invention, the use of at least one compound of general formula I as described above or according to any one of Claims 1 through 22 and/or corresponding enantiomeric, diastereomeric and/or tautomeric forms thereof and/or the pharmaceutically acceptable salts thereof and/or the active ingredient precursors (prodrugs) thereof is made available, characterized in that the CNS disease or CNS-related disease is a disease selected from the group comprising neuropathological, neuropsychiatric and neurodegenerative disorders, neuropathological, neuropsychiatric and neurodegenerative symptoms and/or neuropathological, neuropsychiatric and neurodegenerative dysfunctions.

According to another preferred aspect of the present invention, the use of at least one compound of general formula I as described above or according to any one of Claims 1 through 22 and/or corresponding enantiomeric, diastereomeric and/or tautomeric forms thereof and/or the pharmaceutically acceptable salts thereof and/or the active ingredient precursors (prodrugs) thereof, for treatment and/or prevention of one or more of the CNS diseases or CNS-related diseases listed above is accomplished by modulation of the 5-HT$_5$ receptor activity.

According to another preferred aspect of the present invention, the use of at least one compound of general formula I as described above or according to any one of Claims 1 through 22 and/or corresponding enantiomeric, diastereomeric and/or tautomeric forms thereof and/or the pharmaceutically acceptable salts thereof and/or the active ingredient precursors (prodrugs) thereof, for treatment and/or prevention of one or more of the CNS diseases or CNS-related diseases listed above is accomplished by modulation of the 5-HT$_5$ receptor activity but without or without any significant simultaneous nitric oxide modulation.

According to another preferred aspect of the present invention, the use of at least one compound of general formula I as described above or according to any one of Claims 1 through 22 and/or corresponding enantiomeric, diastereomeric and/or tautomeric forms thereof and/or the pharmaceutically acceptable salts thereof and/or the active ingredient precursors (prodrugs) thereof, for treatment and/or prevention of one or more of the CNS diseases or CNS-related diseases listed above is accomplished by modulation of the 5-HT$_5$ receptor activity but without or without any significant simultaneous interacting or binding to the SH3 protein domain or homologs thereof.

According to another preferred aspect of the present invention, the use of at least one compound of general formula I as described above or according to any one of Claims 1 through 22 and/or corresponding enantiomeric, diastereomeric and/or tautomeric forms thereof and/or the pharmaceutically acceptable salts thereof and/or the active ingredient precursors (prodrugs) thereof, for treatment and/or prevention of one or more of the CNS diseases or CNS-related diseases listed above is accomplished by modulation of the 5-HT$_5$ receptor activity but without or without any significant simultaneous antagonism of the chemokine receptor in particular without antagonizing the chemokine receptor CCR4 and/or CCR5.

According to another preferred aspect of the present invention, the use of at least one compound of general formula I as described above or according to any one of Claims 1 through 22 and/or corresponding enantiomeric, diastereomeric and/or tautomeric forms thereof and/or the pharmaceutically acceptable salts thereof and/or the active ingredient precursors (prodrugs) thereof is made available, characterized in that the CNS disease or CNS-related disease is a disease selected from the group comprising neuropathological, neuropsychiatric and/or neurodegenerative disorders, symptoms and/or dysfunctions are migraines and/or brain injuries.

According to another preferred aspect of the present invention, the use of at least one compound of general formula I as described above or according to any one of Claims 1 through 22 and/or corresponding enantiomeric, diastereomeric and/or tautomeric forms thereof and/or the pharmaceutically acceptable salts thereof and/or the active ingredient precursors (prodrugs) thereof is made available for treatment and/or prevention of one or more of the aforementioned CNS diseases, CNS-related diseases, neuropathological, neuropsychiatric and/or neurodegenerative disorders, symptoms and/or dysfunctions in conjunction with migraines and/or brain injuries by modulation of the 5-HT$_5$ receptor activity.

According to another preferred aspect of the present invention, the use of at least one compound of general formula I as described above or according to any one of Claims 1 through 22 and/or corresponding enantiomeric, diastereomeric and/or tautomeric forms thereof and/or the pharmaceutically acceptable salts thereof and/or the active ingredient precursors (prodrugs) thereof, for treatment and/or prevention of one or more of the aforementioned CNS diseases, CNS-related diseases, neuropathological, neuropsychiatric and/or neurodegenerative disorders, symptoms and/or dysfunctions is accomplished in conjunction with migraines and/or brain injuries by modulation of the 5-HT$_5$ receptor activity but without or without any significant simultaneous nitric oxide modulation, without or without any significant simultaneous interacting or binding to the SH3 protein domain or homologs thereof and/or without or without any significant simultaneous antagonism of the chemokine receptor in particular without antagonizing the chemokine receptor CCR4 and/or CCR5.

According to another preferred aspect of the present invention, the use of at least one compound of general formula I as described above or according to any one of Claims 1 through 22 and/or corresponding enantiomeric, diastereomeric and/or tautomeric forms thereof and/or the pharmaceutically acceptable salts thereof and/or the active ingredient precursors (prodrugs) thereof is made available, characterized in that the CNS disease and/or CNS-related disease and/or neuropathological, neuropsychiatric and/or neurodegenerative disorders, symptoms and/or dysfunctions are selected from the group comprising cerebral ischemia, stroke, epilepsy and seizures in general, psychoses, schizophrenia, autism, OCD syndrome, cognitive disorders, attention disorders, depression, bipolar and unipolar depression, anxiety, dementia, senile dementia, Alzheimer's dementia, demyelinizing diseases, multiple sclerosis and brain tumors.

According to another preferred aspect of the present invention, the use of at least one compound of general formula I as described above or according to any one of Claims 1 through 22 and/or corresponding enantiomeric, diastereomeric and/or tautomeric forms thereof and/or the pharmaceutically acceptable salts thereof and/or the active ingredient precursors (prodrugs) thereof is made available for treatment and/or prevention of one or more of the aforementioned CNS diseases, CNS-related diseases, neuropathological, neuropsychiatric and/or neurodegenerative disorders, symptoms and/or dysfunctions selected from the group comprising cerebral ischemia, stroke, epilepsy and seizures in general, psychoses, schizophrenia, autism, OCD syndrome, cognitive disorders, attention disorders, depression, bipolar and unipolar depression, anxiety, dementia, senile dementia, Alzheimer's dementia, demyelinizing diseases, multiple sclerosis and brain tumors by modulation of the 5-HT$_5$ receptor activity.

According to another preferred aspect of the present invention, the use of at least one compound of general formula I as described above or according to any one of Claims 1 through 22 and/or corresponding enantiomeric, diastereomeric and/or tautomeric forms thereof and/or the pharmaceutically acceptable salts thereof and/or the active ingredient precursors (prodrugs) thereof is made available for treatment and/or prevention of one or more of the aforementioned CNS diseases, CNS-related diseases, neuropathological, neuropsychiatric and/or neurodegenerative disorders, symptoms and/or dysfunctions selected from the group comprising cerebral ischemia, stroke, epilepsy and seizures in general, psychoses, schizophrenia, autism, OCD syndrome, cognitive disorders, attention disorders, depression, bipolar and unipolar depression, anxiety, dementia, senile dementia, Alzheimer's dementia, demyelinizing diseases, multiple sclerosis and brain tumors by modulation of the 5-HT$_5$ receptor activity but without or without any significant simultaneous nitric oxide modulation, without or without any significant simultaneous interacting or binding to the SH3 protein domain or homologs thereof and/or without or without any significant simultaneous antagonism of the chemokine receptor in particular without antagonizing the chemokine receptor CCR4 and/or CCR5.

According to another preferred aspect of the present invention, the use of at least one compound of general formula I as described above or according to any one of Claims 1 through 22 and/or corresponding enantiomeric, diastereomeric and/or tautomeric forms thereof and/or the pharmaceutically acceptable salts thereof and/or the active ingredient precursors (prodrugs) thereof is made available, characterized in that the CNS disease and/or CNS-related disease and/or neuropathological, neuropsychiatric and/or neurodegenerative disorders, symptoms and/or dysfunctions are selected from the group comprising cerebral vascular disorders, pain, pain-related disorders, addiction, drug-related disorders, amnesia, alcoholism, drug abuse, disturbances in the circadian rhythm and Cushing's syndrome.

According to another preferred aspect of the present invention, the use of at least one compound of general formula I as described above or according to any one of Claims 1 through 22 and/or corresponding enantiomeric, diastereomeric and/or tautomeric forms thereof and/or the pharmaceutically acceptable salts thereof and/or the active ingredient precursors (prodrugs) thereof is made available, characterized in that the CNS disease and/or CNS-related disease and/or neuropathological, neuropsychiatric and/or neurodegenerative disorders, symptoms and/or dysfunctions are selected from the group comprising cerebral vascular disorders, pain, pain-related disorders, addiction, drug-related disorders, amnesia, alcoholism, drug abuse, disturbances in the circadian rhythm and Cushing's syndrome by modulation of the 5-HT$_5$ receptor activity.

According to another preferred aspect of the present invention, the use of at least one compound of general formula I as described above or according to any one of Claims 1 through 22 and/or corresponding enantiomeric, diastereomeric and/or tautomeric forms thereof and/or the pharmaceutically acceptable salts thereof and/or the active ingredient precursors (prodrugs) thereof is made available, characterized in that the CNS disease and/or CNS-related disease and/or neuropathological, neuropsychiatric and/or neurodegenerative disorders, symptoms and/or dysfunctions are selected from the group comprising cerebral vascular disorders, pain, pain-related disorders, addiction, drug-related disorders, amnesia, alcoholism, drug abuse, disturbances in the circadian rhythm and Cushing's syndrome by modulation of the 5-HT$_5$ receptor activity but without or without any significant simultaneous nitric oxide modulation, without or without any significant simultaneous interacting or binding to the SH3 protein domain or homologs thereof and/or without or without any significant simultaneous antagonism of the chemokine receptor in particular without antagonizing the chemokine receptor CCR4 and/or CCR5.

According to another preferred aspect of the present invention, the use of at least one compound of general formula I as described above or according to any one of Claims 1 through 22 and/or corresponding enantiomeric, diastereomeric and/or tautomeric forms thereof and/or the pharmaceutically acceptable salts thereof and/or the active ingredient precursors (prodrugs) thereof is made available, characterized in that the treatment and/or prevention is based on a binding affinity for the 5-HT$_{5A}$ receptor of less than or equal to 10 μM (Ki), determined according to a suitable test model.

According to another preferred aspect of the present invention, the use of at least one compound of general formula I as described above or according to any one of Claims 1 through 22 and/or corresponding enantiomeric, diastereomeric and/or tautomeric forms thereof and/or the pharmaceutically acceptable salts thereof and/or the active ingredient precursors (prodrugs) thereof is made available, characterized in that the treatment and/or prevention is based on a binding affinity for the 5-HT$_{5A}$ receptor of less than or equal to 300 nM (Ki), determined according to a suitable test model.

According to another preferred aspect of the present invention, the use of at least one compound of general formula I as described above or according to any one of Claims 1 through 22 and/or corresponding enantiomeric, diastereomeric and/or tautomeric forms thereof and/or the pharmaceutically acceptable salts thereof and/or the active ingredient precursors (prodrugs) thereof is made available, characterized in that the treatment and/or prevention is based modulation of the 5-HT$_5$ receptor activity and additionally on a certain binding affinity for the 5-HT$_{5A}$ receptor.

According to another aspect of the present invention, synthesis of at least one optionally substituted 2-amino-3-benzylquinoline derivative according to general formula I is performed as described above or according to any one of 81 through 7 and 14 through 16 and 18 through 21, characterized by the reaction of optionally substituted 2-aminobenzaldehyde derivatives and optionally substituted 3-arylpropionitrile derivatives under basic or acidic reaction conditions by means of a reaction related to the Friedlander reaction.

According to another aspect of the present invention, synthesis of at least one optionally substituted 2-amino-3-benzylquinoline derivative is performed as described above or according to Claim 23, characterized by the steps of reacting an optionally substituted (2-chloroquinolin-3-yl)(aryl)methanone compound by reaction with primary or secondary amines or ammonia and then reducing the 3-carboxy group (e.g., under Wolff-Kishner conditions).

According to another aspect of the present invention, synthesis of at least one optionally substituted 2-amino-3-benzylquinoline derivative is performed as described above or according to Claim 23, characterized by the steps of reaction of an optionally substituted 2-chloroquinoline compound by orthometallization in position 3, reaction with benzaldehyde derivatives, oxidation to the corresponding optionally substituted chloroquinolin-3-yl(aryl)methanone compound, reaction of primary, secondary amines or ammonia and then reduction of the 3-carboxy groups (e.g., under Wolff-Kishner conditions).

According to another aspect of the present invention, synthesis of at least one optionally substituted 3-benzyl-3,4-dihydroquinazolin-2-amine derivative is performed according to general formula I as described above or according to any one of Claims 1 through 7, and 18 through 21, characterized by the steps of reaction of optionally substituted 2-nitrobenzoic acid derivatives by peptide linkage with an optionally substituted benzylamine derivative, then production of the amide thus formed to the secondary amine followed by reduction of the nitro group and then cyclization with cyanogen bromide.

Each of the definitions of one variable as given above may be combined with any of the definitions of the remaining variables as given above. This is true in particular of the combination of preferred definitions of one variable with any definitions or any preferred definitions of the remaining variables.

According to another aspect of the present invention, synthesis of at least one optionally substituted 3-benzyl-3,4-dihydroquinazolin-2-amine derivative is performed as described above or according to Claim 26, characterized by the steps of reaction of an optionally substituted 2-nitrobenzaldehyde derivative by reductive alkylation with an optionally substituted benzylamine derivative, follows by reduction of the nitro group, cyclization to yield the corresponding 3-aryl-2-(methylthio)-3,4-dihydroquinazoline derivatives with carbon disulfide and methyl iodide and subsequent reaction with primary, secondary amines or ammonia.

According to another aspect of the present invention, the use of at least one quinoline and/or dihydroquinazoline compound of general formula (I) as described above or according to any one of Claims 1 through 21 as a pharmaceutical drug and pharmaceutical compositions containing at least one of these quinoline and dihydroquinazoline compounds and a pharmaceutically acceptable vehicle or diluent is made available.

According to another aspect of the present invention, the use of at least one quinoline and/or dihydroquinazoline compound of general formula (I) as described above or according to any one of Claims 1 through 21 for the production of a medication for treatment of diseases modulated by a 5-$HT_5$ receptor activity is made available.

According to another aspect of the present invention, the use of at least one quinoline and/or dihydroquinazoline compound of general formula (I) as described above or according to any one of Claims 1 through 21 for the production of a medication for treatment of diseases modulated by a 5-$HT_5$ receptor activity, such that the diseases are one or more diseases selected from the group comprising neuropathological, neuropsychiatric and neurodegenerative disorders, symptoms and dysfunctions, is made available.

According to another aspect of the present invention, the use of at least one quinoline and/or dihydroquinazoline compound of general formula (I) as described above or according to any one of Claims 1 through 21 for the production of a medication for treatment of diseases modulated by a 5-$HT_5$ receptor activity, such that the diseases are one or more diseases selected from the group comprising neuropathological, neuropsychiatric and neurodegenerative disorders, symptoms and dysfunctions, in particular the treatment of migraines and brain injuries and/or disorders, is made available.

According to another aspect of the present invention, the use of at least one quinoline and/or dihydroquinazoline compound of general formula (I) as described above or according to any one of Claims 1 through 21 for the production of a medication for treatment of diseases modulated by a 5-$HT_5$ receptor activity, such that the diseases are one or more diseases selected from the group comprising neuropathological, neuropsychiatric and neurodegenerative disorders, symptoms and dysfunctions, in particular brain damage and/or disorders selected from the group comprising cerebral ischemia, stroke, epilepsy and seizures in general, psychoses, schizophrenia, autism, OCD syndrome, cognitive disorders, attention disorders, depression, bipolar and/or unipolar depression, anxiety, dementia, senile dementia, Alzheimer's dementia, demyelinizing diseases, multiple sclerosis and brain tumors, is made available.

According to another aspect of the present invention, the use of at least one quinoline and/or dihydroquinazoline compound of general formula (I) as described above or according to any one of Claims 1 through 21 for the production of a medication for treatment of diseases modulated by a 5-$HT_5$ receptor activity, such that the diseases include one or more diseases selected from the group comprising cerebrovascular disorders, pain, pain-related disorders, addiction, drug-related disorders, amnesia, alcoholism, drug abuse, disorders of the circadian rhythm and Cushing's syndrome, is made available.

According to a preferred embodiment, the inventive use of at least one compound of general formula I as described above for treatment and/or prevention and/or production of a medication for treatment and/or prevention of CNS diseases or CNS-related diseases in a patient requiring such a treatment and/or prevention without or without any significant simultaneous nitric oxide modulation is made available.

According to a preferred embodiment, the inventive use of at least one compound of general formula I as described above for treatment and/or prevention and/or production of a medication for treatment and/or prevention of CNS diseases or CNS-related diseases in a patient requiring such a treatment and/or prevention without or without any significant simultaneous interacting or binding to the SH3 protein domain or homologs thereof is made available.

According to a preferred embodiment, the inventive use of at least one compound of general formula I as described above or treatment and/or prevention and/or production of a medication for treatment and/or prevention of CNS diseases or CNS-related diseases in a patient requiring such a treatment and/or prevention without or without any significant simultaneous antagonism of the chemokine receptor, in particular without antagonizing the chemokine receptor CCR4 and/or CCR5 is made available.

According to a preferred embodiment, the use of at least one compound of general formula I as described above and/or the corresponding enantiomeric, diastereomeric and/or tautomeric forms thereof and/or the pharmaceutically acceptable salts thereof and/or the active ingredient precursors (pro-drugs) thereof is made available, characterized in that the treatment and/or prevention are accomplished by modulation of the 5-$HT_5$ receptor activity.

According to a preferred embodiment, the use of at least one compound of general formula I as described above and/or the corresponding enantiomeric, diastereomeric and/or tautomeric forms thereof and/or the pharmaceutically acceptable salts thereof and/or the active ingredient precursors (pro-drugs) thereof is made available, characterized in that the treatment and/or prevention are accomplished by modulation of the 5-$HT_5$ receptor activity but without or without any significant simultaneous nitric oxide modulation.

According to a preferred embodiment, the use of at least one compound of general formula I as described above and/or the corresponding enantiomeric, diastereomeric and/or tautomeric forms thereof and/or the pharmaceutically acceptable salts thereof and/or the active ingredient precursors (pro-drugs) thereof is made available, characterized in that the treatment and/or prevention are accomplished by modulation of the 5-$HT_5$ receptor activity but without or without any significant simultaneous interacting or binding to the SH3 protein domain or homologs thereof.

According to a preferred embodiment, the use of at least one compound of general formula I as described above and/or the corresponding enantiomeric, diastereomeric and/or tautomeric forms thereof and/or the pharmaceutically acceptable salts thereof and/or the active ingredient precursors (prodrugs) thereof is made available, characterized in that the treatment and/or prevention are accomplished by modulation of the 5-$HT_5$ receptor activity but without or without any significant simultaneous antagonism of the chemokine receptor in particular without antagonizing the chemokine receptor CCR4 and/or CCR5.

According to a preferred embodiment, the use of at least one compound of general formula I as described above and/or the corresponding enantiomeric, diastereomeric and/or tautomeric forms thereof and/or the pharmaceutically acceptable salts thereof and/or the active ingredient precursors (prodrugs) thereof is made available, characterized in that the CNS disease or CNS-related disease is a disease selected from the group comprising neuropathological, neuropsychiatric and neurodegenerative disorders, neuropathological, neuropsychiatric and neurodegenerative symptoms and neuropathological, neuropsychiatric and neurodegenerative dysfunctions.

According to a preferred embodiment, the inventive use for treatment and/or prevention of one or more of the aforementioned CNS diseases or CNS-related diseases is performed by modulation of the 5-$HT_5$ receptor activity.

According to a preferred embodiment, the inventive use for treatment and/or prevention of one or more of the aforementioned CNS diseases or CNS-related diseases is performed by modulation of the 5-$HT_5$ receptor activity but without or without any significant simultaneous nitric oxide modulation.

According to a preferred embodiment, the inventive use for treatment and/or prevention of one or more of the aforementioned CNS diseases or CNS-related diseases is performed by modulation of the 5-$HT_5$ receptor activity but without or without any significant simultaneous interacting or binding to the SH3 protein domain or homologs thereof.

According to a preferred embodiment, the inventive use for treatment and/or prevention of one or more of the aforementioned CNS diseases or CNS-related diseases is performed by modulation of the 5-$HT_5$ receptor activity but without or without any significant simultaneous antagonism of the chemokine receptor in particular without antagonizing the chemokine receptor CCR4 and/or CCR5.

According to a preferred embodiment, the use of at least one compound of general formula I as described above and/or the corresponding enantiomeric, diastereomeric and/or tautomeric forms thereof and/or the pharmaceutically acceptable salts thereof and/or the active ingredient precursors (prodrugs) thereof is made available, characterized in that the CNS disease or CNS-related disease is a disease selected from the group comprising neuropathological, neuropsychiatric and neurodegenerative disorders, symptoms and/or dysfunctions are migraines and/or brain injuries.

According to a preferred embodiment, the inventive use for treatment and/or prevention of one or more of the aforementioned CNS diseases, CNS-related diseases, neuropathological, neuropsychiatric and/or neurodegenerative disorders, symptoms and/or dysfunctions in conjunction with migraines and/or brain injuries is performed by modulation of the 5-$HT_5$ receptor activity.

According to a preferred embodiment, the inventive use for treatment and/or prevention of one or more of the aforementioned CNS diseases, CNS-related diseases, neuropathological, neuropsychiatric and/or neurodegenerative disorders, symptoms and/or dysfunctions in conjunction with migraines and/or brain injuries is performed by modulation of the 5-$HT_5$ receptor activity, but without or without any significant simultaneous nitric oxide modulation, without or without any significant simultaneous interacting or binding to the SH3 protein domain or homologs thereof and/or without or without any significant simultaneous antagonism of the chemokine receptor in particular without antagonizing the chemokine receptor CCR4 and/or CCR5.

According to a preferred embodiment, the use of at least one compound of general formula I as described above and/or the corresponding enantiomeric, diastereomeric and/or tautomeric forms thereof and/or the pharmaceutically acceptable salts thereof and/or the active ingredient precursors (prodrugs) thereof is made available, characterized in that the CNS disease and/or CNS-related disease and/or neuropathological, neuropsychiatric and/or neurodegenerative disorders, symptoms and/or dysfunctions are selected from the group comprising cerebral ischemia, stroke, epilepsy and seizures in general, psychoses, schizophrenia, autism, OCD syndrome, cognitive disorders, attention disorders, depression, bipolar and/or unipolar depression, anxiety, dementia, senile dementia, Alzheimer's dementia, demyelinizing diseases, multiple sclerosis and brain tumors.

According to a preferred embodiment, the inventive use for treatment and/or prevention of one or more of the aforementioned CNS diseases, CNS-related diseases, neuropathological, neuropsychiatric and/or neurodegenerative disorders, symptoms and/or dysfunctions selected from the group comprising cerebral ischemia, stroke, epilepsy and seizures in general, psychoses, schizophrenia, autism, OCD syndrome, cognitive disorders, attention disorders, depression, bipolar and/or unipolar depression, anxiety, dementia, senile dementia, Alzheimer's dementia, demyelinizing diseases, multiple sclerosis and brain tumors is accomplished by modulation of the 5-$HT_5$ receptor activity.

According to a preferred embodiment, the inventive use for treatment and/or prevention of one or more of the aforementioned CNS diseases, CNS-related diseases, neuropathological, neuropsychiatric and/or neurodegenerative disorders, symptoms and/or dysfunctions selected from the group comprising cerebral ischemia, stroke, epilepsy and seizures in general, psychoses, schizophrenia, autism, OCD syndrome, cognitive disorders, attention disorders, depression, bipolar and/or unipolar depression, anxiety, dementia, senile dementia, Alzheimer's dementia, demyelinizing diseases, multiple sclerosis and brain tumors is accomplished by modulation of the 5-$HT_5$ receptor activity but without or without any significant simultaneous nitric oxide modulation, without or without any significant simultaneous interacting or binding to the SH3 protein domain or homologs thereof and/or without or without any significant simultaneous antagonism of the chemokine receptor in particular without antagonizing the chemokine receptor CCR4 and/or CCR5.

According to a preferred embodiment, the use of at least one compound of general formula I as described above and/or corresponding enantiomeric, diastereomeric and/or tautomeric forms thereof and/or the pharmaceutically acceptable salts thereof and/or the active ingredient precursors (prodrugs) thereof is made available, characterized in that the CNS disease and/or CNS-related disease and/or neuropathological, neuropsychiatric and/or neurodegenerative disorders, symptoms and/or dysfunctions are selected from the group comprising cerebral vascular disorders, pain, pain-related disorders, addiction, drug-related disorders, amnesia, alcoholism, drug abuse, disturbances in the circadian rhythm and Cushing's syndrome.

According to a preferred embodiment, the inventive use for treatment and/or prevention of one or more of the aforementioned CNS diseases, CNS-related diseases, neuropathological, neuropsychiatric and/or neurodegenerative disorders, symptoms and/or dysfunctions selected from the group comprising cerebral vascular disorders, pain, pain-related disorders, addiction, drug-related disorders, amnesia, alcoholism, drug abuse, disturbances in the circadian rhythm and Cushing's syndrome is accomplished by modulation of the $5\text{-}HT_5$ receptor activity.

According to a preferred embodiment, the inventive use for treatment and/or prevention of one or more of the aforementioned CNS diseases, CNS-related diseases, neuropathological, neuropsychiatric and/or neurodegenerative disorders, symptoms and/or dysfunctions selected from the group comprising cerebral vascular disorders, pain, pain-related disorders, addiction, drug-related disorders, amnesia, alcoholism, drug abuse, disturbances in the circadian rhythm and Cushing's syndrome is accomplished by modulation of the $5\text{-}HT_5$ receptor activity but without or without any significant simultaneous nitric oxide modulation, without or without any significant simultaneous interacting or binding to the SH3 protein domain or homologs thereof and/or without or without any significant simultaneous antagonism of the chemokine receptor in particular without antagonizing the chemokine receptor CCR4 and/or CCR5.

According to a preferred embodiment, the use of at least one compound of general formula I as described above and/or corresponding enantiomeric, diastereomeric and/or tautomeric forms thereof and/or the pharmaceutically acceptable salts thereof and/or the active ingredient precursors (prodrugs) thereof is made available, characterized in that the treatment and/or prevention is based on a binding affinity for the $5\text{-}HT_{5A}$ receptor of less than or equal to 10 μM (Ki), determined according to a suitable test model.

According to another aspect of the present invention, the use of at least 5-ring heteroaromatic compound of general formula I as described above and/or corresponding enantiomeric, diastereomeric and/or tautomeric forms thereof and/or the pharmaceutically acceptable salts thereof and/or the active ingredient precursors (prodrugs) thereof is made available, in which the radicals $R^1$, $R^2$, $R^3$, $R^4$, $R^5$, $R^6$, $R^7$, $R^8$, $R^9$, $X^1$, $X^2$, $X^3$, $X^4$, $X^5$, W and Z are defined as explained above, for treatment and/or prevention of diseases and/or for production of a medication for treatment and/or prevention of diseases modulated by a $5\text{-}HT_5$ receptor activity and such that the treatment and/or prevention is/are based on a selectivity for the $5\text{-}HT_{5A}$ receptor with a binding affinity (Ki) of less than or equal to 10 μM (Ki) determined according to a suitable test model such that the modulation of the $5\text{-}HT_{5A}$ receptor activity is selected from the group comprising antagonization (antagonist), agonization (agonist), partial agonization (partial agonist), inverse agonization (inverse agonist), partial inverse agonization (partial inverse agonist). Substances having an antagonistic effect on the $5\text{-}HT_{5A}$ receptor, i.e., antagonists or partial agonists are preferred. Antagonists of the $5\text{-}HT_{5A}$ receptor are especially preferred.

According to a preferred embodiment, the use of at least one compound of general formula I as described above and/or corresponding enantiomeric, diastereomeric and/or tautomeric forms thereof and/or the pharmaceutically acceptable salts thereof and/or the active ingredient precursors (prodrugs) thereof is made available, characterized in that the treatment and/or prevention is based on a binding affinity for the $5\text{-}HT_{5A}$ receptor of less than or equal to 300 nM (Ki), determined according to a suitable test model.

According to another aspect of the present invention, the use of at least 5-ring heteroaromatic compound of general formula I as described above and/or corresponding enantiomeric, diastereomeric and/or tautomeric forms thereof and/or the pharmaceutically acceptable salts thereof and/or the active ingredient precursors (prodrugs) thereof is made available, in which the radicals $R^1$, $R^2$, $R^3$, $R^4$, $R^5$, $R^6$, $R^7$, $R^8$, $R^9$, $X^1$, $X^2$, $X^3$, $X^4$, $X^5$, W and Z are defined as explained above, for treatment and/or prevention of diseases and/or for production of a medication for treatment and/or prevention of diseases modulated by a $5\text{-}HT_5$ receptor activity and such that the treatment and/or prevention is/are based on a selectivity for the $5\text{-}HT_{5A}$ receptor with a binding affinity (Ki) of less than or equal to 300 μM (Ki) determined according to a suitable test model such that the modulation of the $5\text{-}HT_{5A}$ receptor activity is selected from the group comprising antagonization (antagonist), agonization (agonist), partial agonization (partial agonist), inverse agonization (inverse agonist), partial inverse agonization (partial inverse agonist). Substances having an antagonistic effect on the $5\text{-}HT_{5A}$ receptor, i.e., antagonists or partial agonists are preferred. Antagonists of the $5\text{-}HT_{5A}$ receptor are especially preferred.

Each of the aforementioned definitions of a variable given above may be combined with any of the aforementioned definitions of the remaining variables. This is true in particular of the combination of preferred definitions of a variable with any or preferred definitions of the remaining variables.

According to a preferred embodiment, the use of at least one compound of general formula I as described above and/or corresponding enantiomeric, diastereomeric and/or tautomeric forms thereof and/or the pharmaceutically acceptable salts thereof and/or the active ingredient precursors (prodrugs) thereof is made available, characterized in that the treatment and/or prevention is based on a modulation of the $5\text{-}HT_5$ receptor activity and additionally on a certain binding affinity for the $5\text{-}HT_{5A}$ receptor.

According to another aspect of the present invention, the use of at least 6-ring heteroaromatic compound of general formula I as described above and/or corresponding enantiomeric, diastereomeric and/or tautomeric forms thereof and/or the pharmaceutically acceptable salts thereof and/or the active ingredient precursors (prodrugs) thereof is made available, in which the radicals $R^1$, $R^2$, $R^3$, $R^4$, $R^5$, $R^6$, $R^7$, $R^8$, $R^9$, $X^1$, $X^2$, $X^3$, $X^4$, $X^5$, W and Z are defined as explained above, for treatment and/or prevention of diseases and/or for production of a medication for treatment and/or prevention of diseases modulated by a $5\text{-}HT_5$ receptor activity such that the modulation of the $5\text{-}HT_5$ receptor activity is selected from the group comprising antagonization (antagonist), agonization (agonist), partial agonization (partial agonist), inverse agonization (inverse agonist), partial inverse agonization (partial inverse agonist). Substances having an antagonistic effect on the $5\text{-}HT_5$ receptor, i.e., antagonists or partial agonists are preferred. Antagonists of the $5\text{-}HT_5$ receptor are especially preferred.

Each of the aforementioned definitions of a variable given above may be combined with any of the aforementioned definitions of the remaining variables. This is true in particular of the combination of preferred definitions of a variable with any or preferred definitions of the remaining variables.

In the sense of the present invention, the term "agonist" refers to a substance that produces an effect on the receptor (here the $5\text{-}HT_5$ receptor) similar to that of the physiological ligand, the term "antagonist" denotes a substance that reduces or cancels the biological effect of an agonist, "partial agonist" refers to a substance that produces a submaximal effect on the receptor such that in the absence of an agonist the partial agonist may have an agonistic effect and in the presence of an agonist the partial agonist may an antagonistic effect, and the term "inverse agonist" refers to a substance that produces a negative effect, "competitive antagonist" refers to a substance having an affinity for the receptor, reversible binding to the receptor (competition with the agonist) and no intrinsic activity on the receptor (relative strength of effect: ability of a substance to trigger an effect in the same receptor position) and "noncompetitive antagonist" refers to a substance with allosteric binding to the receptor and an influence on the intensity of effect (and optionally agonist binding) by a change in conformation of the receptor.

Each of the definitions of one variable as given above may be combined with any of the definitions of the remaining variables as given above. This is true in particular of the combination of preferred definitions of one variable with any definitions or any preferred definitions of the remaining variables.

According to another aspect of the present invention, synthesis of 2-amino-3-benzylquinoline derivative according to general formula I as described above is made available, characterized by the reaction of 2-aminobenzaldehyde derivatives and 3-arylpropionitrile derivatives under basic or acidic reaction conditions by means of a reaction related to the Friedlander reaction.

According to another aspect of the present invention, synthesis of 2-amino-3-benzylquinoline derivative according to general formula I as described above is made available, characterized by the reaction of 2-aminobenzaldehyde derivatives and 3-arylpropionitrile derivatives under basic or acidic reaction conditions by means of a reaction related to the Friedlander reaction.

According to another aspect of the present invention, synthesis of 2-amino-3-benzylquinoline derivative according to general formula I as described above is made available, characterized by the steps of reacting (2-chloroquinolin-3-yl)(aryl)methanone compounds with primary, secondary amines or ammonia and then reducing the 3-carboxy group (e.g., under Wolff-Kishner conditions).

According to another aspect of the present invention, synthesis of 2-amino-3-benzylquinoline derivative according to general formula I as described above is made available, characterized by the steps of reaction of 2-chloroquinoline compounds by orthometallization in position 3, reaction with benzaldehyde derivatives, oxidation to the corresponding chloroquinolin-3-yl-(aryl)methanone compounds, followed by reaction with primary, secondary amines or ammonia and then reduction of the 3-carboxy groups (e.g., under Wolff-Kishner conditions).

According to another aspect of the present invention, synthesis of 3-benzyl-3,4-dihydroquinazolin-2-amine derivatives according to general formula I as described above is made available, characterized by the steps of reacting 2-nitrobenzoic acid derivatives with benzylamine derivatives by peptide linkage, then reducing the amide thus formed to the secondary amine followed by reduction of the nitro group and then cyclization with cyanogen bromide.

According to another aspect of the present invention, synthesis of 3-benzyl-3,4-dihydroquinazolin-2-amine derivatives according to general formula I as described above is made available, characterized by the steps of reacting 2-nitrobenzoaldehyde derivatives with benzylamine derivatives by reductive alkylation followed by reduction of the nitro group, cyclization to the corresponding 3-aryl-2-(methylthio)-3,4-dihydroquinazoline derivatives with carbon disulfide and methyl iodide and then reaction with primary, secondary amines or ammonia.

The present invention also relates to the use of these quinoline and dihydroquinazoline compounds as pharmaceutical drugs and as pharmaceutical compositions containing at least one of these quinoline and dihydroquinazoline compounds as well as a pharmaceutically acceptable vehicle or diluent.

The present invention also relates to the use of these quinoline and dihydroquinazoline compounds for production of a medication for treatment of diseases modulated by a 5-HT$_5$ receptor activity as explained in detail below.

The treatment of neuropathological, neuropsychiatric and neurodegenerative disorders, symptoms and dysfunctions is preferred, in particular the treatment of migraines and brain injuries. Examples of brain injuries and/or disorders include cerebral ischemia, stroke, epilepsy and seizures in general, psychoses, schizophrenia, autism, OCD syndrome, cognitive disorders, attention disorders, depression, bipolar and/or unipolar depression, anxiety, dementia, senile dementia, Alzheimer's dementia, demyelinizing diseases, multiple sclerosis and brain tumors. Also preferred is treatment of cerebrovascular disorders, pain, pain-related disorders, addiction, drug-related disorders, amnesia, alcoholism, drug abuse, disorders of the circadian rhythm and Cushing's syndrome.

DETAILED DESCRIPTION OF THE INVENTION

In preferred embodiments, the radicals of formulas I have the following meanings.

In the present invention the terms that are used have the following meanings as explained below.

An alkyl is an unsubstituted or optionally substituted linear or branched saturated hydrocarbon chain with the stated number of carbon atoms, preferably 1, 2, 3, 4, 5, 6, 7, 8, 9 or 10 carbon atoms, especially preferably 1, 2, 3, 4, 5 or 6, even more preferably 1, 2, 3 or 4 carbon atoms such as methyl, ethyl, propyl, 1-methylethyl, butyl, 1-methylpropyl, 2-methylpropyl, 1,1-dimethylethyl, pentyl, 1-methylbutyl, 2-methylbutyl, 1,2-dimethylpropyl, 1,1-dimethylpropyl, 2,2-dimethylpropyl, 1-ethylpropyl, n-hexyl, 1-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl or 1-ethyl-2-methylpropyl, preferably methyl, ethyl, propyl, n-butyl or isobutyl. The term alkyl should also include halogen-substituted alkyl (haloalkyl).

An alkylene is an unsubstituted or optionally substituted linear or branched alkyl group which is defined as above and in which one hydrogen atom is replaced by a bond. Specific examples include methylene, 1,2-ethylene, 1,2-propylene, 1,3-propylene, 1,2-butylene, 1,3-butylene, 2,3-butylene, 1,4-butylene, 2-methyl-1,3-propylene, 1,2-pentylene, 1,3-pentylene, 1,4-pentylene, 1,5-pentylene, 2,3-pentylene, 2,4-pentylene, 1-methyl-1,4-butylene, 2-methyl-1,4-butylene, 2-methyl-1,3-butylene, 2-ethyl-1,3-propylene, 3,4-hexylene, 3-methyl-2,4-pentylene, 3,5-heptylene, 2-ethyl-1,3-pentylene, 3-ethyl-3,5-heptylene, etc., preferably methylene, 1,2-ethylene and 1,2-propylene. The term alkylene should also include substituted alkylene (haloalkylene).

A cycloalkyl is an unsubstituted or optionally substituted branched or unbranched saturated hydrocarbon ring with 3, 4, 5, 6 or 7, preferably 3, 4, 5 or 6 carbon atoms such as cyclopropyl, cyclobutyl, cyclopentyl, cyclohexyl or cycloheptyl. The term "cycloalkyl" should also include substituted cycloalkyl ("halocycloalkyl").

An alkylene-O-alkyl is a linear or branched saturated alkyl ether chain which has a total of 2 to 12 carbon atoms and one oxygen atom and is unsubstituted or optionally substituted in the alkylene and/or alkyl radical such that both the alkylene radical and the alkyl radical independently of one another contain 1, 2, 3, 4, 5 or 6, more preferably 1, 2, 3 or 4, most preferably 1 or 2 carbon atoms, such that both radicals are defined as above. Preferred examples of alkylene-O-alkyl include methoxymethylene, ethoxymethylene, tert-butoxymethylene, methoxyethylene or ethoxyethylene. The term "alkylene-O-alkyl" should also include halogen-substituted alkylene-O-alkyl in the sense of haloalkylene-O-alkyl or alkylene-O-haloalkyl or haloalkylene-O-haloalkyl.

A thioalkyl is an unsubstituted or optionally substituted linear or branched alkylenesulfanyl chain having 1, 2, 3, 4, 5 or 6 carbon atoms and a sulfur atom. The alkylene radical preferably has 1, 2, 3 or 4, more preferably 1 or 2 carbon atoms, where alkylene is defined as given above. Examples of thioalkyl include thiomethyl or thio-tert-butyl. The term "thioalkyl" should also include halogen-substituted thioalkyl ("halothioalkyl").

An alkenyl is an unsubstituted or optionally substituted branched or unbranched hydrocarbon chain having at least one double bond, having 2, 3, 4, 5 or 6, preferably 2, 3 or 4 carbon atoms. Alkenyl preferably has one or two double bonds, mostly preferably one double bond. Examples of the alkenyl groups include those mentioned above for alkyl, such that these groups have one or two double bonds, e.g., vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl, in particular-2-propenyl, 2-butenyl, 3-methyl-2-butenyl or 3-methyl-2-pentenyl. The term "alkenyl" shall also include halogen-substituted alkenyl ("haloalkenyl").

An alkynyl is an unsubstituted or optionally substituted, branched or unbranched hydrocarbon chain having at least one triple bond with 2, 3, 4, 5 or 6, preferably 2, 3 or 4 carbon atoms. Alkynyl preferably has one or two triple bonds, most preferably one triple bond. Examples of the alkynyl groups include those listed above for alkyl, such that these groups have one or two triple bonds, e.g., ethynyl, 2-pentynyl, 3-pentynyl, 4-pentynyl, 1-methyl-3-butynyl, 2-methyl-3-butynyl, 1-methyl-2-butynyl, 1,1-dimethyl-3-propynyl, 1-ethyl-2-propynyl, 2-hexynyl, 3-hexynyl, 4-hexynyl, 5-hexynyl, 1-methyl-2-pentynyl, 1-methyl-2-pentynyl [sic; duplicate], 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butyryl, 2,2-dimethyl-3-butynyl, 1-ethyl-2-butynyl, 1-ethyl-3-butynyl, 2-ethyl-3-butynyl and 1-ethyl-1-methyl-2-propinyl, preferably ethynyl, 2-propynyl, 2-butynyl, 1-methyl-2-propynyl or 1-methyl-2-butynyl. The term "alkynyl" should also include halogen-substituted alkynyl ("haloalkynyl").

A heterocycloalkyl is an unsubstituted or optionally substituted saturated alkyl ring or an alkyl ring onto which is anellated another unsubstituted or optionally substituted saturated alkyl ring, preferably with a total of 3, 4, 5, 6, 7, 8, 9 or 10 ring atoms, more preferably 3, 4, 5 or 6 ring atoms, most preferably 5 or 6 ring atoms, such that this heterocycloalkyl contains at least one heteroatom, preferably 1, 2 or 3 heteroatoms that may be the same or different and are selected from the group comprising O, N and S, and having 1, 2, 3, 4, 5 or 6, preferably 1, 2, 3, 4 or 5 carbon atoms. The heterocycloalkyl preferably has one or two heteroatoms that may be the same or different and are preferably selected from the group comprising N and O. Examples of a heterocycloalkyl group include N-pyrrolidinyl, N-piperidinyl, N-hexahydroazepinyl, N-morpholinyl or N-piperazinyl, such that in the case of heterocycles containing amino groups, e.g., N-piperazinyl, these amino groups may be replaced by conventional radicals, e.g., methyl, benzyl, Boc (tert-butoxycarbonyl), benzyloxycarbonyl, tosyl(p-toluenesulfonyl), $-SO_2-C_1-C_4$ alkyl, $-SO_2$-phenyl or $-SO_2$-benzyl. The term "heterocycloalkyl" should also include halogen-substituted heterocycloalkyl ("haloheterocycloalkyl").

An aryl is an unsubstituted or optionally substituted aromatic mono-, bi- or polycyclic radical, preferably with 6, 7, 8, 9, 10, 11, 12, 13, 14, 15, 16, 17, 18, 19 or 20 carbon atoms, more preferably 6, 7, 8, 9 or 10 carbon atoms and is preferably selected from phenyl, biphenyl, naphthyl, tetrahydronaphthyl, fluorenyl, indenyl and phenanthrenyl, more preferably from phenyl and naphthyl, e.g., 1-naphthyl or 2-naphthyl. Phenyl is the most preferred.

An alkylene aryl is an aryl bound via $C_1$-$C_6$ alkylene, more preferably $C_1$-$C_4$ alkylene, and optionally substituted in the aryl and/or alkylene radical, such that alkylene and aryl are defined as given above. An alkylene aryl is especially a benzyl or phenethyl, optionally substituted in the aryl radical. The term "alkenylaryl" should also include halogen-substituted alkenylaryl ("haloalkenylaryl").

An aryloxy or O-aryl is an unsubstituted or optionally substituted aryl attached via oxygen and defined as given above, in particular O-phenyl.

A hetaryl (or heteroaryl) is an unsubstituted of optionally substituted mono-, bi- or tricyclic aromatic ring containing at least one heteroatom, preferably 1, 2 or 3 heteroatoms that may be the same or different, more preferably one or two heteroatoms that may be the same or different and are selected from the group comprising O, N and S and preferably 1, 2, 3, 4, 5, 6, 7, 8, 9, 10, 11 or 12, more preferably 1, 2, 3, 4, 5 or 6 carbon atoms. The aromatic ring preferably has five or six members. Hetaryl also comprises the derivatives thereof anellated with aryl, namely an aromatic radical having preferably 6, 7, 8, 9, 10, 11, 12, 13, 14, 15, 16, 17, 18, 19 or 20 carbon atoms, more preferably 6, 7, 8, 9 or 10 carbon atoms, most preferably phenyl which is anellated with this aromatic ring having at least one heteroatom. Hetaryl may also be selected from an aromatic radical preferably having 6, 7, 8, 9, 10, 11, 12, 13, 14, 15, 16, 17, 18, 19 or 20, more preferably 6, 7, 8, 9 or 10 carbon atoms, most preferably phenyl with a heterocycloalkyl group which may be anellated thereon. The heterocycloalkyl group is defined as given above. Hetaryl is preferably selected from 2-furyl, 3-furyl, 2-pyrrolyl, 3-pyrrolyl, 2-thienyl, 3-thienyl, 2-pyridyl, 3-pyridyl, 4-pyridyl, 2-thiazolyl, 4-thiazolyl, 5-thiazolyl, 2-oxazolyl, 4-oxazolyl, 5-oxazolyl, 2-pyrimidyl, 4-pyrimidyl, 5-pyrimidyl, 6-pyrimidyl, 3-pyrazolyl, 4-pyrazolyl, 5-pyrazolyl, 3-isothiazolyl, 4-isothiazolyl, 5-isothiazolyl, 2-imidazolyl, 5-imidazolyl, 3-pyridazinyl, 4-pyridazinyl, 5-pyridazinyl, 6-pyridazinyl, 3-isoxazolyl, 4-isoxazolyl, 5-isoxazolyl, thiadiazolyl, oxadiazolyl, triazinyl, indolinyl, benzothienyl, naphthothienyl, benzofuranyl, chromenyl, indolyl, isoindolyl, indazolyl, quinolyl, isoquinolyl, phthalazinyl, quinoxalinyl, benzimidazolyl and benzoxazolyl, 2,3-dihydro-1,4-benzodioxinyl, 1,3-benzodioxolyl, 2,1,3-benzothiadiazolyl.

The terms "pyridyl" and "pyridinyl" in conjunction with the present invention refer to one and the same radical. The same thing is also true of "pyrimidyl" and "pyrimidinyl."

Alkylene hetaryl is a hetaryl, optionally substituted in the alkenyl and/or hetaryl radical and attached via $C_1$-$C_6$ alkylene, more preferably $C_1$-$C_4$ alkylene. Alkylene hetaryl is preferably optionally substituted —$CH_2$-2-pyridyl, —$CH_2$-3-pyridyl, —$CH_2$-4-pyridyl, —$CH_2$-2-thienyl, —$CH_2$-3-thienyl, —$CH_2$-2-thiazolyl, —$CH_2$-4-thiazolyl, —$CH_2$-5-thiazolyl, —$CH_2$—$CH_2$-2-pyridyl, —$CH_2$—$CH_2$-3-pyridyl, —$CH_2$—$CH_2$-4-pyridyl, —$CH_2$—$CH_2$-2-thienyl, —$CH_2$—$CH_2$-3-thienyl, —$CH_2$—$CH_2$-2-thiazolyl, —$CH_2$—$CH_2$-4-thiazolyl or —$CH_2$—$CH_2$-5-thiazolyl. The term "alkenylhetaryl" should also include halogen-substituted alkenylhetaryl ("haloalkenylhetaryl").

A bicyclic or tricyclic saturated hydrocarbon radical is an unsubstituted or optionally substituted bicycloalkyl or tricycloalkyl radical and has 5, 6, 7, 8, 9, 10, 11, 12, 13, 14, 15, 16, 17 or 18 carbon atoms. In a bicycloalkyl radical, the ring system preferably has 5, 6, 7, 8, 9, 10, 11 or 12 carbon atoms, more preferably 6, 7, 8 9 or 10 carbon atoms. In a tricycloalkyl radical, the ring system preferably has 6, 7, 8, 9, 10, 11, 12, 13, 14, 15 or 16, more preferably 6, 7, 8, 9, 10, 11 or 12 carbon atoms. Examples of a bicycloalkyl radical include indanyl, camphyl and norbornyl. Examples of a tricycloalkyl radical include adamantyl.

A halogen is a halogen atom selected from fluorine, chlorine, bromine or iodine, preferably fluorine, chlorine or bromine, more preferably fluorine or chlorine.

A halogen-substituted alkyl (haloalkyl) refers to an alkyl radical defined as indicated above, partially or completely substituted by fluorine, chlorine, bromine and/or iodine, i.e., for example, $CH_2F$, $CHF_2$, $CF_3$, $CH_2Cl$, 2-fluoroethyl, 2-chloroethyl, 2,2,2-trifluoroethyl. Similarly, the same is also true of the terms "haloalkylene," "haloalkenyl," "haloalkynyl," "haloalkenylaryl," "haloalkenylhetaryl," "haloalkylene-O-alkyl" or "alkylene-O-haloalkyl," "haloalkylene-β-haloalkyl," "halothioalkyl," "halocycloalkyl."

If mentioned in conjunction with the term "optionally substituted," the radical and groups may preferably have one or more substituents, more preferably one, two or three substituents, most preferably one or two substituents. The term "each optionally substituted" should indicate that not only the radical immediately following in the list but also all the radicals listed in the respective group may have the same or different substituents.

Examples of the substituents include: halogen in particular 1, 2, 3, 4 or 5 halogen atoms that may be the same or different per substitution and are selected from the group comprising fluorine, chlorine, bromine and iodine, CN, $CF_3$, $CHF_2$, $OCF_3$, $OCHF_2$, $NO_2$, $NH_2$, OH, COOH, each optionally branched or unbranched, optionally substituted $C_1$-$C_6$ alkyl, $C_3$-$C_7$ cycloalkyl, alkylene-O—$C_1$-$C_6$ alkyl or $C_1$-$C_6$ thioalkyl, O—$C_1$-$C_6$ alkyl, N($C_1$-$C_6$ alkyl)($C_1$-$C_6$ alkyl), NH($C_1$-$C_6$ alkyl), aryl, —O-aryl, $C_1$-$C_6$ alkylene-O-aryl, NHCO—$C_1$-$C_4$ alkyl, NH—$SO_2$—$C_1$-$C_4$ alkyl, CO—$C_1$-$C_6$ alkyl, $SO_2$—$C_1$-$C_6$ alkyl, NHCO-aryl optionally substituted in the aryl radical, $NHSO_2$-aryl, $CONH_2$, $SO_2NH_2$, $SO_2$-aryl, SO—$C_1$-$C_6$ alkyl, $SO_2$—$C_1$-$C_6$ alkyl, SO-aryl, N-pyrrolidinyl, N-piperidinyl and N-morpholinyl. Preferred substituents include F, Cl, $CF_3$, $OCF_3$, $NH_2$, $NO_2$, OH, COOH, $C_1$-$C_4$ alkyl, methoxy, acetyl, NH-acetyl and $SO_2NH_2$.

The term "optionally substituted" alkyl, alkyloxy, alkoxy, aryl and hetaryl should in particular mean, independently of the respective number of carbon atoms per radical, that one or more hydrogen atoms, preferably 1, 2, 3, 4 or 5 hydrogen atoms, may be replaced by halogen atoms that are the same or different and are selected from the group comprising fluorine, chlorine, bromine and iodine, preferably fluorine.

The prefix "$C_1$-$C_6$" means that the radical listed next, e.g., the alkyl radical in $C_1$-$C_6$ alkyl, may have 1, 2, 3, 4, 5 or 6 carbon atoms. Similarly, the same thing also applies to the meaning of the other prefixes used in the present specification and in the Claims, e.g., $C_1$-$C_7$ (3, 4, 5, 6 or 7 carbon atoms), $C_1$-$C_4$ (1, 2, 3 or 4 carbon atoms), $C_2$-$C_6$ (2, 3, 4, 5 or 6 carbon atoms), etc.

The term "three- to seven-membered" carbocycle, heterocycle or ring refers to the total number of ring members, i.e., to a ring having a total of 3, 4, 5, 6 or 7 ring members In the case of ring systems that are anellated together, whereby "anellated" may refer to vicinal ring systems as well as geminal ring systems (i.e., spiro-bridged ring systems), the expression "three- to seven-membered" refers to the total number of ring members, including the ring members which are part of vicinal anellated ring system. Similarly, the same thing also applies to the terms "five- to seven-membered," "five- or six-membered," "four- to seven-membered," etc.

In general, it is true that a radical in parentheses, e.g., the radical ($C_1$-$C_6$ alkyl) in the term "N($C_1$-$C_6$ alkyl)$_2$" together with a numerical value assigned to the term in parentheses denotes a multiple occurrence of the respective radical corresponding to the numerical value, i.e., in the case of the example of a radical "N($C_1$-$C_6$ alkyl)($C_1$-$C_6$ alkyl)" mentioned above, where the repeated occurrence of the radicals may have the same or different meanings independently of one another. The same thing also applies accordingly to all terms according to the diagram "(radical)$_x$," where x=an integer equal to an or greater than 2.

Optical Isomers-Diastereomers-Geometric Isomers-Tautomers

The inventive compounds of general formula I and/or the salt thereof may have in particular an asymmetrical center and may be in the form of racemates and racemic mixtures, individual enantiomers, diastereomeric mixtures and individual diastereomers. The present invention includes all these stereoisomeric forms of the inventive compounds of general formula I.

The inventive compounds of general formula I may be split into their individual stereoisomers by traditional methods, e.g., by fractional crystallization from a suitable solvent, e.g., methanol or ethyl acetate or a mixture thereof or by chiral chromatography using an optically active stationary phase. The absolute stereochemistry can be determined by x-ray crystallography of the individual products or crystalline intermediates which, if necessary, are derivatized with a reactant containing asymmetrical center of a known absolute configuration.

Alternatively, any stereoisomer of an inventive compound of general formula I can be obtained by stereospecific synthesis using optically pure starting materials or reactants having a known absolute configuration or by asymmetrical synthesis methods.

Use of an enantiomer-pure and/or diastereomer-pure compound is preferred. In particular, the inventive compounds of general formula I may also be in the form of various tautomers in which case the type of tautomerism will depend on the nature of the radicals, as is obvious for those skilled in the art. Other tautomer such as keto-enol tautomers may also be present. All the individual possible tautomers as well as mixtures thereof are included as inventive compounds of general formula I.

Salts

The term "pharmaceutically acceptable salts" refers to salts produced from pharmaceutically acceptable physiologically tolerable bases or acids including organic or inorganic bases and organic and inorganic acids.

Salts derived from inorganic bases include aluminum, ammonium, calcium, copper, iron(II), iron(III), lithium, magnesium, manganese, potassium, sodium, zinc and the like. Especially preferred salts include the ammonium, calcium, lithium, magnesium, potassium and sodium salts. Salts derived from pharmaceutically acceptable organic nontoxic bases include salts of primary, secondary and tertiary amines, substituted amines including naturally occurring substituted amines, cyclic amines and basic ion exchange resins, e.g., arginine, betaine, caffeine, choline, N,N'-dibenzylethylenediamine, diethylamine, 2-diethylaminomethanol, 2-dimethylaminoethanol, ethanolamine, ethylenediamine, N-ethylmorpholine, N-ethylpiperidine, glucamine, glucosamine, histidine, hydrabamine, isopropylamine, lysine, methyl glucamine, morpholine, piperazine, piperidine, polyamine urea, procaine, purine, theobromine, triethylamine, trimethylamine, tripropylamine, tromethamine and the like.

If the inventive compounds of general formula I are basic, then the salts may be produced from pharmaceutically acceptable, physiologically tolerable acids, including organic and inorganic acids. Such as include, among others, acetic acid (acetate), benzenesulfonic acid, benzoic acid, camphor sulfonic acid, citric acid, ethanesulfonic acid, formic acid, fumaric acid, gluconic acid glutamic acid hydrobromic acid, hydrochloric acid, lactic acid malic acid, maleic acid, mandelic acid, methanesulfonic acid, malonic acid, nitric acid, pantothenic acid, phosphoric acid, propionic acid, succinic acid, sulfuric acid, tartaric acid, p-toluenesulfonic acid, trifluoroacetic acid and the like. Especially preferred acids include acetic acid, citric acid, fumaric acid, hydrobromic acid, hydrochloric acid, maleic acid, phosphoric acid, sulfuric acid and tartaric acid.

When reference is made to the inventive compounds of general formula I, this is understood to mean that the pharmaceutically acceptable salts thereof are also included.

When reference is made to the inventive compounds of general formula I, this should also be understood to mean that the active ingredient precursors (prodrugs) thereof are also included. The term "prodrugs" is understood to refer to derivatives of the inventive compounds of general formula I which are converted into the inventive compounds of general formula I under physiological conditions, including physical, thermal, chemical or enzymatic conditions after administration in a patient, preferably a human or nonhuman mammal.

Use, Indications and Effects

The subject matter of the present invention is also the use of the inventive compounds of the general formula for the treatment of:

Depression and/or bipolar disorders, e.g., dysthemic disorders, seasonal disorders and/or psychotic disorders Anxiety and/or stress-related disturbances, e.g., general anxiety disorders, panic disorders, compulsion disorders, post-traumatic stress, acute stress disorders and/or social phobia Memory disorders and/or Alzheimer's disease Schizophrenia, psychoses, psychotic disorders and/or psychotic-related disorders.

Cerebrovascular disorders

Pain and/or pain-related disorders, addition and drug-related disorders including medication-related disorders Amnesia Alcoholism or drug abuse including medication abuse Disturbances in the circadian rhythm and/or Cushing's syndrome.

The term "disorder" in the sense according to the present invention refers to anomalies which are regarded as pathological conditions as a rule and may be manifested in the form of certain signs, symptoms and/or dysfunctions. The treatment may be directed at individual disorders, i.e., anomalies and/or pathological conditions, but several anomalies, optionally linked together causally, may also be combined into symptoms, i.e., syndromes which can be treated according to the present invention. This condition may exist preventively, progressively or permanently.

Compounds of the present invention may be used for treatment or prevention of various diseases in the development and/or course of which $5-HT_5$ receptors are involved, i.e., diseases modulated by a $5-HT_5$ receptor activity such as mental disorders. Examples of such mental disorders include, according to the American Psychiatric Association DSM-IV, Diagnostic and Statistical Manual of Mental Disorders, $4^{th}$ edition, 1994: attention disorders and socially dysfunctional behavior; learning disorders, delirium, dementia and amnesia and other cognitive disorders; disorders in conjunction with various substances, e.g., disorders in conjunction with alcohol consumption and alcohol-induced disorders, withdrawal symptoms; schizophrenia and other psychotic disorders, e.g., schizophrenic-form disorders, schizoaffective disorders and delusional disorders; substance-induced psychoses; paranoid disorders; neuroleptic-induced disorders; affective disorders, e.g., depressive disorders (major depression, dysthemic disorder, seasonal affective disorder, unspecified depressive disorder), bipolar disorders (bipolar I disorder, bipolar II disorder, cyclothymic disorder, unspecified bipolar disorder, affective disorder induced by a substance (amphetamine or amphetamine-like substances), unspecified affective disorder); disorders in conjunction with stress, e.g., acute stress disorder; anxiety disorders, e.g., panic disorders without agoraphobia, panic disorders with agoraphobia, agoraphobia without a history of panic disorder, specific phobias, social phobia, compulsion disorder, post-traumatic stress disorder, acute stress disorder, generalized anxiety disorder, substance-induced anxiety disorder; somatoform disorders, e.g., somatization disorder, unspecified somatoform disorder, conversion disorder, pain disorder; eating disorders; sleep disorders, e.g., primary sleep disorders (dyssomnia, parasomnia), sleep disorders in conjunction with another mental disorder.

The subject matter of the invention is in particular also the use of heterocycles of formula I for treatment of neuropathological, neuropsychiatric and neurodegenerative disorders.

Neuropathological disorders are understood to refer to disorders accompanied by neurological deficiencies, i.e., a condition characterized by symptoms of neurological failure.

Treatment of neurodegenerative and/or neuropsychiatric disorders is preferred according to the invention. These disorders occur especially in neuropathological syndromes, usually causing brain damage, e.g., cerebral ischemia, stroke, epilepsy and seizures in general, chronic schizophrenia, other psychotic diseases, depression, anxiety states, bipolar disorders, dementia, in particular Alzheimer's disease, demyelinizing diseases, in particular multiple sclerosis, brain tumors and general inflammatory processes. Another neuropathological disorder is the migraine as well as the signs, symptoms and dysfunctions associated therewith.

According to another aspect of the present invention, neuropathological disorders associated with a glial reaction are treated. The inventive use relates in particular to the modulation of the glial response. An advantageous effect of the binding partners is manifested in preventive or acute treatment of neurological deficiencies such as those observed in patients suffering from psychiatric disorders such as epilepsy, psychosis, e.g., psychoses of the acute exogenous reaction type or concomitant psychoses of an organic and/or exogenous cause, e.g., following trauma, especially cerebral lesions and diffuse brain damage, in metabolic disorders, infections, endocrinopathies; endogenous psychoses such as schizophrenia and schizotypic and delusional disorders; affective disorders such as depression, mania and/or manic depressive states; as well as mixed forms of the psychoses described above; senile dementia and senile dementia of the Alzheimer's type as well as in the treatment or prevention of demyelinization processes.

The inventive quinoline and dihydroquinazoline compounds are effective, in particular with regard to treatment of ischemic damage, e.g., due to the cerebral and medullary trauma and vascular occlusion or heart failure. Strokes in particular should be mentioned here (synonym cerebral apoplexy, cerebral or apoplectic insult, cerebral stroke). Transitory ischemic attacks, reversible ischemic neurological deficiencies, prolonged reversible ischemic neurological deficiencies, partially reversible ischemic neurological symptoms and persistent complete cerebral infarctions can be treated according to the present invention. Treatment of acute forms of these conditions is especially advantageous according to the present invention.

The forms of neuropathological disorders that are preferably treated according to the present invention are based on one or more of the changes in nerve tissue listed below: degeneration or death of neurons, in particular ganglia cells, e.g., tigrolysis, nuclear membrane blurring, plasmolysis or cell shrinkage, cytoplasmic vacuolization and encrustation, parenchymal necroses of the brain, cerebral edema, oxygen deficiency-induced changes in neurons, atrophy, morphological changes, e.g., demyelinization, in particular destruction of the medullary sheath, perivascular infiltrates, glial proliferation and/or glial scarring; degeneration of the substantia nigra.

The indication for treatment according to the present invention is often characterized by a progressive development, i.e., the conditions described above change over a period of time, usually with the severity increasing and in some cases one condition may develop into another or additional conditions may occur in addition to pre-existing conditions. A number of other signs, symptoms and/or dysfunctions associated with the disorders can be treated through the inventive treatment of neuropathological, neuropsychiatric or neurodegenerative disorders and/or the conditions on which they are based, i.e., in particular accompanying the disease conditions described above. These include for example shock lung, loss of cerebral nerves, e.g., retrobulbar neuritis, optic muscle paralysis, scanning speech, spastic paralysis, cerebellar symptoms, disorders of sensibility, the bladder and small intestine, euphoria, dementia; hypokinesia and akinesia, lack of synkinesis, walking in small steps, bent posture of torso and extremities, pro-, retro- and lateropulsion, tremor, Parkinson's mask, monotone speech, depression, apathy, labile or rigid affect, difficulty in spontaneity and decision making, slow cognitive processes, reduced association ability; muscular atrophy.

A treatment in the inventive sense comprises not only the treatment of acute or chronic signs, symptoms and/or dysfunctions but also a preventive treatment (prophylaxis), in particular to prevent a recurrence or phases. The treatment may be symptomatic, e.g., aimed as suppressing symptoms. It may be administered for a short-term, medium-term or even a long-term treatment, e.g., as part of maintenance therapy.

The term "binding partner for 5-$HT_5$ receptors" describes substances that bind to 5-$HT_5$ receptors and therefore can also be referred to as 5-$HT_5$ receptor ligands.

Binding is understood to refer to any molecular interaction between the binding partner and the receptor, in particular under physiological conditions. These are usually classical interactions including electrostatic attraction, hydrogen bridge bonds, hydrophobic binding, van der Waals forces or metal complex-like coordinative bonds. In addition to the reversible molecular interactions mentioned above, irreversible interactions between binding partners and receptors may also be considered, e.g., covalent bonding.

Inventive quinoline and dihydroquinazoline compounds may competitively inhibit the binding of comparative binding partners, e.g., 5-HT (5-hydroxytryptamine) or 5-CT (5-carboxamidotryptamine) to 5-$HT_5$ receptors. Competitive inhibition is understood to refer to the fact that the inventive quinoline and dihydroquinazoline compounds compete with a comparative binding partner, namely in the present case 5-HT or 5-CT, for example, for binding to the receptor.

According to another preferred embodiment, inventive quinoline and dihydroquinazoline compounds inhibit the binding of comparative binding partners such as 5-HT (5-hydroxytryptamine) or 5-CT (5-carboxamidotryptamine) to 5-$HT_5$ receptors noncompetitively. Noncompetitive inhibition is understood to refer to the fact that inventive quinoline and dihydroquinazoline compounds modulate the binding of a comparative binding partner, namely in the present case 5-HT or 5-CT, for example, via its binding to the receptor, in particular reducing its binding affinity.

At least for the case of competitive inhibition, i.e., reversible binding, the principle holds that the displacement of one binding partner by another binding partner with a decreasing binding affinity of one binding partner and/or an increasing binding affinity of the other binding partner with respect to the receptor increases. Expediently, inventive quinoline and dihydroquinazoline compounds therefore have a high binding affinity for 5-$HT_5$ receptors. Such a binding affinity allows on the one hand effective displacement of naturally occurring binding partners for 5-$HT_5$ receptors, e.g., serotonin (5-hydroxytryptamine, 5-HT) itself, such that the required concentration of inventive quinoline and dihydroquinazoline compounds for binding a certain quantity of this binding partner to 5-$HT_5$ receptors decrease with an increase in the binding affinity. With regard to medical use, therefore quinoline and dihydroquinazoline compounds whose binding affinity is so great that they can be administered in reasonable amounts as active ingredients as part of an effective medical treatment are preferred.

Another possibility of expressing the binding affinity is offered by the competition experiments mentioned above with which the concentration of inventive quinoline and dihydroquinazoline compounds that will displace 50% of another comparative binding partner from the receptor binding site ($IC_{50}$ values) is determined in vitro. This makes it possible to evaluate the competitive inhibition of the binding of 5-CT to 5-$HT_5$ receptors to the extent that preferred inventive quinoline and dihydroquinazoline compounds have a 50% of maximal inhibiting constant $IC_{50}$ of less than $10^{-5}M$, preferably less than $10^{-6}M$ and in particular less than $10^{-7}M$. The binding affinity of inventive quinoline and dihydroquinazoline compounds can also be expressed via the inhibiting constant $K_i$; which is generally also determined with competition experiments in vitro. For binding to 5-$HT_5$ receptors, inventive quinoline and dihydroquinazoline compounds preferably have $K_i$ values of less than $10^{-6}M$, advantageously less than $10^{-7}M$ and in particular preferably less than $10^{-8}M$.

Usable binding partners may bind to 5-$HT_5$ with a lower, essentially the same or a higher affinity than to a certain receptor different from 5-$HT_5$. Thus with regard to the inventive use, in particular the binding partners for 5-HT$_5$ receptors include those whose binding affinity for 5-HT$_5$ receptors is so high in comparison with the affinity for 5-HT receptors that they are advantageously suitable for use according to the present invention. This does not necessarily presuppose a comparatively more selective binding to 5-HT$_5$ receptors, although selective binding partners for 5-HT$_5$ receptors constitute a special embodiment of the present invention.

For example, binding partners that have a high affinity for both 5-HT$_5$ receptors and also other 5-HT receptors may be used. A high affinity in this context refers to $K_i$ values usually in the range of $1\text{-}10^{-10}$M to $1\text{-}10^{-6}$M. According to a special embodiment, quinoline and dihydroquinazoline compounds have a binding profile to the 5-HT receptors in the high affinity range such that this binding profile is characterized by a binding affinity for 5-HT$_5$ which is essentially the same as or only slightly lower than other binding affinities in this range. Factors of 10 or less may be advantageous.

Inventive quinoline and dihydroquinazoline compounds have binding affinities for 5-HT$_5$ receptors that are greater than those for one or more 5-HT receptors that are different from 5-HT$_5$, i.e., in particular the receptors to be assigned to the aforementioned 5-HT receptor classes 5-HT$_5$, 5-HT$_2$, 5-HT$_3$, 5-HT$_4$, 5-HT$_6$ and 5-HT$_7$. If the binding affinity for 5-HT$_5$ receptors of a binding partner is greater than that of a 5-HT receptor different from 5-HT$_5$ then we speak of a binding of these binding partners to 5-HT$_5$ receptors that is selective with respect to the 5-HT receptor different from 5-HT$_5$. Special binding partners include those whose binding affinity for 5-HT$_5$ receptors is greater than that for at least one 5-HT receptor. Quinoline and dihydroquinazoline compounds whose binding affinity for 5-HT$_5$ receptors is greater than that for all 5-HT receptors different from 5-HT$_5$ constitute another special class of inventive quinoline and dihydroquinazoline compounds.

Selectivity is understood to refer to the property of a binding partner of preferably binding to 5-HT$_5$ receptors. It is significant for the selectivity described above that the binding affinities for 5-HT$_5$ receptors on the one hand and for one or more 5-HT receptors that are different from 5-HT$_5$ on the other hand are sufficiently different. Affinity differences according to which binding affinity ratios of at least 2, more advantageously of at least 5, especially advantageously of at least 10, preferably of at least 20, especially preferably of at least 50 and in particular of at least 100 are preferred.

According to another embodiment, the inventive quinoline and dihydroquinazoline compounds bind to 5-HT$_5$ receptors selectively with respect to one or more 5-HT receptors different from 5-HT$_5$ with the advantageous binding affinities described above.

According to another embodiment the inventive quinoline and dihydroquinazoline compounds bind to 5-HT$_5$ receptors selectively with respect to all 5-HT receptors different from 5-HT$_5$ with the advantageous binding affinities described above.

Especially advantageous compounds are heterocycles of formula I which bind to 5-HT$_5$ receptors expressed by glial cells and by astrocytes in particular and having the affinities and selectivities described above. According to this invention, the human receptor variant is a preferred target for the inventive quinoline and dihydroquinazoline compounds.

Binding of the inventive heterocycles of formula I to 5-HT$_5$ receptors is linked to an effector function. The binding partners may act agonistically or antagonistically or partially agonistically and/or partially antagonistically. Agonists are compounds according to the present invention which partially or entirely simulate the activity of 5-HT to 5-HT$_5$ receptors. Antagonists are inventive quinoline and dihydroquinazoline compounds which are capable of blocking the agonistic activity of 5-HT to 5-HT$_5$ receptors.

According to a special embodiment of the present invention, heterocycles of formula I are used, their binding to at least 5-HT$_5$ receptors of h5-HT$_5$-transfected CHO or HEK 293 or SHSY-5Y cells inducing a change in the agonist-induced stimulation of GTP binding to membrane-bound G-proteins, a change in the intracellular calcium level, a change in the agonist-induced induction of phospholipase C activity and/or a change in cAMP production. With regard to the change in the intracellular calcium levels, the use of heterocycles of formula I which cause an increase in the intracellular calcium levels constitutes a special embodiment of the invention. This embodiment also includes quinoline and dihydroquinazoline compounds that are effective in known animal models for neurodegenerative and neuropsychiatric processes.

Heterocycles of formula I which are also selective for 5-HT$_5$ receptors with respect to their effect or function in the sense described above are preferred.

Dosage Forms and Formulation

Because of their pharmacological properties, the inventive quinoline and dihydroquinazoline compounds can be used as active ingredients for therapeutic purposes. The inventive quinoline and dihydroquinazoline compounds are preferably converted to a suitable dosage form before being administered. Another subject matter of the present invention is therefore also compositions, in particular pharmaceutical compositions containing at least one inventive quinoline and dihydroquinazoline compound and a pharmaceutically acceptable vehicle or diluent.

The vehicles and diluents that are known to be usable in the field of pharmacy and adjacent fields are pharmaceutically acceptable, in particular those listed in the relevant pharmacopoeias (e.g., DAB (German Pharmacopoeia), Ph. Eur. (Pharmacopoeia Europaea), BP (Baccalaureus Pharmaciae), NF (National Formulary), USP (United States Pharmacopoeia)) as well as other vehicles whose properties do not prevent their physiological use.

Suitable vehicles and excipients may include: wetting agents; emulsifying and suspending agents; preservatives; antioxidants; anti-irritants; chelating agents; pill coating aids; emulsion stabilizers; film-forming agents; gel-forming agents; odor masking agents; taste correcting agents; resins; hydrocolloids; solvents; solubilizers; neutralizing agents; permeation accelerators; pigments; quaternary ammonium compounds; moisturizers and remoisturizers; ointment, cream or oil bases; silicone derivatives; spreading aids; stabilizers; sterilizing agents; suppository bases; tablet excipients such as binders, fillers, lubricants, disintegrants or coatings; propellants; desiccants; opacifiers; thickeners; waxes; plasticizers; white oils. An embodiment in this regard is based on technical knowledge as disclosed, for example, by H. P. Fiedler, Lexicon of Excipients for Pharmacy, Cosmetics and Related Fields, 4$^{th}$ edition, Aulendorf, ECV Editio Cantor Verlag, 1996.

Examples of suitable vehicles and diluents include lactose, dextrose, sucrose, sorbitol, mannitol, starches, gum acacia, calcium phosphate, alginates, gum tragacanth, gelatin, calcium silicate, microcrystalline cellulose, polyvinyl pyrrolidine, cellulose, water syrup, methyl cellulose, methyl and propyl hydroxybenzoates, talc, magnesium stearate and mineral oil.

The inventive quinoline and dihydroquinazoline compounds can be formulated to ensure immediate or delayed release of the active ingredient to the patient.

Examples of suitable pharmaceutical compositions include solid dosage forms, e.g., powders, dusting powders, granules, tablets, especially film tablets, lozenges, sachets, cachets, coated pills, capsules such as hard and soft gelatin capsules, suppositories or vaginal dosage forms; semisolid dosage forms such as ointments, creams, hydrogels, pastes or patches and liquid dosage forms such as solutions, emulsions especially oil in water emulsions, suspension, e.g., lotions, injection and infusion preparations, eye drops and ear drops. Implanted dispensing devices may also be used to administer the inventive quinoline and dihydroquinazoline compounds. Furthermore, liposomes or microspheres may also be used.

The inventive compositions may be administered by the usual routes.

In the production of the inventive compositions, the active ingredients are usually mixed or diluted with a suitable auxiliary substance, in this case also known as an excipient. Excipients may be solid, semisolid or liquid materials that serve as a vehicle, carrier or medium for the active ingredient. Other excipients are added, if necessary, in a known way. Shaping steps, optionally in combination with mixing operations, may be performed, e.g., granulation, compression and the like.

The inventive use of the inventive active ingredients includes a method within the scope of the treatment. An effective amount of at least one heterocycle of formula I, usually formulated in accordance with pharmaceutical practice, is administered to the individual that is to be treated, preferably a mammal, in particular a human being or a commercial or domestic animal.

The invention also relates to the production of agents for treating an individual, preferably a mammal, in particular a human, commercial or domestic animal.

The heterocycles of formula I or the corresponding pharmaceutical composition may be administered orally, rectally, topically, parenterally, including subcutaneously, intravenously and intramuscularly, ocularly, pulmonarily or nasally. Oral administration is preferred.

An effective dose of the active ingredient may depend on the type of heterocycle of formula I, how administered, the disease to be treated and the severity of the disease to be treated. Such an effective dose of the active ingredient can easily be ascertained by those skilled in the art in this field.

The dosage depends on the age, condition and weight of the patient as well as how the dose is administered. As a rule, the daily dose of active ingredient will be between approximately 0.5 and 100 mg/kg body weight for oral administration and between approximately 0.1 and 10 mg/kg body weight for parenteral administration.

Producing the Heterocycles of Formula I

The inventive quinoline compounds can be synthesized by methods like those known in the literature and with which those skilled in the art are familiar. In 1882, P. Friedländer (Ber. (1882), 15, 2572) reported on a reaction of 2-aminobenzaldehyde and acetone to form 2-methyl-quinoline, a reaction that was later named after him. Quinoline derivatives can be synthesized by the Friedländer reaction from 2-aminobenzaldehydes and/or 2-aminophenyl ketones and aldehydes, ketones and nitriles with a vicinal methylene group under basic and/or acidic reaction conditions at room temperature or an elevated temperature (see e.g., Organic Reactions, 1982, vol. 28, 37-131; Can. J. Chem. (2004), 82, 461). Synthesis of 2-aminoquinoline derivatives via this reaction was previously known only with 2-phenylacetamides (Synthesis (1987), 810), 2-cyanoacetamide (Journal of Medicinal Chemistry (1979), 22, 44), malodinitrile (Journal of Organic Chemistry (1953), 18, 1755) or 2-aryloxyacetamides (Synthesis (1987), 810) and 2-aminobenzaldehyde derivatives. Synthesis of 2-amino-3-benzylquinoline derivatives from 2-aminobenzaldehyde derivatives and 3-arylpropionitrile derivatives ($Z=CH_2$) by the Friedländer reaction, however, is novel and is being described here for the first time (diagram 1).

Diagram 1:

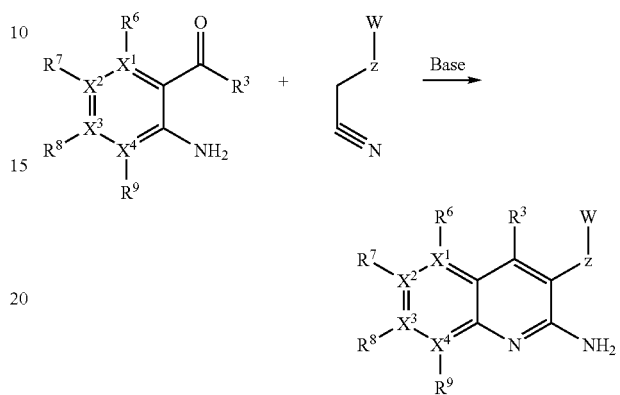

However, the inventive quinoline compounds can also be synthesized from quinoline-3-carbaldehydes, naphtheridine-3-carbaldehydes and/or the analogous ketones and nucleophilic metal organyls (e.g., aryl Grignard compounds) according to diagram 2. Functionalized Grignard reagents can be synthesized, for example, according to the methods described in Angewandte Chemie (2003) 115, 4438-4456.

Diagram 2:

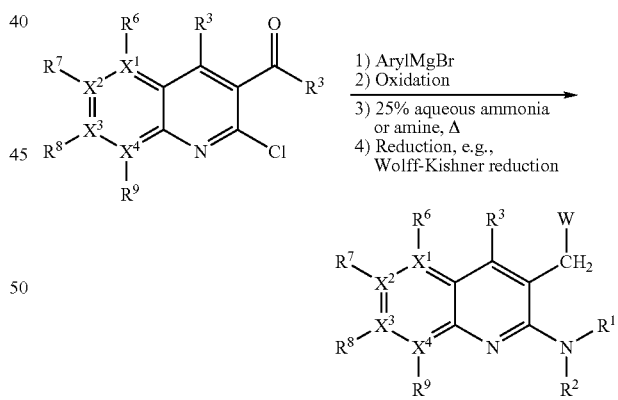

Furthermore, the synthesis of the inventive quinoline compounds from quinolines and/or naphtheridines that have been metallized in position 3 and carbonyl compounds (e.g., benzaldehyde derivatives) according to diagram 3 is also possible. Metallized aryls and hetaryls can also be synthesized by the methods described in Modern Arene Chemistry (2002), 330-367, Journal of Organometallic Chemistry (2002), 653, 150 and Angewandte Chemie (2003), 115, 4438-4456.

Diagram 3:

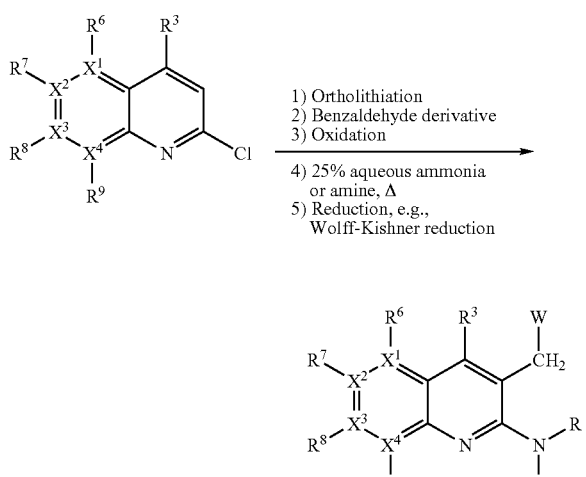

1) Ortholithiation
2) Benzaldehyde derivative
3) Oxidation
4) 25% aqueous ammonia or amine, Δ
5) Reduction, e.g., Wolff-Kishner reduction In addition, quinolines can be synthesized by many other reaction sequences, some of which have been summarized by E. Reimann in Houben-Weyl, Methoden der Organischen Chemie [Methods of Organic Chemistry]), Hetarenes II, part 1, vol. E7a, G. Thieme Verlag, Stuttgart, 1991, pages 290-493.

Synthesis of the inventive dihydroquinazoline compounds can be performed according to the sequences shown in diagrams 4 and 5 (peptide coupling: Bodansky, M., Peptide Chemistry, 1988; formation of 2-amino-3,4-dihydroquinazoline with cyanogen bromide: Chemical & Pharmaceutical Bulletin (1980), 28(5), 1357-64; formation of thiourea: Chemical & Pharmaceutical Bulletin (1988), 36, 2401-9; synthesis of S-methylisothiourea and reaction to yield 2-amino-3,4-dihydroquinazoline: Chemical & Pharmaceutical Bulletin (1980), 28, 1357-64).

Diagram 4:

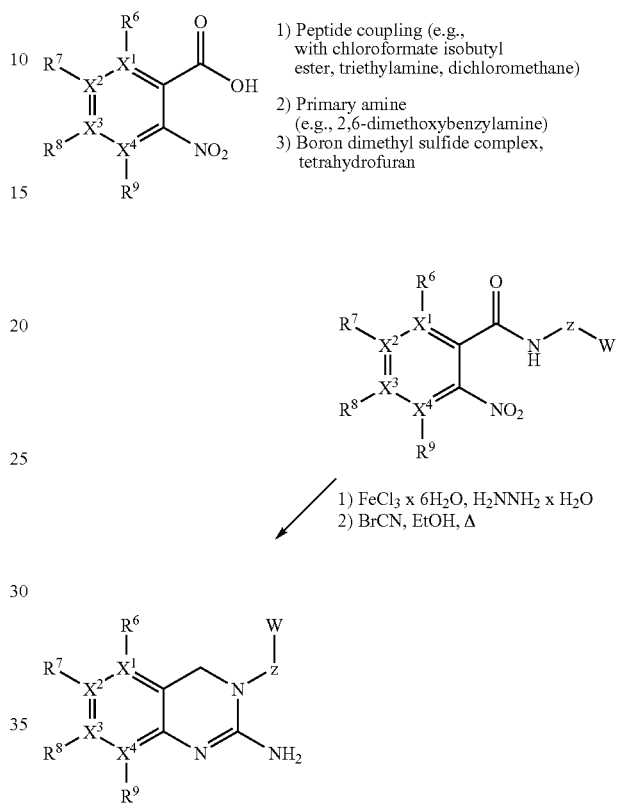

1) Peptide coupling (e.g., with chloroformate isobutyl ester, triethylamine, dichloromethane)
2) Primary amine (e.g., 2,6-dimethoxybenzylamine)
3) Boron dimethyl sulfide complex, tetrahydrofuran 1) $FeCl_3 \times 6H_2O$, $H_2NNH_2 \times H_2O$
2) BrCN, EtOH, Δ

Diagram 5:

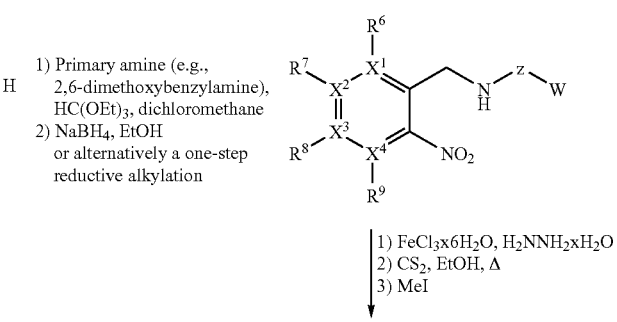

1) Primary amine (e.g., 2,6-dimethoxybenzylamine), $HC(OEt)_3$, dichloromethane
2) $NaBH_4$, EtOH
or alternatively a one-step reductive alkylation 1) $FeCl_3 \times 6H_2O$, $H_2NNH_2 \times H_2O$
2) $CS_2$, EtOH, Δ
3) MeI

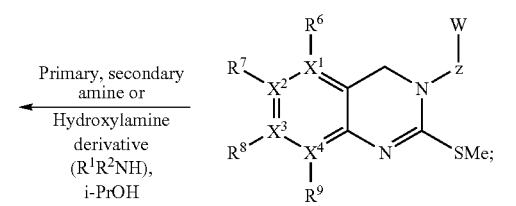

Primary, secondary amine or Hydroxylamine derivative ($R^1R^2NH$), i-PrOH

The inventive heterocycles of formula I and their precursors can be synthesized and derivatized by generally known methods (a) J. March, Advanced Organic Chemistry, New York, 2001; b) Patai, in The Chemistry of Functional Groups: The Chemistry of the Hydroxy Group, 1971; The Chemistry of the Amino Group, 1968; d) Houben-Weyl, Methoden der Organischen Chemie [Methods of Organic Chemistry]). In particular, phenolic hydroxyl groups and other azide groups (e.g., sulfonamides) can be alkylated by the Mitsunobu reaction (Organic Preparations and Procedures International (1996), 28(2), 127-64), aryl halides can be functionalized via palladium-catalyzed coupling reactions (a) Ed.: N. Niyaura, Topics in Current Chemistry, 219, Cross-Coupling Reactions, Springer, 2002; b) J. Tsuji, Palladium Reagents and Catalysts, John Wiley & Sons, 2004; c) Ed.: A. Ricci, Modern Amination methods, Wiley-VCH, 2000) and amine and aniline derivatives can be reductively alkylated, converted to similar amides under peptide linkage conditions and/or converted to similar amides, sulfonamides and/or carbamates by reaction with acid chlorides (e.g., carboxyl chlorides, sulfonyl chlorides or chloroformate esters).

The inventive heterocycles of formula I, just like the intermediates that may also be formed, can be obtained by traditional methods and purified, if necessary, e.g., by recrystallizing from conventional organic solvents, preferably a short-chain alcohol such as ethanol or with the help of chromatographic techniques.

Depending on the starting materials, the inventive heterocycles of formula [sic; formula I] are obtained in free form or already as acid addition salts. The compounds in free form as well as the resulting salts of these compounds according to this invention can be converted by known methods into the desired acid addition salts and/or into the free form.

The following examples illustrate the present invention without restricting it. It should be noted that the notation and the representation of salts with a protonated nitrogen in formulas reflect merely one of several possibilities with regard to the charge distribution that are covered as a whole. This is also true of tautomeric forms.

SYNTHESIS EXAMPLES

3-Arylpropionitriles

2-Chloro-6-methoxybenzaldehyde (Stefano Banfi; Fernando Montanari; Gianluca Pozzi; Silvio Quici, Gazz. Chim. Ital., 1993, 123, 617-622), 2-fluoro-6-methoxybenzaldehyde, 2-methoxybenzaldehyde and 2,6-dimethoxybenzaldehyde (all commercially available) were converted to the corresponding 3-arylpropionitrile derivatives by analogy with the synthesis of compound 13 in the publication by T. Honda et al. (J. Chem. Soc., Perkin Trans. 1, 1990, 5):

3-(2-Methoxyphenyl)propionitrile

ESI-MS [M+H$^+$]=162 Calculated for $C_{10}H_{11}NO$=161

3-(2,6-Dimethoxyphenyl)propionitrile

ESI-MS [M+H$^+$]=192 Calculated for $C_{11}H_{13}NO_2$=191

3-(2-Fluoro-6-methoxyphenyl)propionitrile

ESI-MS [M+H$^+$]=180 Calculated for $C_{10}H_{10}FNO$=179

3-(2-Chloro-6-methoxyphenyl)propionitrile

ESI-MS [M+H$^+$]=196 Calculated for $C_{10}H_{10}ClNO$=195

3-(2-Difluoromethoxyphenyl)propionitrile

ESI-MS [M+H$^+$]=198 Calculated for $C_{10}H_9F_2NO$=197

3-(2-Trifluoromethoxyphenyl)propionitrile

ESI-MS [M+H$^+$]=216 Calculated for $C_{10}H_8F_3NO$=215

3-(2-Ethoxyphenyl)propionitrile

ESI-MS [M+H$^+$]=176 Calculated for $C_{11}H_{13}NO$=175

2-Aminobenzaldehyde derivatives

The 2-aminobenzaldehyde derivatives that were used, inasmuch as they were not commercially available, were synthesized from the corresponding 2-nitrobenzaldehyde derivatives according to the procedure by B. A. Fox and T. L. Threllfall (Org. Syntheses, Coll. vol. V (1962), p. 346) by reduction with iron powder in ethanol and aqueous hydrochloric acid and/or with sodium dithionite in ethanol/water.

6-Amino-1,3-benzodioxole 5-carbaldehyde

ESI-MS [M+H$^+$]=166 Calculated for $C_8H_7NO_3$=165

2-Amino-4,5-dimethoxybenzaldehyde

ESI-MS [M+H$^+$]=182 Calculated for $C_9H_{11}NO_3$=181

2-Amino-5-fluorobenzaldehyde

ESI-MS [M+H$^+$]=140 Calculated for $C_7H_6FNO$=139

2-Amino-4-chlorobenzaldehyde

ESI-MS [M+H$^+$]=156 Calculated for $C_7H_6ClNO$=155

2-Amino-6-chlorobenzaldehyde

ESI-MS [M+H$^+$]=156 Calculated for $C_7H_6ClNO$=155

2-Amino-3-methoxybenzaldehyde

ESI-MS [M+H$^+$]=152 Calculated for $C_8H_9NO_2$=151

2-Aminobenzaldehyde

Product was used as a solution in dioxane in the following reaction without purification.

ESI-MS [M+H$^+$]=122 Calculated for $C_7H_7NO$=121

2-Amino-5-methoxybenzaldehyde

ESI-MS [M+H$^+$]=152 Calculated for $C_8H_9NO_2$=151

2-Amino-5-ethoxybenzaldehyde

ESI-MS [M+H$^+$]=166 Calculated for $C_8H_9NO_2$=165

2-Amino-4-(dimethylamino)benzaldehyde

ESI-MS [M+H$^+$]=165 Calculated for $C_9H_{12}N_2O$=164

2-Amino-5-morpholin-4-ylbenzaldehyde

ESI-MS [M+H$^+$]=[sic; no number] Calculated for C$_{11}$H$_{14}$N$_2$O$_2$=206

2-Amino-5-(2-methoxyethoxy)benzaldehyde

The title compound was obtained from 5-(2-methoxyethoxy)benzaldehyde (synthesized by alkylation of 5-hydroxy-2-nitrobenzaldehyde with 1-bromo-2-methoxyethane in the presence of cesium carbonate in dimethylformamide) by reduction with sodium dithionite in ethanol and water.
ESI-MS [M+H$^+$]=196.1 Calculated for C$_{10}$H$_{13}$NO$_3$=195

2-Amino-5-morpholin-4-ylbenzaldehyde

The title compound was obtained from 5-morpholin-4-yl-2-nitrobenzaldehyde (synthesized by reaction of morphine with 5-fluoro-2-nitrobenzaldehyde in the presence of potassium carbonate in dimethylformamide) by reduction with sodium dithionite in ethanol and water.
ESI-MS [M+H$^+$]=207.1 Calculated for C$_{11}$H$_{14}$N$_2$O$_2$=206

2-Amino-4-fluoro-5-morpholin-4-ylbenzaldehyde

The title compound was obtained from 4-fluoro-5-morpholin-4-yl-2-nitrobenzaldehyde by reduction with sodium dithionite in ethanol and water. 4-Fluoro-5-morpholin-4-yl-2-nitrobenzaldehyde was synthesized by reacting morpholine with 4,5-difluoro-2-nitrobenzaldehyde in the presence of potassium carbonate in dimethylformamide. 4,5-Difluoro-2-nitrobenzaldehyde was obtained by lithium aluminum hydride reduction of 4,5-difluoro-2-nitrobenzoic acid in diethyl ether and subsequent oxidation with sulfur trioxide-pyridine complex.
ESI-MS [M+H$^+$]=225 Calculated for C$_{11}$H$_{13}$FN$_2$O$_2$=224

2-Amino-5-(4-methylpiperazin-1-yl)benzaldehyde

The title compound was obtained 5-(4-methylpiperazin-1-yl)-2-nitrobenzaldehyde (synthesized by reaction of N-methylpiperazine with 5-fluoro-2-nitrobenzaldehyde in the presence of potassium carbonate in dimethylformamide) by reduction with sodium dithionite in ethanol and water.
ESI-MS [M+H$^+$]=220 Calculated for C$_{12}$H$_{17}$N$_3$O=219

Example 1

3-(2-Methoxybenzyl)quinolin-2-amine

Synthesis was performed by analogy with EXAMPLE 2 from 2-chloroquinoline and 2-methoxybenzaldehyde.
ESI-MS [M+H$^+$]=265.2 Calculated for C$_{17}$H$_{16}$N$_2$O=264

Example 2

2-[(2-Aminoquinolin-3-yl)methyl]-3-methoxyphenol

1.1 (2-Chloroquinolin-3-yl)(2,6-dimethoxyphenyl)methanol

At −78° C., a solution of 2-chloroquinoline (1.08 g, 6.6 mmol) in THF (2 mL) was added by drops to a lithium diisopropylamide solution (2M, 4.4 mL; 8.25 mmol) in THF. After stirring for 1 hour at −70° C., the mixture was heated to −20° C. within 30 minutes and then cooled back to −78° C. Next a solution of 2,6-dimethoxybenzaldehyde (1.097 g, 6.6 mmol) in THF (2 mL) was added by drops. The mixture was stirred for 1 hour at −78° C. and then for 12 hours at room temperature.

The mixture was mixed with water while cooling with ice and extracted several times with ethyl acetate. The combined organic phases were washed successively with dilute hydrochloric acid, water and saturated saline solution and then concentrated after drying (sodium sulfate). The residue was stirred with n-pentane and then purified chromatographically (silica gel, dichloromethane, methanol). Yield: 0.5 g (1.5 mmol, 23%).
ESI-MS [M+H$^+$]=330.0 Calculated for C$_{18}$H$_{16}$ClNO$_3$=329

1.2 (2-Chloroquinolin-3-yl)(2,6-dimethoxyphenyl)methanone (2-Chloroquinolin-3-yl)(2,6-dimethoxyphenyl)methanol (0.5 g, 1.5 mmol) and triethylamine (0.84 mL, 6.1 mmol) were dissolved in dimethyl sulfoxide (20 mL) and mixed with a solution of sulfur trioxide-pyridine complex (0.72 g, 4.55 mol) in dimethyl sulfoxide (5 mL) under nitrogen. The batch was stirred at room temperature until the reaction was complete (TLC monitoring). After adding water, the mixture was stirred for 1 hour at room temperature. The precipitated product was filtered with suction, washed with water and dried in a vacuum drying cabinet (20 mbar, 50° C.). Yield: 0.45 g (1.37 mmol, 91%).
ESI-MS [M+H$^+$]=328.1 Calculated for C$_{18}$H$_{14}$ClNO$_3$=327

1.3 (2-Aminoquinolin-3-yl)(2,6-dimethoxyphenyl)methanone (2-Chloroquinolin-3-yl)(2,6-dimethoxyphenyl)methanone (2.0 g, 6.1 mmol) was dissolved in dioxane (15 mL), mixed with 25% aqueous ammonia solution (10 mL) and heated to 150° C. under its own pressure for 24 hours in a pressurized reactor. The reaction mixture was diluted with dichloromethane and washed several times with water. The organic phase was dried (sodium sulfate) and concentrated. The crude product was purified by chromatography (silica gel, dichloromethane, methanol). Yield: 1.15 g (3.73 mmol, 61%).
ESI-MS [M+H$^+$]=309.1 Calculated for C$_{18}$H$_{16}$N$_2$O$_3$=308

1.4 2[(2-Aminoquinolin-3-yl)methyl]-3-methoxyphenol (2-Aminoquinolin-3-yl)(2,6-dimethoxyphenyl)methanone (0.19 g, 0.6 mmol) was dissolved in diethylene glycol (10 mL), mixed with hydrazine hydrate (0.19 mL, 6.1 mmol) and pulverized potassium hydroxide (0.27 g, 6.7 mmol) and heated for 2 hours at 160° C. The same amounts of hydrazine hydrate and potassium hydroxide were added two more times and the reaction mixture was stirred for two more hours each time at 160° C.

After cooling, the batch was mixed with saline solution and extracted repeatedly with ethyl acetate. The combined organic phases were washed with water, dried (sodium sulfate) and concentrated. The slightly contaminated product was recrystallized from methanol. Yield: 40 mg (0.14 mmol, 23%).
ESI-MS [M+H$^+$]=281.0 Calculated for C$_{17}$H$_{16}$N$_2$O$_2$=280

Example 3

3-(2,6-Dimethoxybenzyl)quinolin-2-amine

2-[(2-Aminoquinolin-3-yl)methyl]-3-methoxyphenol (40 mg, 0.14 mmol), triphenylphosphine (56 mg, 0.21 mmol) and methanol (7 µL, 0.22 mmol) were placed in THF (2 mL) at 10° C. and then mixed slowly with azodicarboxylate diisopropyl ester (44 mg, 0.22 mmol) in THF (1 mL). Then the mixture was stirred for 12 hours at room temperature. The batch was mixed with water and extracted with ethyl acetate. The combined organic phases were washed with water, dried (sodium sulfate) and concentrated. The crude product was purified chromatographically (silica gel, dichloromethane, methanol). To remove traces of triphenylphosphine oxide, the slightly contaminated product was dissolved in diethyl ether and extracted with 2N aqueous hydrochloric acid. The aqueous phase was alkalized with dilute sodium hydroxide solution and extracted with dichloromethane. The combined dichloromethane extracts were washed with water until neutral, dried (sodium sulfate) and concentrated (yield: 5 mg, 9%).

ESI-MS [M+H$^+$]=295.1 Calculated for $C_{18}H_{18}N_2O_2$=294

Example 4

3-(2-Ethoxy-6-methoxybenzyl)quinolin-2-amine

Synthesis was performed according to EXAMPLE 3 from 2-[(2-aminoquinolin-3-yl)methyl]-3-methoxyphenol and ethanol.

ESI-MS [M+H$^+$]=309.1 Calculated for $C_{19}H_{20}N_2O_2$=308

Example 5

3-(2-Isopropoxy-6-methoxybenzyl)quinolin-2-amine

Synthesis was performed according to EXAMPLE 3 from 2-[(2-aminoquinolin-3-yl)methyl]-3-methoxyphenol and isopropanol.

ESI-MS [M+H$^+$]=323.1 Calculated for $C_{20}H_{22}N_2O_2$=322

Example 6

7-Methoxy-3-(2-methoxybenzyl)quinolin-2-amine

Synthesis was performed according to EXAMPLE 7 from 2-chloro-7-methoxyquinoline-3-carbaldehyde and 2-methoxyphenyl magnesium bromide.

ESI-MS [M+H$^+$]=295.1 Calculated for $C_{18}H_{18}N_2O_2$=294

Example 7

6-Methoxy-3-(2-methoxybenzyl)quinolin-2-amine

1. (2-Chloro-6-methoxyquinolin-3-yl)(2-methoxyphenyl)methanol

2-Chloro-6-methoxyquinoline-3-carbaldehyde (2.66 g, 12 mmol) was dissolved in THF (40 mL) under nitrogen and cooled to −78° C. At this temperature, a solution of 2-methoxyphenyl magnesium bromide (1M, 12.1 mL, 13.32 mmol) in THF was added by drops. Then the mixture was heated slowly to room temperature. The batch was mixed with water and extracted several times with ethyl acetate. The combined organic phases were washed with water until neutral, dried (sodium sulfate) and concentrated. Yield: 3.9 g (11.8 mmol, 99%).

ESI-MS [M+H$^+$]=330.0 Calculated for $C_{18}H_{16}ClNO_3$=329

2. (2-Chloro-6-methoxyquinolin-3-yl)(2-methoxyphenyl)methanone (2-Chloro-6-methoxyquinolin-3-yl)(2-methoxyphenyl)methanol (3.8 g, 11.5 mmol) and triethylamine (6.4 mL, 46.1 mmol) were dissolved in dimethyl sulfoxide (70 mL). Then a solution of sulfur trioxide-pyridine complex (5.5 g, 34.6 mmol) in dimethyl sulfoxide (80 mL) was added by drops at room temperature. Next the mixture was stirred for 12 hours at room temperature.

The batch was mixed with water and stirred for 2 hours at room temperature. The crystalline raw product was filtered with suction, washed with water and dried in a vacuum drying cabinet (20 mbar, 50° C.). Yield: 3.4 g (10.4 mmol, 90%).

ESI-MS [M+H$^+$]=328.0 Calculated for $C_{18}H_{14}ClNO_3$=327

3. (2-Amino-6-methoxyquinolin-3-yl)(2-methoxyphenyl)methanone (2-Chloro-6-methoxyquinolin-3-yl)(2-methoxyphenyl)methanone (3.4 g, 10.4 mmol) was dissolved in dioxane (25 mL), mixed with 25% aqueous ammonia solution (15 mL) and heated for 30 hours to 150° C. under intrinsic pressure in the pressurized reactor. After cooling, the reaction mixture was diluted with methanol, prepurified with activated carbon and concentrated after filtration. The crude product was dissolved in dichloromethane and washed with water. The dichloromethane solution was dried (sodium sulfate) and concentrated. The crude product was purified chromatographically (silica gel, dichloromethane, 0-2% methanol). Yield: 1.4 g (4.5 mmol, 44%).

ESI-MS [M+H$^+$]=309.0 Calculated for $C_{18}H_{16}N_2O_3$=308

4. 6-Methoxy-3-(2-methoxybenzyl)quinolin-2-amine (2-Amino-6-methoxyquinolin-3-yl)(2-methoxyphenyl)methanone (1.1 g, 3.6 mmol) was dissolved in diethylene glycol (15 mL), mixed with hydrazine hydrate (0.56 mL, 18 mmol) and pulverized potassium hydroxide (1.1 g, 19.8 mmol) and heated to 160° C. for 1.5 hours.

After cooling, the mixture was diluted with ice water and stirred for 30 minutes at room temperature. The batch was extracted several times with ethyl acetate. The combined organic phases were dried (sodium sulfate) and concentrated. The crude product was purified chromatographically (silica gel, dichloromethane, 0-1% methanol). The product was then recrystallized from water/methanol. Yield: 0.11 g (0.37 mmol, 10.4%).

ESI-MS [M+H$^+$]=295.1 Calculated for $C_{18}H_{18}N_2O_2$=294

Example 8

6-Methoxy-3-(2-methoxybenzyl)quinolin-2-amine hydrochloride

ESI-MS [M+H$^+$]=295.1 Calculated for $C_{18}H_{18}N_2O_2$=294

Example 9

6-Chloro-3-(2,6-dimethoxybenzyl)quinolin-2-amine

The title compound was synthesized according to EXAMPLE 11 from 2-amino-5-chlorobenzaldehyde and 3-(2,6-dimethoxyphenyl)propionitrile. Instead of dioxane, tert-butanol was used from [sic; as][1] the solvent.

[1] TN: "aus" (from) appears to be a typo for "als" (as).

ESI-MS [M+H$^+$]=329.1 Calculated for $C_{18}H_{17}ClN_2O_2$=328

Example 10

6-Chloro-3-(2-fluoro-6-methoxybenzyl)quinolin-2-amine

The title compound was synthesized according to EXAMPLE 11 from 2-amino-5-chlorobenzaldehyde and 3-(2-fluoro-6-methoxyphenyl)propionitrile. Instead of dioxane, tert-butanol was used from [sic; as] the solvent. Reaction time: 5 minutes at 120° C.

ESI-MS [M+H$^+$]=317.0 Calculated for $C_{17}H_{14}ClFN_2O$=316

Example 11

6-Chloro-3-(2-methoxybenzyl-quinolin-2-amine

2-Amino-5-chlorobenzaldehyde (78 mg, 0.5 mmol), 3-(2-methoxyphenyl)propionitrile (81 mg, 0.5 mmol) and potassium tert-butylate (112 mg, 1.0 mmol) in dioxane were heated in a microwave (10 minutes, 140° C., 3 bar). The batch was mixed with water, extracted with dichloromethane and the combined organic phases were washed with saturated saline solution. After drying (sodium sulfate), the crude product was purified chromatographically (silica gel, dichloromethane/methanol) and the product purified in this way was stirred with methyl tert-butyl ether to remove 3-(2-methoxyphenyl)propanamide formed during the reaction. Recrystallization from methanol/water was used for the final purification (yield: 32 mg, 21%).

ESI-MS [M+H$^+$]=299.0 Calculated for $C_{17}H_{15}ClN_2O$=298

Example 12

7-(2,6-Dimethoxybenzyl[1.3]dioxolo[4.5-g]quinolin-6-amine

The title compound was synthesized according to EXAMPLE 11 from 6-amino-1,3-benzodioxole 5-carbaldehyde and 3-(2,6-dimethoxyphenyl)propionitrile.

ESI-MS [M+H$^+$]=339.0 Calculated for $C_{19}H_{18}N_2O_4$=338

Example 13

3-(2,6-Dimethoxybenzyl)-6,7-dimethoxy-quinolin-2-amine

The title compound was synthesized according to EXAMPLE 11 from 2-amino-4,5-dimethyl-benzaldehyde and 3-(2,6-dimethoxyphenyl)propionitrile.

ESI-MS [M+H$^+$]=355.1 Calculated for $C_{20}H_{22}N_2O_4$=354

Example 14

7-(2-Methoxybenzyl)[1.3]dioxolo[4.5-g]quinolin-6-amine

The title compound was synthesized according to EXAMPLE 11 from 6-amino-1,3-benzodioxole 5-carbaldehyde and 3-(2-methoxyphenyl)propionitrile.

ESI-MS [M+H$^+$]=309.1 Calculated for $C_{18}H_{16}N_2O_3$=308

Example 15

7-Chloro-3-(2-methoxybenzyl)quinolin-2-amine

The title compound was synthesized according to EXAMPLE 11 from 2-amino-4-chlorobenzaldehyde and 3-(2-methoxyphenyl)propionitrile.

ESI-MS [M+H$^+$]=299.0 Calculated for $C_{17}H_{15}ClN_2O$=298

Example 16

6,7-Dimethoxy-3-(2-methoxybenzyl)quinolin-2-amine

The title compound was synthesized according to EXAMPLE 11 from 2-amino-4,5-dimethoxybenzaldehyde and 3-(2-methoxyphenyl)propionitrile.

ESI-MS [M+H$^+$]=325.1 Calculated for $C_{19}H_{20}N_2O_3$=324

Example 17

7-(2-Fluoro-6-methoxybenzyl)[1.3]dioxolo[4.5-g]quinolin-6-amine

The title compound was synthesized according to EXAMPLE 11 from 6-amino-1,3-benzodioxole 5-carbaldehyde and 3-(2-fluoro-6-methoxyphenyl)propionitrile.

ESI-MS [M+H$^+$]=327.0 Calculated for $C_{18}H_{15}FN_2O_3$=326

Example 18

6-Fluoro-3-(2-methoxybenzyl)quinolin-2-amine

The title compound was synthesized according to EXAMPLE 11 from 2-amino-5-fluorobenzaldehyde and 3-(2-methoxyphenyl)propionitrile.

ESI-MS [M+H$^+$]=283.3 Calculated for $C_{17}H_{15}FN_2O$=282

Example 19

5-Chloro-3-(2-methoxybenzyl)quinolin-2-amine

The title compound was synthesized according to EXAMPLE 11 from 2-amino-6-chlorobenzaldehyde and 3-(2-methoxyphenyl)propionitrile.

ESI-MS [M+H$^+$]=299.0 Calculated for $C_{17}H_{15}ClN_2O$=298

Example 20

5-Chloro-3-(2,6-dimethoxybenzyl)quinolin-2-amine

The title compound was synthesized according to EXAMPLE 11 from 2-amino-4-chlorobenzaldehyde and 3-(2,6-dimethoxyphenyl)propionitrile.

ESI-MS [M+H$^+$]=329.0 Calculated for $C_{18}H_{17}ClN_2O_2$=328

Example 21

3-(2,6-Dimethoxybenzyl)-1,8-naphthyridin-2-amine

The title compound was synthesized according to EXAMPLE 11 from 2-aminopyridine-3-carboxaldehyde and 3-(2,6-dimethoxyphenyl)propionitrile.

ESI-MS [M+H$^+$]=296.1 Calculated for $C_{17}H_{17}N_3O_2$=295

Example 22

3-(2,6-Dimethoxybenzyl)-1,6-naphthyridin-2-amine

The title compound was synthesized according to EXAMPLE 11 from 4-amino-3-pyridine carboxaldehyde hydrochloride and 3-(2,6-dimethoxyphenyl)propionitrile. One equivalent of potassium tert-butylate was additionally used.

ESI-MS [M+H$^+$]=296.1 Calculated for $C_{17}H_{17}N_3O_2$=295

Example 23

3-(2,6-Dimethoxybenzyl)-6-fluoroquinolin-2-amine

The title compound was synthesized according to EXAMPLE 11 from 2-amino-5-fluorobenzaldehyde and 3-(2,6-dimethoxyphenyl)propionitrile.

ESI-MS [M+H$^+$]=313.1 Calculated for $C_{18}H_{17}FN_2O_2$=312

Example 24

6-Fluoro-3-(2-fluoro-6-methoxybenzyl)quinolin-2-amine

The title compound was synthesized according to EXAMPLE 11 from 2-amino-5-fluorobenzaldehyde and 3-(2-fluoro-6-methoxyphenyl)propionitrile. Reaction temperature 100° C.

ESI-MS [M+H$^+$]=301.0 Calculated for $C_{17}H_{14}F_2N_2O$=300

Example 25

2-[(2-Aminoquinolin-3-yl)methyl]phenol 3-(2-Methoxybenzyl)quinolin-2-amine (53 mg, 0.2 mmol) was mixed with boron tribromide solution in dichloromethane (1M, 0.4 mL, 0.4 mmol) in dichloromethane [sic; duplication] at −78° C. After thawing, the mixture was stirred for 12 hours at room temperature. The batch was mixed with water, extracted with dichloromethane and the combined organic phases were washed with sodium hydroxide solution (1M), water and saturated saline solution until neutral. After drying (sodium sulfate), the crude product was stirred with methyl tert-butyl ether and recrystallized from methanol/water (yield: 28 mg, 56%).

ESI-MS [M+H$^+$]=251.1 Calculated for $C_{16}H_{14}N_2O$=250

Example 26

7-Chloro-3-(2-fluoro-6-methoxybenzyl)quinolin-2-amine

The title compound was synthesized according to EXAMPLE 11 from 2-amino-4-chlorobenzaldehyde and 3-(2-fluoro-6-methoxyphenyl)propionitrile.

ESI-MS [M+H$^+$]=317.0 Calculated for $C_{17}H_{14}ClFN_2O$=316

Example 27

7-Chloro-3-(2-chloro-6-methoxybenzyl)quinolin-2-amine

The title compound was synthesized according to EXAMPLE 11 from 2-amino-4-chlorobenzaldehyde and 3-(2-chloro-6-methoxyphenyl)propionitrile.

ESI-MS [M+H$^+$]=333.0 Calculated for $C_{17}H_{14}Cl_2N_2O$=332

Example 28

3-(2-Methoxybenzyl)-N$^7$,N$^7$-dimethylquinolin-2,7-diamine

The title compound was synthesized according to EXAMPLE 11 from 2-amino-4-dimethylaminobenzaldehyde and 3-(2-methoxyphenyl)propionitrile. The reaction was performed thermally (45 min, 70-80° C.).

ESI-MS [M+H$^+$]=308.1 Calculated for $C_{19}H_{21}N_3O$=307

Example 29

3-(2-Fluoro-6-methoxybenzyl)quinolin-2-amine

The title compound was synthesized according to EXAMPLE 11 from 2-aminobenzaldehyde and 3-(2-fluoro-6-methoxyphenyl)propionitrile.

ESI-MS [M+H$^+$]=283.1 Calculated for $C_{17}H_{15}FN_2O$=282

Example 30

3-(2-Chloro-6-methoxybenzyl)quinolin-2-amine

The title compound was synthesized according to EXAMPLE 11 from 2-aminobenzaldehyde and 3-(2-chloro-6-methoxyphenyl)propionitrile.

ESI-MS [M+H$^+$]=299.0 Calculated for $C_{17}H_{15}ClN_2O$=298

Example 31

6-Ethoxy-3-(2-methoxybenzyl)quinolin-2-amine

The title compound was synthesized according to EXAMPLE 11 from 2-amino-5-ethoxybenzaldehyde and 3-(2-methoxyphenyl)propionitrile.

ESI-MS [M+H$^+$]=309.1 Calculated for $C_{19}H_{20}N_2O_2$=308

Example 32

6-Ethoxy-3-(2,6-dimethoxybenzyl)quinolin-2-amine

The title compound was synthesized according to EXAMPLE 11 from 2-amino-5-ethoxybenzaldehyde and 3-(2,6-dimethoxyphenyl)propionitrile.

ESI-MS [M+H$^+$]=339.1 Calculated for $C_{20}H_{22}N_2O_3$=338

Example 33

3-(2-Methoxybenzyl)-1,6-naphthyridin-2-amine

The title compound was synthesized according to EXAMPLE 11 from 4-aminonicotinaldehyde and 3-(2-methoxyphenyl)propionitrile.

ESI-MS [M+H$^+$]=266.0 Calculated for $C_{16}H_{15}N_3O$=265

Example 34

3-(2-Methoxybenzyl)-1,8-naphthyridin-2-amine

The title compound was synthesized according to EXAMPLE 11 from 2-aminopyridin-3-carboxaldehyde and 3-(2-methoxyphenyl)propionitrile.
ESI-MS [M+H$^+$]=266.0 Calculated for $C_{16}H_{15}N_3O$=265

Example 35

3-(2-Fluoro-6-methoxybenzyl)-1,6-naphthyridin-2-amine

The title compound was synthesized according to EXAMPLE 11 from 4-aminonicotinaldehyde and 3-(2-methoxy-6-fluorophenyl)propionitrile.
ESI-MS [M+H$^+$]=284.0 Calculated for $C_{16}H_{14}FN_3O$=283

Example 36

3-(2-Methoxybenzyl)-1,7-naphthyridin-2-amine

The title compound was synthesized according to EXAMPLE 11 from 3-amino-4-pyridine carboxaldehyde and 3-(2-methoxyphenyl)propionitrile.
ESI-MS [M+H$^+$]=266.0 Calculated for $C_{16}H_{15}N_3O$=265

Example 37

3-(2,6-Dimethoxybenzyl)-1,7-naphthyridin-2-amine

The title compound was synthesized according to EXAMPLE 11 from 3-amino-4-pyridine carboxaldehyde and 3-(2,6-dimethoxyphenyl)propionitrile
ESI-MS [M+H$^+$]=296.1 Calculated for $C_{17}H_{17}N_3O_2$=295

Example 38

3-(2-Methoxybenzyl)-1,5-naphthyridin-2-amine

The title compound was synthesized according to EXAMPLE 11 from 3-amino-2-pyridine carboxaldehyde trifluoroacetate (in turn synthesized from (2-formylpyridin-3-yl)carbamate tert-butyl ester by treatment with trifluoroacetic acid) and 3-(2-methoxyphenyl)propionitrile. One equivalent of potassium tert-butylate was additionally used.
ESI-MS [M+H$^+$]=266.0 Calculated for $C_{16}H_{15}N_3O$=265

Example 39

7-Fluoro-3-(2-methoxybenzyl)quinolin-2-amine

The title compound was synthesized according to EXAMPLE 11 from 2-amino-4-fluorobenzaldehyde and 3-(2-methoxyphenyl)propionitrile.
ESI-MS [M+H$^+$]=283.1 Calculated for $C_{17}H_{15}FN_2O$=282

Example 40

7-(2-Chloro-6-methoxybenzyl)[1,3]dioxolo[4,5-g]quinolin-76-amine

The title compound was synthesized according to EXAMPLE 11 from 6-amino-1,3-benzodioxole 5-carbaldehyde and 3-(2-chloro-6-methoxyphenyl)propionitrile.
ESI-MS [M+H$^+$]=343.0 Calculated for $C_{18}H_{15}ClN_2O_3$=342

Example 41

6,7-Difluoro-3-(2-methoxybenzyl)quinolin-2-amine

The title compound was synthesized according to EXAMPLE 11 from 2-amino-4,5-difluorobenzaldehyde and 3-(2-methoxyphenyl)propionitrile.
ESI-MS [M+H$^+$]=301.1 Calculated for $C_{17}H_{14}F_2N2O$=300

Example 42

7-Fluoro-3-(2-fluoro-6-methoxybenzyl)quinolin-2-amine

The title compound was synthesized according to EXAMPLE 11 from 2-amino-4-fluorobenzaldehyde and 3-(2-methoxy-6-fluorophenyl)propionitrile.
ESI-MS [M+H$^+$]=301.1 Calculated for $C_{17}H_{14}F_2N_2O$=300

Example 43

3-(2-Methoxybenzyl)-6-(2-methoxyethoxy)quinolin-2-amine

The title compound was synthesized according to EXAMPLE 11 from 2-amino-5-(2-methoxy-ethoxy)benzaldehyde and 3-(2-methoxyphenyl)propionitrile.
ESI-MS [M+H$^+$]=339.1 Calculated for $C_{20}H_{22}N_2O_3$=338

Example 44

3-(2-Methoxybenzyl)-6-morpholin-4-ylquinolin-2-amine

The title compound was synthesized according to EXAMPLE 11 from 2-amino-5-morpholin-4-ylbenzaldehyde and 3-(2-methoxyphenyl)propionitrile.
ESI-MS [M+H$^+$]=350.1 Calculated for $C_{21}H_{23}N_3O_2$=349

Example 45

3-(2-Methoxy-6-fluorobenzyl)-6-morpholin-4-ylquinolin-2-amine

The title compound was synthesized according to EXAMPLE 11 from 2-amino-5-morpholin-4-ylbenzaldehyde and 3-(2-methoxy-6-fluorophenyl)propionitrile.
ESI-MS [M+H$^+$]=368.1 Calculated for $C_{21}H_{22}FN_3O_2$=367

Example 46

3-(2,6-Dimethoxybenzyl)-1,5-naphthyridin-2-amine

The title compound was synthesized according to EXAMPLE 11 from 3-aminopyridin-2-carbaldehyde and 3-(2,6-dimethoxyphenyl)propionitrile.
ESI-MS [M+H$^+$]=296 Calculated for $C_{17}H_{17}N_3O_2$=295

Example 47

3-(2-Fluoro-6-methoxybenzyl)-1,5-naphthyridin-2-amine

The title compound was synthesized according to EXAMPLE 11 from 3-aminopyridin-2-carbaldehyde and 3-(2-fluoro-6-methoxyphenyl)propionitrile.
ESI-MS [M+H$^+$]=284 Calculated for $C_{16}H_{14}FN_3O$=283

Example 48

3-(2-Methoxybenzyl)-6-(4-methylpiperazin-1-yl)quinolin-2-amine bisfumarate

The title compound was synthesized according to EXAMPLE 11 from 2-amino-5-(4-methylpiperazin-1-yl)benzaldehyde and 3-(2-methoxyphenyl)propionitrile.
ESI-MS [M+H$^+$]=363 Calculated for $C_{22}H_{26}N_4O$=362

Example 49

3-(2-Fluoro-6-methoxybenzyl)-6-(4-methylpiperazin-1-yl)quinolin-2-aminomonofumarate The title compound was synthesized according to EXAMPLE 11 from 2-amino-5-(4-methylpiperazin-1-yl)benzaldehyde and 3-(2-fluoro-6-methoxyphenyl)propionitrile.
ESI-MS [M+H$^+$]=381 Calculated for $C_{22}H_{25}FN_4O$=380

Example 50

7-Fluoro-3-(2-methoxybenzyl)-6-morpholin-4-ylquinolin-2-amine

The title compound was synthesized according to EXAMPLE 11 from 2-amino-4-fluoro-5-morpholin-4-yl-benzaldehyde and 3-(2-methoxyphenyl)propionitrile.
ESI-MS [M+H$^+$]=368 Calculated for $C_{21}H_{22}FN_3O_2$=367

Example 51

8-Methoxy-3-(2-methoxybenzyl)quinolin-2-amine

The title compound was synthesized according to EXAMPLE 11 from 2-amino-3-methoxybenzaldehyde and 3-(2-methoxyphenyl)propionitrile.
ESI-MS [M+H$^+$]=295 Calculated for $C_{18}H_{18}N_2O_2$=294

Example 52

3-(2,6-Dimethoxybenzyl)-8-methoxyquinolin-2-amine hydrochloride

The title compound was synthesized according to EXAMPLE 11 from 2-amino-3-methoxybenzaldehyde and 3-(2,6-dimethoxyphenyl)propionitrile.
ESI-MS [M+H$^+$]=325 Calculated for $C_{19}H_{20}N_2O_3$=324

Example 53

3-[2-(Trifluoromethoxy)benzyl]quinolin-2-amine

The title compound was synthesized according to EXAMPLE 11 from 2-aminobenzaldehyde and 3-(2-trifluoromethoxyphenyl)propionitrile.
ESI-MS [M+H$^+$]=319 Calculated for $C_{18}H_{17}ClN_2O_2$=318

Example 54

3-(2-Isopropoxybenzyl)quinolin-2-amine hydrochloride

The title compound was synthesized from 2-[(2-aminoquinolin-3-yl)methyl]phenol and isopropanol according to EXAMPLE 3.
ESI-MS [M+H$^+$]=293 Calculated for $C_{19}H_{20}N_2O$=292

Example 55

3-(2-Ethoxybenzyl)quinolin-2-amine hydrochloride

The title compound was synthesized from 2-[(2-aminoquinolin-3-yl)methyl]phenol and ethanol according to EXAMPLE 3.
ESI-MS [M+H$^+$]=279 Calculated for $C_{18}H_{18}N_2O$=278

Example 56

3-(2-Fluoro-6-isopropoxybenzyl)quinolin-2-amine hydrochloride

The title compound was synthesized from 2-[(2-aminoquinolin-3-yl)methyl]-3-fluorophenol and isopropanol according to EXAMPLE 3. 2-[(2-Aminoquinolin-3-yl)methyl]-3-fluorophenol was synthesized according to EXAMPLE 25 from 3-(2-fluoro-6-methoxybenzyl)quinolin-2-amine by reaction with boron tribromide.
ESI-MS [M+H$^+$]=311 Calculated for $C_{19}H_{19}FN_2O$=310

Example 57

3-(2-Chloro-6-methoxybenzyl)-1,6-naphthyridin-2-amine

The title compound was synthesized according to EXAMPLE 11 from 4-aminonicotinaldehyde and 3-(2-chloro-6-methoxyphenyl)propionitrile.
ESI-MS [M+H$^+$]=300 Calculated for $C_{16}H_{14}ClN_3O$=299

Example 58

3-(2-Chloro-6-methoxybenzyl)-1,5-naphthyridin-2-amine

The title compound was synthesized according to EXAMPLE 11 from 3-aminopyridine-2-carbaldehyde and 3-(2-chloro-6-methoxyphenyl)propionitrile.
ESI-MS [M+H$^+$]=300 Calculated for $C_{18}H_{14}ClN_3O$=299

Example 59

3-(2-Ethoxy-6-fluorobenzyl)quinolin-2-amine hydrochloride

The title compound was synthesized from 2-[(2-aminoquinolin-3-yl)methyl]-3-fluorophenol and ethanol according to EXAMPLE 3.
ESI-MS [M+H$^+$]=297 Calculated for $C_{18}H_{17}FN_2O$=296

Example 60

3-{2-[2-(Dimethylamino)ethoxy]-6-fluorobenzyl}quinolin-2-amine bishydrochloride

The title compound was synthesized from 2-[(2-aminoquinolin-3-yl)methyl]-3-fluorophenol and 2-(dimethylamino)ethanol according to EXAMPLE 3.
ESI-MS [M+H$^+$]=340 Calculated for $C_{20}H_{22}FN_3O$=339

Example 61

3-[2-(difluoromethoxy)benzyl]quinolin-2-amine

The title compound was synthesized according to EXAMPLE 11 from 2-aminobenzaldehyde and 3-(2-difluoromethoxyphenyl)propionitrile.
ESI-MS [M+H$^+$]=301 Calculated for $C_{17}H_{14}F_2N_2O$=300

Example 62

3-(2-Ethoxygenzyl)-6-morpholin-4-ylquinolin-2-amine monofumarate

The title compound was synthesized according to EXAMPLE 11 from 2-amino-5-morpholin-4-ylbenzaldehyde and 3-(2-ethoxyphenyl)propionitrile.
ESI-MS [M+H$^+$]=323 Calculated for $C_{22}H_{25}N_3O_2$=322

Example 63

3-(2,6-Dimethoxybenzyl)-3,4-dihydroquinazolin-2-amine acetate

1.5 N-(2,6-Dimethoxybenzyl)-2-nitrobenzamide 4 g 2-nitrobenzoic acid (23.93 mmol) and 2.42 g triethylamine were dissolved in 100 mL dichloromethane, mixed with one equivalent isobutyl chloroformate (3.27 g) at 5° C. and stirring was continued for 1 hour at room temperature. Then the mixture was cooled again to 5° C., 4.02 g 2,6-dimethoxybenzylamine was added and the mixture was stirred at room temperature until the reaction was complete. For workup, the mixture was diluted with dichloromethane, washed twice each with 10% citric acid, saturated NaHCO$_3$ and saturated NaCl solution, dried with MgSO$_4$, filtered and concentrated, yielding 7.5 g beige solids that were reacted further directly without any further workup.
ESI-MS [M+H$^+$]=317.15.

1.6 (2,6-Dimethoxybenzyl)(2-nitrobenzyl)amine 7.5 g (23.71 mmol) N-(2,6-dimethoxybenzyl)-2-nitrobenzamide was dissolved in 130 mL THF, then 9.06 g borondimethyl sulfide-complex (2M solution in THF) was added by drops and the mixture was refluxed for 5 hours. Next 50 mL 2N HCl was added and the mixture was heated again at reflux for 30 minutes. For workup, the mixture was poured into water after cooling, a pH of approx. 10 was adjusted by adding 2N NaOH, further extraction was performed with ethyl acetate and the combined organic phases were dried with MgSO$_4$. The crude product obtained by chromatography on silica gel (dichloromethane, 0-5% methanol) after filtration and evaporation yielded the desired amine; 3.58 g as a light yellow oil. ESI-MS [M+H$^+$]=302.15.

1.7 (2-Aminobenzyl)(2,6-dimethoxybenzyl)amine

At 60° C., 2.3 mL hydrazine hydrate was added by drops to a suspension of 3.58 g (11.84 mmol) (2,6-dimethoxybenzyl)(2-nitrobenzyl)amine (Example 1.1), 3.5 g activated carbon and 50 mg FeCl$_3$×6H$_2$O in 60 mL methanol and then the mixture was stirred for 1 hour at 60° C. Cooling, filtering the reaction mixture through Celite and evaporating yielded 2.78 g of the target product as a clear oil. ESI-MS [M+H$^+$]=273.15.

1.8 3-(2,6-Dimethoxybenzyl)-3,4-dihydroquinazolin-2-amine acetate

A mixture of 2.78 g (10.21 mmol) (2-aminobenzyl)(2,6-dimethoxybenzyl)amine and 1.5 g BrCN in 60 mL ethanol was heated at reflux for 10 hours. After evaporation, the resulting residue was dissolved in a small amount of dioxane, mixed with one equivalent 4N HCl in dioxane, the resulting solids were filtered out and dried. The resulting crude product was purified by MPLC (silica gel: Bischoff Prontoprep 60-2540-C18E, 32 μm; mobile phase: CH$_3$CN/H$_2$O+0.1% acetic acid), the resulting product was then dissolved in acetone and converted to the corresponding acetate by adding one equivalent of glacial acetic acid. Stirring the resulting solids [in] n-pentane and drying yielded 580 mg white solids.
ESI-MS [M+H$^+$]=298.15 Calculated for $C_{17}H_{19}N_3O_2$=297
$^1$H-NMR (400 MHz, DMSO-d6), δ (ppm)=1.80 (s, 3H), 3.80 (s, 6H), 4.35 (s, 2H), 4.60 (s, 2H), 6.75 (d, 2H), 6.90 (m, 2H), 7.05 (m, 1H), 7.20 (m, 1H), 7.35 (m, 1H).

The following were synthesized by analogy with EXAMPLE 63:

Example 64

3-(2-Methoxybenzyl)-3,4-dihydroquinazolin-2-amine hydrochloride

ESI-MS [M+H$^+$]=268.15 Calculated for $C_{16}H_{17}N_3O$=267
$^1$H-NMR (400 MHz, DMSO-d6), δ (ppm)=3.80 (s, 3H), 4.50 (s, 2H), 4.70 (s, 2H), 7.05 (m, 2H), 7.15 (m, 2H), 7.23 (m, 1H), 7.28 (m, 1H), 7.35 (m, 1H), 8.05 (s, 2H), 11.10 (s, 1H).

Example 65

7-Chloro-3-(2-methoxybenzyl)-3,4-dihydroquinazolin-2-amine

ESI-MS [M+H$^+$]=302.15 Calculated for $C_{16}H_{16}ClN_3$=301

Example 66

3-(2-Methoxybenzyl)-7-(trifluoromethyl)-3,4-dihydroquinazolin-2-amine hydrochloride

ESI-MS [M+H$^+$]=336.15 Calculated for $C_{17}H_{16}F_3N_3O$=335

Example 67

3-(4-Chloro-2-methoxybenzyl)-3,4-dihydroquinazolin-2-amine hydrochloride

ESI-MS [M+H$^+$]=302.05 Calculated for $C_{16}H_{16}ClN_3O$=301

Example 68

3-(2,3-Dihydro-1-benzofuran-7-ylmethyl)-3,4-dihydroquinazolin-2-amine hydrochloride ESI-MS [M+H$^+$]=280.15 Calculated for C$_{17}$H$_{17}$N$_3$O=279

Example 69

3-[2-(Trifluoromethoxy)benzyl]-3,4-dihydroquinazolin-2-amine

ESI-MS [M+H$^+$]=322.15 Calculated for C$_{16}$H$_{14}$F$_3$N$_3$O=321

Example 70

3-(2,4-Dimethoxybenzyl)-3,4-dihydroquinazolin-2-amine

ESI-MS [M+H$^+$]=298.15 Calculated for C$_{17}$H$_{19}$N$_3$O$_2$=297

Example 71

3-(2,3-Dimethoxybenzyl)-3,4-dihydroquinazolin-2-amine hydrochloride

ESI-MS [M+H$^+$]=298.15 Calculated for C$_{17}$H$_{19}$N$_3$O$_2$=297

Example 72

2-[(2-Aminoquinazolin-3(4H)-yl)methyl]phenol 120 mg (0.45 mmol) 3-(2-methoxybenzyl)-3,4-dihydroquinazolin-2-amine and 5 g pyridine hydrochloride were combined and heated for 4 hours at approx. 140° C. After cooling the melt, the residue was dissolved in water, extracted three times with dichloromethane and the combined organic phases were dried, filtered and evaporated. The resulting crude product was purified over MPLC (silica gel: Bischoff Prontoprep 60-2540-C18E, 32 µm; mobile phase: CH$_3$CN/H$_2$O+0.1% acetic acid) and subsequent lyophilization yielded the target product as a beige white solid; 110 mg.

ESI-MS [M+H$^+$]=254.15 Calculated for C$_{15}$H$_{15}$N$_3$O=253

Example 73

2-(Hydroxyamino)-3-(2-methoxybenzyl)-3,4-dihydroquinazoline 14.1 (2-Methoxybenzyl)(2-nitrobenzyl)amine 2.0 g (66.17 mmol) 2-nitrobenzaldehyde, 9.08 g (66.17 mmol) 2-methoxybenzylamine and 100 mL triethyl orthoformate in 100 mL dichloromethane were stirred for approx. 24 hours at room temperature. The residue obtained after evaporation was dissolved in 190 mL ethanol and mixed by portions with a total of 5.02 g NaBH$_4$ while stirring at room temperature. After approx. 1 hour, the mixture was poured into water, extracted three times with dichloromethane; the combined organic phases were dried with MgSO$_4$, filtered and concentrated until dry; 18.36 g yellow oil. ESI-MS [M+H$^+$]=273.15.

14.2 (2-Aminobenzyl)(2-methoxybenzyl)amine

Reduction of 18.36 g (2-methoxybenzyl)(2-nitrobenzyl)amine as in Example 1.3 and purification of the crude product by chromatography on silica gel (dichloromethane, 3-10% methanol) yielded 11.0 g of a yellowish oil. ESI-MS [M+H$^+$]=243.15.

14.3 3-(2-Methoxybenzyl)-3,4-dihydroquinazolin-2(1H)-thione 4.0 g (16.51 mmol) (2-aminobenzyl)(2-methoxybenzyl)amine in 100 mL ethanol was mixed with 40 mL CS$_2$ and heated at reflux for 8 hours, forming a yellow precipitate. The mixture was evaluated and the resulting solids were recrystallized in ethanol; 4.24 g white solids.

14.4 3-(2-Methoxybenzyl)-2-(methylthio)-3,4-dihydroquinazoline 3.0 g (10.55 mmol) 3-(2-methoxybenzyl)-3,4-dihydroquinazolin-2(1H)-thione was dissolved in 40 mL dichloromethane, 1.31 mL CH$_3$I was added and stirred for approx. 12 hours at room temperature. The reaction mixture was evaporated until dry and the resulting residue was stirred with a mixture of n-pentane/diethyl ether; 3.1 g white solids.

ESI-MS [M+H$^+$]=299.25.

14.5 2-(Hydroxyamino)-3-(2-methoxybenzyl)-3,4-dihydroquinazoline 0.6 g (2.01 mmol) 3-(2-methoxybenzyl)-2-(methylthio)-3,4-dihydroquinazoline and 265 mg hydroxylamine in 10 mL isopropanol were heated at reflux for approx. 36 hours. For workup, the mixture was evaporated, the resulting residue was recrystallized in a mixture of diethyl ether/methyl tert-butyl ether 1:1 and then lyophilized by MPLC (silica gel: Bischoff Prontoprep 60-2540-C18E, 32 µm; mobile phase: CH$_3$CN/H$_2$O+0.1% acetic acid). 300 mg white solids.

ESI-MS [M+H$^+$]=284.15 Calculated for C$_{16}$H$_{17}$N$_3$O$_2$=283

The following substances were synthesized as described in EXAMPLE 73, section 14.1:

Example 74

N-(2,3-Dihydro-1H-inden-2-yl)-3-(2-methoxybenzyl)-3,4-dihydroquinazolin-2-amine acetate ESI-MS [M+H$^+$]=384.25 Calculated for C$_{25}$H$_{25}$N$_3$O=283

Example 75

3-(2-Methoxybenzyl)-2-[(pyridin-3-ylmethyl)amino]-3,4-dihydroquinazoline acetate ESI-MS [M+H$^+$]=359.15 Calculated for C$_{22}$H$_{22}$N$_4$O=358

Example 76

2-(Butylamino)-3-(2-methoxybenzyl)-3,4-dihydroquinazoline hydrochloride

ESI-MS [M+H$^+$]=324.25 Calculated for C$_{20}$H$_{25}$N$_3$O=323

Example 77

2-(Isobutylamino)-3-(2-methoxybenzyl)-3,4-dihydroquinazoline acetate

ESI-MS [M+H$^+$]=324.35 Calculated for C$_{20}$H$_{25}$N$_3$O=323

Example 78

3-(2-Methoxybenzyl)-2-piperazin-1-yl-3,4-dihydroquinazoline hydrochloride tert-butyl-4-[3-(2-methoxybenzyl)-3,4-dihydroquinazolin-2-yl]piperazine 1-carboxylate 6.4 g (26.09 mmol) tert-butyl-4-(aminocarbothioyl)piperazine 1-carboxylate and 3.8 mL $CH_3I$ in 80 mL dichloromethane were stirred for 4 days at room temperature. Evaporation of the mixture yielded the corresponding methyl compound as the hydroiodide which was reacted further without further purification.

5.0 g (20.66 mmol) (2-aminobenzyl)(2-methoxybenzyl)amine and 8 g [4-(tert-butoxycarbonyl)-piperazin-1-yl](methylthio)methane hydroiodide in 100 mL isopropanol were heated at reflux for approx. 60 hours. After the reaction was concluded, the mixture was evaporated and the resulting residue was purified by chromatography on silica geld (dichloromethane, 0 to 3% methanol). 5.96 g beige solids. ESI-MS $[M+H^+]$=437.15.

3-(2-methoxybenzyl)-2-piperazin-1-yl-3,4-dihydroquinazoline

Splitting off the Boc group starting from 5.16 g tert-butyl-4-[3-(2-methoxybenzyl)-3,4-dihydroquinazolin-2-yl]piperazine 1-carboxylate with 4N HCl in dioxane and basic workup yielded the desired product: 3.24 g.
ESI-MS $[M+H^+]$=337.35 Calculated for $C_{20}H_{24}N_4O$=336

Example 79

3-(2-Methoxybenzyl)-2-(4-methylpiperazin-1-yl)-3,4-dihydroquinazoline fumarate Reductive alkylation of 1.0 g (2.97 mmol) 3-(2-methoxybenzyl)-2-piperazin-1-yl-3,4-dihydroquinazoline with 0.31 mL formalin solution and 0.88 g sodium triacetoxyborohydride in 25 mL acetonitrile and purification of the crude product obtained after standard workup by chromatography on silica gel (dichloromethane, 2-5% methanol) yielded 0.46 g yellow oil that was dissolved in diethyl ether and converted to the corresponding fumarate by adding one equivalent of fumaric acid: 0.53 g.
ESI-MS $[M+H^+]$=351.25 Calculated for $C_{21}H_{26}N_4O$=350

Example 80

2-(4-Benzylpiperazin-1-yl)-3-(2-methoxybenzyl)-3,4-dihydroquinazoline fumarate As in EXAMPLE 73, sections 14.1 and 14.2, 0.6 g 3-(2-methoxybenzyl)-2-piperazin-1-yl-3,4-dihydroquinazoline with benzaldehyde in triethyl orthoformate was converted to the corresponding imine and then reduced with $NaBH_4$. Similar workup and conversion like those of the corresponding fumarate yielded 30 mg of the desired product.
ESI-MS $[M+H^+]$=427.15 Calculated for $C_{27}H_{30}N_4O$=426

Example 81

7-Bromo-3-(2,6-dimethoxybenzyl)-3,4-dihydroquinazolin-2-amine

4-Bromo-N-(2,6-dimethoxybenzyl)-2-nitrobenzamide

4-Bromo-2-nitrobenzoic acid (30.0 g, 118.3 mmol) was placed in 300 mL dichloromethane and 16.5 mL triethylamine was added. Then the reaction solution heated up and a change in color from yellow to greenish brown was observed. The mixture was then cooled to 5° C. and isobutyl chloroformate (16 mL, 118.3 mmol) was added by drops without dilution. The reaction mixture was allowed to come to room temperature while stirring and stirring was continued for 1.5 hours. The mixture was cooled again to 5° C. and 2,6-dimethoxybenzylamine (19.8 g, 118.3 mmol) was added by portions. Again 300 mL dichloromethane was added for dilution and stirring was continued for 15 minutes at 5° C. and then for 12 hours at room temperature. The clear reaction mixture ultimately changed color from red to brown and the reaction was monitored by thin-layer chromatography. The batch was extracted with water, the separated organic phase was extracted with 5% citric acid (2×), washed with sodium bicarbonate solution until neutral (1×) and extracted with saturated sodium chloride solution. The organic phase was dried over sodium sulfate, the solvent was removed in vacuo. The residue was dissolved in diethyl ether/pentane solvent and the precipitate which gradually formed therefore was ultimately filtered out. Crystalline 4-bromo-N-(2,6-dimethoxybenzyl)-2-nitrobenzamide was isolated. Yield: 35.4 g (89.6 mmol, 76%).
ESI-MS $[M+H^+]$=396.05 Calculated for $C_{16}H_{15}BrN_2O_5$=395.2

1-(4-Bromo-2-nitrophenyl)-N-(2,6-dimethoxybenzyl)methanamine

4-Bromo-N-(2,6-dimethoxybenzyl)-2-nitrobenzamide (30.0 g, 75.9 mmol) was placed in 600 mL tetrahydrofuran and dissolved; the solution was then heated at reflux. A suspension of dimethylsulfide borane complex (28.8 g, 379.5 mmol) and 30 mL tetrahydrofuran was added slowly by drops to the heated reaction mixture, whereupon foaming was observed and the color changed from yellow to yellowish green. A yellow precipitate was formed. The batch was heated at reflux for 5 hours until the reaction was complete, then stirred further for 12 hours at room temperature and finally heated for 2 hours at 65° C. (TLC monitoring). For workup, the mixture was cooled to 0° C. and 190 mL 2N hydrochloric acid was added by drops slowly with a marked evolution of gas. On the basis of mass spectrometric analyses, 1-(4-bromo-2-nitrophenyl)-N-(2,6-dimethoxybenzyl)methanamine, the desired product, a product-borane complex was also observed (ESI-MS $[M+H^+]$=394.05/396.05). The batch was therefore treated with 2N hydrochloric acid and mixed with water until the entire borane complex had been destroyed. The pH of the solution was adjusted to 11 with 2N sodium hydroxide solution and then was extracted with dichloromethane (3×). The combined organic phases were freed of solvent in vacuo. The residue was purified by column chromatography on silica gel, starting with dichloromethane as the eluent and adding methanol in 5 vol % increments up to pure methanol. Yield: 27.9 g (73.2 mmol, 96%).
ESI-MS $[M+H^+]$=381.05/383.05 Calculated for $C_{16}H_{17}BrN_2O_4$=381.2

5-Bromo-2-{[(dimethoxybenzyl)amino]methyl}aniline 1-(4-Bromo-2-nitrophenyl)-N-(2,6-dimethoxybenzyl)methanamine (23.9 g, 62.7 mmol) was dissolved in 400 mL methanol in the heat. At room temperature, activated carbon (20.0 g) and catalytic amounts of sublimed iron trichloride (0.30 g, 1.85 mmol) were added. Finally, hydrazine hydrate (12.2 mL, 250.8 mmol) was added slowly by drops at 64° C.

After heating for 2 hours at 64° C., the reaction was concluded according to monitoring by TLC. After cooling the reaction mixture to room temperature, the activated carbon was filtered out through a glass suction filter, covered with a 2 cm bed of Cellite and rewashed with heated methanol (3×). The solvent was removed in vacuo and the residue was again dissolved in dichloromethane. The organic phase was extracted with water (2×) and with 2N hydrochloric acid (3×). The desired product was obtained from the acidic aqueous phase while impurities were separated with the organic phase. The hydrochloric acid phase was adjusted to a pH of 11 with 2N sodium hydroxide solution and again extracted with dichloromethane (2×). The organic phase which then contained the product was dried over sodium sulfate, filtered and the solvent was removed in vacuo. Yield: 15.5 g (44.13 mmol, 70%).

ESI-MS [M+H$^+$]=351.05/353.05 Calculated for $C_{16}H_{19}BrN_2O_2$=351.2

5-Bromo-3-(2,6-dimethoxybenzyl)-3,4-dihydro-quinazolin-2-amine

5-Bromo-2-{[(2-dimethoxybenzyl)amino]methyl}aniline (7.50 g, 21.4 mmol) was dissolved in 180 mL dioxane and cyanogen bromide (3.26 g, 29.9 mmol) was added. The reaction mixture was heated for 4.5 hours at reflux. The resulting precipitate was filtered out and rewashed with dioxane (2×), isolated the crude product (8.0 g) after drying in a vacuum drying cabinet at 40° C. For purification and release of the hydrobromide salt, the solids were again dissolved in dichloromethane and alkalized with 2N sodium hydroxide solution. A portion of the product was precipitated immediately, then filtered out and dried. The two phases of the mother liquor were separated and the resulting organic phase was washed with water (2×), dried over sodium sulfate, filtered out and the solvent was removed in vacuo. The isolated solids were combined. Yield: 6.50 g (17.3 mmol, 81%).

ESI-MS [M+H$^+$]=376.05/378.05 Calculated for $C_{17}H_{18}BrN_3O_2$=376.3

Starting with 7-bromo-(2,6-dimethoxybenzyl)-3,4-dihydroquinazolin-2-amine, the inventive compounds according to EXAMPLE 82 through EXAMPLE 88 were synthesized as described below using the corresponding commercially available boric acids or amines.

Example 82

3-(2,6-Dimethoxybenzyl)-7-phenyl-3,4-dihyro-quinazoli-2-aminium acetate

7-Bromo-3-(2,6-dimethoxybenzyl)-3,4-dihydroquinazolin-2-amine (0.400 g, 1.06 mmol) and phenyl boric acid (0.187 g, 1.49 mmol) were dissolved in 20 mL toluene/ethanol (4:1) and 2M potassium carbonate solution (0.205 g, 1.49 mmol) was added. The suspension was divided among three reaction vessels, each of which was also charged with the catalyst 1,1'-bis-(diphenylphosphino)ferrocenyl palladium (II) dichloride.dichloromethane (10 mg, 0.11 mmol) under a nitrogen atmosphere, then sealed and inertized under nitrogen and heated in a CEM microwave at 100° C. (120 watt) for 180 minutes. The course of the reaction was determined by mass spectrometry. The contents of the reaction vessels were diluted with dichloromethane and extracted with 1N sodium hydroxide solution (1×). The basic aqueous phase was extracted again with dichloromethane (2×). The organic phases obtained by workup were combined and dried over sodium sulfate, then filtered out and the solvent was removed in vacuo. The purification was performed with the help of preparative HPLC (Merck, Chromolith RP18) and the eluents acetonitrile and water (0.1M % acetic acid) with a 20% to 50% acetonitrile gradient in 30 minutes. The fractions containing the pure product were combined and lyophilized by freeze drying. Yield: 0.279 g (0.75 mmol, 61%).

ESI-MS [M+H$^+$]=374.15 Calculated for $C_{23}H_{23}N_3O_2$=373.5

Example 83

3-(2,6-Dimethoxybenzyl)-7-(4-methoxyphenyl)-3,4-dihydroquinazolin-2-aminium acetate Synthesis was performed according to EXAMPLE 82 from 7-bromo-3-(2,6-dimethoxybenzyl)-3,4-dihydroquinazolin-2-amine and 4-methoxyphenylboric acid in a CEM microwave at 100° C. (120 watt) for 120 minutes.

ESI-MS [M+H$^+$]=404.15 Calculated for $C_{24}H_{25}N_3O_3$=403.5

Example 84

3-(2,6-Dimethoxybenzyl)-7-methyl-3,4-dihydro-quinazolin-2-aminium acetate

Synthesis was performed according to EXAMPLE 82 from 7-bromo-3-(2,6-dimethoxybenzyl)-3,4-dihydroquinazolin-2-amine and trimethylboroxine in a CEM microwave at 100° C. (120 watt) for a total of 360 minutes (3×120 minutes).

ESI-MS [M+H$^+$]=312.15 Calculated for $C_{18}H_{21}N_3O_2$=311.4

Example 85

3-(2,6-Dimethoxybenzyl)-7-pyridin-3-yl-3,4-dihydroquinazolin-2-aminium acetate

Synthesis was performed according to EXAMPLE 82 from 7-bromo-3-(2,6-dimethoxybenzyl)-3,4-dihydroquinazolin-2-amine and 3-[1.3.2]-dioxaborinan-2-ylpyridine in a CEM microwave at 100° C. (120 watt) for 120 minutes.

ESI-MS [M+H$^+$]=375.15 Calculated for $C_{22}H_{22}N_4O_2$=374.5

Example 86

3-(2,6-Dimethoxybenzyl)-7-(2-thienyl)-3,4-dihydro-quinazolin-2-aminium acetate

Synthesis was performed according to EXAMPLE 82 from 7-bromo-3-(2,6-dimethoxybenzyl)-3,4-dihydroquinazolin-2-amine and thiophene-2-boric acid in a CEM microwave at 100° C. (120 watt) for 120 minutes.

ESI-MS [M+H$^+$]=380.25 Calculated for $C_{21}H_{21}N_3O_2S$=379.5

Example 87

3-(2,6-Dimethoxybenzyl)-7-[4-trifluoromethoxy) phenyl]-3,4-dihydroquinazoline-2-aminium acetate Synthesis was performed according to EXAMPLE 82 from 7-bromo-3-(2,6-dimethoxybenzyl)-3,4-dihydroquinazolin-2-amine and 4-(trifluoromethoxy)phenylboric acid in a CEM microwave at 100° C. (120 watt) for a total of minutes [sic; number omitted].

ESI-MS [M+H$^+$]=458.35 Calculated for C$_{24}$H$_{22}$F$_3$N$_3$O$_3$=457.5

Example 88

7-Anilino-3-(2,6-dimethoxybenzyl)-3,4-dihydro-quinazolin-2-aminium acetate

A three-necked flask was heated under argon and then charged with sodium tert-butylate (0.178 g, 1.99 mol), (R/S)-1,1'-binaphthaline-2,2'-diylphosphate (0.092 g, 0.15 mmol) and tris(dibenzylidene acetone)dipalladium (0) (0.121 g, 0.13 mmol) under a protective atmosphere and suspended in 10 mL toluene. Aniline (0.25 mL, 2.79 mmol) and 7-bromo-3-(2,6-dimethoxybenzyl)-3,4-dihydroquinazolin-2-amine (0.500 g, 1.33 mmol), suspended in 20 mL toluene, were then added one after the other to the starting reagents. The reaction mixture was heated at reflux for 3 hours. The reaction was not yet complete, so that first the mixture had to heated at room temperature for 12 hours and then for 5 hours at reflux. After the reaction was concluded, the mixture was cooled to room temperature, diluted with diethyl ether and the resulting solids were filtered out. For purification, the solids were dissolved in acetonitrile/water (1:1) and acetic acid and purified by preparative HPLC (Merck, Chromolith RP18) with the eluents acetonitrile and water (0.1M % acetic acid) with a gradient of 20% to 50% acetonitrile in 30 minutes. After freeze drying, the desired product was isolated via the lyophilizer. Yield: 50 mg (0.129 mmol, 10%).

ESI-MS [M+H$^+$]=389.15 Calculated for C$_{23}$H$_{24}$N$_4$O$_2$=388.5

Example 89

6-Chloro-3-(2,6-dimethoxybenzyl)-3,4-dihydro-quinazolin-2-amine 9.1
5-Chloro-N-(2,6-dimethoxybenzyl)-2-nitrobenzamide 5-Chloro-2-nitrobenzoic acid (25.0 g, 201.6 mmol) was placed in 250 mL dichloromethane and stirred for 5 minutes. After 17.0 mL triethylamine had been added at 25° C., the yellow suspension dissolved gradually. After storing for 10 minutes, the mixture was cooled to 5° C. Isobutyl chloroformate (16.25 mL, 122.8 mmol) was added by drops without dilution within 15 minutes. The reaction mixture was allowed to reach room temperature while stirring and stirring was continued for 1.5 hours. A light yellow precipitate was formed. The mixture was again cooled to 5° C. and 2,6-dimethoxybenzylamine (20.5 g, 122.8 mmol) was added by portions over a period of 20 minutes. For dilution, another 250 mL dichloromethane was added and the mixture was stirred for 15 minutes at 5° C. and then for 65 hours at room temperature. The reaction was monitored by thin layer chromatography, revealing traces of the starting materials. The batch was mixed with 5% citric acid, whereupon a precipitate formed and was filtered out. Product was still detected in the organic phase, so the organic phase was extracted again with 5% citric acid (1×), washed until neutral with sodium bicarbonate solution (1×) and extracted with sodium chloride solution. The organic phase was dried over sodium sulfate and the solvent was removed in vacuo. The solid yellow residue was suspended in diethyl ether/pentane as solvents, then filtered out and washed with diethyl ether. The two crystal products were combined and a pure 5-chloro-N-(2,6-dimethoxybenzyl)-2-nitrobenzamide was isolated. Yield: 31.3 g (89.2 mmol, 73%).

ESI-MS [M+H$^+$]=351.05/353.05 Calculated for C$_{16}$H$_{15}$ClN$_2$O$_5$=350.8

1-(5-Chloro-2-nitrophenyl)-N-(2,6-dimethoxybenzyl)methanamine

5-Chloro-N-(2,6-dimethoxybenzyl)-2-nitrobenzamide (31.3 g, 89.2 mmol) was placed in suspension in 500 mL tetrahydrofuran and the solution was heated at reflux. A mixture of borane-dimethyl sulfide complex (33.9 g, 446.2 mmol) and 50 mL tetrahydrofuran was added slowly by drops within 45 minutes to the heated reaction mixture. During the addition of the borane complex, a colorless precipitate was formed by flocculation and then went into solution again slowly after the addition was complete. The batch was heated at reflux for a total of 6 hours and stirred for 12 hours at room temperature until achieving complete conversion (TLC monitoring). The mixture was cooled to 0° C. for workup and 42 mL 2N hydrochloric acid was added slowly by drops over a period of 30 minutes, with a great evolution of gas and an increase in temperature to 10° C. due to the exothermic reaction. The reaction mixture was thawed to room temperature. According to the mass spectrometric analysis, the borane-product complex (ESI-MS [M+H$^+$]=349.15/351.15) could not be cleaved completely to the desired product. Therefore the solids obtained after workup had to be treated again in 300 mL tetrahydrofuran with 180 mL 2N hydrochloric acid, by dropwise addition of the acid for 1 hour to the product mixture heated to 50° C. The mixture was stirred for a total of 6 hours at reflux and 12 hours at room temperature. The organic fraction, consisting mainly of tetrahydrofuran, was distilled off in vacuo, the solution was adjusted to a pH of 10 to 11 with 50% sodium hydroxide solution and extracted with dichloromethane (3×). The organic phase was dried over sodium sulfate and filtered out and the solvent was evaporated in vacuo. The isolated yellow oil was stirred into diethyl ether and a yellow precipitant of 1-(5-chloro-2-nitrophenyl)-N-(2,6-dimethoxybenzyl)-methanamine was filtered out. Yield: 19.2 g (57.0 mmol, 64%).

ESI-MS [M+H$^+$]=337.15/339.15 Calculated for C$_{16}$H$_{17}$ClN$_2$O$_4$=336.8

4-Chloro-2-{[(2,6-dimethoxybenzyl)amino]methyl}aniline 1-(5-Chloro-2-nitrophenyl)-N-(2,6-dimethoxybenzyl)methanamine (19.2 g, 57.0 mmol) was dissolved in 400 mL methanol in the heat. Activated carbon (20.0 g) and catalytic amounts of sublimed iron trichloride (0.24 g, 1.48 mmol) were added at room temperature. Finally, hydrazine hydrate (11.10 mL, 228.0 mmol) was added slowly by drops at 64° C. In doing so, it foamed up somewhat. After heating for 2 hours at 64° C., the reaction was concluded. After cooling the reaction mixture to room temperature, the batch was filtered through Hyflo Super Cel and the solid constituents were separated out. The solvent was removed in vacuo. The colorless oil was again dissolved in dichloromethane and extracted with water (3×) and with 2N hydrochloric acid (3×). The hydrochloric two-phase mixture was adjusted to a pH of 11 with 2N sodium hydroxide solution, at which point a bulky colorless precipitate was formed. When dichloromethane was added, the solids dissolved again in the organic phase which was dried over sodium sulfate after separating the aqueous phase, then filtered and freed of the solvent in vacuo. By storing into petroleum ether, a colorless precipitate was obtained from the oily yellow crude product, then filtered with suction and dried. By fractional crystallization of the mother liquor, the yield was further increased. Yield: 11.5 g (37.5 mmol, 66%).

ESI-MS [M+H$^+$]=307.25/309.25 Calculated for C$_{16}$H$_{19}$ClN$_2$O$_2$=306.8

6-Chloro-3-(2,6-dimethoxybenzyl)-3,4-dihydroquinazolin-2-amine 1-(5-Chloro-2-nitrophenyl)-N-(2,6-dimethoxybenzyl) methanamine (6.50 g, 21.2 mmol) was dissolved in 160 mL dioxane and cyanogen bromide (3.24 g, 29.6 mmol) dissolved in 20 mL dioxane was added. A slightly yellowish suspension was formed immediately. The reaction mixture was heated for 2 hours at reflux. The entire reaction mixture was completely dissolved at 85° C. and a colorless precipitate began to form at 75° C. The mixture was cooled to room temperature and stirring was continued for 12 hours. The resulting precipitate was filtered out and rewashed with dioxane (2×), isolating the crude product (8.6 g) after drying in a vacuum drying cabinet at 40° C. For purification and release of the hydrobromide salt, the solids were dissolved in dichloromethane again and alkalized with 2N sodium hydroxide solution. A portion of the product was precipitated immediately, filtered out and dried. The two phases of the mother liquor was separated and the resulting organic phase was washed with water (3×), whereupon a crystal product was again formed from it. The organic aqueous phase was concentrated in vacuo and the solids were filtered out. The two solids that were isolated in succession were combined.

Yield: 6.50 g (19.6 mmol, 93%).

ESI-MS [M+H$^+$]=332.05/334.05 Calculated for C$_{17}$H$_{18}$ClN$_3$O$_2$=331.8

Example 90

7-Chloro-3-(2,6-dimethoxybenzyl)-3,4-dihydroquinazolin-2-amine

As described in EXAMPLE 63, the title compound was synthesized starting from 4-chloro-2-nitrobenzoic acid and 2,6-dimethoxybenzylamine.

ESI-MS [M+H$^+$]=332/334 Calculated for C$_{17}$H$_{18}$ClN$_3$O$_2$=331/333

Example 91

2.1 2-Amino-N-(2-methoxybenzyl)-4-nitrobenzamide

A mixture of 9.3 g 7-nitro-1H-benzo[d][1.3]oxazine-2,4-dione (45 mmol) and 12.3 g 2-methoxybenzylamine (90 mmol) in 200 mL toluene was stirred for 30 minutes at reflux, then mixed with methylene chloride and washed repeated with water. The organic phase was dried, concentrated and the solid residue was dried and reacted further without further purification.

2.2 2-[(2-Methoxybenzylamino)methyl]-5-nitrophenylamine

The title compound was synthesized according to EXAMPLE 63, section 1.6 starting from 2-amino-N-(2-methoxybenzyl)-4-nitrobenzamide and borane-dimethyl sulfide.

2.3 3-(2-Methoxybenzyl)-7-nitro-3,4-dihydroquinazolin-2-amine

The title compound was synthesized according to EXAMPLE 63, section 1.8 starting from 2-[(2-methoxybenzylamino)methyl]-5-nitrophenylamine by reaction with cyanogen bromide.

ESI-MS [M+H$^+$]=313 Calculated for C$_{16}$H$_{16}$N$_4$O$_3$=312

Example 92

N-Cycloheptyl-3-(2,6-dimethoxybenzyl)-3,4-dihydroquinazolin-2-amine hydrochloride A mixture of 657 mg 3-(2,6-dimethoxybenzyl)-2-methylsulfanyl-3,4-dihydroquinazoline (2 mmol, synthesized according to EXAMPLE 73, section 14.4) and 1.7 g cycloheptylamine (15 mmol) was heated for 2 hours at 120° C. without further solvent. After cooling, the batch was mixed with water, adjusted to a pH of 8 with 1M HCl and extracted with methylene chloride. The organic phase was washed again with water, then dried (sodium sulfate), filtered, concentrated and chromatographed on silica gel, yielding 345 mg of the product as a foam. Stirring into a small amount of ethyl acetate yielded 289 mg product as solids.

ESI-MS [M+H$^+$]=394 Calculated for C$_{24}$H$_{31}$N$_3$O$_2$=393

Example 93

3-(2,6-Dimethoxybenzyl)-N-(1-naphthylmethyl)-3,4-dihydroquinazolin-2-amine hydrochloride As described in EXAMPLE 92, the title compound was synthesized from 3-(2,6-dimethoxybenzyl)-2-methylsulfanyl-3,4-dihydroquinazoline and naphth-1-ylmethylamine.

ESI-MS [M+H$^+$]=437 Calculated for C$_{28}$H$_{27}$N$_3$O$_2$=438

Example 94

[3-(2,6-Dimethoxybenzyl)-3,4-dihydroquinazolin-2-yl]pyridin-2-ylmethylamine hydrochloride As described in EXAMPLE 92, the title compound was synthesized from 3-(2,6-dimethoxybenzyl)-2-methylsulfanyl-3,4-dihydroquinazoline and pyridin-2-ylmethylamine.

ESI-MS [M+H$^+$]=389 Calculated for C$_{23}$H$_{24}$N$_4$O$_2$=388

Example 95

N-Benzyl-3-(2,6-dimethoxybenzyl)-3,4-dihydroquinazolin-2-amine hydrochloride As described in EXAMPLE 92, the title compound was synthesized from 3-(2,6-dimethoxybenzyl)-2-methylsulfanyl-3,4-dihydroquinazoline and benzylamine.

ESI-MS [M+H$^+$]=388 Calculated for C$_{24}$H$_{25}$N$_3$O$_2$=387

Example 96

N-(1-Benzylpiperidin-4-yl)-3-(2-methoxybenzyl)-3,4-dihydroquinazolin-2-amine fumarate As described in EXAMPLE 92, the title compound was synthesized from 3-(2-methoxybenzyl)-2-methylsulfanyl-3,4-dihydroquinazoline (EXAMPLE 73, section 14.4) and 1-benzoylpiperidin-4-ylamine.

ESI-MS [M+H$^+$]=441 Calculated for C$_{28}$H$_{32}$N$_4$O=440

Example 97

[3-(2-Methoxybenzyl)-3,4-dihydroquinazolin-2-yl]phenethylamine hydrochloride

As described in EXAMPLE 92, the title compound was synthesized from 3-(2-methoxybenzyl)-2-methylsulfanyl-3,4-dihydroquinazoline (EXAMPLE 73, section 14.4) and phenethylamine.

ESI-MS [M+H$^+$]=372 Calculated for $C_{24}H_{25}N_3O$=371

Example 98

3-(2-Methoxybenzyl)-N-(1-naphthylmethyl)-3,4-dihydroquinazolin-2-amine hydrochloride As described in EXAMPLE 92, the title compound was synthesized from 3-(2-methoxybenzyl)-2-methylsulfanyl-3,4-dihydroquinazoline (EXAMPLE 73, point 14.4) and naphth-1-ylmethylamine.

ESI-MS [M+H$^+$]=372 Calculated for $C_{24}H_{25}N_3O$=371

Example 99

3-(2-Methoxybenzyl)-N-(1-naphthylmethyl)-3,4-dihydroquinazolin-2-amine hydrochloride As described in EXAMPLE 92, the title compound was synthesized from 3-(2-methoxybenzyl)-2-methylsulfanyl-3,4-dihydroquinazoline (EXAMPLE 73, point 14.4) and cycloheptylamine.

ESI-MS [M+H$^+$]=364 Calculated for $C_{23}H_{29}N_3O$=363

Example 100

3-(2-Methoxybenzyl)-N-(2-thienylmethyl)-3,4-dihydroquinazolin-2-amine hydrochloride As described in EXAMPLE 92, the title compound was synthesized from 3-(2-methoxybenzyl)-2-methylsulfanyl-3,4-dihydroquinazoline (EXAMPLE 73, point 14.4) and thien-2-ylmethylamine.

ESI-MS [M+H$^+$]=364 Calculated for $C_{21}H_{21}N_3OS$=363

Example 101

6-Methoxy-3-(2-methoxybenzyl)-3,4-dihydroquinazolin-2-amine

6-Methoxy-3-(2-methoxybenzyl)-3,4-dihydroquinazolin-2-amine was synthesized from 5-methoxy-2-nitrobenzoic acid and 2-methoxybenzylamine by analogy with EXAMPLE 89. The peptide coupling was performed with carbonyl diimidazole and triethylamine in dimethylformamide. The nitro group was reduced with tin(II) chloride instead of iron(III) chloride to form the corresponding aniline. Subsequent cyclization to the dihydroquinazoline with cyanogen bromide was performed using a mixture of dichloromethane and ethanol.

ESI-MS [M+H]=298 Calculated for $C_{17}H_{19}N_3O_2$=297

Example 102

6-Chloro-3-(2-methoxybenzyl)-3,4-dihydroquinazolin-2-amine

6-Chloro-3-(2-methoxybenzyl)-3,4-dihydroquinazolin-2-amine was synthesized from 5-chloro-2-nitrobenzaldehyde and 2-methoxybenzylamine by analogy with EXAMPLE 101. Instead of the peptide coupling and subsequent reduction of the amide, reductive amination was performed with sodium borohydride and trimethyl orthoformate in dichloromethane and ethanol to yield 1-(5-chloro-2-nitrophenyl)-N-(2-methoxybenzyl)methanamine. Reduction of the nitro group and cyclization with cyanogen bromide then yielded the product.

ESI-MS [M+H$^+$]=302 Calculated for $C_{16}H_{16}ClN_3O$=301

2. Functional Assay for Human 5-HT$_{5A}$ Receptor Ligands-Serotonin-Induced Increase in the Binding of GTP Europium General Description:

Simulation of G protein-coupled receptors by suitable agonists leads to the formation of GTP at the α-subunit of trimeric G proteins, followed by dissociation of the GTP-bound α-subunit from the βγ-subunits and activation of signal transduction. By using a europium-labeled GTP analog, GTP-Eu, activation of a G protein-coupled receptor by an agonist can be tracked as an increase in the biding in the GTP-Eu to the receptor G protein complex. After removing the unbound GTP-Eu, bound GTP-Eu can be quantified by measuring the time-resolved fluorescence emission in suitable detection devices.

Cell line: h5-HT$_{5A}$_18.2_SH-sy-5y, a human neuroblastoma cell line, which allows stable expression of human 5-HT$_{5A}$ receptor.

Membrane preparation: Cell membranes are produced according to a standard procedure in the presence of protease inhibitors and partially purified by two successive centrifugation steps at 40,000 g. Aliquots are stored at −80° C.

Assay:

The assay is performed in filter plates with 96 wells (AcroWell 96, Pall Corp.). The receptor membranes diluted in assay buffer (2.5 μM GDP, 100 mM NaCl, 3 mM MgCl$_2$, 50 mM HEPES, pH 7.4) are added to the filter plate (5 μg receptor membrane/well). Test compounds are dissolved in 100% DMSO and serial dilutions are added to the receptor membranes (final DMSO concentration 0.5%). The reaction is initiated by adding serotonin (final concentration 1 μM, total assay volume 100 μL). After an initial incubation period of 30 minutes at 30° C., GTP-Eu (final concentration 10 nM) is added followed by a second incubation period of 30 minutes at 30° C. The reaction is stopped by rapid vacuum filtration and the wells are washed twice with ice-cold assay buffer. Bound GTP-Eu is measured in a VICTOR multilabel counter (Perkin Elmer Corp.) using the time-resolved europium settings. The data is corrected with regard to the nonspecific binding and IC$_{50}$ values are calculated with PRISM4.0 (GraphPad Inc.) using standard nonlinear curve adaptation algorithms. K$_b$ values are calculated from IC$_{50}$ values using the Cheng-Prusoff approximation.

In both assays, different concentrations of the test substances are used and the K$_i$ and IC$_{50}$ values are determined. The affinity of selected compounds is shown in the following table:

TABLE 1

Affinity of selected compounds for 5-HT$_{5A}$ (K$_i$).

| Example No. | 5-HT$_{5A}$ (K$_i$) |
|---|---|
| Example 63 | +++ |
| Example 64 | +++ |

TABLE 1-continued

Affinity of selected compounds for 5-HT$_{5A}$ (K$_i$).

| Example No. | 5-HT$_{5A}$ (K$_i$) |
|---|---|
| Example 65 | +++ |
| Example 66 | +++ |
| Example 67 | +++ |
| Example 68 | +++ |
| Example 69 | +++ |
| Example 70 | ++ |
| Example 71 | ++ |
| Example 72 | ++ |
| Example 73 | ++ |
| Example 74 | +++ |
| Example 75 | ++ |
| Example 76 | ++ |
| Example 77 | ++ |
| Example 78 | ++ |
| Example 79 | ++ |
| Example 80 | ++ |
| Example 81 | +++ |
| Example 82 | +++ |
| Example 83 | ++ |
| Example 84 | +++ |
| Example 85 | +++ |
| Example 86 | +++ |
| Example 87 | +++ |
| Example 88 | +++ |
| Example 89 | +++ |
| Example 1 | +++ |
| Example 2 | +++ |
| Example 3 | +++ |
| Example 4 | +++ |
| Example 5 | +++ |
| Example 6 | +++ |
| Example 7 | +++ |
| Example 8 | +++ |
| Example 9 | +++ |
| Example 9 | +++ |
| Example 11 | +++ |
| Example 12 | +++ |
| Example 13 | +++ |
| Example 14 | +++ |
| Example 15 | +++ |
| Example 16 | +++ |
| Example 17 | +++ |
| Example 18 | +++ |
| Example 19 | +++ |
| Example 20 | +++ |
| Example 21 | ++ |
| Example 22 | +++ |
| Example 23 | +++ |
| Example 24 | +++ |
| Example 25 | +++ |
| Example 26 | +++ |
| Example 27 | +++ |
| Example 28 | +++ |
| Example 29 | +++ |
| Example 30 | +++ |
| Example 31 | +++ |
| Example 32 | +++ |
| Example 33 | +++ |
| Example 34 | ++ |
| Example 35 | +++ |
| Example 36 | +++ |
| Example 37 | +++ |
| Example 38 | +++ |
| Example 39 | +++ |
| Example 40 | +++ |
| Example 41 | +++ |
| Example 42 | +++ |
| Example 43 | +++ |
| Example 44 | +++ |
| Example 45 | +++ |
| Example 90 | +++ |
| Example 99 | ++ |
| Example 100 | ++ |
| Example 91 | +++ |
| Example 92 | +++ |
| Example 93 | ++ |
| Example 94 | ++ |
| Example 95 | ++ |
| Example 96 | ++ |
| Example 97 | ++ |
| Example 98 | ++ |
| Example 46 | +++ |
| Example 47 | +++ |
| Example 48 | +++ |
| Example 49 | +++ |
| Example 50 | +++ |
| Example 51 | +++ |
| Example 52 | +++ |
| Example 53 | +++ |
| Example 54 | +++ |
| Example 55 | +++ |
| Example 56 | +++ |
| Example 57 | +++ |
| Example 58 | +++ |
| Example 59 | +++ |
| Example 60 | +++ |
| Example 61 | +++ |
| Example 62 | +++ |
| Example 101 | +++ |
| Example 102 | +++ |

++ denotes an affinity <10 μM
+++ denotes an affinity <300 nM

The invention claimed is:
1. A compound of general formula I

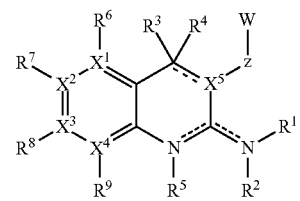

(I)

or an enantiomer, diastereomer or tautomer thereof, or a pharmaceutically acceptable salt thereof, such that the stated radicals have the following definitions:

$R^1$ and
$R^2$ independently of one another denote
hydrogen, a free electron pair, OH, CN or,
in each case optionally substituted, $C_1$-$C_6$ alkyl, O—$C_1$-$C_6$ alkyl, $C_1$-$C_6$ alkylene-O—$C_1$-$C_6$ alkyl, $C_2$-$C_6$ alkenyl, $C_2$-$C_6$ alkynyl, CO—$C_1$-$C_6$ alkyl, CO—O—$C_1$-$C_6$ alkyl, $SO_2$—$C_1$-$C_6$ alkyl, $C_3$-$C_7$ cycloalkyl, $C_1$-$C_4$ alkylene-cycloalkyl, $C_1$-$C_4$ alkylene-aryl, CO—O-arylalkyl, CO—$C_1$-$C_4$ alkylene-aryl, CO-aryl, $SO_2$-aryl, hetaryl, $C_1$-$C_4$ alkylene-hetaryl, CO-hetaryl or $SO_2$—$C_1$-$C_4$ alkylene-aryl, heterocycloalkyl, $C_1$-$C_4$ alkylene-heterocycloalkyl, indanyl, or $R^1$ and $R^2$ together with the nitrogen may form a three to six membered, optionally substituted, saturated or aromatic heterocycle, which may contain another heteroatom selected from the group consisting of O, N and S, such that the heterocycle may optionally be substituted once, twice or three times with the same or different substituents;

$R^3$ denotes
hydrogen, $NO_2$, $NH_2$, OH, CN, $CF_3$, $OCF_3$, $CHF_2$, $OCHF_2$, COOH, O—$CH_2$—COOH, halogen, SH or, in each case optionally substituted, $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-hetaryl or $C_1$-$C_4$ alkylene-aryl or
O—$R_3^1$, CO—$R_3^1$, S—$R_3^1$, SO—$R_3^1$, CO—O—$R_3^1$, $NR_3^4$—CO—O—$R_3^1$, O—$CH_2$—COO—$R_3^1$, $NR_3^2R_3^3$, $CONH_2$, $SO_2NH_2$, $NR_3^4$—CO—$R_3^1$, $SO_2$—$R_3^1$, $NR_3^4$—$SO_2$—$R_3^1$, $SO_2$—$NR_3^2R_3^3$ or CO—$NR_3^2R_3^3$ in which $R_3^1$ denotes,
- in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-aryl, $C_2$-$C_6$ alkylene-aryl or $C_1$-$C_6$ alkylene-hetaryl;

$R_3^2$ denotes
hydrogen, OH, CN or,
- in each case optionally substituted $C_1$-$C_6$ alkyl, $C_2$-$C_6$ alkenyl, $C_2$-$C_6$ alkynyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-aryl, $C_1$-$C_4$ alkylene-hetaryl, $C_1$-$C_6$ alkylene-O—$C_1$-$C_6$ alkyl, CO—$C_1$-$C_6$ alkyl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O—$C_1$-$C_4$ alkylene-aryl, CO—O-hetaryl, CO—O—$C_1$-$C_4$ alkylene-hetaryl, $SO_2$—$C_1$-$C_6$ alkyl, $SO_2$-aryl, $SO_2$-hetaryl, $SO_2$—$C_1$-$C_4$ alkylene-aryl or $SO_2$—$C_1$-$C_4$ alkylene-hetaryl;

$R_3^3$ denotes,
- in each case optionally substituted $C_1$-$C_6$ alkyl, $C_2$-$C_6$ alkenyl, $C_2$-$C_6$ alkynyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-aryl, $C_1$-$C_4$ alkylene-hetaryl, $C_1$-$C_6$ alkylene-O—$C_1$-$C_6$-alkyl, CO—$C_1$-$C_6$ alkyl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O—$C_1$-$C_4$ alkylene-aryl, CO—O-hetaryl, CO—O—$C_1$-$C_4$ alkylene-hetaryl, $SO_2$—$C_1$-$C_6$ alkyl, $SO_2$-aryl, $SO_2$-hetaryl, $SO_2$—$C_1$-$C_4$ alkylene-aryl or $SO_2$—$C_1$-$C_4$ alkylene-hetaryl;

or the radicals $R_3^2$ and $R_3^3$ together with the nitrogen may form a three- to seven-membered, optionally substituted, saturated or aromatic heterocycle, which may contain one, two or three additional heteroatoms, which may be the same or different and are selected from the group consisting of O, N and S, such that optionally two of the substituted radicals on this heterocycle together may form an anellated, optionally substituted, saturated, unsaturated or aromatic carbocycle or heterocycle, such that the heterocycle may contain up to three heteroatoms that are the same or different and are selected from the groups consisting of O, N and S and the cyclic group thereby formed may optionally be substituted and/or another optionally substituted cyclic group may be condensed onto this cyclic group;

$R_3^4$ denotes
hydrogen or,
- in each case optionally substituted $C_1$-$C_6$ alkyl, $C_1$-$C_6$ alkenyl-O—$C_1$-$C_6$ alkyl, $C_2$-$C_6$ alkenyl, $C_3$-$C_{12}$ alkynyl, CO—$C_1$-$C_6$ alkyl, CO—O—$C_1$-$C_6$ alkyl, $SO_2$—$C_1$-$C_6$ alkyl, $C_3$-$C_7$ cycloalkyl, aryl, $C_1$-$C_4$ alkylene-aryl, CO—O-arylalkyl, CO—O—$C_1$-$C_4$ alkylene-aryl, CO—$C_1$-$C_4$ alkylene-aryl, CO-aryl, $SO_2$-aryl, hetaryl, CO-hetaryl or $SO_2$—$C_1$-$C_4$ alkylene-aryl;

$R^4$ denotes
a bond in the ring to $X^5$ while maintaining a C═C double bond for the case when $X^5$═C, $R^5$ denotes
hydrogen, a free electron pair or
in each case optionally substituted O—$C_1$-$C_6$ alkyl, $C_1$-$C_6$ alkyl, CO—$C_1$-$C_6$ alkyl
or —CO—O—$C_1$-$C_6$ alkyl;

$X^1$ denotes C,
$X^2$ denotes C,
$X^3$ denotes C,
$X^4$ denotes C,
in which
$R^6$, $R^7$, $R^8$ and $R^9$ denote,
each independently of one another, the same or different radicals selected from groups 1), 2), 3), 4), 5), 6) or 7), which may be the same or different, such that groups 1) through 7) have the following meanings:

1) hydrogen, halogen, CN, $CF_3$, $CHF_2$, —$OCF_3$, —$NH_2$, —OH or optionally substituted $C_1$-$C_{10}$ alkyl, $C_2$-$C_{10}$ alkenyl, $C_2$-$C_{10}$ alkynyl or $NR_Q^7R_Q^8$ or $NHR_Q^7$,
where $R_Q^7$ and $R_Q^8$ are defined below;

2) phenyl, which may be substituted with one, two or three radicals selected from the group consisting of $R_Q^2$, $R_Q^3$ and $R_Q^4$ such that $R_Q^2$, $R_Q^3$ and $R_Q^4$, each independently of one another, denotes a substituent from the following group:
hydrogen, $NO_2$, $NH_2$, OH, CN, $CF_3$, $CHF_2$, $OCF_3$, $OCHF_2$, COOH, O—$CH_2$—COOH, SH, halogen or
in each case optionally substituted aryl, hetaryl, heterocycloalkyl, $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, $C_1$-$C_4$ alkylene-aryl or $C_1$-$C_4$ alkylene-hetaryl or
O—$R_Q^5$, S—$R_Q^5$, $NR_Q^7R_Q^8$, CO—$OR_Q^6$, $NR_Q^7$—CO—O—$R_Q^6$, O—$CH_2$—COO—$R_Q^6$, $NR_Q^7$—CO—$R_Q^6$, $SO_2$—$R_Q^6$, $NR_Q^7$—$SO_2$—$R_Q^6$, $SO_2NH_2$, $CONH_2$, $SO_2$—$NR_Q^7R_Q^8$ or CO—$NR_Q^7R_Q^8$ or
two radicals selected from the group consisting of $R_Q^2$, $R_Q^3$ and $R_Q^4$ together may form a three- to seven-membered, optionally substituted, saturated, unsaturated or aromatic carbocycle or an optionally substituted, saturated, unsaturated aromatic heterocycle that may contain one, two or three additional heteroatoms, which may be the same or different and are selected from the group consisting of O, N and S and optionally two substituted radicals on this heterocycle together may form an anellated, optionally substituted, saturated, unsaturated or aromatic carbocycle or heterocycle, such that the heterocycle may contain one, two or three heteroatoms that are the same or different and are selected from the group consisting of O, N and S, and the resulting cyclic group may optionally be substituted and/or another optionally substituted cyclic group may be condensed onto this cyclic group;

$R_Q^5$ denotes in each case optionally substituted $C_1$-$C_6$ alkyl, $C_2$-$C_6$ alkenyl, $C_2$-$C_6$ alkynyl, $C_1$-$C_4$ alkylene-$C_3$-$C_7$ cycloalkyl, $C_1$-$C_4$ alkylene-heterocycloalkyl, heterocycloalkyl or hetaryl or $C_1$-$C_4$ alkyl that is optionally substituted once or more with one or more substituents that may be the same or different and are selected from the group consisting of halogen, $NO_2$, $NH_2$, OH, CN, $CF_3$, $CHF_2$, $OCF_3$, $OCHF_2$, NH—($C_1$-$C_6$ alkyl) and N($C_1$-$C_6$ alkyl)$_2$;

$R_Q^6$ denotes in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl or $C_1$-$C_6$ alkylene-O—$C_1$-$C_6$ alkyl;

$R_Q^7$ denotes, independently of the respective incidence, hydrogen, CN or in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_6$ alkylene-O—$C_1$-$C_6$ alkyl, CO—$C_1$-$C_6$ alkyl, $C_1$-$C_4$ alkylene-aryl, $C_1$-$C_4$ alkylene-hetaryl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O—$C_1$-$C_4$ alkylene-aryl, CO—O-hetaryl, CO—O—$C_1$-$C_4$ alkylene-hetaryl, $SO_2$—$C_1$-$C_6$ alkyl, $SO_2$-aryl, $SO_2$-hetaryl, $SO_2$—$C_1$-$C_4$ alkylene-aryl or $SO_2$—$C_1$-$C_4$ alkylene-hetaryl;

$R_Q^8$ denotes, independently of the respective incidence, in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_6$ alkylene-O—$C_1$-$C_6$ alkyl, CO—$C_1$-$C_6$ alkyl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O—$C_1$-$C_4$ alkylene-aryl, CO—O-hetaryl, CO—O—$C_1$-$C_4$ alkylene-hetaryl, $SO_2$—$C_1$-$C_6$ alkyl, $SO_2$-aryl, $SO_2$-hetaryl, $SO_2$—$C_1$-$C_4$ alkylene-aryl or $SO_2$—$C_1$-$C_4$ alkylene-hetaryl;

or the radicals $R_Q^7$ and $R_Q^8$ together with the nitrogen may form a three- to seven-membered, optionally substituted, saturated or aromatic heterocycle that may contain one, two or three other heteroatoms, which may be the same or different and are selected from the group consisting of O, N and S; and optionally two substituted radicals on this heterocycle together may form an anellated, optionally substituted, saturated, unsaturated or aromatic carbocycle or heterocycle, such that the heterocycle may contain one, two or three heteroatoms that are the same or different and are selected from the group consisting of O, N and S, and the cyclic group thereby formed may optionally be substituted or another optionally substituted cyclic group may be condensed onto this cyclic group;

3) a five- or six-membered hetaryl radical, optionally substituted once or twice with substituents that are the same or different and are selected from the group consisting of:

2-thienyl, 3-thienyl, 2-pyrrolyl, 3-pyrrolyl, 2-thiazolyl, 4-thiazolyl, 5-thiazolyl, 2-oxazolyl, 4-oxazolyl, 5-oxazolyl, 1-pyrazolyl, 3-pyrazolyl, 4-pyrazolyl, 5-pyrazolyl, 3-isothiazolyl, 4-isothiazolyl, 5-isothiazolyl, 1-imidazolyl, 2-imidazolyl, 4-imidazolyl, 5-imidazolyl, 2-pyridyl, 3-pyridyl, 4-pyridyl, 2-pyrimidyl, 4-pyrimidyl, 5-pyrimidyl, 6-pyrimidyl, 3-pyridazinyl, 4-pyridazinyl, 5-pyridazinyl, 6-pyridazinyl, 3-isoxazolyl, 4-isoxazolyl, 5-isoxazolyl, thiadiazolyl, oxadiazolyl or triazinyl or their anellated derivatives indazolyl, benzothiophenyl, benzofuranyl, indolinyl, benzimidazolyl, benzothiazolyl, benzoxazolyl, quinolinyl and isoquinolinyl, such that the substituents are selected from the group consisting of halogen, $NO_2$, $NH_2$, OH, CN, $CF_3$, $OCF_3$, $CHF_2$, $OCHF_2$, $C_1$-$C_6$ alkyl, O—$C_1$-$C_6$ alkyl, NH—($C_1$-$C_6$ alkyl), N($C_1$-$C_6$ alkyl)$_2$, NHCO—$C_1$-$C_4$ alkyl, NHSO$_2$—$C_1$-$C_4$ alkyl and $SO_2$—$C_1$-$C_4$ alkyl;

4) two of the radicals $R^6$, $R^7$, $R^8$ or $R^9$ together form a four- to seven-membered, optionally substituted, partially or fully saturated carbocyclic group or a five- or six-membered, optionally substituted, partially or fully saturated heterocyclic group, which may contain one, two or three heteroatoms that are the same or different and are selected from the group consisting of O, N and S;

5) an optionally substituted $C_3$-$C_8$ monocyclic saturated hydrocarbon radical;

6) an optionally substituted four- to seven-membered mono- or bicyclic, partially or fully saturated heterocyclic group, which may contain one, two or three heteroatoms that may be the same or different and are selected from the group consisting of O, N and S, such that this cyclic group may be substituted one or more times, wherein when the heterocyclic group contains a nitrogen atom, this nitrogen atom may be substituted with an $R_Q^7$ radical as defined above;

7) a radical of general formula V

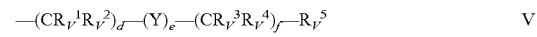

having the indices
d=0, 1, 2, 3 or 4
e=0 or 1
f=0, 1, 2, 3 or 4
where the sum of d, e and f is 1, 2, 3, 4, 5, 6, 7 or 8;

$R_V^1$, $R_V^2$, $R_V^3$, $R_V^4$ independently of one another denote hydrogen, halogen, OH or
in each case optionally substituted $C_1$-$C_4$ alkyl, $C_2$-$C_4$ alkenyl, $C_2$-$C_4$ alkynyl, $C_1$-$C_4$ alkylene-$C_3$-$C_7$ cycloalkyl, $C_3$-$C_7$ cycloalkyl, aryl, $C_1$-$C_4$ alkylene-aryl, hetaryl or $C_1$-$C_4$ alkylene-hetaryl or
independently of one another, two radicals $R_V^1$ and $R_V^2$ or $R_V^3$ and $R_V^4$ together may form a three- to seven-membered, optionally substituted, saturated or unsaturated carbocyclic or heterocyclic group, such that the heterocyclic group may contain one, two or three heteroatoms selected from the group consisting of O, N and S;

$R_V^5$ denotes
a radical as defined above in one of the groups 1), 2), 3), 5) or 6):

Y denotes
—CO—, —O—, —S—, —SO—, —SO$_2$—, —CS—NR$_Y^5$, —COO—, —O—CO—, —CO—NR$_Y^5$, —NR$_Y^5$—CO—, —SO$_2$—NR$_Y^5$, or —NR$_Y^5$—SO$_2$—;

such that
$R_Y^5$ denotes
hydrogen or
optionally substituted $C_1$-$C_6$ alkyl, $C_1$-$C_6$ alkylene-O—$C_1$-$C_6$ alkyl, $C_2$-$C_6$ alkenyl, $C_3$-$C_{12}$ alkynyl, CO—$C_1$-$C_6$ alkyl, CO—O—$C_1$-$C_6$ alkyl, $SO_2$—$C_1$-$C_6$ alkyl, $C_3$-$C_7$ cycloalkyl, aryl, $C_1$-$C_4$ alkylene-aryl, CO—O—$C_1$-$C_4$ alkylene-aryl, CO—$C_1$-$C_4$ alkylene-aryl, CO-aryl, $SO_2$ aryl, hetaryl, CO-hetaryl or $SO_2$—$C_1$-$C_4$ alkylene-aryl;

$X^5$ denotes
C,
Z denotes
a radical of general formula Z1

$$\text{---}(CR_z^1R_z^2)_a\text{---} \quad Z1$$

where
a=1, 2, 3 or 4,
$R_Z^1$, $R_Z^2$ independently of one another denote
hydrogen, halogen, or
in each case optionally substituted $C_1$-$C_4$ alkyl, $C_2$-$C_4$ alkenyl, $C_2$-$C_4$ alkynyl, $C_1$-$C_4$ alkylene-$C_3$-$C_7$ cycloalkyl, $C_3$-$C_7$ cycloalkyl, aryl, $C_1$-$C_4$ alkylene-aryl, or $C_1$-$C_4$ alkylene-hetaryl or
each independently of one another denote two radicals $R_Z^1$ and $R_Z^2$ which together form a three- to seven-membered, optionally substituted, saturated or unsaturated carbocyclic or heterocyclic group, such that the heterocyclic group may contain one, two or three heteroatoms, which may be the same or different and are selected from the group consisting of O, N and S,
W denotes a radical of general formula W $$W$$

in which
A denotes OH, CN, $OCF_3$, $CHF_2$, $CF_3$, $OCHF_2$, COOH, O—$CH_2$—COOH, SH, $C_1$-$C_4$ alkylene-OH, $NR_A^4$—COOH,
or
$R_A^1$, O—$R_A^1$, CO—$R_A^1$, S—$R_A^1$, SO—$R_A^1$, CO—O—$R_A^1$, $NR_A^4$—CO—O—$R_A^1$, O—$CH_2$—COO—$R_A^1$, $NR_A^2R_A^3$, $NR_A^4$—CO—$R_A^1$, $SO_2$—$R_A^1$, $NR_A^4$—$SO_2$—$R_A^1$, $SO_2$—$NR_A^2R_A^3$, CO—$NR_A^2R_A^3$, $C_1$-$C_4$ alkylene-$NR_A^2R_A^3$, $C_1$-$C_4$ alkylene-CO—$NR_A^2R_A^3$, $C_1$-$C_4$ alkylene-$NR_A^2R_A^3$, $C_1$-$C_4$ alkylene-CO—$NR_A^2R_A^3$ or $C_1$-$C_4$ alkylene-O—$R_A^1$;
in which
$R_A^1$ denotes
independently of the respective occurrence, in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-aryl, $C_2$-$C_6$ alkenyl-aryl, $C_1$-$C_6$ alkylene-hetaryl, $C_1$-$C_4$ alkylene-$NR_A^2R_A^3$ or $C_1$-$C_4$ alkylene-O—$C_1$-$C_6$ alkyl;
$R_A^2$ denotes
independently of their respective occurrence, hydrogen, OH, CN
or
in each case optionally substituted $C_1$-$C_6$ alkyl, $C_2$-$C_6$ alkenyl, $C_2$-$C_6$ alkynyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-aryl, $C_1$-$C_4$ alkylene-hetaryl, $C_1$-$C_6$ alkylene-O—$C_1$-$C_6$ alkyl; CO—$C_1$-$C_6$ alkyl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O—$C_1$-$C_4$ alkylene-aryl, CO—O-hetaryl, CO—O—$C_1$-$C_4$ alkylene-hetaryl, $SO_2$—$C_1$-$C_6$ alkyl, $SO_2$-aryl, $SO_2$-hetaryl, $SO_2$—$C_1$-$C_4$ alkylene-aryl or $SO_2$—$C_1$-$C_4$ alkylene-hetaryl;
$R_A^3$ denotes
independently of the respective occurrence, hydrogen or in each case optionally substituted $C_1$-$C_6$ alkyl, $C_2$-$C_6$ alkenyl, $C_2$-$C_6$ alkynyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-aryl, $C_1$-$C_4$ alkylene-hetaryl, $C_1$-$C_6$ alkylene-O—$C_1$-$C_6$ alkyl; CO—$C_1$-$C_6$ alkyl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, CO—O-aryl, CO—O—$C_1$-$C_4$ alkylene-aryl, CO—O-hetaryl, CO—O—$C_1$-$C_4$ alkylene-hetaryl, $SO_2$—$C_1$-$C_6$ alkyl, $SO_2$-aryl, $SO_2$-hetaryl, $SO_2$—$C_1$-$C_4$ alkylene-aryl or $SO_2$—$C_1$-$C_4$ alkylene-hetaryl;
or the radicals $R_A^2$ and $R_A^3$ together with the nitrogen to which they are attached may form a three- to seven-membered, optionally substituted, saturated or aromatic heterocycle, which may contain one, two or three additional heteroatoms, which may be the same or different and are selected from the group consisting of O, N and S; such that two optionally substituted radicals on this heterocycle together may form an anellated, optionally substituted, saturated, unsaturated or aromatic carbocycle or heterocycle, such that the heterocycle may contain one, two or three heteroatoms, which may be the same or different and are selected from the group consisting of O, N and S and such that the cyclic group thereby formed may optionally be substituted and/or another optionally substituted cyclic group may be condensed onto this cyclic group;
$R_A^4$ denotes
independently of the respective occurrence, hydrogen or in each case optionally substituted $C_1$-$C_6$ alkyl, $C_1$-$C_6$ alkenyl-O—$C_1$-$C_6$ alkyl, $C_2$-$C_6$ alkenyl, $C_3$-$C_{12}$ alkynyl, CO—$C_1$-$C_6$ alkyly, CO—O—$C_1$-$C_6$ alkyl, $SO_2$—$C_1$-$C_6$ alkyl, $C_3$-$C_7$ cycloalkyl, aryl, $C_1$-$C_4$ alkylene-aryl, CO—O-arylalkyl, CO—$C_1$-$C_4$ alkylene-aryl, CO-aryl, $SO_2$-aryl, hetaryl, CO-hetaryl or $SO_2$—$C_1$-$C_4$ alkylene-aryl;
B denotes
hydrogen, $NO_2$, $NH_2$, OH, CN, $OCF_3$, $CHF_2$, $CF_3$, $OCHF_2$, COOH, O—$CH_2$—COOH, halogen, SH, $C_1$-$C_4$ alkylene-OH, $NR_A^4$—COOH,
or
in each case optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-hetaryl, $C_1$-$C_4$ alkylene-aryl, O—$R_A^1$, CO—$R_A^1$, S—$R_A^1$, SO—$R_A^1$, CO—O—$R_A^1$, $NR_A^4$—CO—O—$R_A^1$, O—$CH_2$—COO—$R_A^1$, $NR_A^2R_A^3$, $NR_A^4$—CO—$R_A^1$, $SO_2$—$R_A^1$, $NR_A^4$—$SO_2$—$R_A^1$, $SO_2$—$NR_A^2R_A^3$, CO—$NR_A^2R_A^3$, CO—$NR_A^2R_A^3$, $C_1$-$C_4$ alkylene-$NR_A^2R_A^3$, $C_1$-$C_4$ alkylene-CO—$NR_A^2R_A^3$, $C_1$-$C_4$ alkylene-$SO_2$—$NR_A^2R_A^3$ or $C_1$-$C_4$ alkylene-O—$R_A^1$;

or independently of one another, two of the radicals A, B or $R_W$ together with the respective carbon atom to which they are attached may form a five- to seven-membered, optionally substituted, saturated or unsaturated carbocycle or a five- to seven-membered, optionally substituted, saturated or unsaturated or aromatic heterocycle that may contain one, two or three additional heteroatoms, which may be the same or different and are selected from the group consisting of O, N and S; such that optionally two substituted radicals on this carbocycle or heterocycle together may form an anellated, optionally substituted, saturated, unsaturated or aromatic carbocycle or heterocycle, such that the heterocycle may contain one, two or three heteroatoms, which may be the same or different and are selected from the group consisting of O, N and S, and such that the cyclic group thus formed may optionally be substituted and/or another optionally substituted cyclic group may be condensed onto this cyclic group;

$R_W$ denotes hydrogen, OH, halogen, $NO_2$, $NH_2$, CN, $CF_3$, $CHF_2$, $OCF_3$, $OCHF_2$ or in each case optionally substituted $C_1$-$C_6$ alkyl, $C_3$-$C_7$ cycloalkyl, $C_1$-$C_6$ alkylene-O—$C_1$-$C_6$ alkyl, $C_1$-$C_6$ thioalkyl, aryl, hetaryl, O—$C_1$-$C_6$ alkyl, O-aryl, O—$C_1$-$C_4$ alkylene-aryl, O-benzyl, $C_1$-$C_6$ alkylamino, $C_1$-$C_6$ dialkylamino, pyrrolidinyl, piperidinyl, morpholinyl, CO—$C_1$-$C_6$ alkyl, $SO_2$—$C_1$-$C_6$ alkyl, CO-aryl, $SO_2$-aryl, CO—$C_1$-$C_4$ alkylene-aryl, $SO_2$—$C_1$-$C_4$ alkylene-aryl, SO-aryl, $CONH_2$, CONH—$C_1$-$C_6$ alkyl, $SO_2NH$—$C_1$-$C_6$ alkyl, CON—$(C_1$-$C_6$ alkyl$)_2$, $SO_2N$—$(C_1$-$C_6$ alkyl$)_2$, NH—$SO_2$—$C_1$-$C_6$ alkyl or NH—CO—$C_1$-$C_6$ alkyl;

with the provision that when $X^1$, $X^2$, $X^3$, $X^4$ and $X^5$ each equal C, then $R^3$ does not denote COOH, $COOR_3$ or a pharmaceutically acceptable salt thereof.

2. A compound of general formula I according to claim 1, or an enantiomer, diastereomer or tautomer thereof, or a pharmaceutically acceptable salt thereof, in which:

$R^1$ and $R^2$ denote hydrogen, a free electron pair, OH, CN or optionally substituted O—$C_1$-$C_6$ alkyl, $C_1$-$C_6$ alkyl, CO—$C_1$-$C_6$ alkyl, CO—$OC_1$-$C_6$ alkyl.

3. A compound of general formula I according to claim 1, or an enantiomer, diastereomer or tautomer thereof, or a pharmaceutically acceptable salt thereof, in which:

A denotes OH, —O—$C_1$-$C_6$ alkyl, —$OCF_3$, —$OCHF_2$ or optionally substituted —NH—$C_1$-$C_6$ alkyl, —NH—CO—$C_1$-$C_6$ alkyl, —NH—$SO_2$—$C_1$-$C_6$ alkyl, —N($C_1$-$C_6$ alkyl$)_2$, piperidinyl, morpholinyl, —N($C_1$-$C_6$ alkyl)-CO—$C_1$-$C_6$ alkyl or —N($C_1$-$C_6$ alkyl)-$SO_2$—$C_1$-$C_6$ alkyl, $C_1$-$C_4$ alkylene-CO—N($CH_3$)$_2$, $C_1$-$C_4$ alkylene-CO—N-piperidyl, $C_1$-$C_4$ alkylene-CO—N-morpholinyl, $C_1$-$C_4$ alkylene-$SO_2$—N($CH_3$)$_2$, $C_1$-$C_4$ alkylene-$SO_2$—N-piperidyl, $C_1$-$C_4$ alkylene, $SO_2$—N-morpholinyl or $C_1$-$C_4$ alkyl-O—$C_1$-$C_4$ alkyl and, B denotes hydrogen, CN, $CF_3$, $OCF_3$, $OCHF_2$, $CHF_2$, COOH, halogen, or optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-hetaryl, $C_1$-$C_4$ alkylene-aryl, $C_1$-$C_4$ alkylene-$NR_A^2R_A^3$, $C_1$-$C_4$ alkylene-CO—$NR_A^2R_A^3$, $C_1$-$C_4$ alkylene-$SO_2$—$NR_A^2R_A^3$, $NR_A^4$—CO—$R_A^1$, $NR_A^4$—$SO_2$—$R_A^1$, or $C_1$-$C_4$ alkylene-O—$R_A^1$, —O—$R_A^1$ or —$NR_A^2R_A^3$; in which $R_A^1$ denotes independently of its respective occurrence, optionally substituted $C_1$-$C_6$ alkyl, $C_3$-$C_6$ cycloalkyl, $C_1$-$C_4$ alkylene-heterocycloalkyl, aryl, hetaryl, $C_1$-$C_4$ alkylene-aryl, $C_1$-$C_6$ alkylene-hetaryl, $C_1$-$C_4$ alkylene-$NR_A^2R_A^3$, $C_1$-$C_4$ alkylene-CO—$NR_A^2R_A^3$ or $C_1$-$C_4$ alkylene-O—$C_1$-$C_6$ alkyl;

$R_A^2$ denotes independently of its respective occurrence, hydrogen, CN or optionally substituted $C_1$-$C_6$ alkyl, aryl, hetaryl, heterocycloalkyl, $C_1$-$C_4$ alkylene-aryl, $C_1$-$C_4$ alkylene-hetaryl, CO—$C_1$-$C_6$ alkyl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, $SO_2$-aryl or $SO_2$-hetaryl;

$R_A^3$ denotes independently of its respective occurrence, hydrogen or optionally substituted $C_1$-$C_6$ alkyl;

or the radicals $R_A^2$ and $R_A^3$ together with the nitrogen may form a five- or six-membered, optionally substituted, saturated or aromatic heterocycle that may contain another heteroatom that may be the same or different and is selected from the group O, N, S;

$R_A^4$ denotes hydrogen or optionally substituted $C_1$-$C_6$ alkyl;

$R_w$ denotes hydrogen, CN, $CF_3$, $OCF_3$ or optionally substituted $C_1$-$C_6$ alkyl or O—$C_1$-$C_6$ alkyl or independently of one another, two radicals selected from the group consisting of A, B, or $R_w$ together with the respective carbon atom to which they are attached may form a five- or six-membered, optionally substituted, saturated or unsaturated carbocycle or a five- or six-membered, optionally substituted, saturated or unsaturated or aromatic heterocycle, which may contain one, two or three other heteroatoms, which may be the same or different and are selected from the group consisting of O, N and S.

4. A compound of general formula I according to claim 1, or an enantiomer, diastereomer or tautomer thereof or a pharmaceutically acceptable salt thereof in which:

Z denotes —$CH_2$—, —CH($C_1$-$C_3$ alkyl), optionally $C_1$-$C_3$ alkyl-substituted $C_1$-$C_3$ alkylene or —$CH_2$—C—($CH_2$—$CH_2$)—$CH_2$—.

5. A compound of general formula I according to claim 1, or an enantiomer, diastereomer or tautomer thereof or a pharmaceutically acceptable salt thereof in which:

Z denotes —$CH_2$—, —$CH_2$—$CH_2$— or —$CH_2$—$CH_2$—$CH_2$—.

6. A compound of general formula I according to claim 1, or the enantiomer, diastereomer or tautomer thereof, or a pharmaceutically acceptable salt thereof, in which:

Z denotes —$CH_2$—.

7. A compound of general formula I according to claim 1, or the enantiomer, diastereomer or tautomer thereof, or a pharmaceutically acceptable salt thereof, in which the stated radicals are defined as follows:

A denotes optionally substituted —O—$C_1$-$C_6$ alkyl, —$OCF_3$, —$OCHF_2$, —$N(C_1$-$C_3$ alkyl$)_2$, piperidinyl, morpholinyl, and B denotes
hydrogen, CN, $CF_3$, $OCF_3$, —$OCHF_2$, $CHF_2$, COOH, halogen, or optionally substituted $C_1$-$C_6$ alkyl, $C_3$-$C_7$ cycloalkyl, hetaryl, heterocycloalkyl, $C_1$-$C_4$ alkylene-$NR_A^2R_A^3$, $C_1$-$C_4$ alkylene-CO—$NR_A^2R_A^3$, $C_1$-$C_4$ alkylene-$SO_2$—$NR_A^2R_A^3$, $NR_A^4$—CO—$R_A^1$, $NR_A^4$—$SO_2$—$R_A^1$ or $C_1$-$C_4$ alkylene-O—$R_A^1$, —O—$R_A^1$ or —$NR_A^2R_A^3$, in which $R_A^1$ denotes
independently of its respective occurrence, optionally substituted $C_1$-$C_6$ alkyl, $C_3$-$C_6$ cycloalkyl, phenyl, pyridyl, $C_1$-$C_4$ alkylene-$NR_A^2R_A^3$ or $C_1$-$C_4$ alkylene-O—$C_1$-$C_6$ alkyl;

$R_A^2$ denotes
independently of its respective occurrence, hydrogen, CN or optionally substituted $C_1$-$C_6$ alkyl, phenyl or pyridyl;

$R_A^3$ denotes
independently of its respective occurrence, hydrogen or optionally substituted $C_1$-$C_6$ alkyl;
or the radicals $R_A^2$ and $R_A^3$ together with the nitrogen atom to which they are attached may form a five- or six-membered, optionally substituted, saturated heterocycle, which may contain another heteroatom which may be the same or different and is selected from the group consisting of O, N, S;

$R_A^4$ denotes
independently of its respective occurrence, hydrogen or optionally substituted $C_1$-$C_6$ alkyl;

$R_w$ denotes hydrogen or
independently of one another, two radicals selected from the group consisting of A, B and $R_w$ together with the respective carbon atom
to which they are attached may form a five- or six-membered, optionally substituted, saturated or unsaturated or aromatic heterocycle, which may contain one or two or more heteroatoms, which may be the same or different and are selected from the group consisting of O, N and S.

8. A compound of general formula I according to claim 1, or the enantiomer, diastereomer or tautomer thereof, or a pharmaceutically acceptable salt thereof, such that formula I has one of the following meanings IIIa, IIIb, or IIIc (quinoline compound), depending on the meaning of $R^1$, $R^2$ and $R^5$

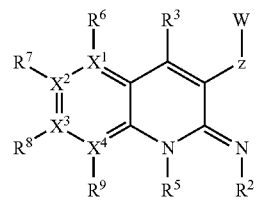
IIIa

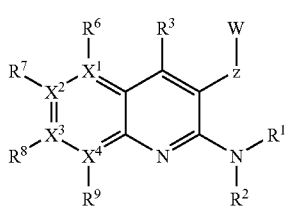
IIIb

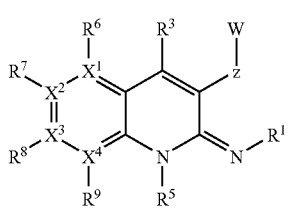
IIIc and $R^1$, $R^2$, $R^5$, $R^6$, $R^7$, $R^8$, $R^9$, $X^1$, $X^2$, $X^3$, $X^4$, Z and W, unless otherwise described above, have same meanings as in claim 1 and in which the stated radicals are defined as follows:
$R^3$ denotes hydrogen, CN, $CF_3$, Cl, F, methoxy, ethoxy, methyl, ethyl, optionally substituted phenyl.

9. A compound of general formula I according to claim 1, or the enantiomer, diastereomer or tautomer thereof, or a pharmaceutically acceptable salt thereof, such that formula I has one of the following meanings IIIa, IIIb or IIIc (quinoline compound), depending on the meaning of $R^1$, $R^2$, and $R^5$

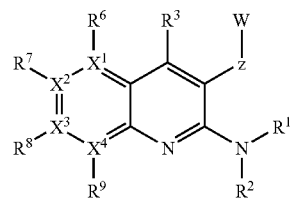
IIIa

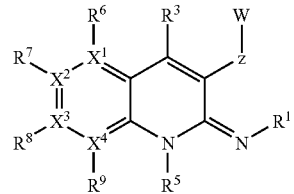
IIIb

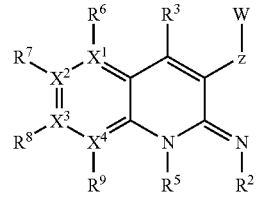
IIIc and $R^1$, $R^2$, $R^3$, $R^5$, $R^6$, $R^7$, $R^8$, $R^9$, Z and W, unless otherwise described above, have the same meanings as in any one of claims 1 through 15, and in which the stated radicals are defined as follows:

$X^1$ denotes C, $X^2$ denotes C, $X^3$ denotes C, $X^4$ denotes C.

10. A compound of general formula I according to claim 1, or the enantiomer, diastereomer or tautomer thereof, or a pharmaceutically acceptable salt thereof, such that formula I has one of the following meanings IIIa, IIIb or IIIc (quinoline compound), depending on the meaning of $R^1$, $R^2$, and $R^5$ IIIa IIIb IIIc in which the radicals $R^1$, $R^2$, $R^3$, $R^5$, $X^1$, $X^2$, $X^3$, $X^4$, Z and W, unless otherwise described above, have the same meanings as in claim 1 and in which the stated radicals are defined as follows:

$R^6$, $R^7$, $R^8$, and $R^9$ denote each independently of the others, a radical that may be the same or different is selected from the same or different radicals of the groups 1), 2), 3), 4), 5), 6) or 7), in which groups 1) through 7) have the following meanings:

1) hydrogen, halogen, CN, $CF_3$, —$OCF_3$, or
   optionally substituted $C_1$-$C_4$ alkyl, $C_2$-$C_4$ alkenyl or $NR_Q^7R_Q^8$
   in which and $R_Q^8$ are defined as shown below
2) phenyl optionally substituted with one, two or three radicals which may be the same or different and are selected from the group consisting of $R_Q^2$, $R_Q^3$ and $R_Q^4$
   in which
   $R_Q^2$, $R_Q^3$ and $R_Q^4$, independently of one another each denote a substituent that may be the same or different and is selected from the following group:
   hydrogen, $NO_2$, $NH_2$, OH, CN, $CF_3$, CHF2, $OCF_3$, $OCHF_2$, COOH, O—$CH_2$—COOH, SH, halogen or optionally substituted hetaryl, heterocycloalkyl, $C_1$-$C_4$ alkyl, O—$R_Q^5$, $NR_Q^7R_Q^8$ or
   two of the radicals from $R_Q^2$, $R_Q^3$ or $R_Q^5$ together with the carbon atom to which they are attached may form a five- or six-membered, optionally substituted, saturated, unsaturated or aromatic heterocycle that may contain one or two additional different or the same heteroatoms selected from the group consisting of O, N and S, in which
   $R_Q^5$ denotes optionally substituted $C_1$-$C_4$ alkyl;
   $R_Q^7$ denotes, independently of its respective occurrence, hydrogen
   Or
   in each case optionally substituted $C_1$-$C_4$ alkyl;
   $R_Q^8$ denotes, independently of its respective occurrence, optionally substituted $C_1$-$C_4$ alkyl, aryl or hetaryl;
   or the radicals $R_Q^7$ and $R_Q^8$ together with the nitrogen atom to which they are attached may form a five- or six-membered, optionally substituted, saturated or aromatic heterocycle, which may contain one or two additional heteroatoms, which may be the same or different and are selected from the group consisting of O, N and S;

3) a five- or six-membered hetaryl radical, which may optionally be substituted once or twice with substituents that may be the same or different and are selected from the group consisting of:
   2-thienyl, 3-thienyl, 2-thiazolyl, 4-thiazolyl, 5-thiazolyl, 1-pyrazolyl, 3-pyrazolyl, 4-pyrazolyl, 5-pyrazolyl, 1-imidazolyl,
   2-imidazolyl, 4-imidazolyl, 5-imidazolyl, 2-pyridyl, 3-pyridyl, 4-pyridyl, in which the substituents are preferably selected from the group consisting of halogen, CN, $CF_3$, $OCF_3$, or optionally substituted $C_1$-$C_3$ alkyl, O—$C_1$-$C_4$ alkyl, NH—($C_1$-$C_4$ alkyl), N($C_1$-$C_4$ alkyl)$_2$;

4) two of the radicals $R^6$, $R^7$, $R^8$ or $R^9$ together may form a five- or six-membered, optionally substituted, partially or fully saturated carbocycle or a five- or six-membered, optionally substituted, partially or fully saturated heterocycle, which may contain one or two heteroatoms that are the same or different and are selected from the group consisting of O, N and S;

5) an optionally substituted $C_3$-$C_5$ monocyclic saturated hydrocarbon radical;

6) an optionally substituted five- or six-membered monocyclic, partially or fully saturated heterocycle selected from the following group:

in which the radical $R_Q^7$, independently of its occurrence, is defined as above;

7) a radical of general formula V $$-(CR_v^1R_v^2)_d-(Y)_e-(CR_v^3R_v^4)_f-R_v^5 \qquad V$$

with the indices
d=0 or 1,
e=0 or 1,
f=0 or 1,
in which the sum of d, e and f is 1, 2 or 3;
$R_v^1$, $R_v^2$, $R_v^3$, $R_v^4$ independently of one another denote hydrogen or optionally substituted $C_1$-$C_4$ alkyl, $R_Y^5$ denotes
a radical selected from radicals as defined above in one or more of the groups 1), 2), 3), 5) or 6);
Y denotes
—CO—, —O—, —S—, —NR$_Y^5$—, —CO—NR$_Y^5$, —NR$_Y^5$-OO—, —SO$_2$—NR$_Y^5$, —NR$_Y^5$—SO$_2$—;
in which
$R_Y^4$ denotes
hydrogen or
optionally substituted $C_1$-$C_6$ alkyl.

11. A compound of general formula I according to claim 1, or the enantiomer, diastereomer or tautomer thereof, or a pharmaceutically acceptable salt thereof, such that formula I has one of the following meanings IIIa, IIIb or IIIc (quinoline compound), depending on the meaning of $R^1$, $R^2$ and $R^5$

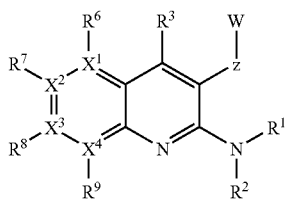
IIIa

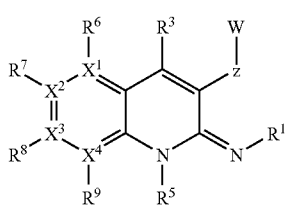
IIIb

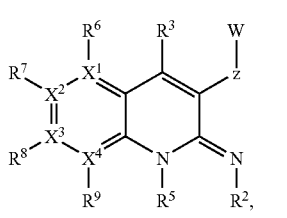
IIIc in which the radicals $R^1$, $R^2$, $R^3$, $R^5$, $X^1$, $X^2$, $X^3$, $X^4$, Z and W, unless otherwise described above, have the same meanings as in claim 1 and in which the stated radicals are defined as follows:

$R^6$, $R^7$, $R^8$ and $R^9$ denote
each independently of one another, a radical selected from the groups 1), 2), 3), 4), 5), 6) or 7) which may be the same or different, such that groups 1) through 7) have the following meanings:
1) hydrogen, Cl, F, CN, CF$_3$, —OCF$_3$, or
optionally substituted $C_1$-$C_4$ alkyl or NR$_Q^7$R$_Q^8$
in which R$_Q^7$ and R$_Q^8$ are defined as shown below,
2) phenyl which may substituted with one, two or three radicals that may be the same or different and are selected from the group consisting of R$_Q^2$, R$_Q^3$ and R$_Q^4$
in which
R$_Q^2$, R$_Q^3$ and R$_Q^4$ each independently of one another denotes a substituent that may be the same or different and is selected from the following group:
hydrogen, CN, CF$_3$, CHF2, OCF$_3$, OCHF$_2$, Cl, F or optionally substituted hetaryl, heterocycloalkyl, $C_1$-$C_4$ alkyl, O—R$_Q^5$, NR$_Q^7$R$_Q^8$ or two of the radicals from R$_Q^2$, R$_Q^3$ or R$_Q^4$ together with the carbon atom to which they are attached may form a five- or six-membered, optionally substituted, saturated, unsaturated or aromatic heterocycle, which may contain one or two additional heteroatoms, which may be the same or different and are selected from the group consisting of O, N and S;
R$_Q^5$ denotes optionally substituted $C_1$-$C_4$ alkyl;
R$_Q^7$ denotes, independently of its respective occurrence, hydrogen or
in each case optionally substituted $C_1$-$C_4$ alkyl;
R$_Q^8$ denotes, independently of its respective occurrence, optionally substituted $C_1$-$C_4$ alkyl, aryl or hetaryl;
or the radicals R$_Q^7$ and R$_Q^8$ together with the nitrogen atom to which they are attached may form a five- or six-membered, optionally substituted, saturated or aromatic heterocycle, which may contain another heteroatom selected from the group consisting of O, N and S;
3) a five- or six-membered hetaryl radical, optionally substituted once or twice with substituents that may be the same or different and are selected from the group consisting of:
2-thienyl, 3-thienyl, 2-thiazolyl, 1-pyrazolyl, 1-imidazolyl, 2-imidazolyl, 2-pyridyl, 3-pyridyl, 4-pyridyl, in which the substituents are preferably selected from the group consisting of Cl, F, CN, CF$_3$, OCF$_3$, or optionally substituted $C_1$-$C_3$ alkyl, O—$C_1$-$C_4$ alkyl, NH—($C_1$-$C_4$ alkyl), N($C_1$-$C_4$ alkyl)$_2$;
4) two of the radicals $R^6$, $R^7$, $R^8$ or $R^9$ together with the respective atom to which they are attached may form an optionally substituted 1,3-dioxolane or morpholine ring;
5) optionally substituted cyclopropyl or cyclopentyl;
6) a five- or six-membered, optionally substituted monocyclic, partially or fully saturated heterocycle selected from the following group:

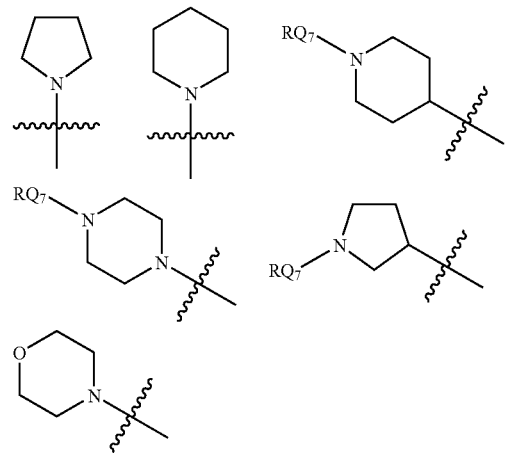

where the R$_Q^7$ radical, independently of its occurrence, is defined as above;
7) a radical of general formula V —(CR$_v^1$R$_v^2$)$_d$—(Y)$_e$—(CR$_v^3$R$_v^4$)$_f$—R$_v^5$    V with the indices
d=0 or 1,
e=0 or 1,
f=0 or 1,
in which the sum of d, e and f is 1 or 2;

$R_v^1, R_v^2, R_v^3, R_v^4$ each denotes hydrogen, $R_v^5$ denotes a radical selected from the radicals as defined above in one or more of groups 1), 2), 3), 5) or 6);

Y denotes

—CO—, —O—, —$NR_Y^5$—;

in which $R_Y^5$ denotes hydrogen or methyl.

12. A compound of general formula I according to claim 1, or the enantiomer, diastereomer or tautomer thereof, or a pharmaceutically acceptable salt thereof, such that formula I has one of the following meanings IIIa, IIIb or IIIc (quinoline compound), depending on the meaning of $R^1$, $R^2$ and $R^5$

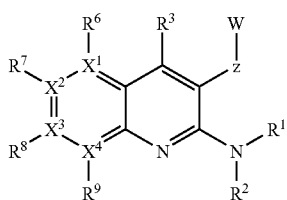

IIIa

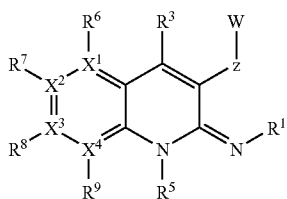

IIIb

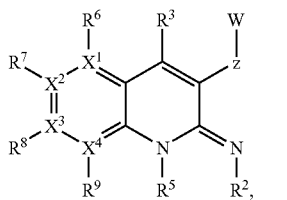

IIIc in which the radicals $R^1, R^2, R^3, R^5, X^1, X^2, X^3, X^4$, Z and W, unless otherwise described above, have the same meanings as in claim 1 and in which the stated radicals are defined as follows:

$R^6$, $R^7$, $R^8$ and $R^9$ denote each independently of one another, a radical selected from the group:

hydrogen, Cl, F, CN, $CF_3$, —$OCF_3$, optionally substituted $C_1$-$C_4$ alkyl, dimethylamino, diethylamino, methoxy, ethoxy, propoxy, isopropoxy, pyrrolidinyl, piperidinyl, morpholinyl or N-methylpiperazinyl or aryl or hetaryl, optionally substituted once or more with substituents that may be the same or different and are selected from Cl, F, methyl or methoxy, the aryl or hetaryl being selected from the group consisting of phenyl, 2-thienyl, 3-thienyl, 2-thiazolyl, 1-imidazolyl, 1-pyrazolyl, 2-pyridyl, 3-pyridyl or 4-pyridyl.

13. A compound of general formula I according to claim 1, or the enantiomer, diastereomer or tautomer thereof, or a pharmaceutically acceptable salt thereof, such that formula I has one of the following meanings IIIa, IIIb or IIIc (quinoline compound), depending on the meaning of $R^1$, $R^2$, and $R^5$

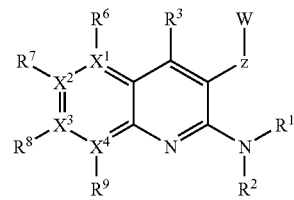

IIIa

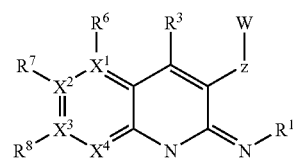

IIIb

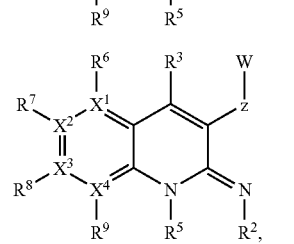

IIIc in which the radicals $R^1, R^2, R^3, R^5, R^6, R^7, R^8, R^9$, Z and W, unless otherwise described above, have the same meanings as in claim 1 and in which the stated radicals are defined as follows:

$R^1$ denotes hydrogen, $R^2$ denotes hydrogen and $R^5$ denotes hydrogen or a free electron pair.

14. A compound of general formula I according to claim 1, or the enantiomer, diastereomer or tautomer thereof, or a pharmaceutically acceptable salt thereof, in which:

$R^1$ and $R^2$ independently denote hydrogen, a free electron pair, OH, CN or optionally substituted O—$C_1$-$C_6$ alkyl, $C_1$-$C_6$ alkyl, CO—$C_1$-$C_6$ alkyl, CO—O—$C_1$-$C_6$ alkyl, $R^3$ denotes hydrogen, CN, $CF_3$, Cl, F, methoxy, ethoxy, methyl, ethyl, optionally substituted phenyl, $R^4$ denotes a bond to $X^5$ while preserving a C=C double bond, $R^5$ denotes hydrogen or a free electron pair, $R^6$, $R^7$, $R^8$ and $R^9$ denote each independently of one another, a radical selected from the group consisting of hydrogen, Cl, F, CN, $CF_3$, —$OCF_3$, optionally substituted $C_1$-$C_4$ alkyl, dimethylamino, diethylamino, methoxy, ethoxy, propoxy, isopropoxy, pyrrolidinyl, piperidinyl, morpholinyl or N-methylpiperazinyl or aryl or hetaryl selected from the group consisting of phenyl, 2-thienyl, 3-thienyl, 2-thiazolyl, 1-imidazolyl, 1-pyrazolyl, 2-pyridyl, 3-pyridyl or 4-pyridyl, each optionally substituted once or more with substituents that may be the same or different and are selected from Cl, F, methyl or methoxy;

$X^1$ denotes C, $X^2$ denotes C, $X^3$ denotes C, $X^4$ denotes C, $X^5$ denotes C, Z denotes —$CH_2$—, —$CH_2$—$CH_2$— or —$CH_2$—$CH_2$—$CH_2$— and W with
A denotes optionally substituted —O—$C_1$-$C_6$ alkyl, —$OCF_3$, —$OCHF_2$, —NH—$C_1$-$C_6$ alkyl, —NH—CO—$C_1$-$C_6$ alkyl, —NH—$SO_2$—$C_1$-$C_6$ alkyl, —N($C_1$-$C_6$ alkyl)$_2$, piperidinyl, morpholinyl, —N($C_1$-$C_6$ alkyl)-CO—$C_1$-$C_6$ alkyl or —N($C_1$-$C_6$ alkyl)-$SO_2$—$C_1$-$C_6$ alkyl, $C_1$-$C_4$ alkylene-CO—N($CH_3$)$_2$, $C_1$-$C_4$ alkylene-CO—N-piperidyl, $C_1$-$C_4$ alkylene-CO—N-morpholinyl, $C_1$-$C_4$ alkylene-$SO_2$—N(CH3)2, $C_1$-$C_4$ alkylene-$SO_2$—N-piperidyl, $C_1$-$C_4$ alkylene, $SO_2$—N-morpholinyl or $C_1$-$C_4$ alkyl-O—$C_1$-$C_4$ alkyl
and
B denotes hydrogen, CN, $CF_3$, $OCF_3$, —$OCHF_2$, $CHF_2$, COOH, halogen, or optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-hetaryl, $C_1$-$C_4$ alkylene-aryl, $C_1$-$C_4$ alkylene-$NR_A^2R_A^3$, $C_1$-$C_4$ alkylene-CO—$NR_A^2R_A^3$, $C_1$-$C_4$ alkylene-$SO_2$—$NR_A^2R_A^3$, $NR_A^4$—CO—$R_A^1$, $NR_A^4$—$SO_2$—$R_A^1$, or $C_1$-$C_4$ alkylene-O—$R_A^1$, —O—$R_A^1$ or —$NR_A^2R_A^3$; in which
$R_A^1$ denotes
optionally substituted $C_1$-$C_6$ alkyl, $C_3$-$C_6$ cycloalkyl, $C_1$-$C_4$ alkylene-heterocycloalkyl, aryl, hetaryl, $C_1$-$C_4$ alkylene-aryl, $C_1$-$C_6$ alkylene-hetaryl, $C_1$-$C_4$ alkylene-$NR_A^2R_A^3$, $C_1$-$C_4$ alkylene-CO—$NR_A^2R_A^3$ or $C_1$-$C_4$ alkylene-O—$C_1$-$C_6$ alkyl;
$R_A^2$ denotes
hydrogen, CN or
optionally substituted $C_1$-$C_6$ alkyl, aryl, hetaryl, heterocycloalkyl, $C_1$-$C_4$ alkylene-aryl, $C_1$-$C_4$ alkylene-hetaryl, CO—$C_1$-$C_6$ alkyl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, $SO_2$-aryl or $SO_2$-hetaryl;
$R_A^3$ denotes
hydrogen or optionally substituted $C_1$-$C_6$ alkyl;
or the radicals $R_A^2$ and $R_A^3$ together with the nitrogen atom to which they are attached may form a five- or six-membered, optionally substituted, saturated or aromatic heterocycle, which may contain another heteroatom that may be the same or different and is selected from the group consisting of O, N and S;
$R_A^4$ denotes
hydrogen or
optionally substituted $C_1$-$C_6$ alkyl;
$R_w$ denotes hydrogen, CN, $CF_3$, $OCF_3$ or
optionally substituted $C_1$-$C_6$ alkyl or O—$C_1$-$C_6$ alkyl
or, independently of one another, two of the radicals A, B, or $R_w$ together with the carbon atom to which they are attached may form a five- or six-membered, optionally substituted, saturated or unsaturated carbocycle or a five- or six-membered, optionally substituted, saturated or unsaturated or aromatic heterocycle, which may contain one, two or three additional heteroatoms, which may be the same or different and are selected from the group consisting of O, N and S.

15. A compound of general formula I according to claim 1, or the enantiomer, diastereomer or tautomer thereof, or a pharmaceutically acceptable salt thereof, in which:
$R^1$ denotes hydrogen,
$R^2$ denotes hydrogen and
$R^3$ denotes hydrogen, CN, $CF_3$, Cl, F, methoxy, ethoxy, methyl, ethyl, optionally substituted phenyl,
$R^4$ denotes a bond to $X^5$ while preserving a C=C double bond, $R^5$ denotes hydrogen or a free electron pair,
$R^6$, $R^7$, $R^8$ and $R^9$
denote, each independently of one another, a radical that may be the same or different and is selected from the group consisting of
hydrogen, Cl, F, CN, $CF_3$, —$OCF_3$, $C_1$-$C_4$ alkyl, dimethylamino, diethylamino, methoxy, ethoxy, propoxy, isopropoxy, pyrrolidinyl, piperidinyl, morpholinyl or N-methylpiperazinyl or
aryl or hetaryl selected from the group consisting of phenyl, 2-thienyl, 3-thienyl, 2-thiazolyl, 1-imidazolyl, 1-pyrazolyl, 2-pyridyl, 3-pyridyl and 4-pyridyl, optionally substituted once or more with substituents that may be the same or different and are selected from Cl, F, methyl or methoxy;
$X^1$ denotes C,
$X^2$ denotes C,
$X^3$ denotes C,
$X^4$ denotes C,
$X^5$ denotes C,
Z denotes —$CH_2$—, and
W with
A denotes optionally substituted —O—$C_1$-$C_6$ alkyl, —$OCF_3$, —$OCHF_2$, —N($C_1$-$C_3$ alkyl)$_2$, piperidinyl or morpholinyl and
B denotes hydrogen, CN, $CF_3$, $OCF_3$, —$OCHF_2$, $CHF_2$, COOH, halogen or optionally substituted $C_1$-$C_6$ alkyl, $C_3$-$C_7$ cycloalkyl, hetaryl, heterocycloalkyl, $C_1$-$C_4$ alkylene-$NR_A^2R_A^3$, $C_1$-$C_4$ alkylene-CO—$NR_A^2R_A^3$, C1-C4 alkylene-$SO_2$—$NR_A^2R_A^3$, $NR_A^4$—CO—$R_A^1$, $NR_A^4$—$SO_2$—$R_A^1$ or $C_1$-$C_4$ alkylene-O—$R_A^1$, —O—$R_A^1$ or —$NR_A^2R_A^3$; in which
$R_A^1$ denotes
optionally substituted $C_1$-$C_6$ alkyl, $C_3$-$C_6$ cycloalkyl, phenyl, pyridyl, $C_1$-$C_4$ alkylene-$NR_A^2R_A^3$ or $C_1$-$C_4$ alkylene-O—$C_1$-$C_6$ alkyl;
$R_A^2$ denotes
hydrogen, CN or optionally substituted $C_1$-$C_6$ alkyl, phenyl or pyridyl;
$R_A^3$ denotes
hydrogen or optionally substituted $C_1$-$C_6$ alkyl;
or the radicals $R_A^2$ and $R_A^3$ together with the nitrogen atom to which they are attached may form a five- to six-membered saturated heterocycle, which may contain another heteroatom that may be the same or different and is selected from the group consisting of O, N and S;
$R_A^4$ denotes
hydrogen or optionally substituted $C_1$-$C_6$ alkyl;
$R_w$ denotes hydrogen
or independently of one another, two of the radicals A, B, or $R_w$ together with the carbon atom to which they are attached may form a five- or six-membered, optionally substituted, saturated or unsaturated or aromatic heterocycle that may contain one or two or three additional
heteroatoms that are the same or different and are selected from the group consisting of O, N and S.

16. A compound of general formula I according to claim 1, or the enantiomer, diastereomer or tautomer thereof, or a pharmaceutically acceptable salt thereof, in which:
$R^1$ denotes hydrogen,
$R^2$ denotes hydrogen and
$R^3$ denotes hydrogen, CN, $CF_3$, Cl, F, methoxy, ethoxy, methyl, ethyl,
optionally substituted phenyl, $R^4$ denotes a bond to $X^5$ while preserving a C=C double bond, $R^5$ denotes hydrogen or a free electron pair, $R^6$, $R^7$, $R^8$ and $R^9$
denote each independently of one another, a radical that may be the same or different and is selected from the group consisting of
hydrogen, Cl, F, CN, $CF_3$, —$OCF_3$, optionally substituted $C_1$-$C_4$ alkyl, dimethylamino, diethylamino, methoxy, ethoxy, propoxy, isopropoxy, pyrrolidinyl, piperidinyl, morpholinyl or N-methylpiperazinyl or aryl or hetaryl selected from the group consisting of phenyl, 2-thienyl, 3-thienyl, 2-thiazolyl, 1-imidazolyl, 1-pyrazolyl, 2-pyridyl, 3-pyridyl and 4-pyridyl, optionally substituted once or more with substituents that may be the same or different and are selected from Cl, F, methyl or methoxy;

$X^1$ denotes C,
$X^2$ denotes C,
$X^3$ denotes C,
$X^4$ denotes C,
$X^5$ denotes C,
Z denotes —$CH_2$—, and
W with A denotes optionally substituted —O—$C_1$-$C_6$ alkyl, —$OCF_3$, —$OCHF_2$, —N($C_1$-$C_3$ alkyl)$_2$, piperidinyl or morpholinyl and B denotes hydrogen, CN, $CF_3$, $OCF_3$, —$OCHF_2$, $CHF_2$, halogen or optionally substituted $C_1$-$C_6$ alkyl, $C_3$-$C_7$ cycloalkyl, $C_1$-$C_4$ alkylene-$NR_A^2R_A^3$, $NR_A^4$—CO—$R_A^1$, $NR_A^4$—$SO_2$—$R_A^1$ or $C_1$-$C_4$ alkylene-O—$R_A^1$, —O—$R_A^1$ or —$NR_A^2R_A^3$; in which $R_A^1$ denotes
optionally substituted $C_1$-$C_6$ alkyl, $C_3$-$C_6$ cycloalkyl, phenyl, pyridyl, $C_1$-$C_4$ alkylene-$NR_A^2R_A^3$ or $C_1$-$C_4$ alkylene-O—$C_1$-$C_6$ alkyl;

$R_A^2$ denotes
hydrogen, CN or optionally substituted $C_1$-$C_6$ alkyl, phenyl or pyridyl;

$R_A^3$ denotes
hydrogen or optionally substituted $C_1$-$C_6$ alkyl;
or the radicals $R_A2$ and $R_A3$ together with the nitrogen atom to which they are attached may form a five- to six-membered, optionally substituted, saturated heterocycle, which may contain another heteroatom that may be the same or different and is selected from the group consisting of O, N and S;

$R_A^4$ denotes
hydrogen or methyl;

$R_w$ denotes hydrogen.

17. A compound of general formula I according to claim 1, or the enantiomer, diastereomer or tautomer thereof, or a pharmaceutically acceptable salt thereof, in which:

$R^1$ and $R^2$ independently of one another denotes
hydrogen, a free electron pair, OH or optionally substituted O—$C_1$-$C_6$ alkyl, $C_1$-$C_6$ alkyl, CO—$C_1$-$C_6$ alkyl, CO—O—$C_1$-$C_6$ alkyl, $R^3$ denotes hydrogen,
$R^4$ denotes hydrogen,
$R^5$ denotes hydrogen or a free electron pair,
$R^6$, $R^7$, $R^8$ and $R^9$
each independently of one another denotes a radical selected from the group consisting of
hydrogen, Cl, F, CN, $CF_3$, —$OCF_3$, $C_1$-$C_4$ alkyl, $NMe_2$, methoxy, ethoxy; phenyl, 2-thienyl, 3-thienyl, 2-pyridyl, 3-pyridyl, 4-pyridyl, morpholinyl or N-methylpiperazinyl, optionally substituted once or more with substituents that may be the same or different and are selected from Cl, F, methyl or methoxy;

$X^1$ denotes C,
$X^2$ denotes C,
$X^3$ denotes C,
$X^4$ denotes C,
$X^5$ denotes C,
Z denotes —$CH_2$—, and
W with A denotes optionally substituted —O—$C_1$-$C_6$ alkyl, —$OCF_3$, —$OCHF_2$, —NH—$C_1$-$C_6$ alkyl, —NH—CO—$C_1$-$C_6$ alkyl, —NH—$SO_2$—$C_1$-$C_6$ alkyl, —N($C_1$-$C_6$ alkyl)$_2$, piperidinyl, morpholinyl, —N($C_1$-$C_6$ alkyl)-CO—$C_1$-$C_6$ alkyl or —N($C_1$-$C_6$ alkyl)-$SO_2$—$C_1$-$C_6$ alkyl, $C_1$-$C_4$ alkylene-CO—N($CH_3$)$_2$, $C_1$-$C_4$ alkylene-CO—N-piperidyl, $C_1$-$C_4$ alkylene-CO—N-morpholinyl, $C_1$-$C_4$ alkylene-$SO_2$—N($CH_3$)$_2$, $C_1$-$C_4$ alkylene-$SO_2$—N-piperidyl, $C_1$-$C_4$ alkylene, $SO_2$—N-morpholinyl or $C_1$-$C_4$ alkyl-O—$C_1$-$C_6$ alkyl and B denotes hydrogen, CN, $CF_3$, $OCF_3$, —$OCHF_2$, $CHF_2$, COOH, halogen, or optionally substituted $C_1$-$C_6$ alkyl, $C_2$-$C_6$ alkenyl, $C_2$-$C_6$ alkynyl, $C_3$-$C_7$ cycloalkyl, $C_1$-$C_4$ alkylene-$C_3$-$C_7$ cycloalkyl, $C_1$-$C_4$ alkylene-heterocycloalkyl, aryl, hetaryl, heterocycloalkyl, $C_1$-$C_4$ alkylene-hetaryl, $C_1$-$C_4$ alkylene-aryl, $C_1$-$C_4$ alkylene-$NR_A^2R_A^3$, $C_1$-$C_4$ alkylene-CO—$NR_A^2R_A^3$, $C_1$-$C_4$ alkylene-$SO_2$—$NR_A^2R_A^3$, $NR_A^4$—CO—$R_A^1$, $NR_A^4$—$SO_2$—$R_A^1$, or $C_1$-$C_4$ alkylene-O—$R_A^1$, —O—$R_A^1$ or —$NR_A^2R_A^3$; in which $R_A^1$ denotes
optionally substituted $C_1$-$C_6$ alkyl, $C_3$-$C_6$ cycloalkyl, $C_1$-$C_4$ alkylene-heterocycloalkyl, aryl, hetaryl, $C_1$-$C_4$ alkylene-aryl, $C_1$-$C_6$ alkylene-hetaryl, $C_1$-$C_4$ alkylene-$NR_A^2R_A^3$, $C_1$-$C_4$ alkylene-CO—$NR_A^2R_A^3$ or $C_1$-$C_4$ alkylene-O—$C_1$-$C_6$ alkyl;

$R_A^2$ denotes
hydrogen, CN or optionally substituted $C_1$-$C_6$ alkyl, aryl, hetaryl, heterocycloalkyl, $C_1$-$C_4$ alkylene-aryl, $C_1$-$C_4$ alkylene-hetaryl, CO—$C_1$-$C_6$ alkyl, CO-aryl, CO-hetaryl, CO—$C_1$-$C_4$ alkylene-aryl, CO—$C_1$-$C_4$ alkylene-hetaryl, CO—O—$C_1$-$C_6$ alkyl, $SO_2$-aryl or $SO_2$-hetaryl;

$R_A^3$ denotes
hydrogen or optionally substituted $C_1$-$C_6$ alkyl;
or the radicals $R_A^2$ and $R_A^3$ together with the nitrogen atom to which they are attached may form a five- or six-membered, optionally substituted, saturated or aromatic heterocycle, which may contain another heteroatom that may be the same or different and is selected from the group consisting of O, N and S;

$R_A^4$ denotes
hydrogen or optionally substituted $C_1$-$C_6$ alkyl;

$R_w$ denotes hydrogen, CN, $CF_3$, $OCF_3$ or
optionally substituted $C_1$-$C_6$ alkyl or O—$C_1$-$C_6$ alkyl
or independently of one another, two of the radicals A, B or $R_w$ together with the carbon atom to which they are attached may form a five- or six-membered, optionally substituted, saturated or unsaturated carbocycle or a five- or six-membered, optionally substituted, saturated or unsaturated or aromatic heterocycle, which may contain one, two or three additional heteroatoms, which may be the same or different and are selected from the group consisting of O, N and S.

18. A compound of general formula I according to claim 1, or the enantiomer, diastereomer or tautomer thereof, or a pharmaceutically acceptable salt thereof, in which:

A denotes optionally substituted —O—C$_1$-C$_3$ alkyl, —O—C$_1$-C$_3$ haloalkyl, —N(C$_1$-C$_3$ alkyl)$_2$, piperidinyl or morpholinyl.

19. A compound of general formula I according to claim 1, or the enantiomer, diastereomer or tautomer thereof, or a pharmaceutically acceptable salt thereof, in which:
A
denotes —O—CH$_3$, —OCF$_3$, —OCHF$_2$, —OCH$_2$F, —O—CH$_2$—CH$_3$, —O—CH$_2$—CF$_3$, —O—CH$_2$—CHF$_2$, —O—CH$_2$—CH$_2$F or O-isopropyl.

20. A compound of general formula I according to claim 1, or the enantiomer, diastereomer or tautomer thereof, or a pharmaceutically acceptable salt thereof, in which:
A denotes —O—CH$_3$, —O—CH$_2$—CH$_3$, —O—CH$_2$—CF$_3$, —O—CH$_2$—CHF$_2$ or —O—CH$_2$—CH$_2$F.

21. A compound of general formula I according to claim 1, or the enantiomer, diastereomer or tautomer thereof, or a pharmaceutically acceptable salt thereof, in which:
A denotes —O—CH$_3$.

22. A pharmaceutical composition containing at least one compound of general formula I according to claim 1 or the enantiomer, diastereomer or tautomer thereof, or a pharmaceutically acceptable salt thereof, and optionally at least one pharmaceutically acceptable vehicle or diluent.

23. A method for synthesizing at least one optionally substituted 2-amino-3-benzylquinoline derivative according to general formula I according to claim 1, characterized by the reaction of optionally substituted 2-aminobenzaldehyde derivatives and optionally substituted 3-arylpropionitrile derivatives under basic or acidic reaction conditions by means of a reaction related to the Friedlander reaction.

24. A method for synthesizing at least one optionally substituted 2-amino-3-benzylquinoline derivative according to claim 23, characterized by the steps of reaction of an optionally substituted (2-chloroquinolin-3-yl) (aryl)methanone compound by reaction with primary, secondary amines or ammonia and then reduction of the 3-carboxy group.

25. A method for synthesizing at least one optionally substituted 2-amino-3-benzylquinoline derivative according to claim 23, characterized by the steps of reaction of an optionally substituted 2-chloroquinoline compound by orthometallization in position 3, reaction with benzaldehyde derivatives, oxidation to the corresponding optionally substituted chloroquinolin-3-yl(aryl)methanone compound, reaction of primary, secondary amines or ammonia and then reduction of the 3-carboxy groups.

26. A method for synthesizing at least one optionally substituted 3-benzyl-3,4-dihydroquinazolin-2-amine derivative according to general formula I according to claim 1, characterized by the steps of reaction of optionally substituted 2-nitrobenzoic acid derivatives by peptide linkage with an optionally substituted benzylamine derivative, then production of the amide thus formed to the secondary amine followed by reduction of the nitro group and then cyclization with cyanogen bromide.

27. A method for synthesizing at least one optionally substituted 3-benzyl-3,4-dihydroquinazolin-2-amine derivative according to claim 26, characterized by the steps of reaction of an optionally substituted 2-nitrobenzaldehyde derivative by reductive alkylation with an optionally substituted benzylamine derivative, follows by reduction of the nitro group, cyclization to yield the corresponding 3-aryl-2-(methylthio)-3,4-dihydroquinazoline derivatives with carbon disulfide and methyl iodide and subsequent reaction with primary, secondary amines or ammonia.

28. A compound of general formula (I) according to claim 1, or a pharmaceutically acceptable salt thereof, selected from the group consisting of:
3-(2-Methoxybenzyl)quinolin-2-amine;
2-[(2-Aminoquinolin-3-yl)methyl]-3-methoxyphenol;
3-(2,6-Dimethoxybenzyl)quinolin-2-amine;
3-(2-Ethoxy-6-methoxybenzyl) quinolin-2-amine;
3-(2-Isopropoxy-6-methoxybenzyl)quinolin-2-amine;
7-Methoxy-3-(2-methoxybenzyl)quinolin-2-amine;
6-Methoxy-3-(2-methoxybenzyl)quinolin-2-amine;
6-Methoxy-3-(2-methoxybenzyl)quinolin-2-amine;
6-Chloro-3-(2,6-dimethoxybenzyl)quinolin-2-amine;
6-Chloro-3-(2-fluoro-6-methoxybenzyl)quinolin-2-amine;
6-Chloro-3-(2-methoxybenzyl-quinolin-2-amine;
7-(2,6-Dimethoxybenzyl)-[1,3]dioxolo[4,5-g]quinolin-6-amine;
3-(2,6-Dimethoxybenzyl)-6,7-dimethoxy-quinolin-2-amine;
7-(2-Methoxybenzyl)-[1,3]dioxolo[4,5-g]quinolin-6-amine;
7-Chloro-3-(2-methoxybenzyl)quinolin-2-amine;
6,7-Dimethoxy-3-(2-methoxybenzyl)quinolin-2-amine;
7-(2-Fluoro-6-methoxybenzyl)-[1,3]dioxolo[4,5-g]quinolin-6-amine;
6-Fluoro-3-(2-methoxybenzyl)quinolin-2-amine;
5-Chloro-3-(2-methoxybenzyl)quinolin-2-amine;
5-Chloro-3-(2,6-dimethoxybenzyl)quinolin-2-amine;
3-(2,6-Dimethoxybenzyl)-6-fluoroquinolin-2-amine;
6-Fluoro-3-(2-fluoro-6-methoxybenzyl)quinolin-2-amine;
2-[(2-Aminoquinolin-3-yl)methyl]phenol;
7-Chloro-3-(2-fluoro-6-methoxybenzyl)quinolin-2-amine;
7-Chloro-3-(2-chloro-6-methoxybenzyl)quinolin-2-amine;
3-(2-Methoxybenzyl)-N$^7$,N$^7$-dimethylquinolin-2,7-diamine;
3-(2-Fluoro-6-methoxybenzyl)quinolin-2-amine;
3-(2-Chloro-6-methoxybenzyl)quinolin-2-amine;
6-Ethoxy-3-(2-methoxybenzyl)quinolin-2-amine;
6-Ethoxy-3-(2,6-dimethoxybenzyl)quinolin-2-amine;
7-Fluoro-3-(2-methoxybenzyl)quinolin-2-amine;
7-(2-Chloro-6-methoxybenzyl)-[1,3]dioxolo[4,5-g]quinolin-6-amine;
6,7-Difluoro-3-(2-methoxybenzyl)quinolin-2-amine;
7-Fluoro-3-(2-fluoro-6-methoxybenzyl)quinolin-2-amine;
3-(2-Methoxybenzyl)-6-(2-methoxyethoxy)quinolin-2-amine;
3-(2-Methoxybenzyl)-6-morpholin-4-ylquinolin-2-amine;
3-(2-Methoxy-6-fluorobenzyl)-6-morpholin-4-ylquinolin-2-amine;
3-(2-Methoxybenzyl)-6-(4-methylpiperazin-1-yl)quinolin-2-amine;
3-(2-Fluoro-6-methoxybenzyl)-6-(4-methylpiperazin-1-yl)quinolin-2-amine;
7-Fluoro-3-(2-methoxybenzyl)-6-morpholin-4-ylquinolin-2-amine;
8-Methoxy-3-(2-methoxybenzyl)quinolin-2-amine;
3-(2,6-Dimethoxybenzyl)-8-methoxyquinolin-2-amine;
3-[2-(Trifluoromethoxy)benzyl]quinolin-2-amine;
3-(2-Isopropoxybenzyl)quinolin-2-amine;
3-(2-Ethoxybenzyl)quinolin-2-amine;
3-(2-Fluoro-6-isopropoxybenzyl)quinolin-2-amine;
3-(2-Ethoxy-6-fluorobenzyl)quinolin-2-amine;

3-{2-[2-(Dimethylamino)ethoxy]-6-fluorobenzyl}quinolin-2-amine;
3-[2-(difluoromethoxy)benzyl]quinolin-2-amine; and
3-(2-Ethoxybenzyl)-6-morpholin-4-ylquinolin-2-amine.

29. A compound of general formula (I) according to claim 1, or a pharmaceutically acceptable salt thereof, selected from the group consisting of:

3-(2,6-Dimethoxybenzyl)-1,8-naphthyridin-2-amine;
3-(2,6-Dimethoxybenzyl)-1,6-naphthyridin-2-amine;
3-(2-Methoxybenzyl)-1,6-naphthyridin-2-amine;
3-(2-Methoxybenzyl)-1,8-naphthyridin-2-amine;
3-(2-Fluoro-6-methoxybenzyl)-1,6-naphthyridin-2-amine;
3-(2-Methoxybenzyl)-1,7-naphthyridin-2-amine;
3-(2,6-Dimethoxybenzyl)-1,7-naphthyridin-2-amine;
3-(2-Methoxybenzyl)-1,5-naphthyridin-2-amine;
3-(2,6-Dimethoxybenzyl)-1,5-naphthyridin-2-amine;
3-(2-Fluoro-6-methoxybenzyl)-1,5-naphthyridin-2-amine;
3-(2-Chloro-6-methoxybenzyl)-1,6-naphthyridin-2-amine;
3-(2-Chloro-6-methoxybenzyl)-1,5-naphthyridin-2-amine;
3-(2,6-Dimethoxybenzyl)-3,4-dihydroquinazolin-2-amine;
3-(2-Methoxybenzyl)-3,4-dihydroquinazolin-2-amine;
7-Chloro-3-(2-methoxybenzyl)-3,4-dihydroquinazolin-2-amine;
3-(2-Methoxybenzyl)-7-(trifluoromethyl)-3,4-dihydroquinazolin-2-amine;
3-(4-Chloro-2-methoxybenzyl)-3,4-dihydroquinazolin-2-amine;
3-(2,3-Dihydro-1-benzofuran-7-ylmethyl)-3,4-dihydroquinazolin-2-amine;
3-[2-(Trifluoromethoxy)benzyl]-3,4-dihydroquinazolin-2-amine;
3-(2,4-Dimethoxybenzyl)-3,4-dihydroquinazolin-2-amine;
3-(2,3-Dimethoxybenzyl)-3,4-dihydroquinazolin-2-amine;
2-[(2-Aminoquinazolin-3(4H)-yl)methyl]phenol;
2-(Hydroxyamino)-3-(2-methoxybenzyl)-3,4-dihydroquinazoline;
N-(2,3-Dihydro-1H-inden-2-yl)-3-(2-methoxybenzyl)-3,4-dihydroquinazolin-2-amine;
3-(2-Methoxybenzyl)-2-[(pyridin-3-ylmethyl)amino]-3,4-dihydroquinazoline;
2-(Butylamino)-3-(2-methoxybenzyl)-3,4-dihydroquinazoline;
2-(Isobutylamino)-3-(2-methoxybenzyl)-3,4-dihydroquinazoline;
3-(2-Methoxybenzyl)-2-piperazin-1-yl-3,4-dihydroquinazoline;
3-(2-Methoxybenzyl)-2-(4-methylpiperazin-1-yl)-3,4-dihydroquinazoline;
2-(4-Benzylpiperazin-1-yl)-3-(2-methoxybenzyl)-3,4-dihydroquinazoline;
7-Bromo-3-(2,6-dimethoxybenzyl)-3,4-dihydroquinazolin-2-amine;
3-(2,6-Dimethoxybenzyl)-7-phenyl-3,4-dihydroquinazolin-2-amine;
3-(2,6-Dimethoxybenzyl)-7-(4-methoxyphenyl)-3,4-dihydroquinazolin-2-amine;
3-(2,6-Dimethoxybenzyl)-7-methyl-3,4-dihydroquinazolin-2-amine;
3-(2,6-Dimethoxybenzyl)-7-pyridin-3-yl-3,4-dihydroquinazolin-2-amine;
3-(2,6-Dimethoxybenzyl)-7-(2-thienyl)-3,4-dihydroquinazolin-2-amine;
3-(2,6-Dimethoxybenzyl)-7-[4-trifluoromethoxy)phenyl]-3,4-dihydroquinazolin-2-amine;
7-Anilino-3-(2,6-dimethoxybenzyl)-3,4-dihydroquinazolin-2-amine;
6-Chloro-3-(2,6-dimethoxybenzyl)-3,4-dihydroquinazolin-2-amine;
7-Chloro-3-(2,6-dimethoxybenzyl)-3,4-dihydroquinazolin-2-amine;
3-(2-Methoxybenzyl)-7-nitro-3,4-dihydroquinazolin-2-amine;
N-Cycloheptyl-3-(2,6-dimethoxybenzyl)-3,4-dihydroquinazolin-2-amine;
3-(2,6-Dimethoxybenzyl)-N-(1-naphthylmethyl)-3,4-dihydroquinazolin-2-amine;
[3-(2,6-Dimethoxybenzyl)-3,4-dihydroquinazolin-2-yl]pyridin-2-ylmethylamine;
N-Benzyl-3-(2,6-dimethoxybenzyl)-3,4-dihydroquinazolin-2-amine;
N-(1-Benzylpiperidin-4-yl)-3-(2-methoxybenzyl)-3,4-dihydroquinazolin-2-amine;
[3-(2-Methoxybenzyl)-3,4-dihydroquinazolin-2-yl]phenethylamine;
3-(2-Methoxybenzyl)-N-(1-naphthylmethyl)-3,4-dihydroquinazolin-2-amine;
3-(2-Methoxybenzyl)-N-(1-naphthylmethyl)-3,4-dihydroquinazolin-2-amine;
3-(2-Methoxybenzyl)-N-(2-thienylmethyl)-3,4-dihydroquinazolin-2-amine;
6-Methoxy-3-(2-methoxybenzyl)-3,4-dihydroquinazolin-2-amine; and
6-Chloro-3-(2-methoxybenzyl)-3,4-dihydroquinazolin-2-amine.

* * * * *

UNITED STATES PATENT AND TRADEMARK OFFICE
CERTIFICATE OF CORRECTION

PATENT NO. : 8,686,002 B2  Page 1 of 1
APPLICATION NO. : 11/990822
DATED : April 1, 2014
INVENTOR(S) : Amberg et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 821 days.

Signed and Sealed this
Thirtieth Day of May, 2017

Michelle K. Lee
*Director of the United States Patent and Trademark Office*